United States Patent
Satagopan et al.

(10) Patent No.: US 9,410,166 B2
(45) Date of Patent: Aug. 9, 2016

(54) ALCOHOL DEHYDROGENASES (ADH) USEFUL FOR FERMENTIVE PRODUCTION OF LOWER ALKYL ALCOHOLS

(71) Applicant: BUTAMAX ADVANCED BIOFUELS LLC, Wilmington, DE (US)

(72) Inventors: Sriram Satagopan, Columbus, OH (US); Daniel P. O'Keefe, Ridley Park, PA (US); Janardhan Gude, Andhrapradesh (IN)

(73) Assignee: Butamax Advanced Biofuels LLC, Wilmington, DE (US)

( * ) Notice: Subject to any disclaimer, the term of this patent is extended or adjusted under 35 U.S.C. 154(b) by 59 days.

(21) Appl. No.: 14/282,722

(22) Filed: May 20, 2014

(65) Prior Publication Data

US 2014/0377824 A1  Dec. 25, 2014

Related U.S. Application Data

(62) Division of application No. 12/980,597, filed on Dec. 29, 2010, now Pat. No. 8,765,433.

(60) Provisional application No. 61/290,636, filed on Dec. 29, 2009.

(51) Int. Cl.
C12N 15/81 (2006.01)
C12P 7/16 (2006.01)
C12N 9/02 (2006.01)

(52) U.S. Cl.
CPC .................. *C12P 7/16* (2013.01); *C12N 9/0004* (2013.01); *C12N 15/81* (2013.01); *Y02E 50/10* (2013.01); *Y02P 20/52* (2015.11)

(58) Field of Classification Search
None
See application file for complete search history.

(56) References Cited

U.S. PATENT DOCUMENTS

| | | |
|---|---|---|
| 4,241,184 A | 12/1980 | Hou et al. |
| 4,266,034 A | 5/1981 | Patel et al. |
| 5,000,000 A | 3/1991 | Ingram et al. |
| 5,028,539 A | 7/1991 | Ingram et al. |
| 5,162,516 A | 11/1992 | Ingram et al. |
| 5,385,833 A | 1/1995 | Bradshaw et al. |
| 5,487,989 A | 1/1996 | Fowler et al. |
| 5,763,236 A | 6/1998 | Kojima et al. |
| 5,821,093 A | 10/1998 | Ingram et al. |
| 5,821,398 A | 10/1998 | Speirs et al. |
| 5,855,881 A | 1/1999 | Loike et al. |
| 6,011,199 A | 1/2000 | Speirs et al. |
| 6,255,092 B1 | 7/2001 | Kojima et al. |
| 6,432,688 B1 | 8/2002 | Ito et al. |
| 6,440,711 B1 | 8/2002 | Dave |
| 6,706,507 B2 | 3/2004 | Kudoh et al. |
| 7,192,772 B1 | 3/2007 | Ingram et al. |
| 7,202,069 B2 | 4/2007 | Kudoh et al. |
| 7,341,859 B2 | 3/2008 | Hummel et al. |
| 7,354,751 B2 | 4/2008 | Nakano |
| 7,371,903 B2 | 5/2008 | Gupta et al. |
| 7,541,173 B2 | 6/2009 | Bramucci et al. |
| 7,569,375 B2 | 8/2009 | Stampfer et al. |
| 7,598,063 B2 | 10/2009 | Yukawa |
| 7,659,104 B2 | 2/2010 | Bramucci et al. |
| 7,659,105 B2 | 2/2010 | Burd et al. |
| 7,750,135 B2 | 7/2010 | Zeikus et al. |
| 7,851,188 B2 | 12/2010 | Donaldson et al. |
| 7,910,342 B2 | 3/2011 | Liao et al. |
| 7,993,889 B1 | 8/2011 | Donaldson et al. |
| 8,017,364 B2 | 9/2011 | Bramucci et al. |
| 8,129,162 B2 | 3/2012 | Li et al. |
| 8,178,328 B2 | 5/2012 | Donaldson et al. |
| 8,188,250 B2 | 5/2012 | Bramucci et al. |
| 8,206,970 B2 | 6/2012 | Eliot et al. |
| 8,222,017 B2 | 7/2012 | Li et al. |
| 8,241,878 B2 | 8/2012 | Anthony et al. |
| 8,273,558 B2 | 9/2012 | Donaldson et al. |
| 8,283,144 B2 | 10/2012 | Donaldson et al. |
| 8,372,612 B2 | 2/2013 | Larossa et al. |
| 8,389,252 B2 | 3/2013 | Larossa |
| 8,455,224 B2 | 6/2013 | Paul |
| 8,455,225 B2 | 6/2013 | Bramucci et al. |
| 8,465,964 B2 | 6/2013 | Anthony et al. |
| 8,518,678 B2 | 8/2013 | Flint et al. |
| 8,557,562 B2 | 10/2013 | Bramucci et al. |
| 8,614,085 B2 | 12/2013 | Van Dyk et al. |
| 8,637,281 B2 | 1/2014 | Paul et al. |
| 8,637,289 B2 | 1/2014 | Anthony et al. |
| 8,652,823 B2 | 2/2014 | Flint et al. |
| 8,669,094 B2 | 3/2014 | Anthony et al. |

(Continued)

FOREIGN PATENT DOCUMENTS

| CS | 197080 | 4/1980 |
|---|---|---|
| EP | 0098136 | 1/1984 |

(Continued)

OTHER PUBLICATIONS

Vallenet, D., et al., 2008, "Comparative analysis of Acinetobacters: Three genomes for three lifestyles", PLoS ONE, vol. 3, Issue 3, E1805 (eleven pages).*
Arfman, et al., Use of the tac Promoter and lacIq for the Controlled Expression of Zymomonas mobilis Fermentative Genes in *Escherichia coli* and Zymomonas mobilis, J. Bacteriol. 174:7370-7378, 1992.
Bellion, et al., Alcohol Dehydrogenases from a Facultative Methylotrophic Bacterium, J. Bacteriol. 135:251-258, 1978.
Bertram, et al., Structure and Regulation of the Candida albicans ADH1 Gene Encoding an Immunogenic Alcohol Dehydrogenase, Yeast 12:115-127, 1996.
Bozzi, et al., Structural and biochemical studies of alcohol dehydrogenase isozymes from Kluyleromyces lactis, Biochim. Biophysica Acta 1339:133-142, 1997.
Branden, et al., Structure of Liver Alcohol Dehydrogenase at 2.9-A Resolution, Proc. Natl. Acad. Sci. USA 70:2439-2442, 1973.
Cannon, et al., The Amino Acid Composition of Horse Liver Alcohol Dehydrogenase, Biochem. Biophys. Res. Comm. 35:403-409, 1969.

(Continued)

*Primary Examiner* — Manjunath Rao
*Assistant Examiner* — William W Moore

(57) ABSTRACT

The invention relates to suitable candidate alcohol dehydrogenase (ADH) enzymes for production of lower alkyl alcohols including isobutanol. The invention also relates to recombinant host cells that comprise such ADH enzymes and methods for producing lower alkyl alcohols in the same.

13 Claims, 15 Drawing Sheets

(56) References Cited

U.S. PATENT DOCUMENTS

| | | |
|---|---|---|
| 8,691,540 B2 | 4/2014 | Bramucci et al. |
| 8,735,114 B2 | 5/2014 | Donaldson et al. |
| 8,765,433 B2 | 7/2014 | Gude et al. |
| 8,785,166 B2 | 7/2014 | Anthony et al. |
| 8,795,992 B2 | 8/2014 | Bramucci et al. |
| 8,828,694 B2 | 9/2014 | Anthony et al. |
| 8,828,704 B2 | 9/2014 | Donaldson et al. |
| 8,871,488 B2 | 10/2014 | Dauner et al. |
| 8,889,385 B2 | 11/2014 | Donaldson et al. |
| 8,895,307 B2 | 11/2014 | Li et al. |
| 8,906,666 B2 | 12/2014 | Alsaker |
| 8,911,981 B2 | 12/2014 | Li et al. |
| 8,940,511 B2 | 1/2015 | Larossa |
| 8,945,859 B2 | 2/2015 | Donaldson et al. |
| 8,945,899 B2 | 2/2015 | Li et al. |
| 8,951,774 B2 | 2/2015 | Donaldson et al. |
| 8,951,937 B2 | 2/2015 | Flint et al. |
| 8,956,850 B2 | 2/2015 | Anthony et al. |
| 8,962,298 B2 | 2/2015 | Donaldson et al. |
| 8,969,065 B2 | 3/2015 | Anthony et al. |
| 8,980,612 B2 | 3/2015 | Donaldson et al. |
| 2002/0037564 A1 | 3/2002 | Blum |
| 2002/0064847 A1 | 5/2002 | Yamamoto et al. |
| 2003/0032153 A1 | 2/2003 | Yamamoto et al. |
| 2003/0171544 A1 | 9/2003 | Riermeier et al. |
| 2007/0031918 A1 | 2/2007 | Dunson et al. |
| 2007/0207529 A1 | 9/2007 | Pfaller et al. |
| 2007/0212766 A1 | 9/2007 | Pfaller et al. |
| 2008/0009046 A1 | 1/2008 | Sturmer et al. |
| 2008/0145904 A1 | 6/2008 | Groger et al. |
| 2008/0176304 A1 | 7/2008 | Lee |
| 2008/0182308 A1 | 7/2008 | Donaldson et al. |
| 2008/0220487 A1 | 9/2008 | Zeikus et al. |
| 2008/0274526 A1 | 11/2008 | Bramucci et al. |
| 2008/0293086 A1 | 11/2008 | Contag |
| 2008/0293101 A1 | 11/2008 | Peters et al. |
| 2009/0017510 A1 | 1/2009 | Gupta et al. |
| 2009/0081746 A1 | 3/2009 | Liao et al. |
| 2009/0148917 A1 | 6/2009 | Gupta et al. |
| 2010/0035317 A1 | 2/2010 | Kawano et al. |
| 2010/0036174 A1 | 2/2010 | Raamsdonk et al. |
| 2010/0062505 A1 | 3/2010 | Gunawardena et al. |
| 2010/0081154 A1 | 4/2010 | Flint et al. |
| 2010/0081179 A1 | 4/2010 | Anthony et al. |
| 2010/0081182 A1 | 4/2010 | Paul et al. |
| 2010/0093020 A1 | 4/2010 | Bramucci et al. |
| 2010/0120105 A1 | 5/2010 | Anthony et al. |
| 2010/0136640 A1 | 6/2010 | Lee et al. |
| 2010/0137655 A1 | 6/2010 | Soucaille |
| 2010/0173286 A1 | 7/2010 | Persson et al. |
| 2010/0190259 A1 | 7/2010 | Javed et al. |
| 2010/0196978 A1 | 8/2010 | Wood et al. |
| 2011/0020888 A1 | 1/2011 | Papoutsakis et al. |
| 2011/0124060 A1 | 5/2011 | Anthony et al. |
| 2011/0136192 A1 | 6/2011 | Paul et al. |
| 2011/0195505 A1 | 8/2011 | Euler et al. |
| 2011/0201072 A1 | 8/2011 | Bastian et al. |
| 2011/0244536 A1 | 10/2011 | Nagarajan et al. |
| 2011/0250610 A1 | 10/2011 | Bramucci et al. |
| 2012/0015416 A1 | 1/2012 | Anthony et al. |
| 2012/0058541 A1 | 3/2012 | Alsaker et al. |
| 2012/0064561 A1 | 3/2012 | Flint et al. |
| 2012/0149080 A1 | 6/2012 | Bramucci et al. |
| 2012/0156735 A1 | 6/2012 | Dauner et al. |
| 2012/0196341 A1 | 8/2012 | Donaldson et al. |
| 2012/0237988 A1 | 9/2012 | Anthony et al. |
| 2012/0258873 A1 | 10/2012 | Gibson et al. |
| 2013/0035515 A1 | 2/2013 | Dobson et al. |
| 2013/0071898 A1 | 3/2013 | Anthony et al. |
| 2013/0171706 A1 | 7/2013 | Donaldson et al. |
| 2013/0203138 A1 | 8/2013 | McElvain et al. |
| 2013/0252296 A1 | 9/2013 | Maggio-Hall et al. |
| 2013/0316414 A1 | 11/2013 | Paul et al. |
| 2014/0004526 A1 | 1/2014 | Dauner et al. |
| 2014/0030782 A1 | 1/2014 | Anthony et al. |
| 2014/0030783 A1 | 1/2014 | Anthony et al. |
| 2014/0038263 A1 | 2/2014 | Flint et al. |
| 2014/0038268 A1 | 2/2014 | Flint et al. |
| 2014/0051133 A1 | 2/2014 | Govindarajan et al. |
| 2014/0051137 A1 | 2/2014 | Flint et al. |
| 2014/0057329 A1 | 2/2014 | Li et al. |
| 2014/0093930 A1 | 4/2014 | Li et al. |
| 2014/0096439 A1 | 4/2014 | Bramucci et al. |
| 2014/0141479 A1 | 5/2014 | Anthony et al. |
| 2014/0170732 A1 | 6/2014 | Bramucci et al. |
| 2014/0186910 A1 | 7/2014 | Rothman et al. |
| 2014/0186911 A1 | 7/2014 | Anthony et al. |
| 2014/0273116 A1 | 9/2014 | Kelly et al. |
| 2014/0273129 A1 | 9/2014 | Bhalla et al. |
| 2014/0308735 A1 | 10/2014 | Anthony et al. |
| 2014/0335582 A1 | 11/2014 | Donaldson et al. |
| 2014/0349349 A1 | 11/2014 | Dauner et al. |
| 2015/0037855 A1 | 2/2015 | Bhadra et al. |
| 2015/0111269 A1 | 4/2015 | Li et al. |
| 2015/0119608 A1 | 4/2015 | Donaldson et al. |
| 2015/0125920 A1 | 5/2015 | Anthony et al. |

FOREIGN PATENT DOCUMENTS

| | | |
|---|---|---|
| EP | 0098137 | 1/1984 |
| EP | 156780 | 8/2005 |
| FR | 2706906 | 12/1994 |
| JP | 54129189 | 10/1979 |
| JP | 11-127883 | 5/1999 |
| JP | 2000-078969 | 3/2000 |
| JP | 2004-254549 | 9/2004 |
| JP | 2005-102511 | 4/2005 |
| JP | 2006-345744 | 12/2006 |
| KR | 2004101797 | 12/2004 |
| KR | 2004104076 | 12/2004 |
| KR | 2005042860 | 5/2005 |
| WO | WO 2005/026338 | 3/2005 |
| WO | WO 2005/040392 | 5/2005 |
| WO | WO 2006/016432 | 2/2006 |
| WO | WO 2007/050671 | 5/2007 |
| WO | WO 2007/130521 | 11/2007 |
| WO | WO 2008/035187 | 3/2008 |
| WO | WO 2008/064817 | 6/2008 |
| WO | WO 2008/074794 | 6/2008 |
| WO | WO 2008/098227 | 8/2008 |
| WO | WO 2009/085953 | 7/2009 |
| WO | WO 2009/086423 | 7/2009 |
| WO | WO 2010/017230 | 2/2010 |
| WO | WO 2010051527 | 5/2010 |
| WO | WO 2010/151525 | 12/2010 |

OTHER PUBLICATIONS

Chinnawirotpisan, et al., Quinoprotein Alcohol Dehydrogenase is Involved in Catabolic Acetate Production, while NAD-Dependent Alcohol Dehydrogenase in Ethanol Assimilation . . . , J. Biosci. Bioengin. 96:564-571, 2003.

Dailly, et al., Novel alcohol dehydrogenase activity in a mutant of *Salmonella* able to use ethanol as sole carbon source, FEMS Microbiol. Lett. 201:41-45, 2001.

Denis, et al., mRNA Levels for the Fermentative Alcohol Dehydrogenase of *Saccharomyces cerevisiae* Decrease upon Growth on a Nonfermentable Carbon Source, J. Biol. Chem. 258:1165-1171, 1983.

Drewke, et al., Overexpression, purification and properties of alcohol dehydrogenase IV from *Saccharomyces cerevisiae*, Biochim. Biophysica Acta 950:54-60, 1988.

Galamba, et al., Molecular and biochemical characterisation of *Mycobacterium smegmatis* alcohol dehydrogenase C, FEMS Microbiol. Lett. 196:51-56, 2001.

Guy, et al., The Structure of an Alcohol Dehydrogenase from the Hyperthermophilic Archaeon Aeropyrum pernix, J. Mol. Biol. 331:1041-1051, 2003.

Hayman, et al., Isolation and Properties of Lens Aldose Reductase, J. Biol. Chem. 240:877-882, 1965.

Hollrigl, et al., TADH, The thermostable alcohol dehydrogenase from *Thermus* sp. ATN1: a versatile new biocatalyst for organic synthesis, Appl. Microbiol. Biotechnol. 81:263-273, 2008.

(56) References Cited

OTHER PUBLICATIONS

Holt, et al., Cloning, sequencing and expression in *Escherichia coli* of the primary alcohol dehydrogenase gene from Thermoanaerobacter ethanolicus JW200, FEMS Microbiol. Lett. 190:57-62, 2000.

Hou, et al., Identification and Purification of a Nicotinamide Adenine Dinucleotide-dependent Secondary Alcohol Dehydrogenase From C1-utilizing Microbes, FEBS Lett. 101:179-183, 1979.

Ismaiel, et al., Purification and characterization of a primary-secondary alcohol dehydrogenase from two strains of Clostridium beijerinckii, J. Bacteriol. 175:5097-5105, 1993.

Jongejan, et al., The enantioselectivity of quinohaemoprotein alcohol dehydrogenases: mechanistic and structural aspects, J. Mol. Catalysis B: Enzymatic 8:121-163, 2000.

Julia, et al., Characterization of three isoenzymes of rat dehydrogenase, Eur. J. Biochem. 162:179-189, 1987.

Karnitz, et al., Identification and Characterization of Three Genes That Affect Expression of ADH2 in *Saccharomyces cerevisiae*, Genetics 132:351-359, 1992.

Kato, et al., Gene Cloning of an Alcohol Dehydrogenase from Thermophilic Alkane-Degrading Bacillus thermoleovorans B23, J. Biosci. Bioeng. 91:100-102, 2001.

Kazuoka, et al., A cold-active and thermostable alcohol dehydrogenase of a psychrotorelant from Antarctic seawater, Flavobacterium frigidimaris KUC-1, Extremophiles 11:257-267, 2007.

Korkhin, et al., NADP-dependent Bacterial Alcohol Dehydrogenases: Crystal Structure, Cofactor-binding and Cofactor Specificity of the ADHs of Clostridium beijerinckii and . . . , J. Mol. Biol. 278:967-981, 1998.

Kreit, et al., Substrate characterization of a NAD-dependent secondary alcohol dehydrogenase from *Rhodococcus* sp. GK1 (CIP 105335), J. Mol. Catalysis B: Enzymatic 19-20:253-259, 2002.

Kumar, et al., Cloning and expression of an NADP+-dependent alcohol dehydrogenase gene of Entamoeba histolytica, Proc. Natl. Acad. Sci. USA 89:10188-10192, 1992.

Larroy, et al., Characterization of the *Saccharomyces cerevisiae* YMR318C (ADH6) gene product as a broad specificity NADPH-dependent alcohol dehydrogenase: relevance in aldehyde . . . , Biochem. J. 361:163-172, 2002.

Larroy, et al., Characterization of a *Saccharomyces cerevisiae* NADP(H)-dependent alcohol dehydrogenase (ADHVII), a member of the cinnamyl alcohol dehydrogenase family, Eur. J. Biochem. 269:5738-5745, 2002.

Larroy, et al., Properties and functional significance of *Saccharomyces cerevisiae* ADHVI, Chemico-Biological Interactions 143-144:229-238, 2003.

Leonardo, et al., Anaerobic Regulation of the adhE Gene, Encoding the Fermentative Alcohol Dehydrogenase of *Escherichia coli*, J. Bacteriol. 175:870-878, 1993.

Mazzoni, et al., Molecular analysis of UASE, a cis element containing stress response elements responsible for ethanol induction of the KlADH4 gene of Kluyveromyces lactis, Res. Microbiol. 151:19-28, 2000.

Nosova, et al., Characteristics of Alcohol Dehydrogenases of Certain Aerobic Bacteria Representing Human Colonic Flora, Alcoholism: Clin Exp. Res. 21:489-494, 1997.

Okuma, et al., Purification and Properties of Alcohol Dehydrogenase from the Acid- and Ethanol-Tolerant Yeast *Candida solicola*, J. Fermentation and Bioengineering 71:309-312, 1991.

Okura, et al., Regeneration of NADH and Ketone Hydrogenation by Hydrogen with the Combination of Hydrogenase and Alcohol Dehydrogenase, Appl. Biochem. Biotechnol. 24/25:425-430, 1990.

Pietruszko, et al., Structure and Function Relationships in Isoenzymes of Horse Liver Alcohol Dehydrogenase, Nature 221:440-443, 1969.

Piskur, et al., How did *Saccharomyces* evolve to become a good brewer? TRENDS Genetics 22:183-186, 2006.

Radianingtyas, et al., Alcohol dehydrogenases from thermophilic and hyperthermophilic archaea and bacteria, FEMS Microbiol. Rev. 27:593-616, 2003.

Rosell, et al., Complete Reversal of Coenzyme Specificity by Concerted Mutation of Three Consecutive Residues in Alcohol Dehydrogenase, J. Biol. Chem. 278:40573-40580, 2003.

Ruohonen, et al., Modifications to the ADHI promoter of *Saccharomyces cerevisiae* for efficient production of heterologous proteins, J. Biotechnol. 39:193-203, 1995.

Saliola, et al., Two mitochondrial alcohol dehydrogenase activities of Kluyveromycee lactis are differently expressed during respiration and fermentation, Mol. Gen. Genet. 249:665-672, 1995.

Shibata, et al., Purification and Molecular Characterization of a Quinoprotein Alcohol Dehydrogenase from Pseudogluconobacter saccharoketogenes IF0 14464, J. Biosci. Bioeng. 92:524-531, 2001.

Sigman, Interactions of Substrates, Inhibitors, and Coenzymes at the Active Site of Horse Liver Alcohol Dehydrogenase, J. Biol. Chem. 242:3815-3824, 1967.

Stibor, et al., Characterization of cold-active dehydrogenases for secondary alcohols and glycerol in psychrotolerant bacteria isolated from Antarctic soil, Enzyme Microbial Technology 32:532-538, 2003.

Sulzenbacher, et al., Crystal Structure of *E. coli* Alcohol Dehydrogenase YqhD: Evidence of a Covalently Modified NADP Coenzyme, J. Mol. Biol. 342:489-502, 2004.

Takeda, et al., Role of Cytochrome c-553(CO), the Second Subunit of Alcohol Dehydrogenase, in the Azide-Insensitive Respiratory Chain and in Oxidative Fermentation . . . , J. Ferment. Bioeng. 74:209-213, 1992.

Takeda, et al., Comparison of the Second Alcohol Dehydrogenase Subunit Gene in Acetic Acid Bacteria, J. Ferment. Bioeng. 75:217-219, 1993.

Branden, et al., X-ray Investigations of Horse Liver Alcohol Dehydrogenase and its Complexes, Arch. Biochem. Biophys. p. 105, 1965.

Trcek, Quick identification of acetic acid bacteria based on nucleotide sequences of the 16S-23S rDNA internal transcribed spacer region and of the PQQ-dependent . . . , Systemic Appl. Microbiol. 28:735-745, 2005.

Velonia, et al., Stereospecificity of Hydrogen Transfer by the NAD+-linked Alcohol Dehydrogenase from the Antarctic Psychrophile *Moraxella* sp. TAE123, Bioorganic Med. Chem. Lett. 9:65-68, 1999.

Walter, et al., Molecular characterization of two Clostridium acetobutylicum ATCC 824 butanol dehydrogenase isozyme genes, J. Bacteriol. 174:7149-7158, 1992.

Welch, et al., Purification and Characterization of the NADH-dependent Butanol Dehydrogenase from Clostridium acetobutylicum (ATCC 824), Arch Biochem. Biophyics 273:309-318, 1989.

Willis, et al., Identification of the Rhizobium meliloti alcohol dehydrogenase gene (adhA) and heterologous expression in Alcaligenes eutrophus, Biochim. Biophysica Acta 1384:197-203, 1998.

Yonetani, et al., Crystallization of Binary and Ternary Complexes of Horse Liver Alcohol Dehydrogenase with DPNH and with DPNH and Isobutyramide, Arch. Biochem. Biophysics 100:554-556, 1963.

Yoshimoto, et al., Identity of the GAM3 Gene with ADR6, Each Required for Transcription of the STA1 or ADH2 Gene in *Saccharomyces cerevisiae*, Biosci. Biotech. Biochem. 56:527-529, 1992.

Youngleson, et al., Molecular analysis and nucleotide sequence of the adh1 gene encoding an NADPH-dependent butanol dehydrogenase in the Gram-positive anaerobe . . . , Gene 78:355-364, 1989.

Britt, et al., Purification and characterisation of an NAD+-dependent secondary alcohol dehydrogenase from Pseudomonas maltophilia MB11L, FEMS Microbiol. Lett. 93:49-55, 1992.

Chen, Alcohol dehydrogenase: multiplicity and relatednes in the solvent-producing clostridia, FEMS Microbiol. Rev. 17:263-273, 1995.

Wales, et al., Comparison of the Primary Structures of NAD(P)-dependent Bacterial Alcohol Dehydrogenases, Enzymology and Molecular Biology of Carbonyl Metabolism 3, Plenum Press, NY 1990, pp. 337-345.

(56) References Cited

OTHER PUBLICATIONS

Indrati, et al., Alcohol dehydrogenase (ADH2) from a mutant strain of Candida guilliermondii A80-03: Purification and characterization, FEMS Microbiol. Lett. 110:179-184, 1993.

Pateman, et al., Molecular Analysis of Alcohol Metabolism in Aspergillus, Mol. Genet. Filamentous Fungi 34:171-184, 1985.

Pateman, et al., Regulation of alcohol dehydrogenase (ADH) and aldehyde dehydrogenase (AldDH) is Aspergillus nidulans, Proc. R. Soc. Lond. B 217:243-264, 1983.

Reid, et al., Molecular Characterization of Microbial Alcohol Dehydrogenases, Crit. Rev. Microbiol. 20:13-56, 1994.

Woods, et al., Regulation of nitrogen metabolism, starch utilisation and the β-hbd-adh1 gene cluster in Clostridium acetobutylicum, FEMS Microbiol. Rev. 17:299-306, 1995.

Leskovac, et al., The three zinc-containing alcohol dehydrogenases from baker's yeast, *Saccharomyces cerevisiae*, FEMS Yeast Res. 2:481-494, 2002.

Li, et al., Crystal Structure of a Thermophilic Alcohol Dehydrogenase Substrate Complex Suggests Determinants of Substrate Specificity and Thermostability, Proteins: Structure, Function, and Genetics 37:619-627, 1999.

Akada, et al., PCR-mediated seamless gene deletion and marker recycling in *Saccharomyces cerevisiae*, Yeast 23:399-405, 2006.

Brutlag, et al., Improved sensitivity of biological sequence database searches, CABIOS 6:237-245, 1990.

Carlini, et al., Guerbet condensation of methanol with n-propanol to isobutyl alcohol over heterogeneous copper chromite/Mg—Al mixed oxides catalysts, J. Mol. Catal. A: Chem. 220:215-220, 2004.

De Smidt, et al., The alcohol dehydrogenases of *Sacchaomyces cerevisiae*: a comprehensive review, FEMS Yeast Res. 8:967-978, 2008.

Dickinson, et al., An investigation of the metabolism of valine to isobutyl alcohol in *Saccharomyces cerevisiae*, J. Biol. Chem. 273:25751-25756, 1998.

Garcia, et al., Fusel alcohols production in beer fermentation processes, Process Biochemistry 29:303-309, 1994.

Green, et al., Inversion of the substrate specificity of yeast alcohol dehydrogenase, J. Biol. Chem. 268:7792-7798, 1993.

Nakamura, et al., Codon usage tabulated from international DNA sequence databases: status for the year 2000, Nucleic Acids Res. 28:292, 2002.

Nevoigt, et al., Engineering of promoter replacement cassettes for fine-tuning of gene expression in *Saccharomyces cerevisiae*, Appl. Environ. Microbiol. 72:5266-5273, 2006.

Oaxaca, et al., Formation of ethanol and higher alcohols by immobilized Zymomonas mobilis in continuous culture, Acta Biotechnol. 11:523-532, 1991.

Racker, Crystalline alcohol dehydrogenase from bakers' yeast, J. Biol. Chem. 184:313-319, 1950.

Sulter et al., Proliferation and metabolic significance of peroxisomes in Candida boidinii during growth on D-alanine or oleic acid as the sole carbon source, Arch. Microbiol. 153:485-489, 1990.

Ausubel et al., Current Protocols in Molecular Biology, published by Greene Publishing Assoc. and Wiley Interscience (1987).

Bellion, et al., Microb. Growth C1 Compd., [Int. Symp.], 7th (1993), 415 32, Editor(s): Murrell, J. Collin; Kelly, Don P. Publisher: Intercept, Andover, UK.

Enzyme Structure and Mechanism, 2nd ed. Ferst, W.H. Freeman: NY, 1985; pp. 98-120.

Sambrook, et al., T. Molecular Cloning: A Laboratory Manual, 2nd ed., Cold Spring Harbor Laboratory: Cold Spring Harbor, NY (1989), particularly 9.50-9.51, 11.7-11.8 and Table 11.1.

Ullmann's Encyclopedia of Industrial Chemistry, 6th edition, 2003, Wiley-VCH Verlag GmbH and Co., Weinheim, Germany, vol. 5, pp. 716-719.

Genbank Database Accession No. B2IGW3, Jun. 10, 2008.

Steen, et al., Metabolic engineerng of *Saccharomyces cerevisiae* for the producton of n-butanol, Microbial Cell Factories 7:36, 2008.

International Search Report and Written Opinion in corresponding PCT/US2010/062390 mailed Aug. 18, 2011.

* cited by examiner

Panel A
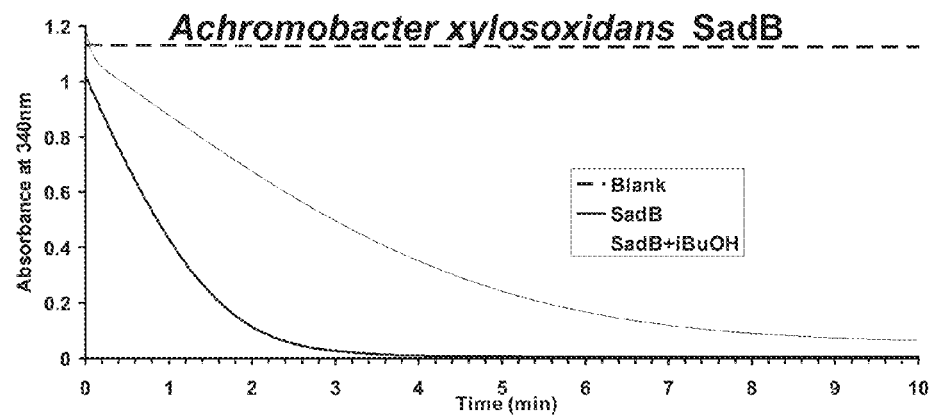
Panel B
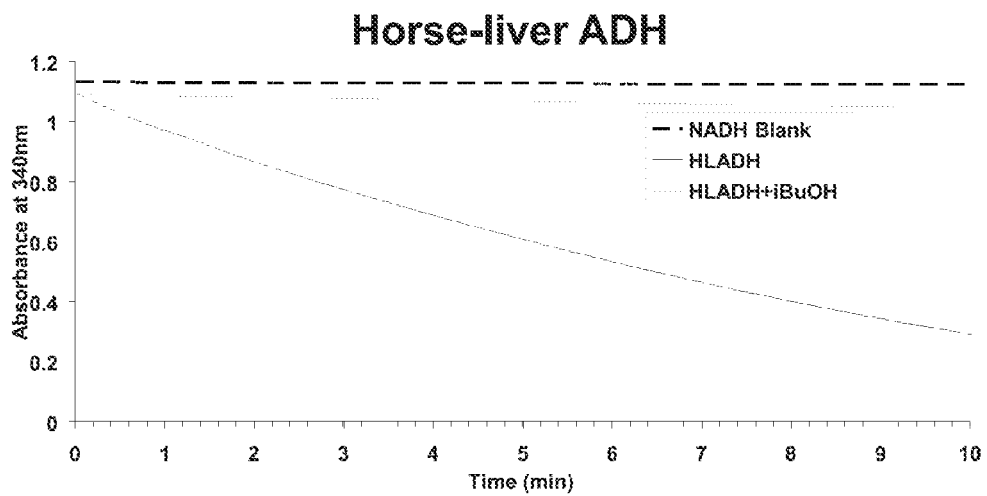
FIG. 1A

Panel C
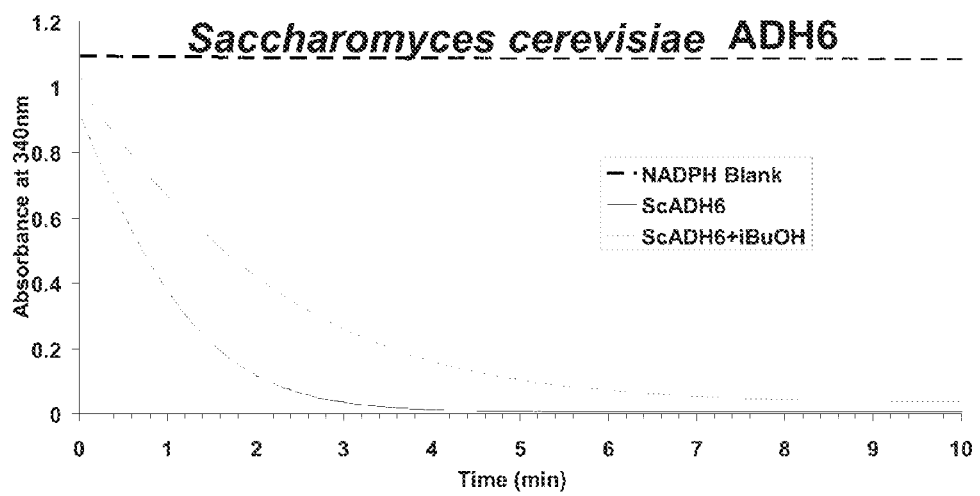
Panel D
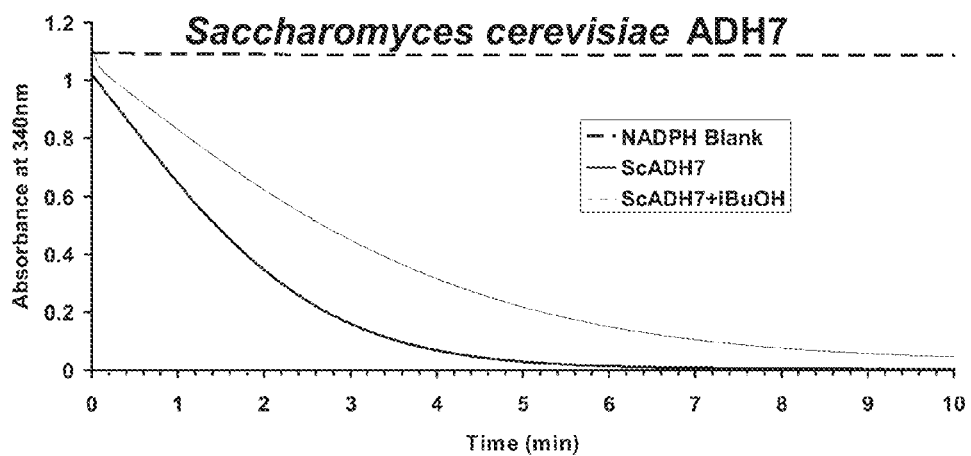
FIG. 1B

Panel E
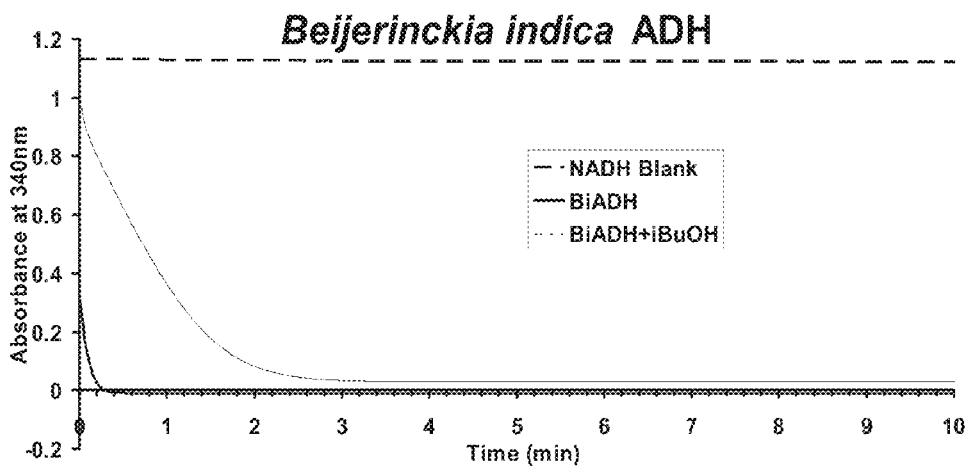
Panel F
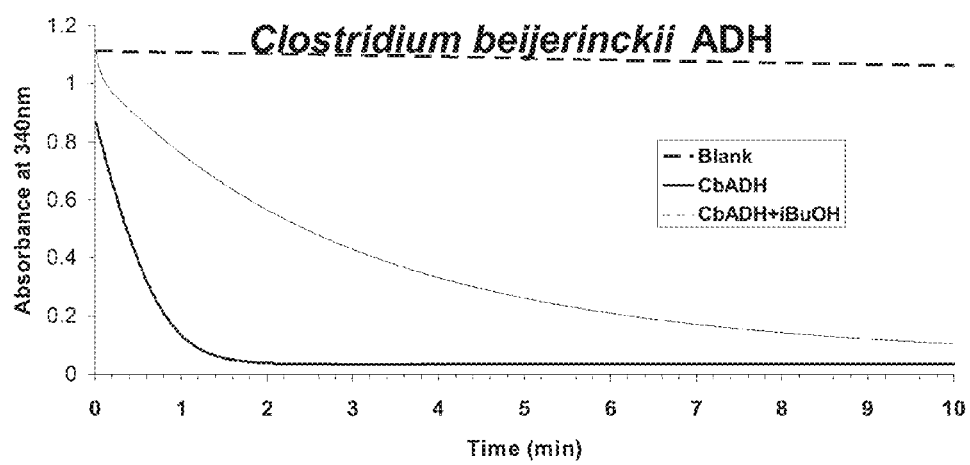
FIG. 1C

Panel G
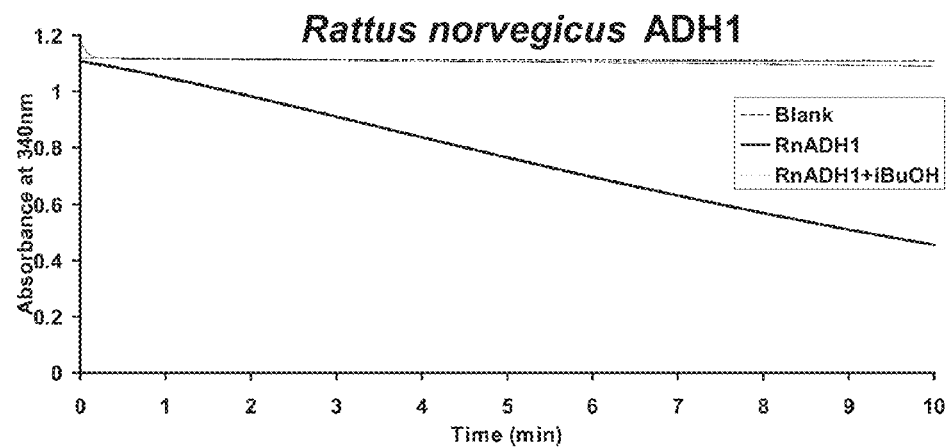
Panel H
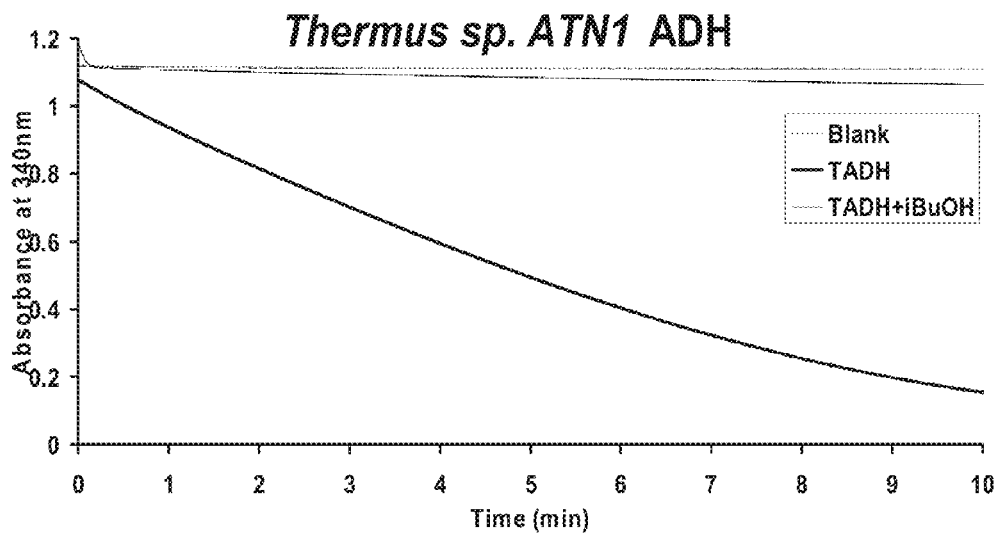
FIG. 1D

```
_aln.pos        10        20        30        40        50        60
1kolA    --------GNRGVVYL-GSGKVEVQKIDYPKMQDPPGKKIEHGVILKVVSTNICGSDQHMVRGRTTAQ-
2ohxA    STACKVIKCKAAVLWEEKKPFSIEEVEVAPP--------KAHEVRIKMVATGICRSDDHVVSGTLVT----
1pedA    --------MRGFAMLGINK-LGWIEKERPVA--------GSYQAIVRPLAVSPCTSDIHTVFEGALGD-
2d8aA    -----EKMVAIMKTKPGYGAELVEVDVPKP--------GPCEVLIKVLATSICGTDLHIYEWNEWAQS
SadB     -----------MKALVYHGDEKISLEDKPKPTLQ-------KPTDVVVRVLKTTICGTDLGIYKGKNPEV-
_consrvd                                                          *  *

_aln.p   70        80        90       100       110       120       130
1kolA    -----VGLVLGHEITGEVIEKCRDVENLQIGDLVSVPFNVACGRCRSCKEM-ETCVCLTVNPARAGGAY--
2ohxA    ---PLPVIAGHEAAGIVESICECVTTVRPGDKVIPLFTPQCGKCRVCKHPEGNFCLKN----DLSMPRGT
1pedA    ---RKNMILGHEAVGEVVEVGSEVKDFKPGDRVIVPCTTPDWRSLEVQAG-FQQHSNG----MLAGWKF-
2d8aA    KIKPPQIMGHEVAGEVVEIGPGVEGIEVGDYVSVETHIVCGKCY---------------TKIF-
SadB     ---ADGRILGHEGVGVIEEVGESVTQFKKGDKVLISCVTSCGSCDYCKKQLYSHCRDG-------GWIL-
_consrvd       ***  *     * *      ** *

_aln.pos        140       150       160       170       180       190       200
1kolA    --------------------GYVDMGDWTGGQAEYVLVPYADFNLLKLPDRDKAMEKIRDLTCLSDILPTGY
2ohxA    MQDGTSRFTCRGKPIHHF-----LGTSTFSQYTVVDE--ISVAKIDA-----ASPLEKVCLIGCGFSTGY
1pedA    -----------------SN----FKDGVFGEYFHVNDADMNLAILPK------DMPLENAVMITDMMTEGF
2d8aA    -----------------GV-----DTDGVPAEYAVVPA--QNIWKNPK----SIPPEYATLQ-EPLGNAV
SadB     -----------------GY-----MIDGVQAEYVRIPHADNSLYKIPQ----TIDDEIAVLLSDILPTGH
_consrvd                              *

_aln.pos        210       220       230       240       250       260       270
1kolA    HGA-VTAGVGPGSTVYVAGAGPVCLAAAASARLLGAAVVIVGDLNPARLAHAKAQGF-EIADLSLDT--
2ohxA    GSAVKVAKVTQGSTCAVFGLGGVCLSVIMGCKAAGAARIIGVDINKDKPAKAKEVGATECVNPQDYKK
1pedA    HGA-ELADIQMGSSVVVIGIGAVGLMGIAGAKLRGAGRIIGVGSRPICVEAAKFYGATDIINYKNG---
2d8aA    DTVLA--GPISGKSVLITGAGPLGLLGIAVAKASGAYPVIVSEPSDPRRELAKKVGADYVINPFEE---
SadB     EIGVQYGNVQPGDAVAIVGAGPVGMSVLLTAQFYSPSTIIVIDMDENRLQLAKELGATHTINSGTE---
_consrvd      *        *  *   *                *         ** *

_aln.pos        280       290       300       310       320       330       340
1kolA    PLHEQIAALLGEPEVDCAVDAVGFEARGHGHEGAKHEAPATVLNSLMQVTRV-AGKIGIPGLYVTEDP
2ohxA    PIQEVLTEMSN-GGVDFSFEVIG---------------RLDTMVTALSCCQEAYGVSVIVGVPP----
1pedA    HIVDQVMKLENGKGVDRVIMAGG---------------GSETLSQAVSMVKP-GGIISNINYHG----
2d8aA    DVVKEVMDITDGNGVDVFLEFSG---------------APKALEQGLQAVTP-AGRVSLLGLY-----
SadB     NVVEAVHRIAA-EGVDVAIEAVG---------------IPATWDICQEIVKP-GAHIANVGVH-----
_consrvd         **       *

_aln.pos        350       360       370       380       390       400
1kolA    GAVDAAAKIGSLSIRFGLG--WAKSESPHTGQF---PVMKYNRALMQAIMWDRINIAEVVGVQVISLD
2ohxA    -------DSQNLSMNP---MLLLSGRTWKGAIFGGFKSKDSVPKLVADFMAKKFALDPLITHVLP-PE
1pedA    -------SGDALLIPRVEWGCGMAHKTIKGGLC--PGGRLRAEMLRDMVVYNRVDLSKLVTHVYHGFD
2d8aA    ---------PGKVTIDFNNLIIFKALTIYGITG--RHLWETWYTVSRLLQSGKLNLDPIITHRYKGFD
SadB     ---------GVKVDFEIQKLWIKNLTITTGLV----NTNTTPMLMKVASTDKLPLKKMITHRFELAE
_consrvd _aln.p   410       420       430
1kolA    DAPRGYGEPDAG--VPKKFVIDPHKTFSA      SEQ ID NO: 79
2ohxA    KINEGFDLLRSG--ESIRTILTF------      SEQ ID NO: 21
1pedA    HIEEALLLMKDKPKDLIKAVVIL------      SEQ ID NO: 29
2d8aA    KYEEAFELMRAGK--TGKVVFML------      SEQ ID NO: 80
SadB     IEHAYQVFLNGAKEKAMKIILSN--AGAA      SEQ ID NO: 26
_consrvd
```

FIG. 3

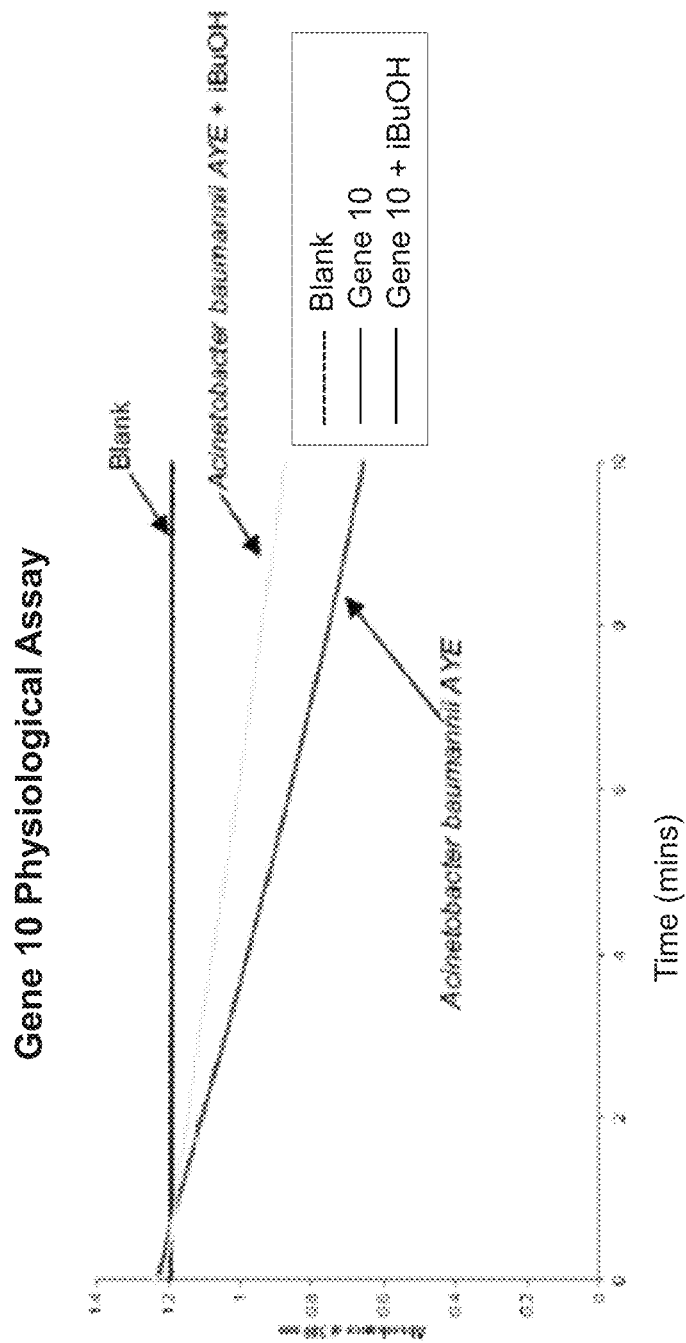

ALCOHOL DEHYDROGENASES (ADH) USEFUL FOR FERMENTIVE PRODUCTION OF LOWER ALKYL ALCOHOLS

This application is a divisional of U.S. patent application Ser. No. 12/980,597, filed on Dec. 29, 2010, now U.S. Pat. No. 8,765,433, issued Jul. 1, 2014 which claims priority to U.S. Provisional Patent Application No. 61/290,636, filed on Dec. 29, 2009, all of which are incorporated by reference in their entirety.

BACKGROUND OF THE INVENTION

1. Field of the Invention

The invention relates to the fields of industrial microbiology and alcohol production. Specifically, the invention relates suitable alcohol dehydrogenases for the production of lower alkyl alcohols via an engineered pathway in microorganisms. More specifically, the invention relates to suitable alcohol dehydrogenases for the production of butanol, particularly isobutanol, via an engineered pathway in microorganisms.

2. Background Art

Butanol is an important industrial chemical, useful as a fuel additive, as a feedstock chemical in the plastics industry, and as a food grade extractant in the food and flavor industry. Each year 10 to 12 billion pounds of butanol are produced by petrochemical means and the need for this commodity chemical will likely increase in the future.

Methods for the chemical synthesis of isobutanol are known, such as oxo synthesis, catalytic hydrogenation of carbon monoxide (Ullmann's Encyclopedia of Industrial Chemistry, 6th edition, 2003, Wiley-VCHVerlag GmbH and Co., Weinheim, Germany, Vol. 5, pp. 716-719) and Guerbet condensation of methanol with n-propanol (Carlini et al., *J. Molec. Catal. A: Chem.* 220:215-220, 2004). These processes use starting materials derived from petrochemicals, are generally expensive, and are not environmentally friendly.

Isobutanol is produced biologically as a by-product of yeast fermentation. It is a component of "fusel oil" that forms as a result of the incomplete metabolism of amino acids by this group of fungi. Isobutanol is specifically produced from catabolism of L-valine. After the amine group of L-valine is harvested as a nitrogen source, the resulting α-keto acid is decarboxylated and reduced to isobutanol by enzymes of the so-called Ehrlich pathway (Dickinson et al., *J. Biol. Chem.* 273:25752-25756, 1998). Yields of fusel oil and/or its components achieved during beverage fermentation are typically low. For example, the concentration of isobutanol produced in beer fermentation is reported to be less than 16 parts per million (Garcia et al., *Process Biochemistry* 29:303-309, 1994). Addition of exogenous L-valine to the fermentation mixture increases the yield of isobutanol, as described by Dickinson et al., supra, wherein it is reported that a yield of isobutanol of 3 g/L is obtained by providing L-valine at a concentration of 20 g/L in the fermentation mixture. In addition, production of n-propanol, isobutanol and isoamylalcohol has been shown by calcium alginate immobilized cells of *Zymomonas mobilis*. A 10% glucose-containing medium supplemented with either L-Leu, L-Ile, L-Val, α-ketoisocaproic acid (α-KCA), α-ketobutyric acid (α-KBA) or α-ketoisovaleric acid (α-KVA) was used (Oaxaca, et al., *Acta Biotechnol.* 11:523-532, 1991). α-KCA increased isobutanol levels. The amino acids also gave corresponding alcohols, but to a lesser degree than the keto acids. An increase in the yield of $C_3$-$C_5$ alcohols from carbohydrates was shown when amino acids leucine, isoleucine, and/or valine were added to the growth medium as the nitrogen source (PCT Publ. No. WO 2005/040392).

Whereas the methods described above indicate the potential of isobutanol production via biological means, these methods are cost prohibitive for industrial scale isobutanol production.

For an efficient biosynthetic process, an optimal enzyme is required at the last step to rapidly convert isobutyraldehyde to isobutanol. Furthermore, an accumulation of isobutyraldehyde in the production host normally leads to undesirable cellular toxicity.

Alcohol dehydrogenases (ADHs) are a family of proteins comprising a large group of enzymes that catalyze the interconversion of aldehydes and alcohols (de Smidt et al., *FEMS Yeast Res.*, 8:967-978, 2008), with varying specificities for different alcohols and aldehydes. There is a need to identify suitable ADH enzymes to catalyze the formation of product alcohols in recombinant microorganisms. There is also a need to identify a suitable ADH enzyme that would catalyze the formation of isobutanol at a high rate, with specific affinity for isobutyraldehyde as the substrate and in the presence of high levels of isobutanol.

BRIEF SUMMARY OF THE INVENTION

One aspect of the invention is directed to a recombinant microbial host cell comprising a heterologous polynucleotide that encodes a polypeptide wherein the polypeptide has alcohol dehydrogenase activity. In embodiments, the recombinant microbial host cell further comprises a biosynthetic pathway for the production of a lower alkyl alcohol, wherein the biosynthetic pathway comprises a substrate to product conversion catalyzed by a polypeptide with alcohol dehydrogenase activity. In embodiments, the polypeptide has alcohol dehydrogenase activity and one or more of the following characteristics: (a) the $K_M$ value for a lower alkyl aldehyde is lower for the polypeptide relative to a control polypeptide having the amino acid sequence of SEQ ID NO: 26; (b) the $K_I$ value for a lower alkyl alcohol for the polypeptide is higher relative to a control polypeptide having the amino acid sequence of SEQ ID NO: 26; and (c) the $k_{cat}/K_M$ value for a lower alkyl aldehyde for the polypeptide is higher relative to a control polypeptide having the amino acid sequence of SEQ ID NO: 26. In embodiments, the polypeptide having alcohol dehydrogenase activity has two or more of the above-listed characteristics. In embodiments, the polypeptide preferentially uses NADH as a cofactor. In embodiments, the polypeptide having alcohol dehydrogenase activity has three of the above-listed characteristics. In embodiments, the biosynthetic pathway for production of a lower alkyl alcohol is a butanol, propanol, isopropanol, or ethanol biosynthetic pathway. In one embodiment, the biosynthetic pathway for production of a lower alkyl alcohol is a butanol biosynthetic pathway.

Accordingly, one aspect of the invention is a recombinant microbial host cell comprising: a biosynthetic pathway for production of a lower alkyl alcohol, the biosynthetic pathway comprising a substrate to product conversion catalyzed by a polypeptide with alcohol dehydrogenase activity and one or more, two or more, or all of the following characteristics: (a) the $K_M$ value for isobutyraldehyde is lower for said polypeptide relative to a control polypeptide having the amino acid sequence of SEQ ID NO: 26; (b) the $K_I$ value for isobutanol for said polypeptide is higher relative to a control polypeptide having the amino acid sequence of SEQ ID NO: 26; and (c) the $k_{cat}/K_M$ value isobutyraldehyde for said polypeptide is higher relative to a control polypeptide having the amino acid sequence of SEQ ID NO: 26. In embodiments, the biosynthetic pathway for production of a lower alkyl alcohol is a butanol, propanol, isopropanol, or ethanol biosynthetic pathway. In embodiments, the polypeptide with alcohol dehydrogenase activity has at least 90% identity to the amino acid sequence of SEQ ID NO: 21, 22, 23, 24, 25, 31, 32, 34, 35, 36, 37, or 38. In embodiments, the polypeptide with alcohol dehydrogenase activity has the amino acid sequence of SEQ ID NO: 31. In embodiments, the polypeptide with alcohol dehydrogenase activity is encoded by a polynucleotide having at least 90% identity to a nucleotide sequence of SEQ ID NO: 1, 2, 3, 4, 5, 6, 11, 12, 14, 15, 16, or 17. In embodiments, polypeptide having alcohol dehydrogenase activity catalyzes the conversion of isobutyraldehyde to isobutanol in the presence of isobutanol at a concentration of at least about 10 g/L, at least about 15 g/L, or at least about 20 g/L.

In embodiments, the biosynthetic pathway for production of a lower alkyl alcohol is an isobutanol biosynthetic pathway comprising heterologous polynucleotides encoding polypeptides that catalyze substrate to product conversions for each step of the following steps: (a) pyruvate to acetolactate; (b) acetolactate to 2,3-dihydroxyisovalerate; (c) 2,3-dihydroxyisovalerate to α-ketoisovalerate; (d) α-ketoisovalerate to isobutyraldehyde; and (e) isobutyraldehyde to isobutanol; and wherein said microbial host cell produces isobutanol. In embodiments, (a) the polypeptide that catalyzes a substrate to product conversion of pyruvate to acetolactate is acetolactate synthase having the EC number 2.2.1.6; (b) the polypeptide that catalyzes a substrate to product conversion of acetolactate to 2,3-dihydroxyisovalerate is acetohydroxy acid isomeroreductase having the EC number 1.1.186; (c) the polypeptide that catalyzes a substrate to product conversion of 2,3-dihydroxyisovalerate to alpha-ketoisovalerate is acetohydroxy acid dehydratase having the EC number 4.2.1.9; and (d) the polypeptide that catalyzes a substrate to product conversion of alpha-ketoisovalerate to isobutyraldehyde is branched-chain alpha-keto acid decarboxylase having the EC number 4.1.1.72. In embodiments, the biosynthetic pathway for production of a lower alkyl alcohol is an isobutanol biosynthetic pathway comprising heterologous polynucleotides encoding polypeptides that catalyze substrate to product conversions for each step of the following steps: (a) pyruvate to acetolactate; (b) acetolactate to 2,3-dihydroxyisovalerate; (c) 2,3-dihydroxyisovalerate to α-ketoisovalerate; (d) α-ketoisovalerate to isobutyryl-CoA; (e) isobutyryl-CoA to isobutyraldehyde; and (f) isobutyraldehyde to isobutanol; and wherein said microbial host cell produces isobutanol. In embodiments, the biosynthetic pathway for production of a lower alkyl alcohol is an isobutanol biosynthetic pathway comprising heterologous polynucleotides encoding polypeptides that catalyze substrate to product conversions for each step of the following steps: (a) pyruvate to acetolactate; (b) acetolactate to 2,3-dihydroxyisovalerate; (c) 2,3-dihydroxyisovalerate to α-ketoisovalerate; (d) α-ketoisovalerate to valine; (e) valine to isobutylamine; (e) isobutylamine to isobutyraldehyde; and (f) isobutyraldehyde to isobutanol; and wherein said microbial host cell produces isobutanol.

Also provided herein are recombinant microbial host cells comprising a biosynthetic pathway for the production of a lower alkyl alcohol and a heterologous polynucleotide encoding a polypeptide with alcohol dehydrogenase activity having at least 85% identity to the amino acid sequence of SEQ ID NO: 21, 22, 23, 24, 25, 31, 32, 34, 35, 36, 37, or 38. In embodiments, the biosynthetic pathway for the production of a lower alkyl alcohol is a 2-butanol biosynthetic pathway comprising heterologous polynucleotides encoding polypeptides that catalyze substrate to product conversions for each of the following steps: (a) pyruvate to alpha-acetolactate; (b) alpha-acetolactate to acetoin; (c) acetoin to 2,3-butanediol; (d) 2,3-butanediol to 2-butanone; and (e) 2-butanone to 2-butanol. In embodiments, (a) the polypeptide that catalyzes a substrate to product conversion of pyruvate to acetolactate is acetolactate synthase having the EC number 2.2.1.6; (b) the polypeptide that catalyzes a substrate to product conversion of acetolactate to acetoin is acetolactate decarboxylase having the EC number 4.1.1.5; (c) the polypeptide that catalyzes a substrate to product conversion of acetoin to 2,3-butanediol is butanediol dehydrogenase having the EC number 1.1.1.76 or EC number 1.1.1.4; (d) the polypeptide that catalyzes a substrate to product conversion of butanediol to 2-butanone is butanediol dehydratase having the EC number 4.2.1.28; and (e) the polypeptide that catalyzes a substrate to product conversion of 2-butanone to 2-butanol is 2-butanol dehydrogenase having the EC number 1.1.1.1. In embodiments, the polypeptide having alcohol dehydrogenase activity comprises an amino acid sequence with at least 95% identity to the amino acid sequence of SEQ ID NO: 21, 22, 23, 24, 25, 27, 31, 32, 34, 35, 36, 37, or 38. In embodiments, the polypeptide having alcohol dehydrogenase activity comprises an amino acid sequence with at least 95% identity to the amino acid sequence of SEQ ID NO: 31.

In embodiments, the biosynthetic pathway for the production of a lower alkyl alcohol is a 1-butanol biosynthetic pathway comprises heterologous polynucleotides encoding polypeptides that catalyze substrate to product conversions for each of the following steps: (a) acetyl-CoA to acetoacetyl-CoA; (b) acetoacetyl-CoA to 3-hydroxybutyryl-CoA; (c) 3-hydroxybutyryl-CoA to crotonyl-CoA; (d) crotonyl-CoA to butyryl-CoA; (e) butyryl-CoA to butyraldehyde; and (f) butyraldehyde to 1-butanol; and wherein said microbial host cell produces 1-butanol. In embodiments, (a) the polypeptide that catalyzes a substrate to product conversion of acetyl-CoA to acetoacetyl-CoA is acetyl-CoA acetyltransferase having the EC number 2.3.1.9 or 2.3.1.16; (b) the polypeptide that catalyzes a substrate to product conversion of acetoacetyl-CoA to 3-hydroxybutyryl-CoA is 3-hydroxybutyryl-CoA dehydrogenase having the EC number 1.1.1.35, 1.1.1.30, 1.1.1.157, or 1.1.1.36; (c) the polypeptide that catalyzes a substrate to product conversion of 3-hydroxybutyryl-CoA to crotonyl-CoA is crotonase having the EC number 4.2.1.17 or 4.2.1.55; (d) the polypeptide that catalyzes a substrate to product conversion of crotonyl-CoA to butyryl-CoA is butyryl-CoA dehydrogenase having the EC number 1.3.1.44 or 1.3.1.38; (e) the polypeptide that catalyzes a substrate to product conversion of butyryl-CoA to butyrylaldehyde is butyraldehyde dehydrogenase having the EC number 1.2.1.57; and (f) the polypeptide that catalyzes a substrate to product conversion of butyrylaldehyde to 1-butanol is 1-butanol dehydrogenase. In embodiments, the polypeptide having alcohol dehydrogenase activity comprises an amino acid sequence with at least 95% identity to the amino acid sequence of SEQ ID NO: 21, 22, 23, 24, 25, 27, 31, 32, 34, 35, 36, 37, or 38. In embodiments, the polypeptide having alcohol dehydrogenase activity comprises an amino acid sequence with at least 95% identity to the amino acid sequence of SEQ ID NO: 31.

In embodiments, the recombinant microbial host cell is selected from the group consisting of: bacteria, cyanobacteria, filamentous fungi and yeasts. In embodiments, the host cell is a bacterial or cyanobacterial cell. In embodiments, the genus of the host cells is selected from the group consisting of: *Salmonella, Arthrobacter, Bacillus, Brevibacterium,*

*Clostridium, Corynebacterium, Gluconobacter, Nocardia, Pseudomonas, Rhodococcus, Streptomyces, Zymomonas, Escherichia, Lactobacillus, Enterococcus, Alcaligenes, Klebsiella, Serratia, Shigella, Alcaligenes, Erwinia, Paenibacillus,* and *Xanthomonas.* In embodiments, the genus of the host cells provided herein is selected from the group consisting of: *Saccharomyces, Pichia, Hansenula, Yarrowia, Aspergillus, Kluyveromyces, Pachysolen, Rhodotorula, Zygosaccharomyces, Galactomyces, Schizosaccharomyces, Torulaspora, Debaryomyces, Williopsis, Dekkera, Kloeckera, Metschnikowia, Issatchenkia,* and *Candida.*

Another aspect of the present invention is a method for producing isobutanol comprising: (a) providing a recombinant microbial host cell comprising an isobutanol biosynthetic pathway, the pathway comprising a heterologous polypeptide which catalyzes the substrate to product conversion of isobutyraldehyde to isobutanol wherein the polypeptide has at least 90% identity to the amino acid sequence of SEQ ID NO: 21, 22, 23, 24, 25, 27, 31, 32, 34, 35, 36, 37, or 38; and (b) contacting the host cell of (a) with a carbon substrate under conditions whereby isobutanol is produced. In embodiments, the heterologous polypeptide which catalyzes the substrate to product conversion of isobutyraldehyde to isobutanol has at least 90% identity to the amino acid sequence of SEQ ID NO: 31. Another aspect is a method for producing 2-butanol comprising: (a) providing a recombinant microbial host cell comprising a 2-butanol biosynthetic pathway, the pathway comprising a heterologous polypeptide having at least 90% identity to the amino acid sequence of SEQ ID NO: 21, 22, 23, 24, 25, 27, 31, 32, 34, 35, 36, 37, or 38; and (b) contacting the host cell of (a) with a carbon substrate under conditions whereby 2-butanol is produced. In embodiments, the heterologous polypeptide has at least 90% identity to the amino acid sequence of SEQ ID NO: 31. Another aspect is a method for producing 1-butanol comprising: (a) providing a recombinant microbial host cell comprising a 1-butanol biosynthetic pathway, the pathway comprising a heterologous polypeptide having at least 90% identity to the amino acid sequence of SEQ ID NO: 21, 22, 23, 24, 25, 27, 31, 32, 34, 35, 36, 37, or 38; and (b) contacting the host cell of (a) with a carbon substrate under conditions whereby 1-butanol is produced. In embodiments, the heterologous polypeptide has at least 90% identity to the amino acid sequence of SEQ ID NO: 31.

Also provided herein are methods for the production of a lower alkyl alcohol comprising: (a) providing a recombinant host cell provided herein; (b) contacting said host cell with a fermentable carbon substrate in a fermentation medium under conditions whereby the lower alkyl alcohol is produced; and (c) recovering said lower alkyl alcohol. In embodiments, said fermentable carbon substrate is selected from the group consisting of: monosaccharides, oligosaccharides, and polysaccharides. In embodiments, monosaccharide is selected from the group consisting: glucose, galactose, mannose, rhamnose, xylose, and fructose. In embodiments, said oligosaccharide is selected from the group consisting of: sucrose, maltose, and lactose. In embodiments, polysaccharide is selected from the group consisting of: starch, cellulose, and maltodextrin. In embodiments, the conditions are anaerobic, aerobic, or microaerobic. In embodiments, said lower alkyl alcohol is produced at a titer of at least about 10 g/L, at least about 15 g/L, or at least about 20 g/L. In embodiments, said lower alkyl alcohol is selected from the group consisting of: butanol, isobutanol, propanol, isopropanol, and ethanol.

In embodiments, isobutanol is produced. In embodiments, the method for producing isobutanol comprises: (a) providing a recombinant host cell comprising a heterologous polypeptide which catalyzes the substrate to product conversion of isobutyraldehyde to isobutanol and which has one or more of the following characteristics: (i) the $K_M$ value of a lower alkyl aldehyde is lower for the polypeptide relative to a control polypeptide having the amino acid sequence of SEQ ID NO: 26; (ii) the $K_I$ value for a lower alkyl aldehyde for the polypeptide is higher relative to control polypeptide having the amino acid sequence of SEQ ID NO: 26; (iii) the $k_{cat}/K_M$ value for a lower alkyl aldehyde for the polypeptide is higher relative to a control polypeptide having the amino acid sequence of SEQ ID NO: 26; and (b) contacting the host cell of (a) with a carbon substrate under conditions whereby isobutanol is produced.

In embodiments, 1-butanol is produced. In embodiments, the method for producing 1-butanol comprises: (a) providing a recombinant microbial host cell comprising a heterologous polypeptide which catalyzes the substrate to product conversion of butyraldehyde to 1-butanol and which has one or more of the following characteristics: (i) the $K_M$ value for a lower alkyl aldehyde is lower for the polypeptide relative to a control polypeptide having the amino acid sequence of SEQ ID NO: 26; (ii) the $K_I$ value for a lower alkyl alcohol for the polypeptide is higher relative to a control polypeptide having the amino acid sequence of SEQ ID NO: 26; and (iii) the $k_{cat}/K_M$ value for a lower alkyl aldehyde for the polypeptide is higher relative to a control polypeptide having the amino acid sequence of SEQ ID NO: 26; and (b) contacting the host cell of (a) with a carbon substrate under conditions whereby 1-butanol is produced.

Also provided herein are methods for screening candidate polypeptides having alcohol dehydrogenase activity, said method comprising: a) providing a candidate polypeptide and a cofactor selected from the group consisting of NADH and NADPH; b) monitoring a change in $A_{340\,nm}$ over time in the presence or absence of a lower alkyl alcohol for the candidate polypeptide; and c) selecting those candidate polypeptides where the change in $A_{340\,nm}$ is a decrease, and the decrease is faster in the absence of the lower alkyl alcohol with respect to the decrease in the presence of the lower alkyl alcohol. In embodiments, the methods further comprise (d) providing a control polypeptide having the amino acid sequence of either SEQ ID NO: 21 or 26 and NADH; (e) monitoring a change in $A_{340\,nm}$ over time in the presence or absence of a lower alkyl alcohol for the control polypeptide; (f) comparing the changes observed in (e) with the changes observed in (b); and (g) selecting those candidate polypeptides where the decrease in $A_{340\,nm}$ in the absence of the lower alkyl alcohol is faster than the decrease observed for the control polypeptide. In embodiments, the methods further comprise (d) providing a control polypeptide having the amino acid sequence of either SEQ ID NO: 21 or 26 and NADH; (e) monitoring a change in $A_{340\,nm}$ over time in the presence or absence of a lower alkyl alcohol for the control polypeptide; (f) comparing the changes observed in (e) with the changes observed in (b); and (g) selecting those candidate polypeptides where the decrease in $A_{340\,nm}$ in the presence of the lower alkyl alcohol is faster than the decrease observed for the control polypeptide.

Also provided herein is use of an alcohol dehydrogenase having at least about 80% identity to an amino acid sequence of SEQ ID NO: 21, 22, 23, 24, 25, 26, 27, 28, 29, 30, 31, 32, 33, 34, 35, 36, 37, 38, 39, or 40 in a microbial host cell to catalyze the conversion of isobutyraldehyde to isobutanol; wherein said host cell comprises an isobutanol biosynthetic pathway.

BRIEF DESCRIPTION OF THE
DRAWINGS/FIGURES AND SEQUENCES

FIGS. 1A to 1D shows the results of semi-physiological time-course assays showing isobutyraldehyde reduction by NAD(P)H, catalyzed by ADH candidate enzymes in the presence and absence of isobutanol. Enzymatic activity is measured by following changes in absorbance at 340 nm. In each panel, $A_{340\,nm}$ of NADH or NADPH alone, in the presence of all other reactants except the enzyme, was used as a control. Panel A shows the change in absorbance at 340 nm over time for *Achromobacter xylosoxidans* SadB. Panel B shows the change in absorbance at 340 nm over time for horse liver ADH. Panel C shows the change in absorbance at 340 nm over time for *Saccharomyces cerevisiae* ADH6. Panel D shows the change in absorbance at 340 nm over time for *Saccharomyces cerevisiae* ADH7. Panel E shows the change in absorbance at 340 nm over time for *Beijierickia indica* ADH. Panel F shows the change in absorbance at 340 nm over time for *Clostridium beijerinckii* ADH. Panel G shows the change in absorbance at 340 nm over time for *Rattus norvegicus* ADH. Panel H shows the change in absorbance at 340 nm over time for *Therm.* sp. ATN1 ADH.

FIG. 3 is an alignment of the polypeptide sequences of *Pseudomonas putida* formaldehyde dehydrogenase (1kolA) (SEQ ID NO: 79), horse liver ADH (2ohxA) (SEQ ID NO: 21), *Clostridium beijerinckii* ADH (1pedA) (SEQ ID NO: 29), *Pyrococcus horikoshii* L-theronine 3-dehydrogenase (2d8aA) (SEQ ID NO: 80), and *Achromobacter xylosoxidans* SadB (SEQ ID NO: 26).

Figure 6:
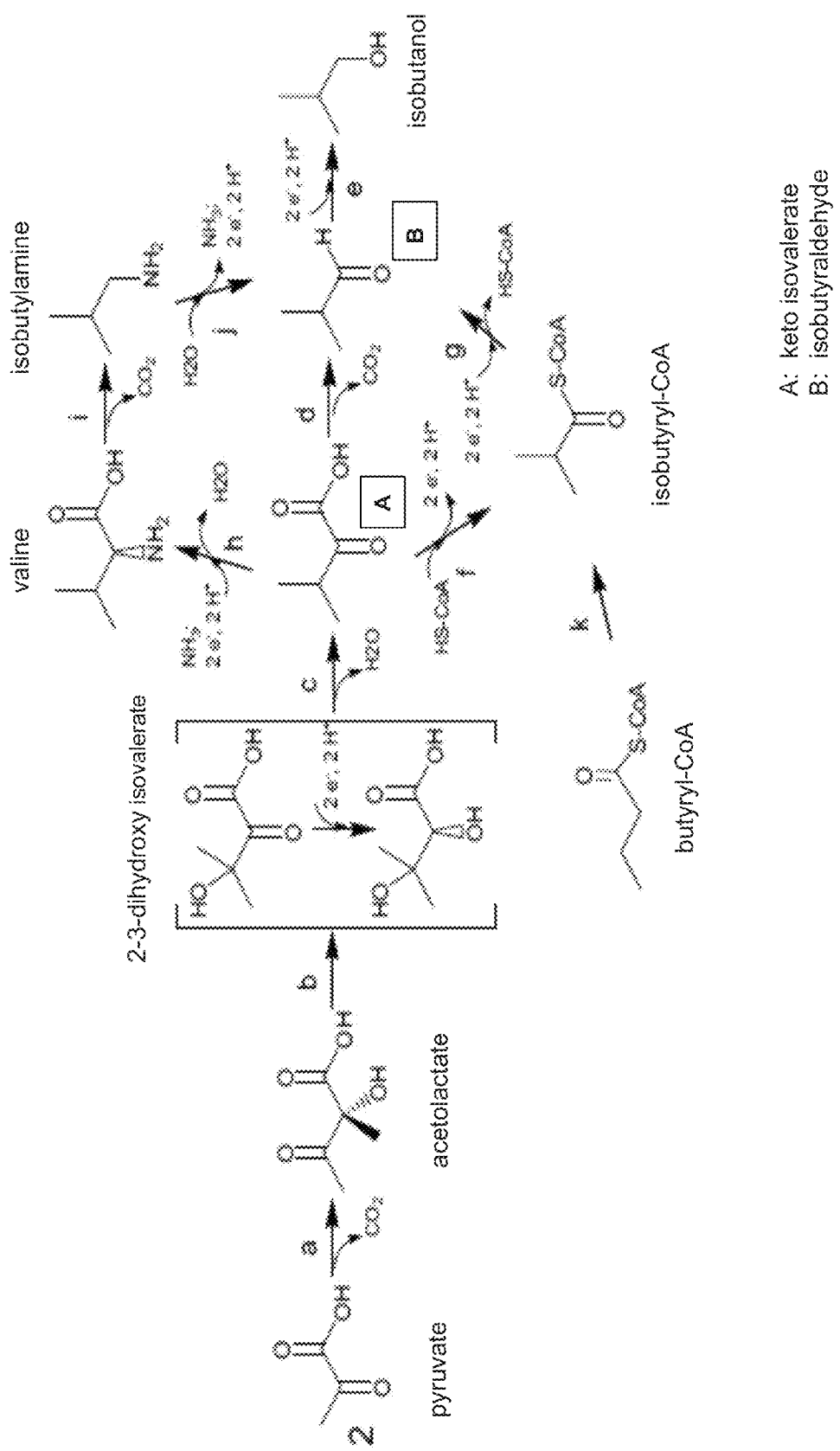

FIG. 6 is an illustration of example pyruvate to isobutanol biosynthetic pathways. The steps labeled "a," "b," "c," "d," "e," "f," "g," "h," "i," "j," and "k" represent the substrate to product conversions catalyzed by the following enzymes: a→acetolactate synthase; b→ketol-acid reductoisomerase or acetohydroxy acid isomeroreductase; c→acetohydroxy acid dehydratase; d→branched-chain keto acid decarboxylase; e→branched-chain alcohol dehydrogenase; f→branched-chain keto acid dehydrogenase; g→acylating aldehyde dehydrogenase; h→valine dehydrogenase or transaminase; i→valine decarboxylase; j→omega transaminase; and k→isobutyryl-CoA mutase.

Figure 7A:
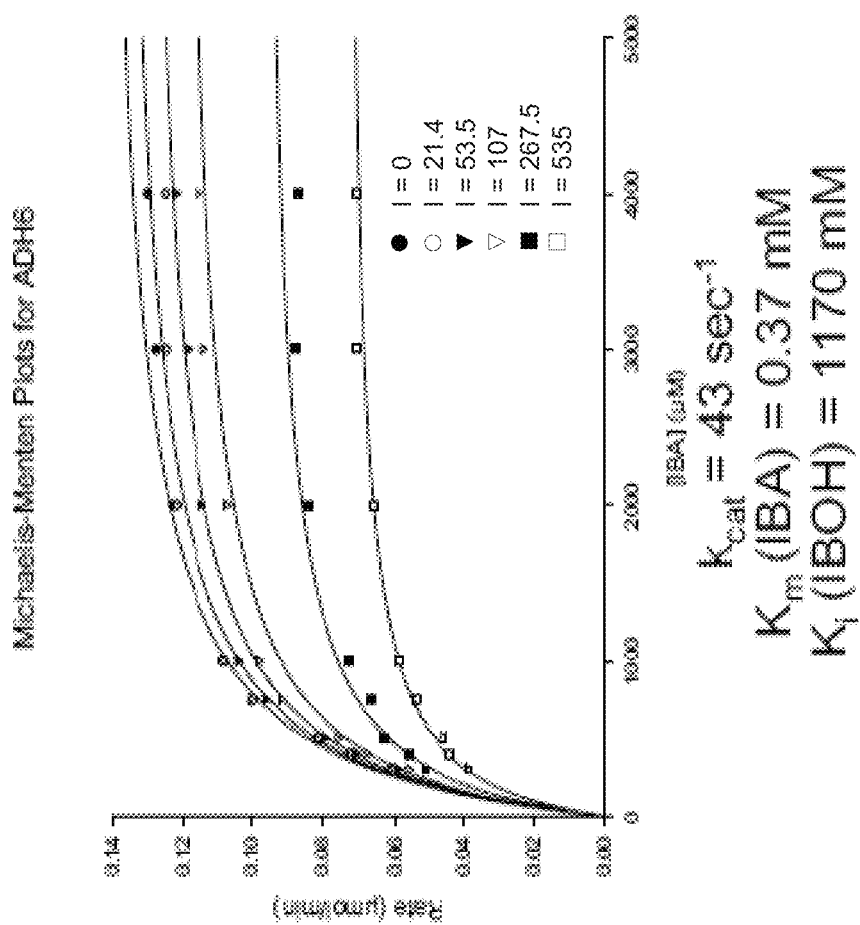
Figure 7B:
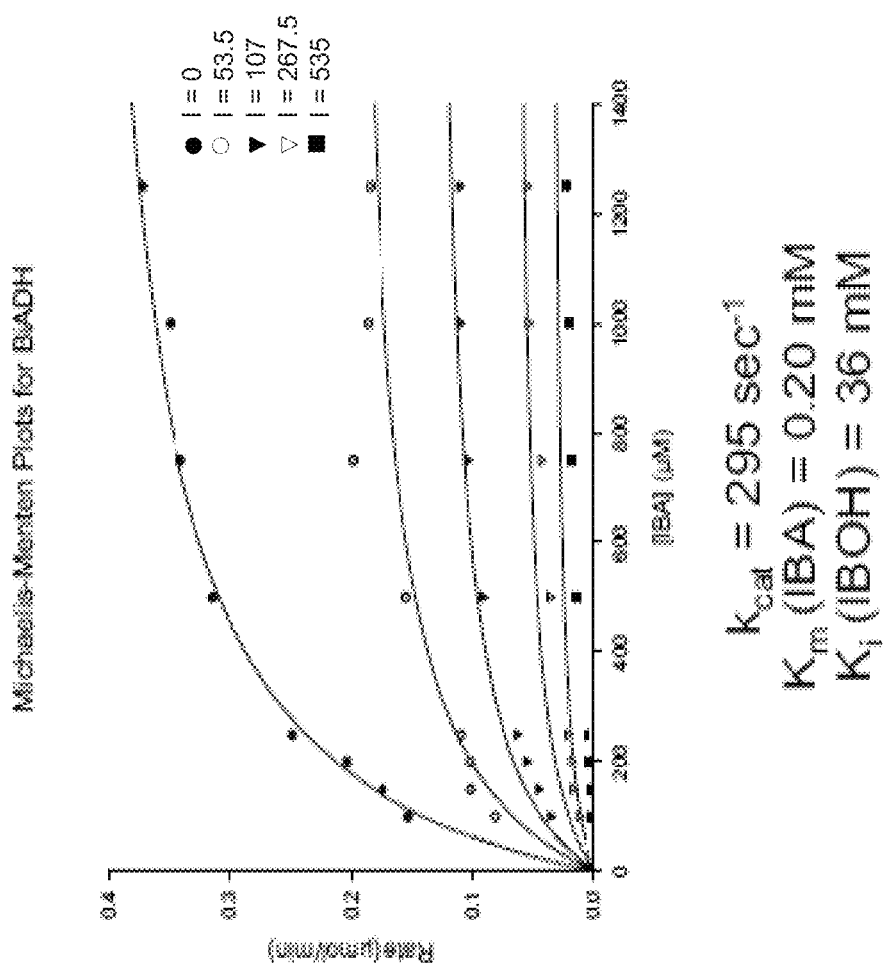

FIGS. 7A and 7B show the Michaelis-Menten plots describing the properties of the enzymes pertaining to isobutyraldehyde reduction. FIG. 7A shows results of assays to determine the $K_I$ for isobutanol for ADH6 and FIG. 7B shows results of assays to determine the $K_I$ for isobutanol for BiADH.

Figure 8A:
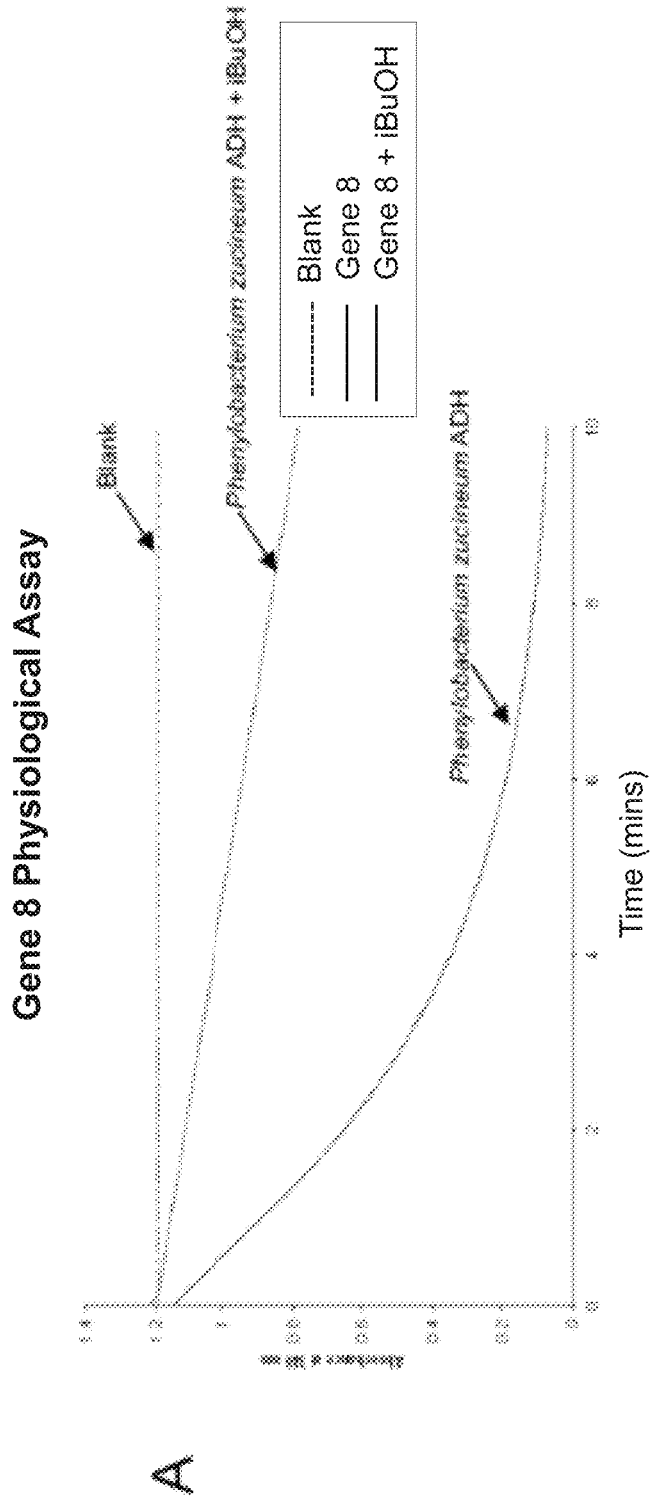
Figure 8B:
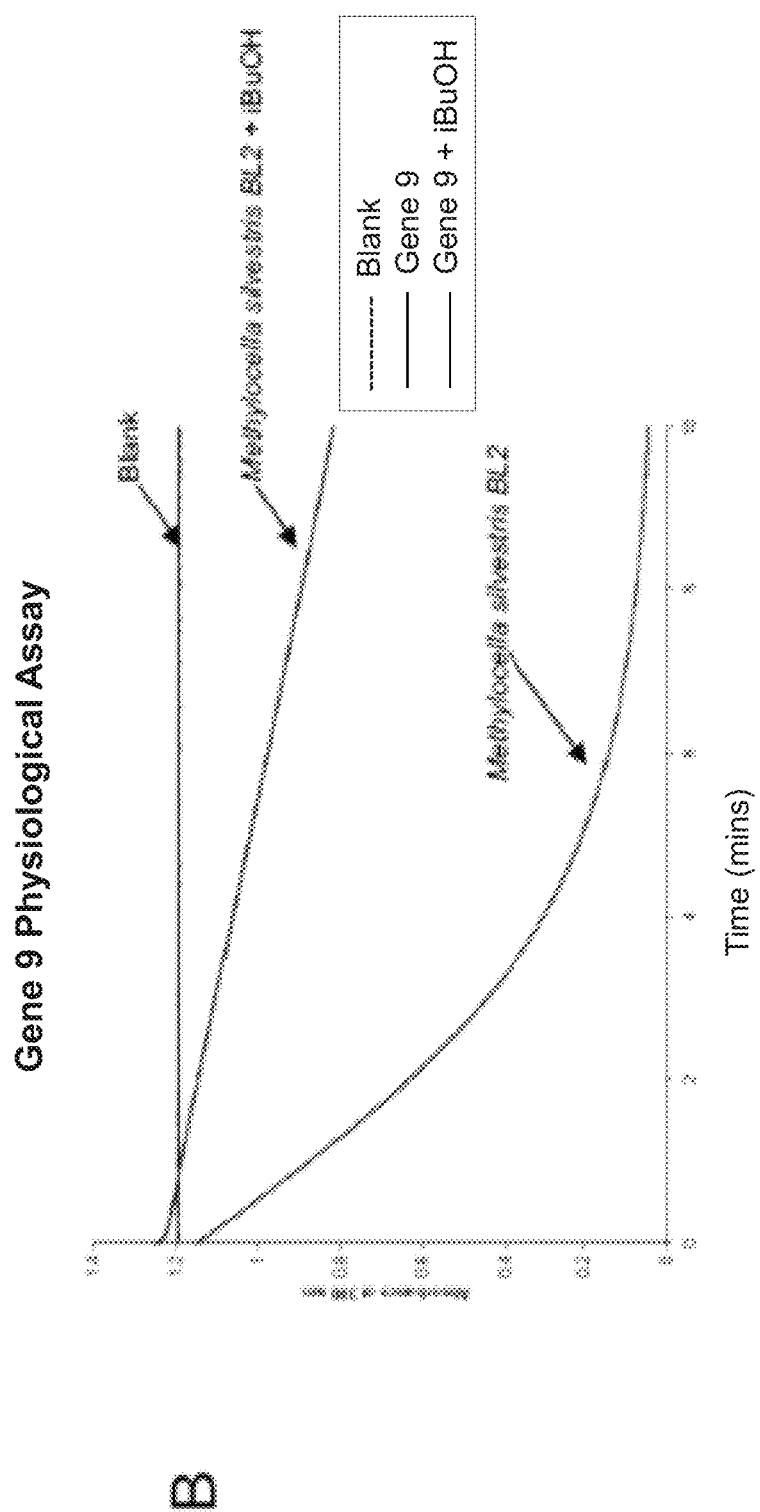

FIGS. 8A to 8C show the results of semi-physiological time-course assays, which were as described for FIG. 1. FIG. 8A shows the change in absorbance at 340 nm over time for the ADH from *Phenylobacterium zucineum*. FIG. 8B shows the change in absorbance at 340 nm over time for *Methylocella silvestris* BL2. FIG. 8C shows the change in absorbance at 340 nm over time for *Acinetobacter baumannii* AYE.

Figure 9:
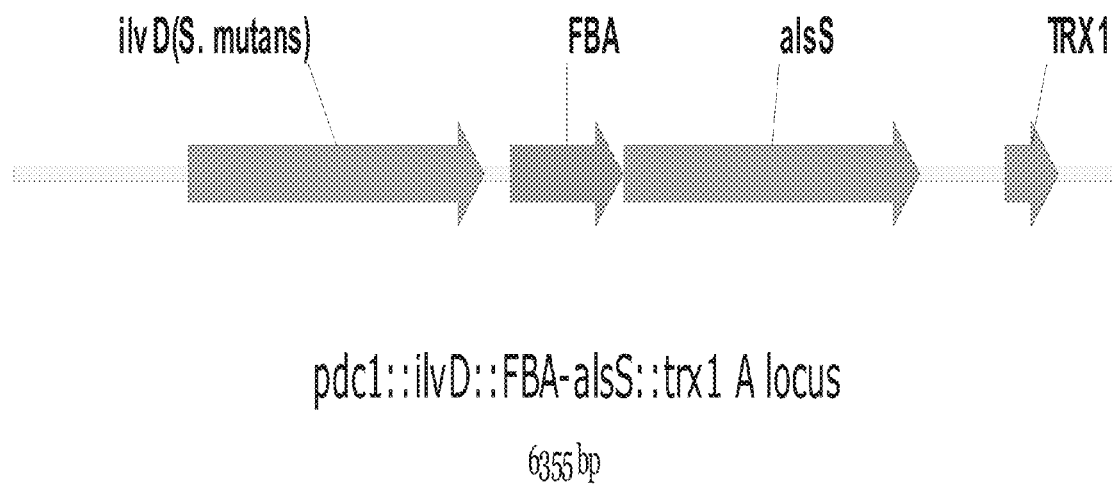

FIG. 9 depicts the pdc1::ilvD::FBA-alsS::trx1A locus. The alsS gene integration in the pdc1-trx1 intergenic region is considered a "scarless" insertion since vector, marker gene and loxP sequences are lost.

The following sequences provided in the accompanying sequence listing, filed electronically herewith and incorporated herein by reference, conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1 and 7-20 are codon-optimized polynucleotide sequences.

SEQ ID NOs: 2 and 3 are polynucleotide sequences from *Saccharomyces cerevisiae*.

SEQ ID NOs: 4 and 5 are polynucleotide sequences from *Clostridium acetobutylicum*.

SEQ ID NO: 6 is a polynucleotide sequence from *Achromobacter xylosoxidans*.

SEQ ID NOs: 21-40 and 79-80 are polypeptide sequences.

SEQ ID NOs: 41-50 and 52-57 and 59-74 and 77-78 are primers.

SEQ ID NO: 51 is the sequence of the pRS423::TEF(M4)-xpk1+ENO1-eutD plasmid.

SEQ ID NO: 58 is the sequence of the pUC19-URA3::pdc1::TEF(M4)-xpk1::kan plasmid.

SEQ ID NO: 75 is the sequence of the pLH468 plasmid.

SEQ ID NO: 76 is the BiADH coding region (codon optimized for yeast) plus 5'homology to GPM promoter and 3'homology to ADH1 terminator.

SEQ ID NO: 81 is the sequence of the pRS426::GPD-xpk1+ADH-eutD plasmid.

DETAILED DESCRIPTION OF THE INVENTION

The stated problems are solved as described herein by devising and using a suitable screening strategy for evaluating various candidate ADH enzymes. The screening strategy can be used to identify ADH enzymes having desirable characteristics. These identified ADH enzymes can be used to enhance the biological production of lower alkyl alcohols, such as isobutanol. Also provided are recombinant host cells that express the identified desirable ADH enzymes and provided methods for producing lower alkyl alcohols using the same.

The present invention describes a method for screening large numbers of alcohol dehydrogenase (ADH) enzymes for their ability to rapidly convert isobutyraldehyde to isobutanol in the presence of high concentrations of isobutanol. Also described in the present invention is a new ADH that is present in the bacterium *Beijerinckia indica* subspecies indica ATCC 9039. The *Beijerinckia indica* ADH enzyme can be used in the production of isobutanol from isobutyraldehyde in a recombinant microorganism having an isobutyraldehyde source.

The present invention meets a number of commercial and industrial needs. Butanol is an important industrial commodity chemical with a variety of applications, where its potential as a fuel or fuel additive is particularly significant. Although only a four-carbon alcohol, butanol has an energy content similar to that of gasoline and can be blended with any fossil fuel. Butanol is favored as a fuel or fuel additive as it yields only $CO_2$ and little or no $SO_2$ or $NO_2$ when burned in the standard internal combustion engine. Additionally butanol is less corrosive than ethanol, the most preferred fuel additive to date.

In addition to its utility as a biofuel or fuel additive, butanol has the potential of impacting hydrogen distribution problems in the emerging fuel cell industry. Fuel cells today are plagued by safety concerns associated with hydrogen transport and distribution. Butanol can be easily reformed for its hydrogen content and can be distributed through existing gas stations in the purity required for either fuel cells or vehicles.

The present invention produces butanol from plant derived carbon sources, avoiding the negative environmental impact associated with standard petrochemical processes for butanol production. In one embodiment, the present invention provides a method for the selection and identification of ADH enzymes that increase the flux in the last reaction of the isobutanol biosynthesis pathway; the conversion of isobutyraldehyde to isobutanol. In one embodiment, the present invention provides a method for the selection and identification of ADH enzymes that increase the flux in the last reaction of the 1-butanol biosynthesis pathway; the conversion of butyrylaldehyde to 1-butanol. In one embodiment, the present invention provides a method for the selection and identification of ADH enzymes that increase the flux in the last reaction of the 2-butanol biosynthesis pathway; the conversion of 2-butanone to 2-butanol. Particularly useful ADH enzymes are those that are better able to increase the flux in the isobutyraldehyde to isobutanol conversion reaction when compared to known control ADH enzymes. The present invention also provides for recombinant host cells expressing such identified ADH enzymes and methods for using the same.

The following definitions and abbreviations are to be used for the interpretation of the claims and the specification.

The term "invention" or "present invention" as used herein is meant to apply generally to all embodiments of the invention as described in the claims as presented or as later amended and supplemented, or in the specification.

The term "isobutanol biosynthetic pathway" refers to the enzymatic pathway to produce isobutanol from pyruvate.

The term "1-butanol biosynthetic pathway" refers to the enzymatic pathway to produce 1-butanol from pyruvate.

The term "2-butanol biosynthetic pathway" refers to the enzymatic pathway to produce 2-butanol from acetyl-CoA.

The term "NADH consumption assay" refers to an enzyme assay for the determination of the specific activity of the alcohol dehydrogenase enzyme, which is measured as a stoichiometric disappearance of NADH, a cofactor for the enzyme reaction, as described in Racker, *J Biol. Chem.*, 184: 313-319 (1950).

"ADH" is the abbreviation for the enzyme alcohol dehydrogenase.

The terms "isobutyraldehyde dehydrogenase," "secondary alcohol dehydrogenase," "butanol dehydrogenase," "branched-chain alcohol dehydrogenase," and "alcohol dehydrogenase" will be used interchangeably and refer the enzyme having the EC number, EC 1.1.1.1 (Enzyme Nomenclature 1992, Academic Press, San Diego). Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as an electron donor.

As used herein, "heterologous" refers to a polynucleotide, gene or polypeptide not normally found in the host organism but that is introduced or is otherwise modified. "Heterologous polynucleotide" includes a native coding region from the host organism, or portion thereof, that is reintroduced or otherwise modified in the host organism in a form that is different from the corresponding native polynucleotide as well as a coding region from a different organism, or portion thereof "Heterologous gene" includes a native coding region, or portion thereof, that is reintroduced or is otherwise modified from the source organism in a form that is different from the corresponding native gene as well as a coding region from a different organism. For example, a heterologous gene may include a native coding region that is a portion of a chimeric gene including non-native regulatory regions that is reintroduced into the native host. "Heterologous polypeptide" includes a native polypeptide that is reintroduced or otherwise modified in the host organism in a form that is different from the corresponding native polypeptide as well as a polypeptide from another organism.

The term "carbon substrate" or "fermentable carbon substrate" refers to a carbon source capable of being metabolized by host organisms of the present invention. Non-limited examples of carbon sources that can be used in the invention include monosaccharides, oligosaccharides, polysaccharides, and one-carbon substrates or mixtures thereof.

The terms "$k_{cat}$" and "$K_M$" and $K_I$" are known to those skilled in the art and are described in Enzyme Structure and Mechanism, 2nd ed. (Ferst, W.H. Freeman: NY, 1985; pp 98-120). The term "$k_{cat}$," often called the "turnover number," is defined as the maximum number of substrate molecules converted to product molecules per active site per unit time, or the number of times the enzyme turns over per unit time. $k_{cat}=V_{max}/[E]$, where [E] is the enzyme concentration (Ferst, supra).

The term "catalytic efficiency" is defined as the $k_{cat}/K_M$ of an enzyme. "Catalytic efficiency" is used to quantitate the specificity of an enzyme for a substrate.

The term "specific activity" means enzyme units/mg protein where an enzyme unit is defined as moles of product formed/minute under specified conditions of temperature, pH, [S], etc.

The terms "slow," "slower," "faster," or "fast" when used in reference to an enzyme activity relates to the turnover number of the enzyme as compared with a standard.

The term "control polypeptide" refers to a known polypeptide having known alcohol dehydrogenase activity. Non-limiting examples of control polypeptides suitable for use in the invention include *Achromobacter xylosoxidans* SadB and horse liver ADH.

The term "lower alkyl alcohol" refers to any straight-chain or branched, saturated or unsaturated, alcohol molecule with 1-10 carbon atoms.

The term "lower alkyl aldehyde" refers to any straight-chain or branched, saturated or unsaturated, aldehyde molecule with 1-10 carbon atoms.

The term "butanol" as used herein refers to 1-butanol, 2-butanol, isobutanol, or mixtures thereof.

The term "biosynthetic pathway for production of a lower alkyl alcohol" as used herein refers to an enzyme pathway to produce lower alkyl alcohols. For example, isobutanol biosynthetic pathways are disclosed in U.S. Patent Application Publication No. 2007/0092957, which is incorporated by reference herein.

As used herein, the term "yield" refers to the amount of product per amount of carbon source in g/g. The yield may be exemplified for glucose as the carbon source. It is understood unless otherwise noted that yield is expressed as a percentage of the theoretical yield. In reference to a microorganism or metabolic pathway, "theoretical yield" is defined as the maximum amount of product that can be generated per total amount of substrate as dictated by the stoichiometry of the metabolic pathway used to make the product. For example, the theoretical yield for one typical conversion of glucose to isopropanol is 0.33 mg. As such, a yield of isopropanol from glucose of 29.7 mg would be expressed as 90% of theoretical or 90% theoretical yield. It is understood that while in the present disclosure the yield is exemplified for glucose as a carbon source, the invention can be applied to other carbon sources and the yield may vary depending on the carbon source used. One skilled in the art can calculate yields on various carbon sources. The term "NADH" means reduced nicotinamide adenine dinucleotide.

The term "NADPH" means reduced nicotinamide adenine dinucleotide phosphate.

The term "NAD(P)H" is used to refer to either NADH or NADPH.

Polypeptides and Polynucleotides for Use in the Invention

The ADH enzymes used in the invention comprise polypeptides and fragments thereof. As used herein, term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids.

A polypeptide of the invention may be of a size of about 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

Also included as polypeptides of the present invention are derivatives, analogs, or variants of the foregoing polypeptides, and any combination thereof. The terms "active variant," "active fragment," "active derivative," and "analog" refer to polypeptides of the present invention and include any polypeptides that are capable of catalyzing the reduction of a lower alkyl aldehyde. Variants of polypeptides of the present invention include polypeptides with altered amino acid sequences due to amino acid substitutions, deletions, and/or insertions. Variants may occur naturally or be non-naturally occurring. Non-naturally occurring variants may be produced using art-known mutagenesis techniques. Variant polypeptides may comprise conservative or non-conservative amino acid substitutions, deletions and/or additions. Derivatives of polypeptides of the present invention, are polypeptides which have been altered so as to exhibit additional features not found on the native polypeptide. Examples include fusion proteins. Variant polypeptides may also be referred to herein as "polypeptide analogs." As used herein a "derivative" of a polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

A "fragment" is a unique portion of an ADH enzyme which is identical in sequence to but shorter in length than the parent sequence. A fragment may comprise up to the entire length of the defined sequence, minus one amino acid residue. For example, a fragment may comprise from 5 to 1000 contiguous amino acid residues. A fragment may be at least 5, 10, 15, 16, 20, 25, 30, 40, 50, 60, 75, 100, 150, 250 or at least 500 contiguous amino acid residues in length. Fragments may be preferentially selected from certain regions of a molecule. For example, a polypeptide fragment may comprise a certain length of contiguous amino acids selected from the first 100 or 200 amino acids of a polypeptide as shown in a certain defined sequence. Clearly these lengths are exemplary, and any length that is supported by the specification, including the Sequence Listing, tables, and figures, may be encompassed by the present embodiments.

Alternatively, recombinant variants encoding these same or similar polypeptides can be synthesized or selected by making use of the "redundancy" in the genetic code. Various codon substitutions, such as the silent changes which produce various restriction sites, may be introduced to optimize cloning into a plasmid or viral vector or expression in a host cell system. Mutations in the polynucleotide sequence may be reflected in the polypeptide or domains of other peptides added to the polypeptide to modify the properties of any part of the polypeptide, to change characteristics such as the $K_M$ for a lower alkyl aldehyde, the $K_M$ for a lower alkyl alcohol, the $K_I$ for a lower alkyl alcohol, etc.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are preferably in the range of about 1 to about 20 amino acids, more preferably 1 to 10 amino acids. The variation allowed may be experimentally determined by systematically making insertions, deletions, or substitutions of amino acids in a polypeptide molecule using recombinant DNA techniques and assaying the resulting recombinant variants for activity.

By a polypeptide having an amino acid or polypeptide sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the references sequence.

As a practical matter, whether any particular polypeptide is at least 80%, 85%, 90%, 95%, 96%, 97%, 98%, or 99% identical to a reference polypeptide can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., *Comp. Appl. Biosci.* 6:237-245 (1990). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty-0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to be made for the purposes of the present invention.

Polypeptides useful in the invention include those that are at least about 80%, 85%, 90%, 95%, 96%, 97%, 98%, 99%, or 100% identical to the sequences set forth in Table 5, including active variants, fragments, or derivatives thereof. The invention also encompasses polypeptides comprising amino acid sequences of Table 5 with conservative amino acid substitutions.

In one embodiment of the invention, polypeptides having alcohol dehydrogenase activity to be expressed in the recombinant host cells of the invention have amino acid sequences that are at least about 80%, 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO 34, SEQ ID NO: 35, SEQ ID NO: 36, SEQ ID NO: 37, SEQ ID NO: 38, SEQ ID NO: 39, and SEQ ID NO: 40. In another embodiment of the invention, a polypeptide having alcohol dehydrogenase activity to be expressed in the recombinant host cells of the invention has an amino acid sequence selected from the group consisting of: SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO 34, SEQ ID NO: 35, SEQ ID NO: 36, SEQ ID NO: 37, SEQ ID NO: 38, SEQ ID NO: 39, and SEQ ID NO: 40, or an active variant, fragment or derivative thereof. In one embodiment, polypeptides having alcohol dehydrogenase activity are encoded by polynucleotides that have been codon-optimized for expression in a specific host cell.

In one embodiment of the invention, polypeptides having alcohol dehydrogenase activity to be expressed in the recombinant host cells of the invention comprise a amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 22. In another embodiment, the polypeptide comprises the amino acid sequence of SEQ ID NO: 22 or an active variant, fragment or derivative thereof.

In one embodiment of the invention, polypeptides having alcohol dehydrogenase activity to be expressed in the recombinant host cells of the invention comprise a amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 23. In another embodiment, the polypeptide comprises the amino acid sequence of SEQ ID NO: 23 or an active variant, fragment or derivative thereof.

In one embodiment of the invention, polypeptides having alcohol dehydrogenase activity to be expressed in the recombinant host cells of the invention comprise a amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 31. In another embodiment, the polypeptide comprises the amino acid sequence of SEQ ID NO: 31 or an active variant, fragment or derivative thereof.

In one embodiment of the invention, polypeptides having alcohol dehydrogenase activity to be expressed in the recombinant host cells of the invention comprise a amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 29. In another embodiment, the polypeptide comprises the amino acid sequence of SEQ ID NO: 29 or an active variant, fragment or derivative thereof.

ADH enzymes suitable for use in the present invention and fragments thereof are can be encoded by polynucleotides. The term "polynucleotide" is intended to encompass a singular nucleic acid as well as plural nucleic acids, and refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. Polynucleotides according to the present invention further include such molecules produced synthetically. Polynucleotides of the invention may be native to the host cell or heterologous. In addition, a polynucleotide or a nucleic acid may be or may include a regulatory element such as a promoter, ribosome binding site, or a transcription terminator.

As used herein, a "coding region" or "ORF" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' non-translated regions, and the like, are not part of a coding region.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters." It is further recognized that since in most cases the exact boundaries of regulatory sequences have not been completely defined, DNA fragments of different lengths may have identical promoter activity.

In certain embodiments, the polynucleotide or nucleic acid is DNA. In the case of DNA, a polynucleotide comprising a nucleic acid, which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of affecting transcription of that nucleic acid. Other transcription control elements, besides a promoter, for example enhancers, operators, repressors, and transcription termination signals, can be operably associated with the polynucleotide. Suitable promoters and other transcription control regions are disclosed herein.

A variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence).

In other embodiments, a polynucleotide of the present invention is RNA, for example, in the form of messenger RNA (mRNA). RNA of the present invention may be single stranded or double stranded.

Polynucleotide and nucleic acid coding regions of the present invention may be associated with additional coding regions which encode secretory or signal peptides, which direct the secretion of a polypeptide encoded by a polynucleotide of the present invention.

As used herein, the term "transformation" refers to the transfer of a nucleic acid fragment into the genome of a host organism, resulting in genetically stable inheritance. Host organisms containing the transformed nucleic acid fragments are referred to as "recombinant" or "transformed" organisms.

The term "expression," as used herein, refers to the transcription and stable accumulation of sense (mRNA) or antisense RNA derived from the nucleic acid fragment of the invention. Expression may also refer to translation of mRNA into a polypeptide.

The terms "plasmid," "vector," and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The term "artificial" refers to a synthetic, or non-host cell derived composition, e.g., a chemically-synthesized oligonucleotide.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As a practical matter, whether any particular nucleic acid molecule or polypeptide is at least 80%, 85%, 90%, 95%, 96%, 97%, 98%, or 99% identical to a nucleotide sequence or polypeptide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., Comp. Appl. Biosci. 6:237-245 (1990). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty-30, Randomization Group Length=0, Cutoff Score=1, Gap Penalty=5, Gap Size Penalty=0.05, Window Size=500 or the length of the subject nucleotide sequences, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

Polynucleotides useful in the invention include those that are at least about 80%, 85%, 90%, 95%, 96%, 97%, 98%, 99%, or 100% identical to the nucleotide sequences set forth in Table 4, below, including variants, fragments or derivatives thereof that encode polypeptides with active alcohol dehydrogenase activity.

The terms "active variant," "active fragment," "active derivative," and "analog" refer to polynucleotides of the present invention and include any polynucleotides that encode polypeptides capable of catalyzing the reduction of a lower alkyl aldehyde. Variants of polynucleotides of the present invention include polynucleotides with altered nucleotide sequences due to base pair substitutions, deletions, and/or insertions. Variants may occur naturally or be non-naturally occurring. Non-naturally occurring variants may be produced using art-known mutagenesis techniques. Derivatives of polynucleotides of the present invention, are polynucleotides which have been altered so that the polypeptides they encode exhibit additional features not found on the native polypeptide. Examples include polynucleotides that encode fusion proteins. Variant polynucleotides may also be referred to herein as "polynucleotide analogs." As used herein a "derivative" of a polynucleotide refers to a subject polynucleotide having one or more nucleotides chemically derivatized by reaction of a functional side group. Also included as "derivatives" are those polynucleotides which contain one or more naturally occurring nucleotide derivatives. For example, 3-methylcytidine may be substituted for cytosine; ribothymidine may be substituted for thymidine; and N4-acetylcytidine may be substituted for cytosine.

A "fragment" is a unique portion of the polynucleotide encoding the ADH enzyme which is identical in sequence to but shorter in length than the parent sequence. A fragment may comprise up to the entire length of the defined sequence, minus one nucleotide. For example, a fragment may comprise from 5 to 1000 contiguous nucleotides. A fragment used as a probe, primer, or for other purposes, may be at least 5, 10, 15, 16, 20, 25, 30, 40, 50, 60, 75, 100, 150, 250 or at least 500 contiguous nucleotides. Fragments may be preferentially selected from certain regions of a molecule. For example, a polynucleotide fragment may comprise a certain length of contiguous nucleotides selected from the first 100 or 200 nucleotides of a polynucleotide as shown in a certain defined sequence. Clearly these lengths are exemplary, and any length that is supported by the specification, including the Sequence Listing, tables, and figures, may be encompassed by the present embodiments.

In one embodiment of the invention, polynucleotide sequences suitable for expression in recombinant host cells of the invention comprise nucleotide sequences that are at least about 80%, 85%, 90%, 95%, 96%, 97%, 98%, 99% or 100% identical to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO 14, SEQ ID NO: 15, SEQ ID NO: 16, SEQ ID NO: 17, SEQ ID NO: 18, SEQ ID NO: 19, and SEQ ID NO: 20. In another embodiment of the invention, a polynucleotide sequence suitable for expression in recombinant host cells of the invention can be selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO 14, SEQ ID NO: 15, SEQ ID NO: 16, SEQ ID NO: 17, SEQ ID NO: 18, SEQ ID NO: 19, and SEQ ID NO: 20 or an active variant, fragment or derivative thereof. In one embodiment, polynucleotides have been codon-optimized for expression in a specific host cell.

In one embodiment of the invention, the polynucleotide sequence suitable for expression in recombinant host cells of the invention has a nucleotide sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 2. In another embodiment, the polynucleotide comprises the nucleotide sequence of SEQ ID NO: 2 or an active variant, fragment or derivative thereof.

In one embodiment of the invention, the polynucleotide sequence suitable for expression in recombinant host cells of the invention has a nucleotide sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 3. In another embodiment, the polynucleotide comprises the nucleotide sequence of SEQ ID NO: 3 or an active variant, fragment or derivative thereof.

In one embodiment of the invention, the polynucleotide sequence suitable for expression in recombinant host cells of the invention has a nucleotide sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 11. In another embodiment, the polynucleotide comprises the nucleotide sequence of SEQ ID NO: 11 or an active variant, fragment or derivative thereof.

In one embodiment of the invention, the polynucleotide sequence suitable for expression in recombinant host cells of the invention has a nucleotide sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 9. In another embodiment, the polynucleotide comprises the nucleotide sequence of SEQ ID NO: 9 or an active variant, fragment or derivative thereof.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein the term "codon optimized coding region" means a nucleic acid coding region that has been adapted for expression in the cells of a given organism by replacing at least one, or more than one, or a significant number, of codons with one or more codons that are more frequently used in the genes of that organism.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA Ter | TGA Ter |
| | TTG Leu (L) | TCG Ser (S) | TAG Ter | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database" available at the Kazusa DNA Research Institute, Japan, and these tables can be adapted in a number of ways. See Nakamura, Y., et al. Nucl. Acids Res. 28:292 (2000). Codon usage tables for yeast, calculated from GenBank Release 128.0 [15 Feb. 2002], are reproduced below as Table 2. This table uses mRNA nomenclature, and so instead of thymine (T) which is found in DNA, the tables use uracil (U) which is found in RNA. The Table has been adapted so that frequencies are calculated for each amino acid, rather than for all 64 codons.

TABLE 2

Codon Usage Table for *Saccharomyces cerevisiae* Genes

| Amino Acid | Codon | Number | Frequency per thousand |
|---|---|---|---|
| Phe | UUU | 170666 | 26.1 |
| Phe | UUC | 120510 | 18.4 |
| Total | | | |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Total | | | |
| Ile | AUU | 196893 | 30.1 |
| Ile | AUC | 112176 | 17.2 |
| Ile | AUA | 116254 | 17.8 |

TABLE 2-continued

Codon Usage Table for *Saccharomyces cerevisiae* Genes

| Amino Acid | Codon | Number | Frequency per thousand |
|---|---|---|---|
| Total | | | |
| Met | AUG | 136805 | 20.9 |
| Total | | | |
| Val | GUU | 144243 | 22.1 |
| Val | GUC | 76947 | 11.8 |
| Val | GUA | 76927 | 11.8 |
| Val | GUG | 70337 | 10.8 |
| Total | | | |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Total | | | |
| Pro | CCU | 88263 | 13.5 |
| Pro | CCC | 44309 | 6.8 |
| Pro | CCA | 119641 | 18.3 |
| Pro | CCG | 34597 | 5.3 |
| Total | | | |
| Thr | ACU | 132522 | 20.3 |
| Thr | ACC | 83207 | 12.7 |
| Thr | ACA | 116084 | 17.8 |
| Thr | ACG | 52045 | 8.0 |
| Total | | | |
| Ala | GCU | 138358 | 21.2 |
| Ala | GCC | 82357 | 12.6 |
| Ala | GCA | 105910 | 16.2 |
| Ala | GCG | 40358 | 6.2 |
| Total | | | |
| Tyr | UAU | 122728 | 18.8 |
| Tyr | UAC | 96596 | 14.8 |
| Total | | | |
| His | CAU | 89007 | 13.6 |
| His | CAC | 50785 | 7.8 |
| Total | | | |
| Gln | CAA | 178251 | 27.3 |
| Gln | CAG | 79121 | 12.1 |
| Total | | | |
| Asn | AAU | 233124 | 35.7 |
| Asn | AAC | 162199 | 24.8 |
| Total | | | |
| Lys | AAA | 273618 | 41.9 |
| Lys | AAG | 201361 | 30.8 |
| Total | | | |
| Asp | GAU | 245641 | 37.6 |
| Asp | GAC | 132048 | 20.2 |
| Total | | | |
| Glu | GAA | 297944 | 45.6 |
| Glu | GAG | 125717 | 19.2 |
| Total | | | |
| Cys | UGU | 52903 | 8.1 |
| Cys | UGC | 31095 | 4.8 |
| Total | | | |
| Trp | UGG | 67789 | 10.4 |
| Total | | | |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Total | | | |
| Gly | GGU | 156109 | 23.9 |
| Gly | GGC | 63903 | 9.8 |
| Gly | GGA | 71216 | 10.9 |
| Gly | GGG | 39359 | 6.0 |
| Total | | | |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences, e.g., the "backtranslation" function (Entelechon GmbH, Regensburg, Germany) and the "backtranseq" function available (NRC Saskatoon Bioinformatics, Saskatoon, Saskatchewan, Canada). Constructing a rudimentary algorithm to assign codons based on a given frequency can also easily be accomplished with basic mathematical functions by one of ordinary skill in the art.

Codon-optimized coding regions can be designed by various methods known to those skilled in the art including software packages such as "synthetic gene designer" (University of Maryland, Baltimore, Md.).

Standard recombinant DNA and molecular cloning techniques used here are well known in the art and are described by Sambrook et al. (Sambrook, Fritsch, and Maniatis, Molecular Cloning: A Laboratory Manual, Second Edition, Cold Spring Harbor Laboratory Press, Cold Spring Harbor, N.Y., 1989) (hereinafter "Maniatis"); and by Silhavy et al. (Silhavy et al., Experiments with Gene Fusions, Cold Spring Harbor Laboratory Press Cold Spring Harbor, N.Y., 1984); and by Ausubel, F. M. et al., (Ausubel et al., Current Protocols in Molecular Biology, published by Greene Publishing Assoc. and Wiley-Interscience, 1987).

Alcohol Dehydrogenase (ADH) Enzymes

Alcohol dehydrogenases (ADH) are a broad class of enzymes that catalyze the interconversion of aldehydes to alcohols as part of various pathways in cellular milieu. ADH enzymes are universal and are classified into multiple families based on either the length of the amino-acid sequence or the type of metal cofactors they use.

Figure 2:
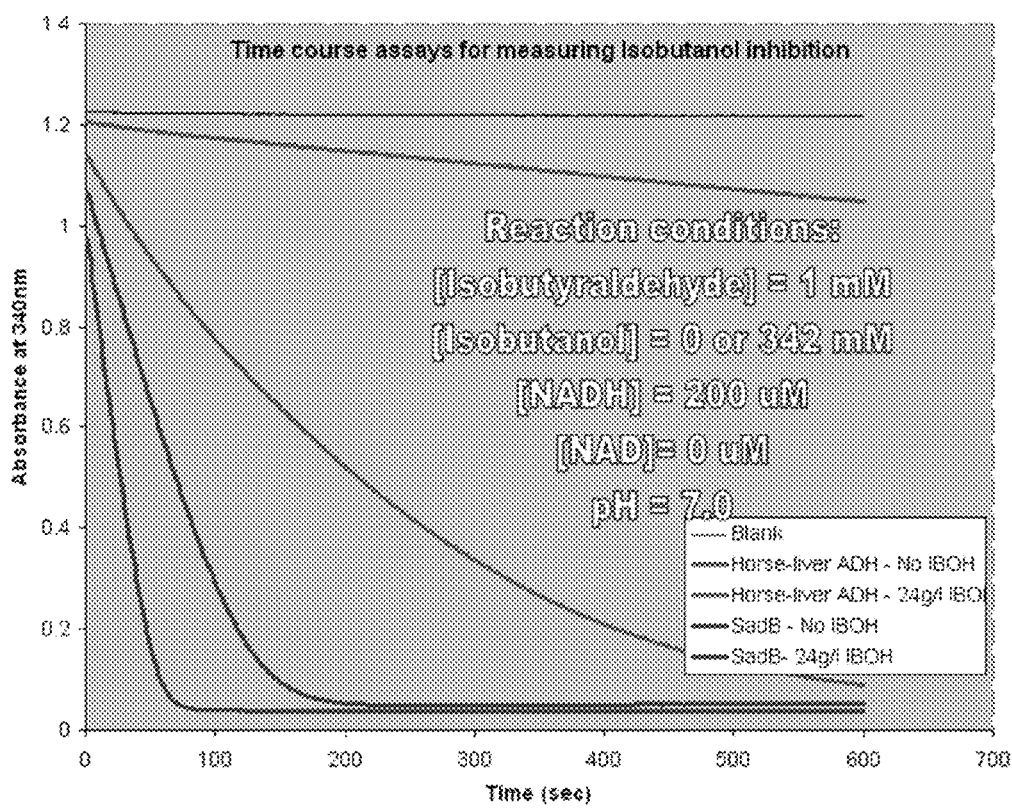
FIG. 2 shows the results of semi-physiological time-course assays comparing the level of isobutanol inhibition observed with horse liver ADH and *Achromobacter xylosoxidans* SadB in the same figure. The assays are as described for FIG. 1.
Figure 4:
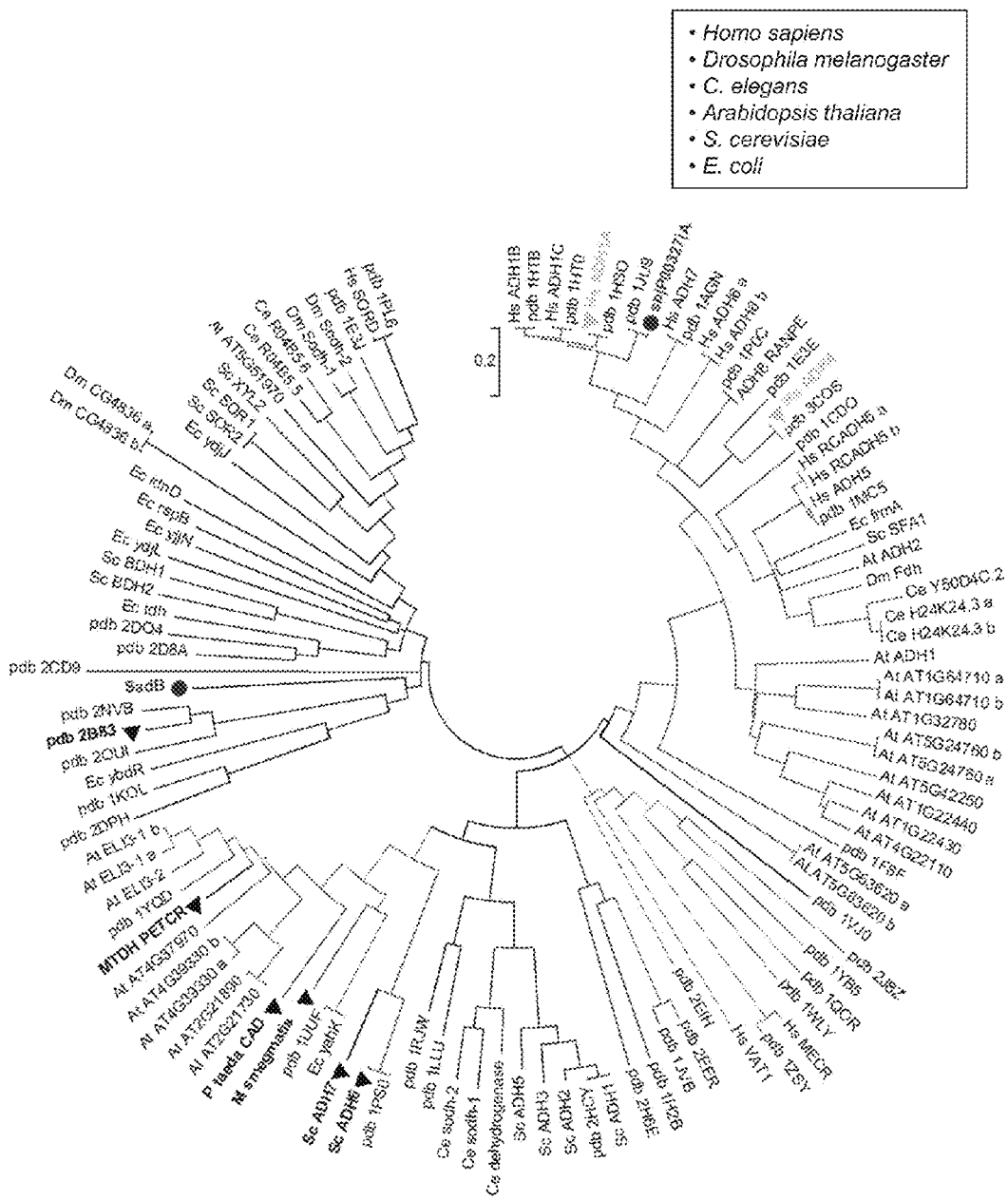
FIG. 4 is a phylogenetic tree of oxidoreductase enzymes obtained as hits from (i) a protein BLAST search for similar sequences in *Saccharomyces cerevisiae, E. coli, Homo sapiens, C. elegans, Drosophila melanogaster,* and *Arabidopsis thaliana,* and (ii) a protein BLAST search of Protein Data Bank (PDB) for similar sequences using horse liver ADH and *Achromobacter xylosoxidans* SadB as queries.

More than 150 structures are available in the Protein Data Bank (PDB) for a variety of ADH enzymes. The enzymes are highly divergent and different ADHs exist as oligomers with varying subunit compositions. FIG. 4 shows the phylogenetic relationship of oxidoreductase enzymes in *Saccharomyces cerevisiae*, *E. coli*, *Homo sapiens*, *C. elegans*, *Drosophila melanogaster*, and *Arabidopsis thaliana* that are related to horse liver ADH and *Achromobacter xylosoxidans* SadB.

Figure 5:
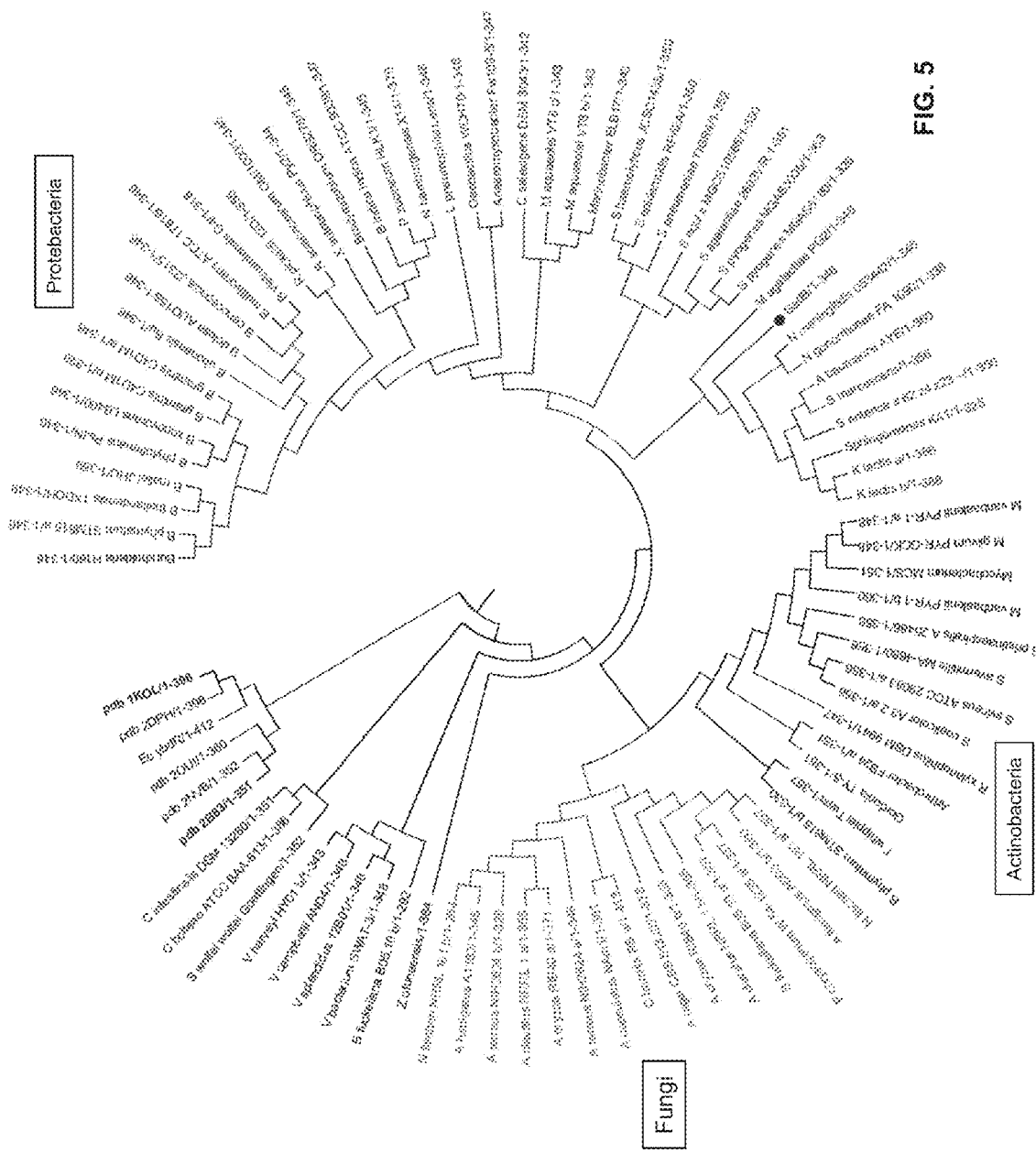
FIG. 5 is a phylogenetic tree of oxidoreductase enzyme sequences more closely related in sequence to *Achromobacter xylosoxidans* SadB among hits from a protein BLAST search of nonredundant protein sequence database (nr) at NCBI using *Achromobacter xylosoxidans* SadB as query.

FIG. 5 shows the phylogenetic relationship of specific ADH enzyme sequences more closely related to *Achromobacter xylosoxidans* SadB by sequence.

In one embodiment, ADH enzymes suitable for use in the present invention have a very high $k_{cat}$ for the conversion of a lower alkyl aldehyde to a corresponding lower alkyl alcohol. In another embodiment, ADH enzymes suitable for use have a very low $k_{cat}$ for the conversion of a lower alkyl alcohol to a corresponding lower alkyl aldehyde. In another embodiment, ADH enzymes suitable for use have a low $K_M$ for lower alkyl aldehydes. In another embodiment, suitable ADH enzymes have a high $K_M$ for lower alkyl alcohols. In another embodiment, suitable ADH enzymes preferentially use NADH as a cofactor during reduction reactions. In another embodiment, suitable ADH enzymes have one or more of the following characteristics: a very high $k_{cat}$ for the conversion of a lower alkyl aldehyde to a corresponding lower alkyl alcohol; a very low $k_{cat}$ for the conversion of a lower alkyl alcohol to a corresponding lower alkyl aldehyde; a low $K_M$ for lower alkyl aldehydes; a high $K_M$ for lower alkyl alcohols; and preferential use of NADH as a cofactor during reduction reactions. In another embodiment, suitable ADH enzymes have a high $K_I$ for lower alkyl alcohols. In another embodiment, suitable ADH enzymes have two or more of the above characteristics.

In one embodiment, ADH enzymes suitable for use in the present invention oxidize cofactors in the presence and absence of a lower alkyl alcohol faster relative to control polypeptides. In one embodiment, the control polypeptide is *Achromobacter xylosoxidans* SadB having the amino acid sequence of SEQ ID NO: 26.

In another embodiment, suitable ADH enzymes have $K_M$ for a lower alkyl aldehyde that are lower relative to a control polypeptide. In another embodiment, suitable ADH enzymes have a $K_M$ for a lower alkyl aldehyde that is at least about 5%, 10%, 15%, 20%, 25%, 30%, 35%, 40%, 50%, 60%, 70%, 80%, or 90% lower relative to a control polypeptide. In one embodiment, the control polypeptide is *Achromobacter xylosoxidans* SadB having the amino acid sequence of SEQ ID NO: 26. In one embodiment, the lower alkyl aldehyde is isobutyraldehyde.

In another embodiment, suitable ADH enzymes have a $K_I$ for a lower alkyl alcohol that is higher relative to a control polypeptide. In another embodiment, suitable ADH enzymes have a lower alkyl alcohol $K_I$ that is at least about 10%, 50%, 100%, 200%, 300%, 400%, or 500% higher relative to a control polypeptide. In one embodiment, the control polypeptide is *Achromobacter xylosoxidans* SadB having the amino acid sequence of SEQ ID NO: 26. In one embodiment, the lower alkyl alcohol is isobutanol.

In another embodiment, suitable ADH enzymes have a $k_{cat}/K_M$ for a lower alkyl aldehyde that is higher relative to a control polypeptide. In another embodiment, suitable ADH enzymes have a $k_{cat}/K_M$ that is at least about 10%, 50%, 100%, 200%, 300%, 400%, 500%, 600%, 800%, or 1000% higher relative to a control polypeptide. In one embodiment, the control polypeptide is *Achromobacter xylosoxidans* SadB having the amino acid sequence of SEQ ID NO: 26. In one embodiment, the lower alkyl aldehyde is isobutyraldehyde.

In another embodiment, suitable ADH enzymes have two or more of the above characteristics. In another embodiment, suitable ADH enzymes have three or more of the above characteristics. In another embodiment, suitable ADH enzymes have all four of the above characteristics. In one embodiment, suitable ADH enzymes preferentially use NADH as a cofactor.

In one embodiment, suitable ADH enzymes for use in the present invention catalyze reduction reactions optimally at host cell physiological conditions. In another embodiment, suitable ADH enzymes for use in the present invention catalyze reduction reactions optimally from about pH 4 to about pH 9. In another embodiment, suitable ADH enzymes for use in the present invention catalyze reduction reactions optimally from about pH 5 to about pH 8. In another embodiment, suitable ADH enzymes for use in the present invention catalyze reduction reactions optimally from about pH 6 to about pH 7. In another embodiment, suitable ADH enzymes for use in the present invention catalyze reduction reactions optimally from about pH 6.5 to about pH 7. In another embodiment, suitable ADH enzymes for use in the present invention catalyze reduction reactions optimally at about pH 4, 4.5, 5, 5.5, 6, 6.5, 7, 7.5, 8, 8.5, or 9. In another embodiment, suitable ADH enzymes for use in the present invention catalyze reduction reactions optimally at about pH 7.

In one embodiment, suitable ADH enzymes for use in the present invention catalyze reduction reactions optimally at up to about 70° C. In another embodiment, suitable ADH enzymes catalyze reduction reactions optimally at about 10° C., 15° C., 20° C., 25° C., 30° C., 35° C., 40° C., 45° C., 50° C., 55° C., 60° C., 65° C., or 70° C. In another embodiment, suitable ADH enzymes catalyze reduction reactions optimally at about 30° C.

In one embodiment, suitable ADH enzymes for use in the present invention catalyze the conversion of an aldehyde to an alcohol in the presence of a lower alkyl alcohol at a concentration up to about 50 g/L. In another embodiment, suitable ADH enzymes catalyze the conversion of an aldehyde to an alcohol in the presence of a lower alkyl alcohol at a concentration of at least about 10 g/L, 15 g/L, 20 g/L, 25 g/L, 30 g/L, 35 g/L, 40 g/L, 45 g/L, or 50 g/L. In another embodiment, suitable ADH enzymes catalyze the conversion of an aldehyde to an alcohol in the presence of a lower alkyl alcohol at a concentration of at least about 20 g/L. In some embodiments, the lower alkyl alcohol is butanol. In some embodiments, the lower alkyl aldehyde is isobutyraldehyde and the lower alkyl alcohol is isobutanol.

Recombinant Host Cells for ADH Enzyme Expression

One aspect of the present invention is directed to recombinant host cells that express ADH enzymes having the above-outlined activities. Non-limiting examples of host cells for use in the invention include bacteria, cyanobacteria, filamentous fungi and yeasts.

In one embodiment, the recombinant host cell of the invention is a bacterial or a cyanobacterial cell. In another embodiment, the recombinant host cell is selected from the group consisting of: *Salmonella, Arthrobacter, Bacillus, Brevibacterium, Clostridium, Corynebacterium, Gluconobacter, Nocardia, Pseudomonas, Rhodococcus, Streptomyces, Zymomonas, Escherichia, Lactobacillus, Enterococcus, Alcaligenes, Klebsiella, Serratia, Shigella, Alcaligenes, Erwinia, Paenibacillus*, and *Xanthomonas*. In some embodiments, the recombinant host cell is *E. coli, S. cerevisiae*, or *L. plantarum*.

In another embodiment, the recombinant host cell of the invention is a filamentous fungi or yeast cell. In another embodiment, the recombinant host cell is selected from the group consisting of: *Saccharomyces, Pichia, Hansenula, Yarrowia, Aspergillus, Kluyveromyces, Pachysolen, Rhodotorula, Zygosaccharomyces, Galactomyces, Schizosaccharomyces, Torulaspora, Debayomyces, Williopsis, Dekkera, Kloeckera, Metschnikowia, Issatchenkia*, and *Candida*.

In one embodiment, the recombinant host cell of the invention produces a lower alkyl alcohol at a yield of greater than about 25%, 30%, 35%, 40%, 45%, 50%, 55%, 60%, 65%, 70%, 75%, or 90% of theoretical. In one embodiment, the recombinant host cell of the invention produces a lower alkyl alcohol at a yield of greater than about 25% of theoretical. In another embodiment, the recombinant host cell of the invention produces a lower alkyl alcohol at a yield of greater than about 40% of theoretical. In another embodiment, the recombinant host cell of the invention produces a lower alkyl alcohol at a yield of greater than about 50% of theoretical. In another embodiment, the recombinant host cell of the invention produces a lower alkyl alcohol at a yield of greater than about 75% of theoretical. In another embodiment, the recombinant host cell of the invention produces a lower alkyl alcohol at a yield of greater than about 90% of theoretical. In some embodiments, the lower alkyl alcohol is butanol. In some embodiments, the lower alkyl alcohol is isobutanol.

Non-limiting examples of lower alkyl alcohols produced by the recombinant host cells of the invention include butanol, propanol, isopropanol, and ethanol. In one embodiment, the recombinant host cells of the invention produce isobutanol. In another embodiment, the recombinant host cells of the invention do not produce ethanol.

U.S. Publ. No. 2007/0092957 A1 discloses the engineering of recombinant microorganisms for production of isobutanol (2-methylpropan-1-ol). U.S. Publ. No. 2008/0182308 A1 discloses the engineering of recombinant microorganisms for production of 1-butanol. U.S. Publ. Nos. 2007/0259410 A1 and 2007/0292927 A1 disclose the engineering of recombinant microorganisms for production of 2-butanol. Multiple pathways are described for biosynthesis of isobutanol and 2-butanol. The last step in all described pathways for all three products is the reduction of a more oxidized moiety to the alcohol moiety by an enzyme with butanol dehydrogenase activity. The methods disclosed in these publications can be used to engineer the recombinant host cells of the present invention. The information presented in these publications is hereby incorporated by reference in its entirety.

In embodiments, the recombinant microbial host cell produces isobutanol. In embodiments, the recombinant microbial host cell comprises at least two heterologous polynucleotides encoding enzymes which catalyze a substrate to product conversion selected from the group consisting of: pyruvate to acetolactate; acetolactate to 2,3-dihydroxyisovalerate; 2,3-dihydroxyisovalerate to alpha-ketoisovalerate; alpha-ketoisovalerate to isobutyraldehyde, and isobutyraldehyde to isobutanol. In embodiments, the recombinant microbial host cell comprises at least three heterologous polynucleotides encoding enzymes which catalyze a substrate to product conversion selected from the group consisting of: pyruvate to acetolactate; acetolactate to 2,3-dihydroxyisovalerate; 2,3-dihydroxyisovalerate to alpha-ketoisovalerate; alpha-ketoisovalerate to isobutyraldehyde, and isobutyraldehyde to isobutanol. In embodiments, the recombinant microbial host cell comprises at least four heterologous polynucleotides encoding enzymes which catalyze a substrate to product conversion selected from the group consisting of: pyruvate to acetolactate; acetolactate to 2,3-dihydroxyisovalerate; 2,3-dihydroxyisovalerate to alpha-ketoisovalerate; alpha-ketoisovalerate to isobutyraldehyde, and isobutyraldehyde to isobutanol. In embodiments, the recombinant microbial host cell comprises heterologous polynucleotides encoding enzymes which catalyze the conversion of pyruvate to acetolactate; acetolactate to 2,3-dihydroxyisovalerate; 2,3-dihydroxyisovalerate to alpha-ketoisovalerate; alpha-ketoisovalerate to isobutyraldehyde, and isobutyraldehyde to isobutanol. In embodiments, (a) the polypeptide that catalyzes a substrate to product conversion of pyruvate to acetolactate is acetolactate synthase having the EC number 2.2.1.6; (b) the polypeptide that catalyzes a substrate to product conversion of acetolactate to 2,3-dihydroxyisovalerate is acetohydroxy acid isomeroreducatase having the EC number 1.1.186; (c) the polypeptide that catalyzes a substrate to product conversion of 2,3-dihydroxyisovalerate to alpha-ketoisovalerate is acetohydroxy acid dehydratase having the EC number 4.2.1.9; and (d) the polypeptide that catalyzes a substrate to product conversion of alpha-ketoisovalerate to isobutyraldehyde is branched-chain alpha-keto acid decarboxylase having the EC number 4.1.1.72.

In embodiments, the recombinant microbial host cell further comprises at least one heterologous polynucleotide encoding an enzyme which catalyzes a substrate to product conversion selected from the group consisting of: pyruvate to alpha-acetolactate; alpha-acetolactate to acetoin; acetoin to 2,3-butanediol; 2,3-butanediol to 2-butanone; and 2-butanone to 2-butanol; and wherein said microbial host cell produces 2-butanol. In embodiments, (a) the polypeptide that catalyzes a substrate to product conversion of pyruvate to acetolactate is acetolactate synthase having the EC number 2.2.1.6; (b) the polypeptide that catalyzes a substrate to product conversion of acetolactate to acetoin is acetolactate decarboxylase having the EC number 4.1.1.5; (c) the polypeptide that catalyzes a substrate to product conversion of acetoin to 2,3-butanediol is butanediol dehydrogenase having the EC number 1.1.1.76 or EC number 1.1.1.4; (d) the polypeptide that catalyzes a substrate to product conversion of butanediol to 2-butanone is butanediol dehydratase having the EC number 4.2.1.28. In embodiments, (e) the polypeptide that catalyzes a substrate to product conversion of 2-butanone to 2-butanol is 2-butanol dehydrogenase having the EC number 1.1.1.1.

In embodiments, the recombinant microbial host cell further comprises at least one heterologous polynucleotide encoding an enzyme which catalyzes a substrate to product conversion selected from the group consisting of: acetyl-CoA to acetoacetyl-CoA; acetoacetyl-CoA to 3-hydroxybutyryl-CoA; 3-hydroxybutyryl-CoA to crotonyl-CoA; crotonyl-CoA to butyryl-CoA; butyryl-CoA to butyraldehyde; butyraldehyde to 1-butanol; and wherein said microbial host cell produces 1-butanol. In embodiments, (a) the polypeptide that catalyzes a substrate to product conversion of acetyl-CoA to acetoacetyl-CoA is acetyl-CoA acetyltransferase having the EC number 2.3.1.9 or 2.3.1.16; (b) the polypeptide that catalyzes a substrate to product conversion of acetoacetyl-CoA to 3-hydroxybutyryl-CoA is 3-hydroxybutyryl-CoA dehydrogenase having the EC number 1.1.1.35, 1.1.1.30, 1.1.1.157, or 1.1.1.36; (c) the polypeptide that catalyzes a substrate to product conversion of 3-hydroxybutyryl-CoA to crotonyl-CoA is crotonase having the EC number 4.2.1.17 or 4.2.1.55; (d) the polypeptide that catalyzes a substrate to product conversion of crotonyl-CoA to butyryl-CoA is butyryl-CoA dehydrogenase having the EC number 1.3.1.44 or 1.3.1.38; (e) the polypeptide that catalyzes a substrate to product conversion of butyryl-CoA to butyrylaldehyde is butyraldehyde dehydrogenase having the EC number 1.2.1.57. In embodiments, (f) the polypeptide that catalyzes a substrate to product conversion of butyrylaldehyde to 1-butanol is 1-butanol dehydrogenase having the EC number 1.1.1.1.

In some embodiments, the recombinant microbial host cell further comprises at least one modification which improves carbon flow to the isobutanol pathway. In some embodiments, the recombinant microbial host cell further comprises at least one modification which improves carbon flow to the 1-butanol pathway. In some embodiments, the recombinant microbial host cell further comprises at least one modification which improves carbon flow to the 2-butanol pathway.

Methods for Producing Lower Alkyl Alcohols

Another aspect of the present invention is directed to methods for producing lower alkyl alcohols. These methods primarily employ the recombinant host cells of the invention. In one embodiment, the method of the present invention comprises providing a recombinant host cell as discussed above, contacting the recombinant host cell with a fermentable carbon substrate in a fermentation medium under conditions whereby the lower alkyl alcohol is produced and recovering the lower alkyl alcohol.

Carbon substrates may include, but are not limited to, monosaccharides (such as fructose, glucose, mannose, rhamnose, xylose or galactose), oligosaccharides (such as lactose, maltose, or sucrose), polysaccharides such as starch, maltodextrin, or cellulose or mixtures thereof and unpurified mixtures from renewable feedstocks such as cheese whey permeate, cornsteep liquor, sugar beet molasses, and barley malt. Other carbon substrates may include ethanol, lactate, succinate, or glycerol.

Additionally, the carbon substrate may also be a one carbon substrate such as carbon dioxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeasts are known to utilize the carbon from methylamine to form trehalose or glycerol (Bellion et al., Microb. Growth C1 Compd., [Int. Symp.], 7th (1993), 415 32, Editor(s): Murrell, J. Collin; Kelly, Don P. Publisher: Intercept, Andover, UK). Similarly, various species of *Candida* will metabolize alanine or oleic acid (Sulter et al., Arch. Microbiol. 153:485-489 (1990)). Hence, it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose, or mixtures of these with C5 sugars such as xylose and/or arabinose for yeasts cells modified to use C5 sugars. Sucrose may be derived from renewable sugar sources such as sugar cane, sugar beets, cassava, sweet sorghum, and mixtures thereof. Glucose and dextrose may be derived from renewable grain sources through saccharification of starch based feedstocks including grains such as corn, wheat, rye, barley, oats, and mixtures thereof. In addition, fermentable sugars may be derived from renewable cellulosic or lignocellulosic biomass through processes of pretreatment and saccharification, as described, for example, in U.S. Publ. No. 2007/0031918 A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

The carbon substrates may be provided in any media that is suitable for host cell growth and reproduction. Non-limiting examples of media that can be used include M122C, MOPS, SOB, TSY, YMG, YPD, 2XYT, LB, M17, or M9 minimal media. Other examples of media that can be used include solutions containing potassium phosphate and/or sodium phosphate. Suitable media can be supplemented with NADH or NADPH.

The fermentation conditions for producing a lower alkyl alcohol may vary according to the host cell being used. In one embodiment, the method for producing a lower alkyl alcohol is performed under anaerobic conditions. In one embodiment, the method for producing a lower alkyl alcohol is performed under aerobic conditions. In one embodiment, the method for producing a lower alkyl alcohol is performed under microaerobic conditions.

In one embodiment, the method for producing a lower alkyl alcohol results in a titer of at least about 20 g/L of a lower alkyl alcohol. In another embodiment, the method for producing a lower alkyl alcohol results in a titer of at least about 30 g/L of a lower alkyl alcohol. In another embodiment, the method for producing a lower alkyl alcohol results in a titer of about 10 g/L, 15 g/L, 20 g/L, 25 g/L, 30 g/L, 35 g/L or 40 g/L of a lower alkyl alcohol.

Non-limiting examples of lower alkyl alcohols produced by the methods of the invention include butanol, isobutanol, propanol, isopropanol, and ethanol. In one embodiment, isobutanol is produced.

In embodiments, isobutanol is produced. In embodiments, the method for producing isobutanol comprises:
 (a) providing a recombinant host cell comprising a heterologous polypeptide which catalyzes the substrate to product conversion of isobutyraldehyde to isobutanol and which has one or more of the following characteristics:
  (i) the $K_M$ value of a lower alkyl aldehyde is lower for the polypeptide relative to a control polypeptide having the amino acid sequence of SEQ ID NO: 26;
  (ii) the $K_I$ value for a lower alkyl aldehyde for the polypeptide is higher relative to control polypeptide having the amino acid sequence of SEQ ID NO: 26;
  (iii) the $k_{cat}/K_M$ value for a lower alkyl aldehyde for the polypeptide is higher relative to a control polypeptide having the amino acid sequence of SEQ ID NO: 26; and
 (b) contacting the host cell of (a) with a carbon substrate under conditions whereby isobutanol is produced.

In embodiments, 2-butanol is produced. In embodiments, the method for producing 2-butanol comprises:
 (a) providing a recombinant microbial host cell comprising a heterologous polypeptide which catalyzes the substrate to product conversion of 2-butanone to 2-butanol and which has one or more of the following characteristics:
  (i) the $K_M$ value for a lower alkyl aldehyde is lower for the polypeptide relative to a control polypeptide having the amino acid sequence of SEQ ID NO: 26;
  (ii) the $K_I$ value for a lower alkyl alcohol for the polypeptide is higher relative to a control polypeptide having the amino acid sequence of SEQ ID NO: 26; and
  (iii) the $k_{cat}/K_M$ value for a lower alkyl aldehyde for the polypeptide is higher relative to a control polypeptide having the amino acid sequence of SEQ ID NO: 26; and
 (b) contacting the host cell of (a) with a carbon substrate under conditions whereby 2-butanol is produced.

In embodiments, 1-butanol is produced. In embodiments, the method for producing 1-butanol comprises:
 (a) providing a recombinant microbial host cell comprising a heterologous polypeptide which catalyzes the substrate to product conversion of butyraldehyde to 1-butanol and which has one or more of the following characteristics:
  (i) the $K_M$ value for a lower alkyl aldehyde is lower for the polypeptide relative to a control polypeptide having the amino acid sequence of SEQ ID NO: 26;

(ii) the $K_I$ value for a lower alkyl alcohol for the polypeptide is higher relative to a control polypeptide having the amino acid sequence of SEQ ID NO: 26; and (iii) the $k_{cat}/K_M$ value for a lower alkyl aldehyde for the polypeptide is higher relative to a control polypeptide having the amino acid sequence of SEQ ID NO: 26; and (b) contacting the host cell of (a) with a carbon substrate under conditions whereby 1-butanol is produced.

Biosynthetic Pathways

Recombinant microbial production hosts expressing a 1-butanol biosynthetic pathway (Donaldson et al., U.S. Patent Application Publication No. US20080182308A1, incorporated herein by reference), a 2-butanol biosynthetic pathway (Donaldson et al., U.S. Patent Publication Nos. US 20070259410A1 and US 20070292927, and US 20090155870, all incorporated herein by reference), and an isobutanol biosynthetic pathway (Maggio-Hall et al., U.S. Patent Publication No. US 20070092957, incorporated herein by reference) have been described in the art. Certain suitable proteins having the ability to catalyze the indicated substrate to product conversions are described therein and other suitable proteins are described in the art. The skilled person will appreciate that polypeptides having the activity of such pathway steps can be isolated from a variety of sources and can be used in a recombinant host cell disclosed herein. For example, US Published Patent Application Nos. US20080261230 and US20090163376, US20100197519, and U.S. application Ser. No. 12/893,077 describe acetohydroxy acid isomeroreductases; US20070092957 and US20100081154, describe suitable dihydroxyacid dehydratases.

Equipped with this disclosure, a person of skill in the art will be able to utilize publicly available sequences to construct relevant pathways in the host cells provided herein. Additionally, one of skill in the art, equipped with this disclosure, will appreciate other suitable isobutanol, 1-butanol, or 2-butanol pathways.

Isobutanol Biosynthetic Pathway

Isobutanol can be produced from carbohydrate sources with recombinant microorganisms by through various biosynthetic pathways. Suitable pathways converting pyruvate to isobutanol include the four complete reaction pathways shown in FIG. 6. A suitable isobutanol pathway (FIG. 6, steps a to e), comprises the following substrate to product conversions:

a) pyruvate to acetolactate, as catalyzed for example by acetolactate synthase,
b) acetolactate to 2,3-dihydroxyisovalerate, as catalyzed for example by acetohydroxy acid isomeroreductase,
c) 2,3-dihydroxyisovalerate to α-ketoisovalerate, as catalyzed for example by acetohydroxy acid dehydratase,
d) α-ketoisovalerate to isobutyraldehyde, as catalyzed for example by a branched-chain keto acid decarboxylase, and
e) isobutyraldehyde to isobutanol, as catalyzed for example by, a branched-chain alcohol dehydrogenase.

Another suitable pathway for converting pyruvate to isobutanol comprises the following substrate to product conversions (FIG. 6, steps a,b,c,f,g,e):

a) pyruvate to acetolactate, as catalyzed for example by acetolactate synthase,
b) acetolactate to 2,3-dihydroxyisovalerate, as catalyzed for example by acetohydroxy acid isomeroreductase,
c) 2,3-dihydroxyisovalerate to α-ketoisovalerate, as catalyzed for example by acetohydroxy acid dehydratase,
f) α-ketoisovalerate to isobutyryl-CoA, as catalyzed for example by a branched-chain keto acid dehydrogenase,
g) isobutyryl-CoA to isobutyraldehyde, as catalyzed for example by an acylating aldehyde dehydrogenase, and
e) isobutyraldehyde to isobutanol, as catalyzed for example by, a branched-chain alcohol dehydrogenase.

The first three steps in this pathway (a,b,c) are the same as those described above.

Another suitable pathway for converting pyruvate to isobutanol comprises the following substrate to product conversions (FIG. 6, steps a,b,c,h,i,j,e):

a) pyruvate to acetolactate, as catalyzed for example by acetolactate synthase,
b) acetolactate to 2,3-dihydroxyisovalerate, as catalyzed for example by acetohydroxy acid isomeroreductase,
c) 2,3-dihydroxyisovalerate to α-ketoisovalerate, as catalyzed for example by acetohydroxy acid dehydratase,
h) α-ketoisovalerate to valine, as catalyzed for example by valine dehydrogenase or transaminase,
i) valine to isobutylamine, as catalyzed for example by valine decarboxylase,
j) isobutylamine to isobutyraldehyde, as catalyzed for example by omega transaminase, and
e) isobutyraldehyde to isobutanol, as catalyzed for example by, a branched-chain alcohol dehydrogenase.

The first three steps in this pathway (a,b,c) are the same as those described above.

A fourth suitable isobutanol biosynthetic pathway comprises the substrate to product conversions shown as steps k,g,e in FIG. 6.

1-Butanol Biosynthetic Pathway

An example of a suitable biosynthetic pathway for production of 1-butanol is disclosed in U.S. Patent Application Publication No. US 2008/0182308 A1. As disclosed this publication, steps in the disclosed 1-butanol biosynthetic pathway include conversion of:

acetyl-CoA to acetoacetyl-CoA, as catalyzed for example by acetyl-CoA acetyltransferase;
acetoacetyl-CoA to 3-hydroxybutyryl-CoA, as catalyzed for example by 3-hydroxybutyryl-CoA dehydrogenase;
3-hydroxybutyryl-CoA to crotonyl-CoA, as catalyzed for example by crotonase;
crotonyl-CoA to butyryl-CoA, as catalyzed for example by butyryl-CoA dehydrogenase;
butyryl-CoA to butyraldehyde, as catalyzed for example by butyraldehyde dehydrogenase; and
butyraldehyde to 1-butanol, as catalyzed for example by butanol dehydrogenase.

2-Butanol Biosynthetic Pathway

An example of a suitable biosynthetic pathway for production of 2-butanol is described by Donaldson et al. in U.S. Patent Application Publication Nos. US20070259410A1 and US 20070292927A1, and in PCT Publication WO 2007/130521, all of which are incorporated herein by reference. Steps of a suitable 2-butanol biosynthetic pathway comprises the following substrate to product conversions:

a) pyruvate to alpha-acetolactate, which may be catalyzed, for example, by acetolactate synthase;
b) alpha-acetolactate to acetoin, which may be catalyzed, for example, by acetolactate decarboxylase;
c) acetoin to 2,3-butanediol, which may be catalyzed, for example, by butanediol dehydrogenase;
d) 2,3-butanediol to 2-butanone, which may be catalyzed, for example, by butanediol dehydratase; and
e) 2-butanone to 2-butanol, which may be catalyzed, for example, by 2-butanol dehydrogenase.

Additional Modifications

Additional modifications that may be useful in cells provided herein include modifications to reduce pyruvate decarboxylase and/or glycerol-3-phosphate dehydrogenase activity as described in US Patent Application Publication No. 20090305363 (incorporated herein by reference), modifications to a host cell that provide for increased carbon flux through an Entner-Doudoroff Pathway or reducing equivalents balance as described in US Patent Application Publication No. 20100120105 (incorporated herein by reference). Yeast strains with increased activity of heterologous proteins that require binding of an Fe—S cluster for their activity are described in US Application Publication No. 20100081179 (incorporated herein by reference). Other modifications include modifications in an endogenous polynucleotide encoding a polypeptide having dual-role hexokinase activity, described in U.S. Provisional Application No. 61/290,639, integration of at least one polynucleotide encoding a polypeptide that catalyzes a step in a pyruvate-utilizing biosynthetic pathway described in U.S. Provisional Application No. 61/380,563 (both referenced provisional applications are incorporated herein by reference in their entirety). Additional modifications that may be suitable for embodiments herein are described in U.S. application Ser. No. 12/893,089.

Additionally, host cells comprising at least one deletion, mutation, and/or substitution in an endogenous gene encoding a polypeptide affecting Fe—S cluster biosynthesis are described in U.S. Provisional Patent Application No. 61/305,333 (incorporated herein by reference), and host cells comprising a heterologous polynucleotide encoding a polypeptide with phosphoketolase activity and host cells comprising a heterologous polynucleotide encoding a polypeptide with phosphotransacetylase activity are described in U.S. Provisional Patent Application No. 61/356,379.

Identification and Isolation of High Activity ADH Enzymes

The present invention is directed to devising a strategy and identifying several ADH enzymes with superior properties towards the conversion of isobutyraldehyde to isobutanol in a host organism that has been engineered for isobutanol production. The process of ADH candidate selection involves searching among the naturally existing enzymes. Enzymes are identified based on their natural propensity to utilize aldehydes as preferred substrates and convert them to the respective alcohols with reasonably high $k_{cat}$ and/or low $K_M$ values for the corresponding aldehyde substrates, as documented by literature examples. Once a set of candidates is identified, the strategy involves using this set to isolate closely-related homologues via bioinformatics analysis. Therefore, in one embodiment, the screening method of the invention comprises performing a bioinformatics or literature search for candidate ADH enzymes. In one embodiment, the bioinformatics search uses a phylogenetic analysis.

The protein-encoding DNA sequences of the candidate genes are either amplified directly from the host organisms or procured as codon-optimized synthetic genes for expression in a host cell, such as *E. coli*. Various ADH candidates utilized herein are listed in Table 3.

TABLE 3

| Gene | Polynucleotide SEQ ID NO: | Polypeptide SEQ ID NO: |
|---|---|---|
| Horse-liver ADH | 1 | 21 |
| *Saccharomyces cerevisiae* ADH6 | 2 | 22 |
| *Saccharomyces cerevisiae* ADH7 | 3 | 23 |
| *Clostridium acetobutylicum* BdhA | 4 | 24 |
| *Clostridium acetobutylicum* BdhB | 5 | 25 |
| *Achromobacter xylosoxidans* SadB | 6 | 26 |
| *Bos taurus* ARD | 7 | 27 |
| *Rana perezi* ADH8 | 8 | 28 |
| *Clostridium beijerinckii* ADH | 9 | 29 |
| *Entamoeba histolytica* ADH1 | 10 | 30 |
| *Beijerinckia indica* ADH | 11 | 31 |
| *Rattus norvegicus* ADH1 | 12 | 32 |
| *Thermus* sp. ATN1 ADH | 13 | 33 |
| *Phenylobacterium zucineum* HLK1 ADH | 14 | 34 |
| *Methylocecila silvestris* BL2 ADH | 15 | 35 |
| *Acinetobacter baumannii* AYE ADH | 16 | 36 |
| *Geobacillus* sp. WCH70 ADH | 17 | 37 |
| *Vanderwaltozyma polyspora* DSM 70294 ADH | 18 | 38 |
| *Mucor circinelloides* ADH | 19 | 39 |
| *Rhodococcus erythropolis* PR4 ADH | 20 | 40 |

The present invention is not limited to the ADH enzymes listed in Table 3. Additional candidates can be identified based on sequence homologies to these candidates or candidates can be derived from these sequences via mutagenesis and/or protein evolution. Suitable ADH enzymes include ADH enzymes having at least about 95% identity to the sequences provided herein.

Tables 4 and 5 provide the polynucleotide (codon-optimized for expression *E. coli* except for SEQ ID NOs. 2, 3, 4, 5, and 6) and polypeptides sequences of the candidate ADH enzymes presented in Table 3, respectively.

TABLE 4

| SEQ ID NO | POLYNUCLEOTIDE SEQUENCE |
|---|---|
| 1 | atgtcaacagccggtaaagttattaagtgtaaagcggcagttttgtgggaagagaaaaagccgtttagcat<br>agaagaagtagaagtagcgccaccaaaagcacacgaggttagaatcaagatggttgccaccggaatct<br>gtagatccgacgaccatgtggtgagtggcactctagttactcctttgccagtaatcgcgggacacgaggc<br>tgccggaatcgttgaatccataggtgaaggtgttaccactgttcgtcctggtgataaagtgatcccactgttc<br>actcctcaatgtgtaagtgtagagtctgcaaacatcctgagggtaatttctgccttaaaaatgatttgtctat<br>gcctagaggtactatgcaggatggtacaagcagatttacatgcagagggaaacctatacaccatttccttg<br>gtacttctacattttcccaatacacagtggtggacgagatatctgtcgctaaaatcgatgcagatcaccact<br>ggaaaaagtttgcttgatagggtgcggattttccaccggttacggttccgcagttaaagttgcaaaggttac<br>acagggttcgacttgtgcagtattcggtttaggaggagtaggactaagcgttattatggggtgtaaagctg<br>caggcgcagcgaggattataggtgtagacatcaataaggacaaatttgcaaaagctaaggaggtcggg<br>gctactgaatgtgttaaccctcaagtattaagaaaccaatacaagaagtccttactgaaatgtcaaacggt<br>ggagttgatttctcttttgaagttataggccgtcttgatactatggtaactgcgttgtcctgctgtcaagaggc |

TABLE 4-continued

| SEQ ID NO | POLYNUCLEOTIDE SEQUENCE |
|---|---|
| | atatggagtcagtgtgatcgtaggtgttcctcctgattcacaaaatttgtcgatgaatcctatgctgttgctaa
gcggtcgtacatggaagggagctatatttggcggttttaagagcaaggatagtgttccaaaacttgttgcc
gactttatggcgaagaagtttgctcttgatcctttaattacacatgtattgccattcgagaaaatcaatgaagg
gtttgatttgttaagaagtggtgaatctattcgtacaattttaacttttga |
| 2 | atgtcttatcctgagaaatttgaaggtatcgctattcaatcacacgaagattggaaaaacccaaagaagac
aaagtatgacccaaaaccattttacgatcatgacattgacattaagatcgaagcatgtggtgtctgcggtag
tgatattcattgtgcagctggtcattggggcaatatgaagatgccgctagtcgttggtcatgaaatcgttggt
aaagttgtcaagctagggcccaagtcaaacagtgggttgaaagtcggtcaacgtgttggtgtaggtgctc
aagtatttcatgatggaatgtgaccgttgtaagaatgataatgaaccatactgcaccaagtttgttaccaca
tacagtcagcctttatgaagacggctatgtgtcgcagggtggctatgcaaactacgtcagagttcatgaaca
ttttgtggtgcctatcccagagaatattccatcacatttggctgctccactattatgtggtggtttgactgtgta
ctctccattggttcgtaacggttgcggtccaggtaaaaaagttggtatagttggtcttggtggtatcggcagt
atgggtacattgatttccaaagccatgggggcagagacgtatgttatttctcgttctttcttcgagaaaaagagaa
gatgcaatgaagatgggcgccgatcactacattgctacattagaagaaggtgattggggtgaaaagtact
ttgacaccttcgacctgattgtagtctgtgatcctcccttaccgacattgacttcaacattatgccaaaggct
atgaaggttggtggtagaattgtctcaatctctataccagaacaacacgaaatgttatcgctaaagccatat
ggcttaaaggctgtctccatttcttacagtgctttaggttccatcaaagaattgaaccaactcttgaaattagt
ctctgaaaaagatatcaaaatttgggtggaaacattacctgttggtgaagccggcgtccatgaagccttcg
aaaggatggaaaagggtgacgttagatatagatttaccttagtcggctacgacaaagaattttcagactag |
| 3 | atgctttacccagaaaaatttcagggcatcggtatttccaacgcaaaggattggaagcatcctaaattagtg
agttttgacccaaaaacccttttggcgatcatgacgttgatgttgaaattgaagcctgtggtatctgcggatctg
attttcatatagccgttggtaattggggtccagtcccagaaaatcaaatccttggacatgaaataattggccg
cgtggtgaaggttggatccaagtgccacactggggtaaaaatcggtgaccgtgttggtgttggtgcccaa
gccttggcgtgttttgagtgtgaacgttgcaaaagtgacaacgagcaatactgtaccaatgaccacgttttg
actatgtggactccttacaaggacggctacatttcacaaggaggctttgcctcccacgtgaggcttcatga
acacttttgctattcaaataccagaaaatattccaagtccgctagccgctccattattgtgtggtggtattacag
ttttctctccactactaagaaatggctgtggtccaggtaagagggtaggtattgttggcatcggtggtattgg
gcatatggggattctgttggctaaagctatgggagccgaggtttatgcgttttcgcgaggccactccaagc
gggaggattctatgaaactcggtgctgatcactatattgctatgttggaggataaaggctggacagaacaa
tactctaacgcttttggaccttatgtcgtttgctcatcatctttgtcgaaagttaattttgacagtatcgttaagat
tatgaagattggaggctccatcgtttcaattgctgctcctgaagttaatgaaaagcttgttttaaaaccgttgg
gcctaatgggagtatcaatctcaagcagtgctatcggatctaggaaggaaatcgaacaactattgaaatta
gtttccgaaaagaatgtcaaaatatgggtggaaaaacttccgatcagcgaagaaggcgtcagccatgcct
ttacaaggatggaaagcggagacgtcaaatacagatttactttggtcgattatgataagaaattccataaat
ag |
| 4 | atgctaagttttgattattcaataccaactaaagtttttttgggaaaaggaaaaatagacgtaattggagaaga
aattaagaaatatggctcaagagtgcttatagtttatggcggaggaagtataaaaaggaacggtatatatg
atagagcaacagctatattaaaagaaaacaatatagattctatgaactttcaggagtagagccaaatccta
ggataacaacagtaaaaaaaggcatagaaatatgtagagaaaataatgtggatttagtattagcaatagg
ggaggaagtgcaatagactgttctaaggtaattgcagctggtttattatgatggcgatacatgggacat
ggttaaagatccatctaaaataactaaagttatccaattgcaagtatacttactattcagcaacagggtctg
aaatggatcaaattgcagtaatttcaaatatggagactaatgaaaagcttggagtaggacatgatgatatga
gacctaaattttcagtgttagatcctacatatactttacagtacctaaaaatcaaacagcagcgggaacag
ctgacattatgagtcacaccttttgaatcttacttttagtggtgttgaaggtgatatgtgcaggacggtatacga
gaagcaatcttaagaacatgtataaagtatggaaaaatagcaatggagaagactgatgattacgaggcta
gagctaatttgatgtgggcttcaagtttagctataaatggtctattatcacttggtaaggatagaaaatggagt
tgtcatcctatggaacacgagttaagtgcatattatgatataacacatggtgtaggacttgcaattttaacacc
taattggatggaatatattctaaatgacgatacacttcataaatttgtttcttatggaattaaatgttggggaata
gacaagaacaaagataactatgaaatagcacgagaggctattaaaaatacgaggaatacttttaattcatt
gggtattccttcaaagcttagagaagttggaataggaaaagataaactagaactaatggcaaagcaagct
gttagaaattctggaggaacaataggaagtttaagaccaatataagcagaggatgttcttgagatatttaaa
aaatcttattaa |
| 5 | atggttgatttcgaatattcaataccaactagaattttttttcggtaaagataagataaatgtacttggaagaga
gcttaaaaaaatatggttctaaagtgcttatagtttatggtggaggaagtataaagagaaatggaatatatgat
aaagctgtaagtatacttgaaaaaaacagtattaaattttatgaacttgcaggagtagagccaaatccaaga
gtaactacagttgaaaaaggagttaaaatatgtagaaaatggagttgagtagtactagctagctataggtgg
aggaagtgcaatagattgcgcaaaggttatagcagcagcatgtgaatatgatggaaatccatgggatatt
gtgttagatggctcaaaaataaaaagggtgcttcctatagctagtatattaaccattgctgcaacaggatca
gaaatggatacgtgggcagtaataaataatgatacaaacgaaaaactaattgcggcacatccagata
tggctcctaagttttctatattagatccaacgtatacgtataccgtacctaccaatcaaacagcagcaggaa
cagctgatattatgagtcatatatttgaggtgtatttagtaatacaaaacagcatatttgcaggatagaatg
gcagaagcgttattaagaacttgtattaaatatggaggaatagctcttgagaagccgatgattatgaggc
aagagccaatctaatgtgggcttcaagtcttgcgataaatggacttttaacatatggtaaagacactaattgg
agtgtacacttaatggaacatgaattaagtgatattacgacatacaccacggcgtagggcttgcaattttaa
cacctaattggatggagtataattttaaataatgatacagtgtacaagtttgttgaatatggtgtaaatgtttggg
gaatagcaaagaaaaaatcactatgacatagcacatcaagcaatacaaaaaacaagagattactttgt
aaatgtactaggtttaccatctagactgagagatgttggaattgaagaagaaaattggacataatggcaa
aggaatcagtaaagcttacaggaggaaccataggaaacctaagaccagtaaacgcctccgaagtcctac
aaatattcaaaaaatctgtgtaa |
| 6 | atgaaagctctggtttatcacggtgaccacaagatctcgcttgaagacaagcccaagcccaccatcaaa
agcccacggatgtagtagtacgggttttgaagaccacgatctgcggcacggatctcggcatctacaaag
gcaagaatccagaggtcgccgacgggcgcatcctgggccatgaaggggtaggcgtcatcgaggaagt |

TABLE 4-continued

| SEQ ID NO | POLYNUCLEOTIDE SEQUENCE |
|---|---|
|  | gggcgagagtgtcacgcagttcaagaaaggcgacaaggtcctgatttcctgcgtcacttatgcggctcg<br>tgcgactactgcaagaagcagctttactcccattgccgcgacggcgggtggatcctgggttacatgatcg<br>atggcgtgcaggccgaatacgtccgcatcccgcatgccgacaacagcctctacaagatcccccagaca<br>attgacgacgaaatcgccgtcctgctgagcgacatcctgcccaccggccacgaaatcggcgtccagtat<br>gggaatgtccagccgggcgatgcggtggctattgtcggcgcgggccccgtcggcatgtccgtactgttg<br>accgcccagttctactcccctcgaccatcatcgtgatcgacatggacgagaatcgcctccagctcgcca<br>aggagctcggggcaacgcacaccatcaactccggcacggagaacgttgtcgaagccgtgcataggatt<br>gcgcagagggagtcgatgttgcgatcgaggcggtgggcataccggcgacttgggacatctgccagg<br>agatcgtcaagcccggcgcgcacatcgccaacgtcggcgtgcatggcgtcaaggttgacttcgagattc<br>agaagctctggatcaagaacctgacgatcaccacgggactggtgaacacgaacacgacgcccatgctg<br>atgaaggtcgcctcgaccgacaagcttccgttgaagaagatgattacccatcgcttcgagctggccgaga<br>tcgagcacgcctatcaggtattcctcaatggcgccaaggagaaggcgatgaagatcatcctctcgaacg<br>caggcgctgcctga |
| 7 | atggcggcgagctgcattttgctgcacaccggtcaaaagatgccgctgatcggtctgggcacctggaaat<br>ctgacccaggtcaagtgaaggcggcaattaagtatgcgctgagcgtcggttatcgtcacattgactgcgc<br>ggcaatctacggcaatgaaaccgagattggcgaggcgttgaaagaaacgtcggtccgggtaagctgg<br>tcccgcgtgaagaactgtttgtcacgagcaagctgtggaataccaagcaccaccccggaggacgtggaa<br>ccggctctgcgcaaaaccctggccgatctgcagttggagtacttggatctgtatttgatgcactggccgtat<br>gcgtttgaacgcggtgactctccgttcccgaagaacgccgacggcaccatccgttacgacagcactcatt<br>ataaagaaacctggcgtgcgctggaggcgctggttgcaaaaggtctggtcgtgccctgggttttgagca<br>attttaattctcgtcagatcgacgatgttctgagcgtggcctctgtggctccggctgtgttgcaggtcgagtg<br>tcaccttatctggcgcaaaacgagctgatcgctcattgtcaagcgctaatctgaaagtgaccgcgtact<br>ccccgctgggtagcagcgaccgcgcctggcgtgatccggaagaacctgttctgctgaaagaaccggtc<br>gtgctggcgctggctgaaaagcacggtcgcagcccagcgcagatcttgctgcgttggcaagttcagcgc<br>aaagtttcttgcatcccgaaatctgtcacgccgagccgtattctggagaacattcaagttttcgacttcaccttt<br>tagcccggaagaaatgaagcagctggacgccctgaacaagaatctgcgttttattgtgccgatgttgacc<br>gtggacggcaagcgcgttccgcgtgacgcgggtcaccgttgtatccatttaacgatccgtactaatga |
| 8 | atgtgcaccgccggtaaagatattacgtgtaaagcggcggtcgcttgggagccgcataaaccgctgtcc<br>ctggaaacgatcacggttgcacctccaaaagcgcatgaggtgcgtattaaaatcctggcgtctggcatct<br>gcggtagcgacagcagcgttctgaaagagatcatcccgagcaagttcccggtgattctgggtcatgagg<br>cggtgggcgtggttgagagcatcggtgcgggcgttacgtgcgtgaaaccgggtgacaaggtgatcccg<br>ctgttcgtgccgcaatgtggttcttgtcgcgcatgtaaaagcagcaatagcaacttctgtgagaagaatgat<br>atgggcgcgaaaacgggtttgatggcagacatgaccagccgttttacgtgccgtggtaagccgatttata<br>atctggtgggcaccagcacctttacggagtacacggttgtggccgatatcgcggtcgcaaagatcgacc<br>caaaagcccgctggagagctgcctgatcggttgtggttttgcgacgggttatggtgcagcggttaacac<br>ggccaaagttacccctggcagcacctgtgcagtgtttggcctgggcggtgttggtttcagcgctattgttg<br>gttgtaaagcagctggcgcatcccgtattattggcgttggtactcataaggataagttcccgaaagcaatc<br>gaactgggcgcaactgagtgcctgaatccgaaggactatgacaaaccgatctatgaggttatttgcgaga<br>aaaccaatggcggtgtggattacgcggtcgagtgtgcgggtcgtattgaaactatgatgaacgcattgca<br>gtcgacctattgcggttctggcgttactgttgtgttgggtctggcgagcccgaacgagcgtctgccgctgg<br>acccgttgttgctgctgacgggccgttccctgaaaggtagcgtgttggcggctttaaaggtgaagaagtt<br>agccgtctggtggatgactacatgaagaagaagatcaatgttaatttcctggtgagcaccaaactgacgct<br>ggatcagatcaacaaagcgttcgaattgctgagcagcggtcaaggcgttcgtagcattatgatctactaat<br>ga |
| 9 | atgaaaggtttcgctatgttgggtattaataagctgggttggattgagaaagagcgtccggtcgcaggcag<br>ctatgatgcaatcgttcgtccgttggccgttagcccgtgcacgagcgacattcatacggtgttcgagggtg<br>cactgggtgaccgtaagaacatgatcctgggtcatgaggccgttggtgaagttgtcgaagtcggtagcga<br>agtcaaagattttaaaccgggcgaccgtgtcatcgttccatgcacgacgccagattggcgtagcctggag<br>gtgcaggcaggtttccagcagcatagcaatggcatgctgctggctggctggaaattctctaatttcaaggatgg<br>tgtgttcggtgaatatttccacgtgaacgacgctgacatgaacctggctatcctgccgaaggatatgccgc<br>tggagaacgcggtgatgatcacggatatgatgactacgggtttcatggtgcggagctggcggacatcca<br>aatgggtagcagcgtggtcgtcatcggcatcggcgctgtgggtctgatgggcattgcaggcgcaaaact<br>gcgcggtgcgggtcgtatcatcgtgtgggtagccgccctatctcgcgtggaggcggcgaagttttacgg<br>tgcgactgacattctgaactataagaacggtcacattgttgatcaagtgatgaagctgaccaacggtaaag<br>gcgtggatcgcgttatcatggcgggtggtggttcggaaacgctgagccaggcagttagcatggtcaagc<br>cgggtggcattatcagcaatattaattaccacggtagcggtgatgcgctgctgatcccacgtgtcgagtgg<br>ggttgtggtatggcacacaagaccattaaaggcggtctgtgcccgggtggtcgttgcgtgcggaaatgc<br>tgcgtgatatggttgtctataaccgtgttgacctgagcaagctggtgacgcacgtctatcacgcgtttgacc<br>atatcgaagaggcgttgctgctgatgaaggataaaccgaaggacctgattaaagcggtcgtgatcctgta<br>atga |
| 10 | atgaagggcctggcgatgctgggatcggtcgtattggttggattgaaaagaaaatcccggagtgcggc<br>ccactggatgcgttggtccgtcgctggcgctggccccgtgcaccagcgacacccacaccgtgtgggc<br>tggcgcaatcggcgaccgtcacgacatgattctgggtcacgaagcggtcggtcagatcgtgaaggtgg<br>gttccctggtgaagcgtctgaaggttggcgataaggtgatcgtcccggcgattactccggactgggtga<br>agaagaaagccaacgtggttacccgatgcatagcggtggtatgctgggcggctggaagttctccaatttc<br>aaggacggtgtcttttccgaggtgttccacgtgaacgaggcggatgctaacctggcactgctgccgcgtg<br>atattaaacctgaagatgcggtcatgctgagcgacatggtgaccaccggctttcacggtgccgaattggc<br>gaatattaaactgggtgataccgtggcgttattggtatcggccccagtgggtctgatgagcgtggctggtg<br>cgaatcacctgggtgccggtcgcatcttcgcggttggtagccgcaaacactgttgtgatatcgctctggaa<br>tacggcgcgactgatattatcaattacaagaatggcgacattgtggagcaaattttgaaggcgaccgatgg<br>taaaggcgttgacaaggttgttattgcaggtggcgatgttcatacgtttgcacaagcggtcaagatgattaa<br>accgggtagcgatattggtaacgtgaattatctgggtgaaggcgataacattgacattccgcgtagcgaat<br>ggggtgtgggcatgggtcataaacacatccacggtggtttgactcctggcggtcgtgtccgcatggaaaa |

TABLE 4-continued

| SEQ ID NO | POLYNUCLEOTIDE SEQUENCE |
|---|---|
|  | gtttggcttcgctgattagcaccggcaaactggacaccagcaaactgattactcatcgtttcgagggcctgg<br>agaaggtggaagatgccttgatgctgatgaagaacaagccggcagatctgattaagccggttgtccgtat<br>tcactatgacgatgaagatacgttgcactaatga |
| 11 | atgaaagcactggtttaccgtggccctggccaaaagctggtggaagaacgtcaaaagccggagctgaa<br>agagccaggcgacgcgattgtgaaagtcaccaaaacgaccatctgtggtacggacttgcacattctgaa<br>gggcgatgtggcgacgtgtaagccgggtcgcgtgctgggcacgaaggtgtgggtgttattgaaagcgt<br>tggcagcggcgttaccgcgttccaaccgggtgatcgcgtcctgatctcttgtatttctagctgtggcaagtg<br>cagatttgtcgccgtggcatgtttagccactgtaccactggcggctggattctgggtaatgagattgacgg<br>tacgcaggcagagtacgttcgtgtcccgcatgccgacacctctctgtatcgtattccagcgggtgcggac<br>gaagaggcgctggtgatgctgagcgatatcctgccgaccggtttcgagtgtggtgtcctgaatggtaagg<br>ttgcgcctggcagcagcgttgcgatcgttggcgcaggccctgtcggtttggccgcattgctgacggcgc<br>agttctactctccggcagagattatcatgattgatctggacgacaaccgcctgggcctggcgaagcaattc<br>ggcgcaacgctaccgttaatagcaccggtggtaacgcagcagcagaaggtcaaggctctgacggagg<br>gcctgggtgttgacacggctattgaggctgttggcatcccggccaccttcgagctgtgccagaacattgtg<br>gctccgggtggcactattgcgaatgtcggccgttcacggttcgaaagtggatctgcatctggaatctctgtg<br>gagccataatgtgactatcacgacgcgtctggtggacacggcaacgacgccgatgctgctgaaaaccgt<br>gcaatctcataaactggacccgagccgtctgatcacccatcgttttagcctggaccaaatcctggatgcgt<br>acgaaacgtttggtcaggccgcaagcacccaggcgctgaaggttattatcagcatggaggcgtaatga |
| 12 | atgagcaccgcaggtaaagtgattaaatgcaaagcagcagttctgtgggaaccgcataaaccgtttacca<br>ttgaagatattgaagttgcacctccgaaagcacatgaagtgcatttaaaatggttgcaaccggtgtttgtc<br>gttctgatgatcatgcagttagcggtagcctgtttacaccgctgcctgcagttctgggtcatgaaggtgcag<br>gtattgttgaaagcattggtgaaggtgttacctgtgttaaaccgggtgataaagtgattccgctgttttctccg<br>cagtgtggtaaatgtcgcatttgcaaacatccggaaagcaatctgtgttgccagaccaaaaatctgaccca<br>gccgaaaggtgcactgctggatggcaccagccgttttagctgtcgtggtcaaaagcgattcatcattttattag<br>caccagcaccttttagccagtataccgtggttgatgatattgccgtggcaaaaattgatgcagcagcaccgc<br>tggataaagtttgtctgattggtgtggttttagcaccggttatggtagcgcagttcaggttgcaaaagttaca<br>ccgggtagcacctgtgcagttttttggtctgggtggtgttggtctgagcgttgttattggttgtaaaaccgcag<br>gcgcagcaaaaattattgccgtggatattaataaagataatttgccaaagcaaagaactgggtgcaac<br>cgattgtattaatccgcaggattataccaaaccgattcaggaagttctgcaggaaatgaccgatggtggtg<br>tggattttagcttttgaagtgattggtcgtctggataccatgaccagcgcactgctgagctgtcatagcgcat<br>gtggtgttagcgttattgttggtgttcctccgagcgcacagagcctgagcgttaatccgatgagcctgctgc<br>tgggtcgtacctggaaaggtgcaattttttggtggctttaaaagcaaagatgccgttccgaaactggttgca<br>gatttttatggccaaaaaatttccgctggaaccgctgattacccatgttctgccgtttgaaaaaattaatgaag<br>ccttttgatctgctgcgtgcaggtaaaagcattcgtaccgtgctgaccttttaataa |
| 13 | atgcgtgcagttgtgtttgaaaacaaagaacgcgtggccgttaaagaagttaacgcaccgcgtctgcagc<br>atccgctggatgcactggttcgtgttcatctggcaggtatttgtggtagcgatctgcatctgtatcatggtaa<br>aattccggttctgcctggtagcgttctgggtcatgaatttgttggtcaggttgaagcagttggtgaaggtatt<br>caggatctgcagcctggtgattgggttgttggtccgtttcatattgcatgtggccacctgtccgtattgtcgtcg<br>tcatcagtataatctgtgtgaacgtggtggtgtttatggttatggtccgatgtttggtaatctgcagggtgcac<br>aggcagaaaattctcgtgttccgtttagcaatgtgaatctgcgtgaaaaccaatgattggaagtcctctccgaac<br>gtgcaatttttttgccggtgatattctgagcaccgccatggtggtctgattcagggtcagctgcgtcctggtg<br>atagcgttgcagttattggtgcaggtccggttggtctgatggcaattgaagttgcacaggttctgggtgcaa<br>gcaaaattctggccattgatcgtattccggaacgtctggaacgtgcagcaagcctgggtgcaattccgatt<br>aatgccgaacaggaaaatccggttcgtcgcgttcgtagcgaaaccaatgataaggtccggatctggttc<br>tggaagccgttggtggtgcagcaaaccctgagcctggcactggaaatggttcgtcctggtggtcgtgttag<br>cgcagttggtgttgataatgcaccgagctttccgtttccgctggcaagcggtctggttaaagatctgacgttt<br>cgtattggtctggcaaatgtgcatctgtatattgatgcagttctggcactgctggccagcggtcgtctgcag<br>ccggaacgtattgttagccattatctgccgctggaagaagcacctcgcggttacgaactgtttgatcgcaa<br>agaagcactgaaagttctgctggttgtgcgtggttaataa |
| 14 | atgaaagcactggtttatggtggtccgggtcagaaaagcctggaagatcgtccgaaaccggaactgcag<br>gcaccgggtgatgcaattgttcgtattgtgaaaaccaccatttgtggcaccgatctgcatattctgaaaggt<br>gatgttgcaacctgtgcaccgggtcgtattctgggtcatgaaggtgttggtattgttgatagcgtggttgca<br>gcagttaccgcatttcgtccgggtgatcatgttctgattagctgtattagcgcctgtgtaaatgtgattattg<br>ccgtcgtggtatgtatagccattgtacaaccggtggatggattctgggtaatgaaattgatggcacccagg<br>cagaatatgttcgtacaccgcatgcagataccagcctgtatccggttccggcaggcgcagatgaagagg<br>cactggttatgctgagcgatattctgccgaccggttttgaatgtggtgtgctgaatggtaaagttgcaccgg<br>gtggcaccgttgcaattgttggtgcaggtccgattggtctggcagcactgctgaccgcacagttttattctc<br>cggcagaaattattatgattgatctggatgataatcgtctgggtattgcacgtcagtttggtgcaacccagac<br>cattaatagcggtgatggtcgtcagcagaaaccgttaaagcactgaccggtggtcgtggtgttgatacc<br>gcaattgaagcagttggtgttccggcaaccttttgaactgtcgtcaggatctggttggtcctggtggttattg<br>caaatattggtgtgcatggtcgtaaagttgatctgcatctggatcgtctgtggagccagaatattgcaattac<br>cacccgtctggttgataccgttagcaccccgatgctgctgaaaaccgttcagagccgtaaactggacccg<br>agccagctgattacccatcgttttcgcctggatgaaattctggcagcctatgataccttttgcacgtgcagca<br>gatacccaggcactgaaagttattattgcagcctaataa |
| 15 | atgaaagcactggtttatcatggtccgggtcagaaaagcactggaagaacgtccgaaaccgcagattgaa<br>gcaagcggtgatgccattgttaaaattgtgaaaaccaccatttgtggcaccgatctgcatattctgaaaggt<br>gatgttgcaacctgtgcaccgggtcgtattctgggtcatgaaggtgtgggtattattgatagcgttggtgcc<br>ggttaccgcatttcagccggtgatcgtgttctgattagctgtattagcagctgtgcaaatgtgattattgt<br>cgtcgtggtctgtatagccattgtacaaccggtggttggattctgggtaatgaaattgatggcacccagc<br>agaatatgttcgtacaccgcatgcagataccagcctgtatcgtattccggcaggcgcagatgaagaggca<br>ctggttatgctgagcgatattctgccgaccggttttgaatgtggtgtgctgaatggtaaagttgaaccggt<br>agcaccgttgcaattgttggtgcaggtccgattggtctggcagcactgctgaccgcacagttttatgcacc |

TABLE 4-continued

| SEQ ID NO | POLYNUCLEOTIDE SEQUENCE |
|---|---|
| | gggtgatattattatgattgatctggatgataatcgtctggatgttgcacgtcgttttggtgcaacccatacca ttaatagcggtgatggtaaagcagcagaagcagttaaagcactgaccggtggtattggtgttgataccgc aattgaagccgttggtattccggcaaccttctgctgtgtgaagatattgttgcaccgggtggtgttattgca aatgttggtgtgcatggtgttaaagttgatctgcatctggaacgtctgtgggcacataatattaccattacca cccgtctggttgataccgttaccaccccgatgctgctgaaaaccgttcagagcaaaaaactggacccgct gcagctgattacccatcgttttaccctggatcatattctggatgcctatgataccttagccgtgcagcagat accaaagccctgaaagttattgtgagcgcctaataa |
| 16 | atggaaaatattatgaaagcaatggtgtattatggcgatcatgatattcgttttgaagaacgcaaaaaaccg gaactgattgatccgaccgatgccattattaaaatgaccaaaaccaccatttgtggcaccgatctgggtatt tataaaggcaaaaatccggaaattgaacagaaagaacaggaaaaaaacggcagctttaatggtcgtattc tgggtcatgaaggtattggtattgtggagcagattggtagcagcgtgaaaaacattaaagtgggcgataa agttattgttagctgcgttagccgttgtggcacctgtgaaaattgtgccaaacagctgtatagccattgtcgt aatgatggtggttggattatggcgtatatgattgatggcaccaggcagatatgttcgtaccccgtttgca gataccagcctgtatgttctgccggaaggtctgaatgaagatgttgcagttctgctgtctgatgcactgccg accgcacatgaaattggtgttcagaatggcgatattaaaccgggtgatacccgttgcaattgttggtgcaggt ccggttggtatgagcgcactgctgaccgctcagttttatagcccgagccagattattatgattgatatggat gaaaatcgtctggcaatggcaaaagaactgggtgcaaccgataccattaatagcggcaccgaagatgca attgcacgtgttatggaactgaccaatcagcgtggtgttgattgtgcaattgaagccgttggtattgaaccg acctgggatatttgtcagaatattgtgaaagaaggtggtcatctggcaaatgttggtgttcatggcaaaagc gtgaattttagcctggaaaaactgtggattaaaaatctgaccattaccaccggtctggttaatgcaaatacc accggtatgctgctgaaaagctgttgtagcggtaaactgccgatgaaaaactggcaacccatcatttttaa atttaatgaaattgaaaaggccatgatgtgtgtttattaatgcagccaaagaaaaagccatgaaagtgattatt gattttaataa |
| 17 | atgaaagcactgacctatctgggtccgggtaaaaaagaagtgatggaaaaaccgaaaccgaaaattgaa aaagaaaccgatgccattgtgaaaattaccaaaaccaccatttgtggcaccgatctgcatattctgagcgg tgatgttccgaccgttgaagaaggtcgtattctgggtcatgaaggtgtgggtattattgaagaagttggctct ggcgttaaaaattttaaaaaaggcgatcgcgttctgattagctgtattaccagctgtggcaaatgcgaaaat tgcaaaaaaggcctgtatgcccattgtgaagatggtggttggattctgggccatctgattgatggcaccca ggcagaatatgttcgtattccgcatgcagataatagcctgtatccgattccggaaggtgttgatgaagagg cactggttatgctgagcgatattctgccgaccggttttgaaattggtgtgctgaatgtaaagttcagcctgg tcagaccgttgcaattattggtgcaggtccggttggtatggcagcactgctgaccgcacagttttattctcc ggcagaaattattatggtggatctggatgataatcgtctggaagtggccaaaaatttggtgcaacccagg ttgttaatagcgcagatgataaagccgtggaaaaaattatggaactgaccggtggcaaaggtggtgtt gcaatggaagcagttggtattccggtgacctttgatatttgccaggaaattgttaaacctggcggttatattg caaatattggcgtgcatggtaaaagcgtggaatttcatattgaaaaactgtggattcgcaacattaccctga ccaccggtctggttaataccacctctacccgatgctgctgaaaaccgttcagagcaaaaaactgaaacc ggaacagctgattacccatcgttttgccttgccgatattatgaaagcctatgaagtgtttggtaatgcagcc aaagaaaaagccctgaaagtgattattagcaatgattaataa |
| 18 | atgagctatccggaaaaatttcagggtattggcattaccaatcgcgaagattggaaacatccgaaaaaagt gaccttgaaccgaaacagtttaatgataaagatgtggatattaaaattgaagcctgcggtgttttgttct gatgttcattgtgcagcaagccattggggtccggttgcagaaaaacaggttgtgggccatgaaattattgg tcgtgtgctgaaagttggtccgaaatgtaccaccggtattaaagttggtgatcgtgttggtgttggtgcaca ggcatggtcttgtctggaatgtagccgttgcaaaagcgataatgaaagctattgtccgaaaagcgtttgga cctatagcattccgtatattgatggttatgttagccagggtggttatgcaaacgcatattcgcctgcatgaacat tttgcaattccgattccggataaactgagcaatgaactggcagcaccgctgctgtgtggtggtattaccgttt attctccgctgctgcgtaatggttgtggtccgggtaaaaaagttggtattgtgggcattggtggtattggtca catgggtctgctgtttgcaaaaggtatgggtgccgaagtttatgcatttagccgcacccatagcaaagagg cagacgccaaaaaactgggtgccgatcattttattgcaacctggaagataaagattggaccaccaaatat tttgataccctggatctgctggttattgtgcaagcagcctgaccgatattaattttgatgaactgaccaaaatt atgaaagtgaataccaaattattagcattagcgcaccggcagcagataagttctgaccctgaaaccgtt tggtctgattggtgtgaccattggtaatagcgcaattggtagccgtcgtgaaattgaacatctgctgaatttt gtggccgaaaagatattaaaccgtgggttgaaaccctgccggttggtgaagccggtgttaatgaagcat tgaacgcatggataaaggtgatgtgaaatatcgttttaccctggtggattttgataaagaatttggcaattaa taa |
| 19 | atgagcgaagaaaccttaccgcatgggcatgtaaaagcaaaagcgcaccgctggaaccgatggaaat gaccttttgccattgggatgatgatatggttcagatggatgttgatttgttggtgtttggtgccaccgatctgca taccgttgatgaaggttgggctccgaccgaatttccgtgtgttgtgggccatgaaattattggcaatgtgac caaagtgggtaaaaatgtgaccgtattaaagttggtgatcgttgtgtgttggttgtcagagcgcaagctg tggtaaatgcgattttttgcaaaaaaggcatggaaaatctgtgtagcacccatgcagtttggacctttaatgat cgctatgataatgccaccaaagataaaaaccatggtggctttgcaaaaaaatggcgtgcatcaggattt tgttgttcatgtgccgatggattttctccggaagttgcagcaagcttctgtggtggtggttaccacctatgc accgctgaaacgttatggtgttggtaaaggtagcaaagttgcagttctgggtctgggtggtctgggccatttt tggtgttcagtgggcaaaagcaatgggtgcagaagttgttgcctttgacgtgattccggataaagtggatg atgccaaaaaactgggcgtgatgattatgtctgatgcagaaagaagagcagatggaaccgcattataat accttacccatattctggccaccaaattgtgaataaatgctggatcagtattttaaaatgctgaaaaataa tggcatttttatgctgtgcgatattccggaagttccgctgagcggtatgagcgcatttgttatggcaggtaaa cagctgaccattgcaggcacctttattggtagcccgagcgttattcaggaatgtctggattttgcagccaag cataatgttcgtacctgggttaataccttccgatggaaaaaattaatgaagcctttgaatttgttcgtcaggc aaaaccgcgttatcgtgccgttgtgatgaattaataa |
| 20 | atgtttaccgttaatgcacgtagcaccagcgcaccgggtgcaccgtttgaagcagttgttattgaacgtcgt gatccgggtccgggtgatgttgttattgatattgcctttagcggtatttgtcataccgatgttagccgtgcacg tagcgaatttggcaccacccattatccgctggttccgggtcatgaaattgccggtgttgttagcaaagttgg |

TABLE 4-continued

| SEQ ID NO | POLYNUCLEOTIDE SEQUENCE |
|---|---|
| | ttccgatgttaccaaatttgcagttggtgatcgtgttggtgttggttgtattgttgatagctgccgtgaatgtga<br>ttattgtcgtgcaggtctggaaccgtattgtcgtaaagatcatgtgcgcacctataatagcatgggtcgtgat<br>ggtcgtattaccctgggtggttatagcgaaaaaattgtggtggataaggttatgttctgcgtattccggatg<br>caattccgctggatcaggcagcaccgctgctgtgtgcaggtattaccatgtattctccgctgcgtcattgga<br>aagcaggtccgggtagccgtattgcaattgttggttttggtggtctgggtcatgttggtgttgcaattgcacg<br>tgcactgggtgcacataccaccgttttgatctgacgatggataaacatgatgatgcaattcgtctgggtgc<br>agatgattatcgtctgagcaccgatgcaggcattttaaagaatttgaaggtgcctttgaactgattgttagc<br>accgttccggcaaatctggattatgacctgtttctgaaaatgctggcactggatggcacctttgttcagctgg<br>gtgttccgcataatccggttagcctggatgtttttagcctgttttataatcgtcgtagcctggcaggcaccctg<br>gttggtggtattggtgaaacccaggaaatgctggattttgcgcagaacatagcattgttgccgaaattgaa<br>accgttggtgccgatgaaattgatagcgcctatgatcgtgttgcagccggtgatgttcgttatcgtatggttc<br>tggatgttggcaccctggcaacccagcgttaataa |

TABLE 5

| SEQ ID NO | POLYPEPTIDE SEQUENCE |
|---|---|
| 21 | MSTAGKVIKCKAAVLWEEKKPFSIEEVEVAPPKAHEVRIKMVATG<br>ICRSDDHVVSGTLVTPLPVIAGHEAAGIVESIGEGVTTVRPGDKVIP<br>LFTPQCGKCRVCKHPEGNFCLKNDLSMPRGTMQDGTSRFTCRGK<br>PIHHFLGTSTFSQYTVVDEISVAKIDAASPLEKVCLIGCGFSTGYGS<br>AVKVAKVTQGSTCAVFGLGGVGLSVIMGCKAAGAARIIGVDINK<br>DKFAKAKEVGATECVNPQDYKKPIQEVLTEMSNGGVDFSFEVIGR<br>LDTMVTALSCCQEAYGVSVIVGVPPDSQNLSMNPMLLLSGRTWK<br>GAIFGGFKSKDSVPKLVADFMAKKFALDPLITHVLPFEKINEGFDL<br>LRSGESIRTILTF |
| 22 | MSYPEKFEGIAIQSHEDWKNPKKTKYDPKPFYDHDIDIKIEACGVC<br>GSDIHCAAGHWGNMKMPLVVGHEIVGKVVKLGPKSNSGLKVGQ<br>RVGVGAQVFSCLECDRCKNDNEPYCTKFVTTYSQPYEDGYVSQG<br>GYANYVRVHEHFVVPIPENIPSHLAAPLLCGGLTVYSPLVRNGCGP<br>GKKVGIVGLGGIGSMGTLISKAMGAETYVISRSSRKREDAMKMG<br>ADHYIATLEEGDWGEKYFDTFDLIVVCASSLTDIDFNIMPKAMKV<br>GGRIVSISIPEQHEMLSLKPYGLKAVSISYSALGSIKELNQLLKLVSE<br>KDIKIWVETLPVGEAGVHEAFERMEKGDVRYRFTLVGYDKEFSD |
| 23 | MLYPEKFQGIGISNAKDWKHPKLVSFDPKPFGDHDVDVEIEACGI<br>CGSDPHIAVGNWGPVPENQILGHEIIGRVVKVGSKCHTGVKIGDR<br>VGVGAQALACFECERCKSDNEQYCTNDHVLTMWTPYKDGYISQ<br>GGFASHVRLHEHFAIQIPENIPSPLAAPLLCGGITVFSPLLRNGCGP<br>GKRVGIVGIGGIGHMGILLAKAMGAEVYAFSRGHSKREDSMKLG<br>ADHYIAMLEDKGWTEQYSNALDLLVVCSSSLSKVNFDSIVKIMKI<br>GGSIVSIAAPEVNEKLVLKPLGLMGVSISSSAIGSRKEIEQLLKLVSE<br>KNVKIWVEKLPISEEGVSHAFTRMESGDVKYRFTLVDYDKKFHK |
| 24 | MLSFDYSIPTKVFFGKGKIDVIGEEIKKYGSRVLIVYGGGSIKRNGI<br>YDRATAILKENNIAFYELSGVEPNPRITTVKKGIEICRENNVDLVLA<br>IGGGSAIDCSKVIAAGVYYDGDTWDMVKDPSKITKVLPIASILTLS<br>ATGSEMDQIAVISNMETNEKLGVGHDDMRPKFSVLDPTYTFTVPK<br>NQTAAGTADIMSHTFESYFSGVEGAYVQDGIREAILRTCIKYGKIA<br>MEKTDDYEARANLMWASSLAINGLLSLGKDRKWSCHPMEHELS<br>AYYDITHGVGLAILTPNWMEYILNDDTLHKFVSYGINVWGIDKNK<br>DNYEIAREAIKNTREYFNSLGIPSKLREVGIGKDKLELMAKQAVRN<br>SGGTIGSLRPINAEDVLEIFKKSY |
| 25 | MVDFEYSIPTRIFFGKDKINVLGRELKKYGSKVLIVYGGGSIKRNGI<br>YDKAVSILEKNSIKFYELAGVEPNPRVTTVEKGVKICRENGVEVVL<br>AIGGGSAIDCAKVIAAACEYDGNPWDIVLDGSKIKRVLPIASILTIA<br>ATGSEMDTWAVINNMDTNEKLIAAHPDMAPKFSILDPTYTYTVPT<br>NQTAAGTADIMSHIFEVYFSNTKTAYLQDRMAEALLRTCIKYGGI<br>ALEKPDDYEARANLMWASSLAINGLLTYGKDTNWSVHLMEHELS<br>AYYDITHGVGLAILTPNWMEYILNNDTVYKFVEYGVNVWGIDKE<br>KNHYDIAHQAIQKTRDYFVNVLGLPSRLRDVGIEEEKLDIMAKES<br>VKLTGGTIGNLRPVNASEVLQIFKKSV |
| 26 | MKALVYHGDHKISLEDKPKPTLQKPTDVVVRVLKTTICGTDLGIY<br>KGKNPEVADGRILGHEGVGVIEEVGESVTQFKKGDKVLISCVTSC<br>GSCDYCKKQLYSHCRDGGWILGYMIDGVQAEYVRIPHADNSLYK<br>IPQTIDDEIAVLLSDILPTGHEIGVQYGNVQPGDAVAIVGAPVGM<br>SVLLTAQFYSPSTIIVIDMDENRLQLAKELGATHTINSGTENVVEA<br>VHRIAAEGVDVAIEAVGIPATWDICQEIVKPGAHIANVGVHGVKV<br>DFEIQKLWIKNLTITTGLVNTNTTPMLMKVASTDKLPLKKMITHRF<br>ELAEIEHAYQVFLNGAKEKAMKIILSNAGAA |

TABLE 5-continued

| SEQ ID NO | POLYPEPTIDE SEQUENCE |
|---|---|
| 27 | MAASCILLHTGQKMPLIGLGTWKSDPGQVKAAIKYALSVGYRHID
CAAIYGNETEIGEALKENVGPGKLVPREELFVTSKLWNTKHHPED
VEPALRKTLADLQLEYLDLYLMHWPYAFERGDSPFPKNADGTIRY
DSTHYKETWRALEALVAKGLVRALGLSNFNSRQIDDVLSVASVRP
AVLQVECHPYLAQNELIAHCQARNLEVTAYSPLGSSDRAWRDPEE
PVLLKEPVVLALAEKHGRSPAQILLRWQVQRKVSCIPKSVTPSRIL
ENIQVFDFTFSPEEMKQLDALNKNLRFIV
PMLTVDGKRVPRDAGHPLYPFNDPY |
| 28 | MCTAGKDITCKAAVAWEPHKPLSLETITVAPPKAHEVRIKILASGI
CGSDSSVLKEIIPSKFPVILGHEAVGVVESIGAGVTCVKPGDKVIPL
FVPQCGSCRACKSSNSNFCEKNDMGAKTGLMADMTSRFTCRGKP
IYNLVGTSTFTEYTVVADIAVAKIDPKAPLESCLIGCGFATGYGAA
VNTAKVTPGSTCAVFGLGGVGFSAIVGCKAAGASRIIGVGTHKDK
FPKAIELGATECLNPKDYDKPIYEVICEKTNGGVDYAVECAGRIET
MMNALQSTYCGSGVTVVLGLASPNERLPLDPLLLLTGRSLKGSVF
GGFKGEEVSRLVDDYMKKKINVNFLVSTKLTLDQINKAFELLSSG
QGVRSIMIY |
| 29 | MKGFAMLGINKLGWIEKERPVAGSYDAIVRPLAVSPCTSDIHTVFE
GALGDRKNMILGHEAVGEVVEVGSEVKDFKPGDRVIVPCTTPDW
RSLEVQAGFQQHSNGMLAGWKFSNFKDGVFGEYFHVNDADMNL
AILPKDMPLENAVMITDMMTTGFHGAELADIQMGSSVVVIGIGAV
GLMGIAGAKLRGAGRIIGVGSRPICVEAAKFYGATDILNYKNGHIV
DQVMKLTNGKGVDRVIMAGGGSETLSQAVSMVKPGGIISNINYH
GSGDALLIPRVEWGCGMAHKTIKGGLCPGGRLRAEMLRDMVVY
NRVDLSKLVTHVYHGFDHIEEALLLMKDKPKDLIKAVVIL |
| 30 | MKGLAMLGIGRIGWIEKKIPECGPLDALVRPLALAPCTSDTHTVW
AGAIGDRHDMILGHEAVGQIVKVGSLVKRLKVGDKVIVPAITPDW
GEEESQRGYPMHSGGMLGGWKFSNFKDGVFSEVFHVNEADANL
ALLPRDIKPEDAVMLSDMVTTGFHGAELANIKLGDTVCVIGIGPV
GLMSVAGANHLGAGRIFAVGSRKHCCDIALEYGATDIINYKNGDI
VEQILKATDGKGVDKVVIAGGDVHTFAQAVKMIKPGSDIGNVNY
LGEGDNIDIPRSEWGVGMGHKHIHGGLTPGGRVRMEKLASLISTG
KLDTSKLITHRFEGLEKVEDALMLMKNKPADLIKPVVRIHYDDED
TLH |
| 31 | MKALVYRGPGQKLVEERQKPELKEPGDAIVKVTKTTICGTDLHIL
KGDVATCKPGRVLGHEGVGVIESVGSGVTAFQPGDRVLISCISSCG
KCSFCRRGMFSHCTTGGWILGNEIDGTQAEYVRVPHADTSLYRIP
AGADEEALVMLSDILPTGFECGVLNGKVAPGSSVAIVGAGPVGLA
ALLTAQFYSPAEIIMIDLDDNRLGLAKQFGATRTVNSTGGNAAAE
VKALTEGLGVDTAIEAVGIPATFELCQNIVAPGGTIANVGVHGSKV
DLHLESLWSHNVTITTRLVDTATTPMLLKTVQSHKLDPSRLITHRF
SLDQILDAYETFGQAASTQALKVIISMEA |
| 32 | MSTAGKVIKCKAAVLWEPHKPFTIEDIEVAPPKAHEVRIKMVATG
VCRSDDHAVSGSLFTPLPAVLGHEGAGIVESIGEGVTCVKPGDKVI
PLFSPQCGKCRICKHPESNLCCQTKNLTQPKGALLDGTSRFSCRGK
PIHHFISTSTFSQYTVVDDIAVAKIDAAAPLDKVCLIGCGFSTGYGS
AVQVAKVTPGSTCAVFGLGGVGLSVVIGCKTAGAAKIIAVDINKD
KPFAKAKELGATDCINPQDYTKPIQEVLQEMTDGGVDFSFEVIGRL
DTMTSALLSCHSACGVSVIVGVPPSAQSLSVNPMSLLLGRTWKGA
IFGGFKSKDAVPKLVADFMAKKFPLEPLITHVLPFEKINEAFDLLR
AGKSIRTVLTF |
| 33 | MRAVVFENKERVAVKEVNAPRLQHPLDALVRVHLAGICGSDLHL
YHGKIPVLPGSVLGHEFVGQVEAVGEGIQDLQPGDWVVGPFHIAC
GTCPYCRRHQYNLCERGGVYGYGPMFGNLQGAQAEILRVPFSNV
NLRKLPPNLSPERAIFAGDILSTAYGGLIQGQLRPGDSVAVIGAGPV
GLMAIEVAQVLGASKILAIDRIPERLERAASLGAIPINAEQENPVRR
VRSETNDEGPDLVLEAVGGAATLSLALEMVRPGGRVSAVGVDNA
PSFPFPLASGLVKDLTFRIGLANVHLYIDAVLALLASGRLQPERIVS
HYLPLEEAPRGYELFDRKEALKVLLVVRG |
| 34 | MKALVYGGPGQKSLEDRPKPELQAPGDAIVRIVKTTICGTDLHILK
GDVATCAPGRILGHEGVGIVDSVGAAVTAFRPGDHVLISCISACGK
CDYCRRGMYSHCTTGGWILGNEIDGTQAEYVRTPHADTSLYPVP
AGADEEALVMLSDILPTGFECGVLNGKVAPGGTVAIVGAGPIGLA
ALLTAQFYSPAEIIMIDLDDNRLGIARQFGATQTINSGDGRAAETV
KALTGGRGVDTAIEAVGVPATFELCQDLVGPGGVIANIGVHGRKV
DLHLDRLWSQNIAITTRLVDTVSTPMLLKTVQSRKLDPSQLITHRF
RLDEILAAYDTFARAADTQALKVIIAA |

TABLE 5-continued

| SEQ ID NO | POLYPEPTIDE SEQUENCE |
|---|---|
| 35 | MKALVYHGPGQKALEERPKPQIEASGDAIVKIVKTTICGTDLHILK GDVATCAPGRILGHEGVGIIDSVGAGVTAFQPGDRVLISCISSCGK CDYCRRGLYSHCTTGGWILGNEIDGTQAEYVRTPHADTSLYRIPA GADEEALVMLSDILPTGFECGVLNGKVEPGSTVAIVGAGPIGLAAL LTAQFYAPGDIIMIDLDDNRLDVARRFGATHTINSGDGKAAEAVK ALTGGIGVDTAIEAVGIPATFLLCEDIVAPGGVIANVGVHGVKVDL HLERLWAHNITITTRLVDTVTTPMLLKTVQSKKLDPLQLITHRFTL DHILDAYDTFSRAADTKALKVIVSA |
| 36 | MENIMKAMVYYGDHDIRFEERKKPELIDPTDAIIKMTKTTICGTDL GIYKGKNPEIEQKEQEKNGSFNGRILGHEGIGIVEQIGSSVKNIKVG DKVIVSCVSRCGTCENCAKQLYSHCRNDGGWIMGYMIDGTQAEY VRTPFADTSLYVLPEGLNEDVAVLLSDALPTAHEIGVQNGDIKPG DTVAIVGAGPVGMSALLTAQFYSPSQIIMIDMDENRLAMAKELGA TDTINSGTEDAIARVMELTNQRGVDCAIEAVGIEPTWDICQNIVKE GGHLANVGVHGKSVNFSLEKLWIKNLTITTGLVNANTTGMLLKS CCSGKLPMEKLATHHFKFNEIEKAYDVFINAAKEKAMKVIIDF |
| 37 | MKALTYLGPGKKEVMEKPKPKIEKETDAIVKITKTTICGTDLHILS GDVPTVEEGRILGHEGVGIIEEVGSGVKNFKKGDRVLISCITSCGK CENCKKGLYAHCEDGGWILGHLIDGTQAEYVRIPHADNSLYPIPE GVDEEALVMLSDILPTGFEIGVLNGKVQPGQTVAIIGAGPVGMAA LLTAQFYSPAEIIMVDLDDNRLEVAKKFGATQVVNSADGKAVEKI MELTGGKGVDVAMEAVGIPVTFDICQEIVKPGGYIANIGVHGKSV EFHIEKLWIRNITLTTGLVNTTSTPMLLKTVQSKKLKPEQLITHRFA FADIMKAYEVFGNAAKEKALKVIISND |
| 38 | MSYPEKFQGIGITNREDWKHPKKVTFEPKQFNDKDVDIKIEACGV CGSDVHCAASHWGPVAEKQVVGHEIIGRVLKVGPKCTTGIKVGD RVGVGAQAWSCLECSRCKSDNESYCPKSVWTYSIPYIDGYVSQG GYASHIRLHEHFAIPIPDKLSNELAAPLLCGGITVYSPLLRNGCGPG KKVGIVGIGGIGHMGLLFAKGMGAEVYAFSRTHSKEADAKKLGA DHFIATLEDKDWTTKYFDTLDLLVICASSLTDINFDELTKIMKVNT KIISISAPAADEVLTLKPFGLIGVTIGNSAIGSRREIEHLLNFVAEKDI KPWVETLPVGEAGVNEAFERMDKGDVKYRFTLVDFDKEFGN |
| 39 | MSEETFTAWACKSKSAPLEPMEMTFCHWDDDMVQMDVICCGVC GTDLHTVDEGWGPTEFPCVVGHEIIGNVTKVGKNVTRIKVGDRCG VGCQSASCGKCDFCKKGMENLCSTHAVWTFNDRYDNATKDKTY GGFAKKWRGNQDFVVHVPMDFSPEVAASFLCGGVTTYAPLKRY GVGKGSKVAVLGLGGLGHFGVQWAKAMGAEVVAFDVIPDKVD DAKKLGCDDYVLMQKEEQMEPHYNTFTHILATKIVNKCWDQYF KMLKNNGIFMLCDIPEVPLSGMSAFVMAGKQLTIAGTFIGSPSVIQ ECLDFAAKHNVRTWVNTFPMEKINEAFEFVRQAKPRYRAVVMN |
| 40 | MFTVNARSTSAPGAPFEAVVIERRDPGPGDVVIDIAFSGICHTDVS RARSEFGTTHYPLVPGHEIAGVVSKVGSDVTKFAVGDRVGVGCIV DSCRECDYCRAGLEPYCRKDHVRTYNSMGRDGRITLGGYSEKIV VDEGYVLRIPDAIPLDQAAPLLCAGITMYSPLRHWKAGPGSRIAIV GFGGLGHVGVAIARALGAHTTVFDLTMDKHDDAIRLGADDYRLS TDAGIFKEFEGAFELIVSTVPANLDYDLFLKMLALDGTFVQLGVPH NPVSLDVFSLFYNRRSLAGTLVGGIGETQEMLDFCAEHSIVAEIET VGADEIDSAYDRVAAGDVRYRMVLDVGTLATQR |

In one embodiment, the method for screening candidate polypeptides having alcohol dehydrogenase activity comprises:

(a) measuring the rate of cofactor oxidation by a lower alkyl aldehyde for the candidate polypeptides in the presence or absence of a lower alkyl alcohol; and (b) selecting only those candidate polypeptides that oxidize a cofactor faster relative to a control polypeptide in the presence or absence of a lower alkyl alcohol. In one embodiment, (b) comprises selecting only those candidate polypeptides that oxidize a cofactor faster relative to a control polypeptide in both the presence and absence of a lower alkyl alcohol. In one embodiment, the cofactor is NADH. In another embodiment, the cofactor is NADPH. In yet another embodiment, the control polypeptide is HLADH having the amino acid sequence of SEQ ID NO: 21. In yet another embodiment, the control polypeptide is *Achromobacter xylosoxidans* SadB having the amino acid sequence of SEQ ID NO: 26. In another embodiment, step (a) comprises monitoring a change in A340 nm.

In another embodiment, the method for screening candidate polypeptides having alcohol dehydrogenase activity comprises:

(a) measuring one or more of the following values for the candidate polypeptides:
   (i) the $K_M$ value for a lower alkyl aldehyde;
   (ii) the $K_I$ value for a lower alkyl alcohol; and
   (iii) $k_{cat}/K_M$; and (b) selecting only those candidate polypeptides having one or more of the following characteristics:
   (i) the $K_M$ value for a lower alkyl aldehyde is lower relative to a control polypeptide;
   (ii) the $K_I$ value for a lower alkyl alcohol is higher relative to a control polypeptide; and (iii) the $k_{cat}/K_M$ value for a lower alkyl aldehyde is higher relative to a control polypeptide.

In yet another embodiment, the control polypeptide is *Achromobacter xylosoxidans* SadB having the amino acid sequence of SEQ ID NO: 26. In another embodiment, the selected candidate polypeptides have two or more of the above characteristics. In another embodiment, the selected candidate polypeptides have three or more of the above characteristics. In another embodiment, the selected candidate polypeptides preferentially use NADH as a cofactor.

In one embodiment of the invention, polynucleotide sequences suitable for use in the screening methods of the invention comprise nucleotide sequences that are at least about 80%, 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO 14, SEQ ID NO: 15, SEQ ID NO: 16, SEQ ID NO: 17, SEQ ID NO: 18, SEQ ID NO: 19, and SEQ ID NO: 20. In another embodiment of the invention, a polynucleotide sequence suitable for use in the screening methods of the invention can be selected from the group consisting of: SEQ ID NO: 1, SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO 14, SEQ ID NO: 15, SEQ ID NO: 16, SEQ ID NO: 17, SEQ ID NO: 18, SEQ ID NO: 19, and SEQ ID NO: 20 or an active variant, fragment or derivative thereof. In one embodiment, polynucleotides have been codon-optimized for expression in a specific host cell.

In one embodiment of the invention, candidate polypeptides suitable for use in the screening methods of the invention have amino acid sequences that are at least about 80%, 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO 34, SEQ ID NO: 35, SEQ ID NO: 36, SEQ ID NO: 37, SEQ ID NO: 38, SEQ ID NO: 39, and SEQ ID NO: 40. In another embodiment of the invention, a candidate polypeptide suitable for use in the screening methods of the invention has an amino acid sequence selected from the group consisting of: SEQ ID NO: 21, SEQ ID NO: 22, SEQ ID NO: 23, SEQ ID NO: 24, SEQ ID NO: 25, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO 34, SEQ ID NO: 35, SEQ ID NO: 36, SEQ ID NO: 37, SEQ ID NO: 38, SEQ ID NO: 39, and SEQ ID NO: 40, or an active variant, fragment or derivative thereof. In one embodiment, candidate polypeptides suitable for use in the screening methods of the invention have been codon-optimized for expression in a specific host cell.

In one embodiment of the invention, the polynucleotide sequence suitable for use in the screening methods of the invention has a nucleotide sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 2. In another embodiment, the polynucleotide comprises the nucleotide sequence of SEQ ID NO: 2 or an active variant, fragment or derivative thereof.

In one embodiment of the invention, candidate polypeptides for use in the screening methods comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 22. In another embodiment, the candidate polypeptide comprises the amino acid sequence of SEQ ID NO: 22 or an active variant, fragment or derivative thereof.

In one embodiment of the invention, the polynucleotide sequence suitable for use in the screening methods has a nucleotide sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 3. In another embodiment, the polynucleotide comprises the nucleotide sequence of SEQ ID NO: 3 or an active variant, fragment or derivative thereof.

In one embodiment of the invention, candidate polypeptides for use in the screening methods comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 23. In another embodiment, the candidate polypeptide comprises the amino acid sequence of SEQ ID NO: 23 or an active variant, fragment or derivative thereof.

In one embodiment of the invention, the polynucleotide sequence for use in the screening methods has a nucleotide sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 11. In another embodiment, the polynucleotide comprises the nucleotide sequence of SEQ ID NO: 11 or an active variant, fragment or derivative thereof.

In one embodiment of the invention, candidate polypeptides for use in the screening methods comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 31. In another embodiment, the candidate polypeptide comprises the amino acid sequence of SEQ ID NO: 31 or an active variant, fragment or derivative thereof.

In one embodiment of the invention, the polynucleotide sequence for use in the screening methods has a nucleotide sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 9. In another embodiment, the polynucleotide comprises the nucleotide sequence of SEQ ID NO: 9 or an active variant, fragment or derivative thereof.

In one embodiment of the invention, candidate polypeptides for use in the screening methods comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 29. In another embodiment, the candidate polypeptide comprises the amino acid sequence of SEQ ID NO: 29 or an active variant, fragment or derivative thereof.

In another embodiment, the method for screening candidate polypeptides results in selected candidate polypeptides being able to catalyze the conversion of an aldehyde to an alcohol at a temperature up to about 70° C. In another embodiment, the screening method results in selected candidate polypeptides being able to catalyze the conversion of an aldehyde to an alcohol at a temperature of about 10° C., 15° C., 20° C., 25° C., 30° C., 35° C., 40° C., 45° C., 50° C., 55° C., 60° C., 65° C., or 70° C. In another embodiment, the screening method results in selected candidate polypeptides being able to catalyze the conversion of an aldehyde to an alcohol at a temperature of about 30° C.

In another embodiment, the method for screening candidate polypeptides results in selected candidate polypeptides being able to catalyze the conversion of an aldehyde to an alcohol at a pH from about 4 to about 9. In another embodiment, the screening method results in selected candidate polypeptides being able to catalyze the conversion of an aldehyde to an alcohol at pH from about 5 to about 8. In another embodiment, the screening method results in selected candidate polypeptides being able to catalyze the conversion of an aldehyde to an alcohol at a pH from about 6 to about 7. In another embodiment, the screening method results in selected candidate polypeptides being able to catalyze the conversion of an aldehyde to an alcohol at a pH from about 6.5 to about 7. In another embodiment, the screening method results in selected candidate polypeptides being able to catalyze the conversion of an aldehyde to an alcohol at a pH of about 4, 4.5, 5, 5.5, 6, 6.5, 7, 7.5, 8, 8.5, or 9. In another embodiment, the screening method results in selected candidate polypeptides being able to catalyze the conversion of an aldehyde to an alcohol at a pH of about 7.

In another embodiment, the method for screening candidate polypeptides results in selected candidate polypeptides that can catalyze the conversion of an aldehyde to an alcohol in the presence of a lower alkyl alcohol at a concentration up to about 50 g/L. In another embodiment, the screening method results in selected candidate polypeptides being able to catalyze the conversion of an aldehyde to an alcohol at a concentration of about 10 g/L, 15 g/L, 20 g/L, 25 g/L, 30 g/L, 35 g/L, 40 g/L, 45 g/L, or 50 g/L. In another embodiment, the screening method results in selected candidate polypeptides being able to catalyze the conversion of an aldehyde to an alcohol at a concentration of at least about 20 g/L.

Non-limiting examples of lower alkyl alcohols that can be used in the screening methods of the invention include butanol, isobutanol, propanol, isopropanol, and ethanol. In one embodiment, the lower alkyl alcohol used in the screening method is isobutanol.

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes.

EXAMPLES

The present invention is further defined in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook et al. (Sambrook, J., Fritsch, E. F. and Maniatis, T. (Molecular Cloning: A Laboratory Manual; Cold Spring Harbor Laboratory Press, Cold Spring Harbor, 1989, here in referred to as Maniatis) and by Ausubel et al. (Ausubel et al., Current Protocols in Molecular Biology, pub. by Greene Publishing Assoc. and Wiley-Interscience, 1987).

Materials and methods suitable for the maintenance and growth of bacterial cultures are well known in the art. Techniques suitable for use in the following examples may be found as set out in Manual of Methods for General Bacteriology (Phillipp et al., eds., American Society for Microbiology, Washington, D.C., 1994) or by Thomas D. Brock in (Brock, Biotechnology: A Textbook of Industrial Microbiology, Second Edition, Sinauer Associates, Inc., Sunderland, Mass. (1989). All reagents, restriction enzymes and materials used for the growth and maintenance of bacterial cells were obtained from Sigma-Aldrich Chemicals (St. Louis, Mo.), BD Diagnostic Systems (Sparks, Md.), Invitrogen (Carlsbad, Calif.), HiMedia (Mumbai, India), SD Fine chemicals (India), or Takara Bio Inc. (Shiga, Japan), unless otherwise specified.

The meaning of abbreviations is as follows: "sec" means second(s), "min" means minute(s), "h" means hour(s), "nm" means nanometers, "uL" means microliter(s), "mL" means milliliter(s), "mg/mL" means milligram per milliliter, "L" means liter(s), "nm" means nanometers, "mM" means millimolar, "M" means molar, "mmol" means millimole(s), "μmole" means micromole(s), "kg" means kilogram, "g" means gram(s), "μg" means microgram(s) and "ng" means nanogram(s), "PCR" means polymerase chain reaction, "OD" means optical density, "OD600" means the optical density measured at a wavelength of 600 nm, "kDa" means kilodaltons, "g" can also mean the gravitation constant, "bp" means base pair(s), "kbp" means kilobase pair(s), "kb" means kilobase, "%" means percent, "% w/v" means weight/volume percent, "% v/v" means volume/volume percent, "HPLC" means high performance liquid chromatography, "g/L" means gram per liter, "μg/L" means microgram per liter, "ng/μL" means nanogram per microliter, "pmol/μL" means picomol per microliter, "RPM" means rotation per minute, "pmol/min/mg" means micromole per minute per milligram, "w/v" means weight per volume, "v/v" means volume per volume.

Example 1

Selection of Potential Isobutyraldehyde Dehydrogenases for Screening

This example describes the basis for the selection of several ADH candidate enzymes for identifying efficient isobutyraldehyde dehydrogenases. *Clostridium acetobutylicum* Butanol Dehydrogenase A and B (BdhA and BdhB) were chosen for analysis based on the literature evidence. *Achromobacter xylosoxidans* was selected by enriching an environmental sludge sample on medium containing 1-butanol. The organism was then cultured and used to purify protein fraction that contained butanol dehydrogenase activity, subsequent to which the gene corresponding to the Secondary Alcohol Dehydrogenase B (SadB) was cloned as described in U.S. Patent Application Publication No. US 2009-0269823 A1. The horse-liver ADH enzyme (HLADH) is commercially available and was reported to have isobutanol oxidation activity by Green et al. in *J. Biol. Chem.* 268:7792 (1993).

Desirable properties of an ideal isobutyraldehyde dehydrogenase candidate for the isobutanol production pathway have been described above.

An extensive literature search identified those candidate ADH enzymes with either a high $k_{cat}$ and/or low $K_M$ values for isobutyraldehyde or other closely-related aldehydes, or with a lower $k_{cat}$ and/or higher $K_M$ for isobutanol or other closely-related alcohols. Protein BLAST searches against nonredundant protein sequence database (nr) at NCBI were performed using horse liver ADH, *Achromobacter xylosoxidans* SadB, and *Saccharomyces cerevisiae* ADH6 as queries, respectively. All the BLAST hits were collected and combined, from which sequences with more than 95% sequence identity to each other were removed. Multiple sequence alignment (MSA) was created from the set of remaining 95%-nonredundant sequences and a phylogenetic tree was generated from the MSA using the neighbor joining method. Similarly, MSA and phylogenetic tree were generated separately for a number of selected ADH enzymes to identify closely-related homologs of each enzyme where the alignment consisted of only the BLAST hits obtained using the target enzyme as the query. These enzymes included *Achromobacter xylosoxidans* SadB, *Saccharomyces cerevisiae* ADH6, and *Saccharomyces cerevisiae* ADH7. Based on these analyses several candidates were selected (Table 3) for evaluation of performance.

Example 2

Cloning, Protein Expression and Purification, and Screening for a Suitable Isobutyraldehyde Dehydrogenase This example describes preparation of ADH-gene constructs for over-expression/purification and measurement of enzyme activities using a time-course assay. Horse-liver ADH (HLADH; A-6128) was purchased from Sigma. *Achromobacter xylosoxidans* SadB (SadB), *Saccharomyces cerevisiae* ADH6 (ScADH6) and ADH7 (ScADH7), *Entamoeba histolytica* ADH1 (EhADH1), *Bos Taurus* Aldehyde Reductase (BtARD), *Beijerinckia indica* subsp. Indica ATCC 9039 (BiADH), *Clostridium beijerinckii* ADH (CbADH), *Rana perezi* ADH8 (RpADH8), *Rattus norvegicus* ADH1 (RnADH1), *Thermus* sp. ATN1 ADH (TADH), *Phenylobacterium zucineum* HLK1 ADH (PzADH), *Methylocella silvestris* BL2 ADH (MsADH), *Acinetobacter baumannii* AYE ADH (AbADH), *Geobacillus* sp. WCH70 ADH (GbADH), *Vanderwaltozyma polyspora* DSM 70294 ADH (VpADH), *Mucor circinelloides* ADH (McADH), and *Rhodococcus erythropolis* PR4 ADH (ReADH) were the candidates for which subclones were prepared for protein expression and purification.

Construction of Plasmid Constructs Expressing ADH Candidates

The gene-coding regions of EhADH1, BtARD, CbADH, BiADH, and RpADH8 were synthesized by DNA 2.0 (Menlo Park, Calif.) and those of RnADH1, TADH, PzADH, MsADH, AbADH, GbADH, VpADH, McADH, and ReADH were synthesized by GENEART AG (Germany) after optimizing the codons for expression in *Escherichia coli*. The amino-acid sequences for these candidates were procured from the Genbank Protein database and provided to DNA 2.0 or Geneart AG for codon optimization. Each coding region was flanked by XhoI and KpnI sites at the 5' and 3' ends of the coding sequence, respectively. These constructs were cloned and supplied in either DNA 2.0's vector pJ201 or Geneart's pMA vector.

The plasmids were transformed into chemically competent TOP10 cells (Invitrogen) and amplified by growing the transformants in liquid LB media containing either 25 mg/ml Kanamycin or 100 mg/ml Ampicillin. The plasmids, which were purified from overnight cultures (grown at 37° C.), were restricted with XhoI (NEB; R0146) and KpnI (NEB; R0142) and ligated into the corresponding sites in-frame with an N-terminal hexa-histidine tag in the vector pBADHisA (Invitrogen; V43001) using the DNA ligation kit Version 2.1 from Takara Bio Inc. (6022).

The ligation products were transformed into chemically competent TOP10 cells (Invitrogen; C4040-50). The transformed cells were streaked on a plate containing the LB medium plus 100 mg/mL ampicillin. Clones containing the ADH inserts were confirmed by restriction digestion with XhoI/KpnI. Plasmids with the correct insert contained the expected 1.2 kbp band in each case. The cloned sequence was confirmed via DNA sequencing. The resulting clones were named as pBADHisA::EhADH1, pBADHisA::BtARD, pBADHisA::CbADH, pBADHisA::BiADH, pBADHisA::RpADH8, pBADHisA::RnADH1, pBADHisA::TADH, pBADHisA::PzADH, pBADHisA::MsADH, pBADHisA::AbADH, pBADHisA::GbADH, pBADHisA::VpADH, pBADHisA::McADH, and pBADHisA::ReADH, respectively.

SadB, an enzyme which was previously examined, was PCR-amplified with KOD polymerase enzyme (Novagen), as per the procedure mentioned in the product manual, from pTrc99a::SadB using primers SadBXhoI-f (CCATGGAATCTCGAGATGAAAGCTCTGGTTTACC, SEQ ID NO: 41) and SadBKpnI-r (GATCCCCGGGTACCGAGCTCGAATTC, SEQ ID NO: 42) to introduce XhoI and KpnI sites at the 5' and 3' ends, respectively. After confirmation of the PCR product via agarose-gel electrophoresis, the 1.2-kb PCR product was restricted with XhoI and KpnI and cloned into pBADHisA as described above for the other candidate genes. The genes for ScADH6 and ScADH7 were each amplified from 100 ng of genomic DNA of the yeast wild-type strain BY4741 (ATCC 201388) using primers ADH6_XhoI_f (CAAGAAAACTCGAGATCATGTCTTATCCTGAG, SEQ ID NO: 43) and ADH6_KpnI_r (GAGCTTGGTACCCTAGTCTGAAAATTCTTTG, SEQ ID NO: 44) for ScADH6 and ADH7_XhoI_f (CTGAAAAACTCGAGAAAAAAATGCTTTACCC, SEQ ID NO: 45) and ADH7_KpnI_r (GAAAAATATTAGGTACCTAGACTATTTATGG, SEQ ID NO: 46) for ScADH7. The strategy and PCR conditions were identical to those used for the amplification of SadB. The genes were then cloned into the XhoI and KpnI sites of pBADHisA, as per the procedure described above. The plasmids containing SadB, ScADH6 and ScADH7 were labeled as pBADHisA::SadB, pBADHisA::ScADH6 and pBADHisA:: ScADH7, respectively.

Expression of Recombinant ADHs in *E. coli*

For the data shown, either BL21-CodonPlus (Invitrogen; 230240) or a proprietary *E. coli* strain were used for the overexpression of ADH enzymes. However, it is believed that commercially available strains, such as BL21-codon plus, are suitable for overexpression of ADH enzymes.

Expression plasmids (pBADHisA plasmids) containing ADH genes were prepared from 3-mL overnight cultures of Top10 transformants using Qiaprep spin miniprep kit (Qiagen, Valencia Calif.; 27106) following manufacturer's instructions. One ng of each of the plasmid was transformed into either BL21-CodonPlus or proprietary *E. coli* electrocompetent cells using a Bio RAD Gene Pulser II (Bio-Rad Laboratories Inc, Hercules, Calif.) by following the manufacturer's directions. The transformed cells were spread onto agar plates containing the LB medium plus 100 µg/mL of each of ampicillin and spectinomycin. The plates were incubated overnight at 37° C. Colonies from these plates innoculated in 3.0 mL of the LB medium containing 100 µg/mL of each of ampicillin and spectinomycin, at 37° C. while shaking at 250 rpm. Cells from these starter cultures (grown overnight) were used to innoculate 1-L media at a dilution of 1:1000. The cells were induced with 0.02% Arabinose after the culture reached an OD of ~0.8. The induction was carried out at 37° C. while shaking at 250 rpm overnight. The cells were then harvested by centrifugation at 4000 g for 10 min at 4° C. The cells were lysed by treatment with 40 ml of Bug-Buster master mix (Novagen; 71456-4), in the presence of Complete, EDTA-free Protease Inhibitor Cocktail tablets (Roche; 11873580001) and 1 mg/ml Lysozyme, by placing on a rocker at 4° C. for 30 min. The cell debris was removed by centrifugation at 16,000 g for 20 min at 4° C.

The total protein concentration in samples was measured by the Bradfords Assay using Bradford's dye concentrate (Bio-Rad). The samples and protein standards (Bovine Serum Albumin, BSA) were set up in either individual cuvettes (1-mL reactions) or a 96-well microplate following the manufacturer's protocol. The concentrations of proteins were calculated from absorbance values at 595 nm, measured using either a Cary 100 Bio UV-Visible spectrophotometer (Varian, Inc.) or a SpectraMax plate reader (Molecular Devices Corporation, Sunnyvale, Calif.).

ADH Enzyme Purification and Activity Assays

Cell-free extracts prepared from 1-liter cultures as per the procedure described above, was directly used to purify the various expressed ADH enzymes via IMAC (immobilized metal affinity chromatography) affinity chromatography on 5-mL HisTrap FF columns (GE Healthcare Life Sciences; 175255-01). The entire procedure was carried out using an AKTAexplorer 10 S (GE Healthcare Life Sciences; 18-1145-05) FPLC system. The extracts were mixed with 30 mM Imidazole and loaded onto the HisTrap columns. Upon loading, the column was washed with 50 mM Sodium phosphate buffer, pH 8.0, containing 30 mM Imidazole (approximately ~10-20 column volumes) to get rid of unbound and non-specifically bound proteins. The ADH protein was then eluted with a gradient of 30 mM to 500 mM Imidazole over 20 column volumes. The peak fractions were electrophoresed on 10% Bis-Tris SDS-PAGE gels (Invitrogen; NP0301) using Invitrogen's XCell SureLock Mini-Gel apparatus (EI0001). Upon coomassie staining and destaining, it could be ascertained that the fractions were more than 95% pure and contained only the ADH protein. Activity assays were carried out to ensure that the purified proteins were active.

As a routine practice, the crude extracts and purified proteins were assayed for butanol oxidation activity, in order to ensure that the recombinant proteins were active throughout the purification process. In the reductive direction, isobutyraldehyde reduction assays were carried out with NADH or NADPH as the cofactor and an excess of the isobutyraldehyde substrate (40 mM). In each case, enzymatic activity was measured for 1 min at 30° C. in 1-ml reactions by following the decrease or increase in the absorbance at 340 nm using a Cary Bio 100 UV-Visible spectrophotometer (Varian Inc.), depending on whether the NADH/NADPH is being consumed (absorbance is decreased) or generated (absorbance is increased) in the reaction. Alcohol oxidation activities were carried out in 50 mM sodium phosphate buffer at pH 8.8 and aldehyde reduction reactions were assayed in 100 mM potassium phosphate buffer at pH 7.0. Depending on the nature of reaction being carried out, the enzyme and cofactor stocks were diluted in the reaction buffers at the respective pHs. Either buffer or cell extract prepared from the proprietary E. coli strain (with no ADH plasmid) was used as the negative control for assays with purified protein and cell-free extracts, respectively.

In initial experiments, there were insufficient levels of protein expression with EhADH1 and RpADH8. Subsequently, the activity assays failed to detect ADH activity in the cell extracts expressing these enzymes. Likewise initially, although the BtARD showed good levels of protein expression and the protein could be purified to homogeneity, it had no detectable activity under the conditions used for the assay. It is believed that one of skill in the art could further optimize expression and assay conditions for these candidates. Sufficient amounts of active protein could be purified with all other enzymes for which data are presented. Cofactor specificities were measured with all these enzymes in isobutyraldehyde reduction reactions (as in proc mentioned above), using either NADH or NADPH as cofactors. In each case, at least a 10-fold difference was observed in the activity numbers, when either NADH or NADPH was used as a cofactor, as against the number corresponding to the other form of the cofactor. Table 6 summarizes the cofactor preferences for some of the ADH enzymes.

TABLE 6

| CANDIDATE ADH | COFACTOR PREFERENCE |
| --- | --- |
| Horse-liver ADH | NADH |
| Saccharomyces cerevisiae ADH6 | NADPH |
| Saccharomyces cerevisiae ADH7 | NADPH |
| Achromobacter xylosoxidans SadB | NADH |
| Beijerickia indica ADH | NADH |
| Clostridium beijerinckii ADH | NADPH |
| Rattus norvegicus ADH1 | NADH |
| Thermus sp. ATN1 ADH | NADH |
| Phenylobacterium zucineum HLK1 ADH | NADH |
| Methylocella silvestris BL2 ADH | NADH |
| Acinetobacter baumannii AYE ADH | NADH |
| Geobacillus sp. WCH70 ADH | NADPH |
| Mucor circinelloides ADH | NADH |

Screening Purified ADH Candidates Using a Semi-Physiological Time-Course Assay

The ideal way to characterize and compare various ADH candidates would be to calculate and compare the full set of kinetic constants, i.e., $k_{cat}$ values for aldehyde reduction and alcohol oxidation, $K_M$ values for isobutyraldehyde, isobutanol, NAD(P) and NAD(P)H, and $K_I$ values for isobutyraldehyde and isobutanol. A detailed characterization for numerous candidates would require considerable expenditure of time, effort and money. Thus, a qualitative assay was developed to allow for quick and efficient comparison of several candidates. A semi-physiological assay was designed to compare the performance of various enzymes. The assays entail the initiation of all reactions with a constant amount of each enzyme. In this case, 1 ug of each enzyme was used to initiate reactions that contained isobutyraldehyde and NADH at concentrations 1 mM and 200 µM, respectively. Each reaction's time course was followed for 10 min by measuring the decrease in absorbance at 340 nm, as the reaction proceeds towards equilibrium. An enzyme with a high $k_{cat}$ would drive the reaction towards equilibrium faster than an enzyme with a lower $k_{cat}$. A parallel assay was also carried out under identical conditions, but with the inclusion of 321 mM isobutanol (24 g/L) in the reaction. An enzyme that is relatively uninhibited by this concentration of isobutanol would have a time course that closely mimics the time course in the absence of isobutanol. FIG. 1 compares time courses exhibited by the ADH candidate enzymes in these assays.

Based on the results presented in FIG. 1, it is inferred that the Beijerickia indica ADH is likely to have the highest $k_{cat}$ for the isobutyraldehyde reduction reaction and ADH6 is likely to be the least inhibited by isobutanol in the reaction.

Example 3

Identification of *Beijerinckia indica* ADH with a High $k_{cat}$ and a Low $K_M$ for Isobutyraldehyde Kinetic constants of the ADH enzymes were calculated and compared to identify those candidate ADH enzymes with the most desirable properties for the conversion of isobutyraldehyde to isobutanol in the last step of the engineered pathway for isobutanol production. The assays for determining the kinetic constants were carried out using initial rates from the assays described above. Decreases in NADH can be correlated with aldehyde being consumed (Biochemistry by Voet and Voet, John Wiley & Sons, Inc.) However, the amount of a given enzyme used in the reaction was in the range of 0.1 to 5 µg. The concentration of a given enzyme was such that it was conducive for the measurement of initial velocities over a 1-min time course. For each enzyme, Michaelis-Menten plots were generated with a broad range of substrate concentrations. Rough estimates of $K_M$ were obtained, based on which the assays were redesigned so as to use substrate concentrations in the range 0.5 to 10 times the $K_M$ value, to be able to obtain the appropriate kinetic constants. Isobutyraldehyde (isobutanal) reduction reactions were carried out at 30° C. in 100 mM Potassium phosphate buffer, pH 7.0, containing 200 µM NADH. When calculating the $K_I$ for isobutanol, the same reactions were carried out in the presence of varying concentrations of isobutanol (generally 0-535 mM) in the reaction (see FIG. 7, for example). Reactions with isobutanol substrate were performed at 30° C. in 50 mM Sodium phosphate buffer, pH 8.8, containing 7.5 mM NAD. The Enzyme kinetics module (Version 1.3) of SigmaPlot 11 (Systat Software, Inc.) was used to fit data to Michaelis-Menten equations and calculate the kinetic constants. Kinetic constants obtained for the indicated ADH enzymes are given in Table 7. The $k_{cat}/K_M$ is derived from the individual numbers of $k_{cat}$ and $K_M$ and not an experimentally determined value. The ratios of the $K_M$, $K_I$ and $k_{cat}/K_M$ for each candidate enzyme as compared to the same parameter for SadB are given in Table 9.

and is preferred. The enzyme RnADH1 appears to have a low $K_M$ value for isobutyraldehyde and consequently may have a high catalytic efficiency. However, the low $K_M$ value precludes an accurate determination of its $K_M$ value via spectrophotometric assays. Nevertheless, the enzyme's performance in the isobutanol production host may be limited more by the $k_{cat}$ if the intracellular steady-state levels of isobutyraldehyde are in excess of its $K_M$ value. Comparing BiADH with SadB, the former's catalytic efficiency for isobutyraldehyde reduction is ~12 times more than that of the latter although it is more sensitive to isobutanol than SadB. With regard to the nucleotide cofactor, SadB has a lower $K_M$ value for NADH when compared with BiADH. ScADH6 has a high $K_I$ value for isobutanol, indicating that this enzyme is likely to function in vivo, unfettered by the presence of isobutanol at concentrations that are expected in an isobutanol production host. Among the candidates analyzed so far, SadB has the least catalytic efficiency for isobutanol oxidation ($k_{cat}/K_M$=0.083), followed by BiADH (1.91) and HLADH (12.5).

Example 4

Seven additional candidate ADH enzymes were synthesized, expressed, and assayed according to methods such as described in Example 2. Kinetic constants obtained for the indicated ADH enzymes (*Phenylobacterium zucineum* HLK1 ADH (PzADH), *Methylocella silvestris* BL2 ADH (MsADH), *Acinetobacter baumannii* AYE ADH (AbADH), *Geobacillus* sp. WCH70 ADH (GbADH), and *Mucor circinelloides* ADH (McADH)) are given in Table 8. A comparison of $K_M$, $K_I$, and $k_{cat}/K_M$ for each candidate enzyme as compared to the same parameter for SadB are given in Table 9 as a percentage of the values determined (Table 7) for SadB. Percentages less than 100 indicate a value less than that

TABLE 7

| Enzyme | $k_{cat}$ (sec$^{-1}$) | $K_M$ (Isobututanal) mM) | $K_I$ (Isobutanol) (mM) | $k_{cat}/K_M$ | Other enzymatic properties and cofactor preference |
|---|---|---|---|---|---|
| HLADH* | 8 | 0.1 | 2 | 82 | [Isobutanol oxidation: $k_{cat}$ = 5 sec$^{-1}$; $K_M$ = 0.4 mM] |
| SadB* | 109 | 1 | 180 | 105 | $K_M$ (NADH) = 0.02 mM [Isobutanol oxidation: $k_{cat}$ = 2 sec$^{-1}$; $K_M$ = 24 mM] |
| ScADH6 | 47 | 0.6 | 1170 | 81 | NADPH specific |
| ScADH7* | 36 | 0.3 | 88 | 120 | NADPH specific |
| BiADH | 283 | 0.2 | 36 | 1252 | $K_M$ (NADH) = 0.06 mM [Isobutanol oxidation: $k_{cat}$ = 9 sec$^{-1}$; $K_M$ = 4.7 mM] |
| CbADH | 123 | 1.5 | ND | 85 | NADPH specific |
| TADH | 15 | 1.3 | ND | 11 | NADH specific |
| RnADH1 | ~5 | ≤0.003 | ND | ~1667 | NADH specific |

For those enzymes marked with an asterisk in Table 7, at least 3 assays were performed with separate preparations of the enzyme. All other numbers are values from either one assay or are averages from 2 assays performed with the same enzyme sample.

The data for *Beijerickia indica* ADH (BiADH) shows the highest number for the $k_{cat}$ and a reasonably high $k_{cat}/K_M$, determined for SadB; percentages higher than 100 indicate a value greater than that determined for SadB. There was no expression for *Rhodococcus erythropolis* PR4 ADH (ReADH) and no detectable activity for *Vanderwaltozyma polyspora* DSM 70294 ADH (VpADH) in these assays. determined for SadB; percentages higher than 100 indicate a value greater than that determined for SadB. There was no expression for *Rhodococcus erythropolis* PR4 ADH

TABLE 8

| Enzyme | $k_{cat}$ (sec-1) | $K_M$ (Isobututanal) (mM) | $K_I$ (Isobutanol) (mM) | $k_{cat}/K_M$* | Other enzymatic properties and cofactor preference |
|---|---|---|---|---|---|
| PzADH | 30 | 0.1 | 13 | 321 | NADH specific No measureable conversion of isobutanol to isobutyraldehyde |
| MsADH | 33 | 0.06 | 19 | 530 | NADH specific No measureable conversion of isobutanol to isobutyraldehyde |
| AbADH | 99 | 10 | 305 | 10 | NADH specific No measureable conversion of isobutanol to isobutyraldehyde |
| GbADH | 32 | 0.4 | 13 | 72 | NADPH specific No measureable conversion of isobutanol to isobutyraldehyde |
| McADH | 151 | 30 | 79 | 5 | NADH specific No measureable conversion of isobutanol to isobutyraldehyde |

TABLE 9

Indicated parameter as a percentage of the same parameter determined for SadB

| Enzyme | $k_{cat}$ | $K_M$ | $K_I$ | $k_{cat}/K_M$ |
|---|---|---|---|---|
| HLADH | 7% | 10% | 1% | 78% |
| SadB | 100% | 100% | 100% | 100% |
| ScADH6 | 43% | 60% | 650% | 77% |
| ScADH7 | 33% | 30% | 49% | 114% |
| BiADH | 260% | 20% | 20% | 1192% |
| CbADH | 113% | 150% | ND | 81% |
| TADH | 14% | 130% | ND | 10% |
| RnADH1 | 5% | <1% | ND | 1588% |
| PzADH | 28% | 10% | 7% | 243% |
| MsADH | 30% | 6% | 11% | 532% |
| AbADH | 91% | 1020% | 169% | 9% |
| GbADH | 29% | 44% | 7% | 69% |
| McADH | 138% | 3000% | 44% | 5% |

Example 5

Construction of *S. cerevisiae* Strain PNY2211

PNY2211 was constructed in several steps from *S. cerevisiae* strain PNY1507 as described in U.S. Appl. No. 61/380,563, filed Sep. 7, 2010, and in the following paragraphs. First the strain was modified to contain a phosphoketolase gene. Construction of phosphoketolase gene cassettes and integration strains was previously described in U.S. Appl. No. 61/356,379, filed Jun. 18, 2010. Next, an acetolactate synthase gene (alsS) was added to the strain, using an integration vector previously described in U.S. Appl. No. 61/308,563. Finally, homologous recombination was used to remove the phosphoketolase gene and integration vector sequences, resulting in a scarless insertion of alsS in the intergenic region between pdc1Δ::ilvD (a previously described deletion/insertion of the PDC1 ORF in U.S. Appl. No. 61/308,563) and the native TRX1 gene of chromosome XII. The resulting genotype of PNY2211 is MATa ura3Δ::loxP his3Δ pdc6Δ pdc1Δ:: P[PDC1]-DHAD|ilvD_Sm-PDClt-P[FBA1]-ALS|alsS_Bs-CYClt pdc5Δ::P[PDC5]-ADH|sadB_Ax-PDC5t d2Δ::loxP fra2Δ adh1Δ::UAS(PGK1)P[FBA1]-kivD_L1(y)-ADHlt.

A phosphoketolase gene cassette was introduced into PNY1507 by homologous recombination. The integration construct was generated as follows. The plasmid pRS423::CUP1-alsS+FBA-budA (as described in U.S. Publ. No. 2009/0305363 A1) was digested with NotI and XmaI to remove the 1.8 kb FBA-budA sequence, and the vector was religated after treatment with Klenow fragment. Next, the CUP1 promoter was replaced with a TEF1 promoter variant (M4 variant described by Nevoigt et al. *Appl. Environ. Microbiol.* 72(8): 5266-5273 (2006)) via DNA synthesis and vector construction service from DNA2.0 (Menlo Park, Calif.). The resulting plasmid, pRS423::TEF(M4)-alsS was cut with StuI and MluI (removes 1.6 kb portion containing part of the alsS gene and CYC1 termintor), combined with the 4 kb PCR product generated from pRS426::GPD-xpk1+ADH-eutD (SEQ ID NO: 81; the plasmid is described in U.S. Appl. No. 61/356,379) with primers N1176 and N1177 (SEQ ID NOs: 47 and 48, respectively) and an 0.8 kb PCR product DNA generated from yeast genomic DNA (ENO1 promoter region) with primers N822 and N1178 (SEQ ID NOs: 49 and 50, respectively) and transformed into *S. cerevisiae* strain BY4741 (ATCC#201388; gap repair cloning methodology, see Ma and Botstein). Transformants were obtained by plating cells on synthetic complete medium without histidine. Proper assembly of the expected plasmid (pRS423::TEF(M4)-xpk1+ENO1-eutD, SEQ ID No: 51) was confirmed by PCR using primers N821 and N1115 (SEQ ID NOs: 52 and 53, respectively) and by restriction digest (BglI). Two clones were subsequently sequenced. The 3.1 kb TEF(M4)-xpk1 gene was isolated by digestion with SacI and NotI and cloned into the pUC19-URA3::ilvD-TRX1 vector described in U.S. Appl. No. 61/356,379 (Clone A, cut with AflII). Cloning fragments were treated with Klenow fragment to generate blunt ends for ligation. Ligation reactions were transformed into *E. coli* Stbl3 cells, selecting for ampicillin resistance.

Insertion of TEF(M4)-xpk1 was confirmed by PCR using primers N1110 and N1114 (SEQ ID NOs: 54 and 55, respectively). The vector was linearized with AflII and treated with Klenow fragment. The 1.8 kb KpnI-HincII geneticin resistance cassette described in U.S. Appl. No. 61/356,379 was cloned by ligation after Klenow fragment treatment. Ligation reactions were transformed into *E. coli* Stb13 cells, selecting for ampicillin resistance. Insertion of the geneticin cassette was confirmed by PCR using primers N160SeqF5 and BK468 (SEQ ID NOs: 56 and 57, respectively). The plasmid sequence is provided as SEQ ID NO: 58 (pUC19-URA3::pdc1::TEF(M4)-xpk1::kan).

The resulting integration cassette (pdc1::TEF(M4)-xpk1::KanMX::TRX1) was isolated (AscI and NaeI digestion generated a 5.3 kb band that was gel purified) and transformed into PNY1507 using the Zymo Research Frozen-EZ Yeast Transformation Kit (Cat. No. T2001). Transformants were selected by plating on YPE plus 50 µg/ml G418. Integration at the expected locus was confirmed by PCR using primers N886 and N1214 (SEQ ID NOs: 59 and 60, respectively). Next, plasmid pRS423::GAL1p-Cre, encoding Cre recombinase, was used to remove the loxP-flanked KanMX cassette (vector and methods described in U.S. Appl. No. 61/308,563). Proper removal of the cassette was confirmed by PCR using primers oBP512 and N160SeqF5 (SEQ ID NOs: 61 and 62, respectively). Finally, the alsS integration plasmid described in U.S. Appl. No. 61/308,563 (pUC19-kan::pdc1::FBA-alsS::TRX1, clone A) was transformed into this strain using the included geneticin selection marker. Two integrants were tested for acetolactate synthase activity by transformation with plasmids pYZ090ΔalsS and pBP915 (plasmids described in U.S. Appl. No. 61/308,563, transformed using Protocol #2 in "Methods in Yeast Genetics" 2005. Amberg, Burke and Strathern) and evaluation of growth and isobutanol production in glucose-containing media (methods for growth and isobutanol measurement are described in U.S. Appl. No. 61/308,563 and U.S. Publ. No. 2007/0092957 A1). One of the two clones was positive and was named PNY2218. An isolate of PNY2218 containing the plasmids pYZ090ΔalsS and pBP915 was designated PNY2209.

PNY2218 was treated with Cre recombinase and resulting clones were screened for loss of the xpk1 gene and pUC19 integration vector sequences by PCR using primers N886 and N160SeqR5 (SEQ ID NOs: 59 and 56, respectively). This leaves only the alsS gene integrated in the pdc1-TRX1 intergenic region after recombination the DNA upstream of xpk1 and the homologous DNA introduced during insertion of the integration vector (a "scarless" insertion since vector, marker gene and loxP sequences are lost, see FIG. 9). Although this recombination could have occurred at any point, the vector integration appeared to be stable even without geneticin selection and the recombination event was only observed after introduction of the Cre recombinase. One clone was designated PNY2211.

Example 6

Construction of *Saccharomyces cerevisiae* Strain PNY1540

The purpose of this example is to describe the construction of *Saccharomyces cerevisiae* strain PNY1540 from strain PNY2211. This strain was derived from CEN.PK 113-7D (CBS 8340; Centraalbureau voor Schimmelcultures (CBS) Fungal Biodiversiry Centre, Netherlands) and is described in Example 5 above. PNY1540 contains a deletion of the sadB gene, from *Achromobacter xylosoxidans*, which had been integrated at the PDC5 locus in PNY2211. The deletion, which completely removed the entire coding sequence, was created by homologous recombination with a PCR fragment containing regions of homology upstream and downstream of the target gene and a URA3 gene for selection of transformants. The URA3 gene was removed by homologous recombination to create a scarless deletion.

The scarless deletion procedure was adapted from Akada et al. 2006 *Yeast* v23 p399. The PCR cassette for the scarless deletion was made by combining four fragments, A-B-U-C, by overlapping PCR. The PCR cassette contained a selectable/counter-selectable marker, URA3 (Fragment U), consisting of the native CEN.PK 113-7D URA3 gene, along with the promoter (250 bp upstream of the URA3 gene) and terminator (150 bp downstream of the URA3 gene). Fragments A and C, each 500 bp long, corresponded to the 500 bp immediately upstream of the target gene (Fragment A) and the 3' 500 bp of the target gene (Fragment C). Fragments A and C were used for integration of the cassette into the chromosome by homologous recombination. Fragment B (254 bp long) corresponded to the sequence immediately downstream of the target gene and was used for excision of the URA3 marker and Fragment C from the chromosome by homologous recombination, as a direct repeat of the sequence corresponding to Fragment B was created upon integration of the cassette into the chromosome. Using the PCR product ABUC cassette, the URA3 marker was first integrated into and then excised from the chromosome by homologous recombination. The initial integration deleted the gene, excluding the 3' 500 bp. Upon excision, the 3' 500 bp region of the gene was also deleted.

sadB Deletion

The four fragments for the PCR cassette for the scarless sadB deletion were amplified using Phusion High Fidelity PCR Master Mix (New England BioLabs; Ipswich, Mass.) and CEN.PK 113-7D genomic DNA as template for Fragment U and PNY1503 genomic DNA as template for Fragments A, B, and C. Genomic DNA was prepared with a Gentra Puregene Yeast/Bact kit (Qiagen; Valencia, Calif.). sadB Fragment A was amplified with primer oBP540 (SEQ ID NO: 63) and primer oBP835 (SEQ ID NO: 64), containing a 5' tail with homology to the 5' end of sadB Fragment B. sadB Fragment B was amplified with primer oBP836 (SEQ ID NO: 65), containing a 5' tail with homology to the 3' end of sadB Fragment A, and primer oBP837 (SEQ ID NO: 66), containing a 5' tail with homology to the 5' end of sadB Fragment U. sadB Fragment U was amplified with primer oBP838 (SEQ ID NO: 67), containing a 5' tail with homology to the 3' end of sadB Fragment B, and primer oBP839 (SEQ ID NO: 68), containing a 5' tail with homology to the 5' end of sadB Fragment C. sadB Fragment C was amplified with primer oBP840 (SEQ ID NO: 69), containing a 5' tail with homology to the 3' end of sadB Fragment U, and primer oBP841 (SEQ ID NO: 70). PCR products were purified with a PCR Purification kit (Qiagen). sadB Fragment AB was created by overlapping PCR by mixing sadB Fragment A and sadB Fragment B and amplifying with primers oBP540 (SEQ ID NO: 63) and oBP837 (SEQ ID NO: 66). sadB Fragment UC was created by overlapping PCR by mixing sadB Fragment U and sadB Fragment C and amplifying with primers oBP838 (SEQ ID NO: 67) and oBP841 (SEQ ID NO: 70). The resulting PCR products were purified on an agarose gel followed by a Gel Extraction kit (Qiagen). The sadB ABUC cassette was created by overlapping PCR by mixing sadB Fragment AB and sadB Fragment UC and amplifying with primers oBP540 (SEQ ID NO: 63) and oBP841 (SEQ ID NO: 70). The PCR product was purified with a PCR Purification kit (Qiagen).

Competent cells of PNY2211 were made and transformed with the sadB ABUC PCR cassette using a Frozen-EZ Yeast Transformation II kit (Zymo Research; Orange, Calif.). Transformation mixtures were plated on synthetic complete media lacking uracil supplemented with 1% ethanol at 30 C. Transformants with a sadB knockout were screened for by PCR with primers Ura3-end (SEQ ID NO: 71) and oBP541 (SEQ ID NO: 72). A correct transformant was grown in YPE (1% ethanol) and plated on synthetic complete medium containing 5-fluoro-orotic acid (0.1%) at 30 C to select for isolates that lost the URA3 marker. The deletion and marker removal were confirmed by PCR with primers oBP540 (SEQ ID NO: 63) and oBP541 (SEQ ID NO: 72) using genomic DNA prepared with a YeaStar Genomic DNA Kit (Zymo Research). The absence of the sadB gene from the isolate was demonstrated by a negative PCR result using primers specific for the deleted coding sequence of sadB, oBP530 (SEQ ID NO: 73) and oBP531 (SEQ ID NO: 74). A correct isolate was selected as strain PNY1540 (BP1746).

Example 7

Construction of a Yeast Shuttle Vector Carrying a Gene Encoding the B. indica ADH and a Negative Control Vector The plasmid pLH468 (SEQ ID NO: 75), as described in U.S. Publ. No. 2009/0305363 A1, is an E. coli/yeast shuttle vector that carries 3 chimeric genes encoding enzymes that comprise part of an isobutanol production pathway (dihydroxyacid dehydratase, aKIV decarboxylase and isobutanol dehydrogenase). The existing isobutanol dehydrogenase gene was replaced by the B. indica ADH using gap repair cloning methodology. The B. indica ADH coding region with suitable 5' and 3' flanking sequences was first obtained via DNA synthesis (DNA2.0, Menlo Park, Calif.) with yeast codon optimization. The sequence is provided (SEQ ID NO:76). The vector μLH468 was linearized with Bsu36I and transformed along with the B. indica ADH (released from the supplier's cloning vector with EcoRI and BamHI) into yeast strain BY4741. Transformants were plated on synthetic complete medium without histidine (Teknova Cat. No. C3020). Plasmids were prepared from several transformants using a Zymoprep™ Yeast Plasmid Miniprep kit (Zymo Research Cat. No. D2004). PCR (with primers N1092 and N1093, SEQ ID NOs: 77 and 78) and restriction enzyme digestion (with KpnI) were used to confirm incorporation of BiADH in the intended location. This plasmid is referred to as pLH468::BiADH.

A second vector was constructed that eliminated the most of the original isobutanol dehydrogenase gene (hADH) from pLH468. This was done by releasing a 808 bp fragment via digestion with Bsu36I and PacI, filling in the ends of the DNA with Klenow fragment and re-ligating the vector. The ligation reaction was transformed into E. coli Stb13 cells. Loss of the hADH gene was confirmed by EcoRI digestion of isolated plasmid cones. One successful clone was selected for the experiment described in Example 8, below. The plasmid is referred to as μLH468ΔhADH.

Example 8

Isobutanologen Strains Carrying BiADH Display Better Glucose-Dependent Growth, Higher Glucose Consumption and Higher Isobutanol Titer and Yield than Control Strains The plasmids pLH468::BiADH and pLH468ΔhADH were each transformed along with a second isobutanol pathway plasmid (pYZ090ΔalsS, U.S. Appl. No. 61/380,563) into PNY1540. Transformations were plated on synthetic complete medium lacking histidine and uracil, containing 1% ethanol as carbon source. Several transformants were patched to fresh plates. After 48 hours, patches (3 of each strain) were used to inoculate synthetic complete medium (minus histidine and uracil) containing 0.3% glucose and 0.3% ethanol as carbon sources. After 24 hours, growth in this medium was similar for all replicates of both strains. Cultures were then sub-cultured into synthetic complete medium (minus histidine and uracil) containing 2% glucose and 0.05% ethanol as carbon sources. Cultures (starting optical density (OD) at 600 nm was 0.2, culture volume was 20 ml in 125 ml tightly-capped flasks) were incubated 48 hours. Samples were collected for HPLC analysis at the time of subculture and again after 48 hours. The final ODs were also determined. The average 48 h OD for the BiADH strain was 3.3 (+/−0.1) compared to 2.37 (+/−0.07) for the no ADH control. Thus inclusion of BiADH increased OD by 39% under these conditions. Similarly, glucose consumption (assessed by HPLC compared to samples collected immediately after sub-culturing) was increased by 69% (81+/−1 mM vs. 47.9+/−0.6 mM). Isobutanol titers were 4-fold higher and molar yields (i.e. yield of isobutanol per mole of glucose consumed) were doubled as shown in table below. In the no ADH control strain, significant carbon from the isobutanol pathway accumulated as isobutyrate, indicating that aldehyde dehydrogenases were acting upon isobutyraldehyde.

TABLE 10

| | Isobutanol (mM) | Isobutyrate (mM) | Isobutyraldehyde (mM) |
|---|---|---|---|
| TITERS | | | |
| PNY1540/ pLH468::BiADH | 32.3 (±0.6) | 10.9 (±0.3) | ND |
| PNY1540/ pLH468ΔADH | 6.2 (±0.2) | 18.4 (±0.4) | 2.1 (±0.4) |
| MOLAR YIELDS | | | |
| PNY1540/ pLH468::BiADH | 0.401 (±0.006) | 0.135 (±0.005) | ND |
| PNY1540/ pLH468ΔADH | 0.129 (±0.004) | 0.384 (±0.004) | 0.044 (±0.008) |

What is claimed is:

1. A recombinant microbial host cell comprising a biosynthetic pathway for production of isobutanol, the biosynthetic pathway comprising a substrate to product conversion catalyzed by a polypeptide with alcohol dehydrogenase activity, wherein the polypeptide with alcohol dehydrogenase activity has at least 90% identity to the amino acid sequence of SEQ ID NO: 36 and a $K_I$ value for isobutanol that is higher relative to a control polypeptide having the amino acid sequence of SEQ ID NO:26.

2. The recombinant microbial host cell of claim 1, wherein the polypeptide with alcohol dehydrogenase activity has at least 95% identity to the amino acid sequence of SEQ ID NO: 36.

3. The recombinant microbial host cell of claim 1, wherein the polypeptide with alcohol dehydrogenase activity has the amino acid sequence of SEQ ID NO: 36.

4. The recombinant host cell of claim 1, wherein the polypeptide with alcohol dehydrogenase activity is encoded by a polynucleotide having at least 85% identity to the nucleotide sequence of SEQ ID NO: 16.

5. The recombinant microbial host cell of claim 1, wherein the polypeptide with alcohol dehydrogenase activity uses NADH as a cofactor.

6. The recombinant microbial host cell of claim 1, wherein the polypeptide having alcohol dehydrogenase activity catalyzes the conversion of isobutyraldehyde to isobutanol in the presence of isobutanol at a concentration of 15 g/L.

7. The recombinant microbial host cell of claim 1, wherein the biosynthetic pathway for production of isobutanol comprises heterologous polynucleotides encoding polypeptides that catalyze substrate to product conversions for each step of the following steps:
    (a) pyruvate to acetolactate;
    (b) acetolactate to 2,3-dihydroxyisovalerate;
    (c) 2,3-dihydroxyisovalerate to α-ketoisovalerate;
    (d) α-ketoisovalerate to isobutyraldehyde; and
    (e) isobutyraldehyde to isobutanol;
    wherein the substrate to product conversion of step (e) is catalyzed by the polypeptide with alcohol dehydrogenase activity of claim 1 and the microbial host cell produces isobutanol.

8. The recombinant microbial host cell of claim 1, wherein the biosynthetic pathway for production of isobutanol comprises heterologous polynucleotides encoding polypeptides that catalyze substrate to product conversions for each step of the following steps:
    (a) pyruvate to acetolactate;
    (b) acetolactate to 2,3-dihydroxyisovalerate;
    (c) 2,3-dihydroxyisovalerate to α-ketoisovalerate;
    (d) α-ketoisovalerate to isobutyryl-CoA;
    (e) isobutyryl-CoA to isobutyraldehyde; and
    (f) isobutyraldehyde to isobutanol;
    wherein the substrate to product conversion of step (e) is catalyzed by the polypeptide with alcohol dehydrogenase activity of claim 1 and the microbial host cell produces isobutanol.

9. The recombinant microbial host cell of claim 1, wherein the biosynthetic pathway for production of isobutanol comprises heterologous polynucleotides encoding polypeptides that catalyze substrate to product conversions for each step of the following steps:
    (a) pyruvate to acetolactate;
    (b) acetolactate to 2,3-dihydroxyisovalerate;
    (c) 2,3-dihydroxyisovalerate to α-ketoisovalerate;
    (d) α-ketoisovalerate to valine;
    (e) valine to isobutylamine;
    (f) isobutylamine to isobutyraldehyde; and
    (g) isobutyraldehyde to isobutanol;
    wherein the substrate to product conversion of step (e) is catalyzed by the polypeptide with alcohol dehydrogenase activity of claim 1 and the microbial host cell produces isobutanol.

10. The recombinant host cell of claim 1, wherein the genus of the host cell is selected from the group consisting of: *Saccharomyces, Pichia, Hansenula, Yarrowia, Aspergillus, Kluyveromyces, Pachysolen, Rhodotorula, Zygosaccharomyces, Galactomyces, Torulaspora, Schizosaccharomyces, Debayomyces, Williopsis, Dekkera, Kloeckera, Metschnikowia, Issatchenkia,* and *Candida*.

11. A method for producing isobutanol comprising:
    (a) providing a recombinant microbial host cell comprising an isobutanol biosynthetic pathway, the pathway comprising a heterologous polypeptide which catalyzes the substrate to product conversion of isobutyraldehyde to isobutanol wherein the polypeptide has at least 90% identity to the amino acid sequence of SEQ ID NO: 36 and a $K_I$ value for isobutanol that is higher relative to a control polypeptide having the amino acid sequence of SEQ ID NO:26, and (b) contacting the host cell of (a) with a carbon substrate under conditions whereby isobutanol is produced.

12. The method of claim 11, wherein the heterologous polypeptide which catalyzes the substrate to product conversion of isobutyraldehyde to isobutanol has at least 95% identity to the amino acid sequence of SEQ ID NO: 36.

13. The method of claim 11, wherein the heterologous polypeptide which catalyzes the substrate to product conversion of isobutyraldehyde to isobutanol has the amino acid sequence of SEQ ID NO: 36.

* * * * *

SEQUENCE LISTING

```
<160> NUMBER OF SEQ ID NOS: 81

<210> SEQ ID NO 1
<211> LENGTH: 1128
<212> TYPE: DNA
<213> ORGANISM: Artificial sequence
<220> FEATURE:
```

<223> OTHER INFORMATION: Codon-optimized polynucleotide sequence-Horse-
       liver ADH

<400> SEQUENCE: 1

| | | | | | |
|---|---|---|---|---|---|
| atgtcaacag | ccggtaaagt | tattaagtgt | aaagcggcag | ttttgtggga | agagaaaaag | 60 |
| ccgtttagca | tagaagaagt | agaagtagcg | ccaccaaaag | cacacgaggt | tagaatcaag | 120 |
| atggttgcca | ccggaatctg | tagatccgac | gaccatgtgg | tgagtggcac | tctagttact | 180 |
| cctttgccag | taatcgcggg | acacgaggct | gccggaatcg | ttaatccat | aggtgaaggt | 240 |
| gttaccactg | ttcgtcctgg | tgataaagtg | atcccactgt | tcactcctca | atgtggtaag | 300 |
| tgtagagtct | gcaaacatcc | tgagggtaat | ttctgcctta | aaaatgattt | gtctatgcct | 360 |
| agaggtacta | tgcaggatgg | tacaagcaga | tttacatgca | gagggaaacc | tatacaccat | 420 |
| ttccttggta | cttctacatt | tcccaatac | acagtggtgg | acgagatatc | tgtcgctaaa | 480 |
| atcgatgcag | cttcaccact | ggaaaaagtt | tgcttgatag | ggtgcggatt | tccaccggt | 540 |
| tacggttccg | cagttaaagt | tgcaaaggtt | acacagggtt | cgacttgtgc | agtattcggt | 600 |
| ttaggaggag | taggactaag | cgttattatg | gggtgtaaag | ctgcaggcgc | agcgaggatt | 660 |
| ataggtgtag | acatcaataa | ggacaaattt | gcaaaagcta | aggaggtcgg | ggctactgaa | 720 |
| tgtgttaacc | ctcaagatta | taagaaacca | atacaagaag | tccttactga | aatgtcaaac | 780 |
| ggtgagttg | atttctcttt | tgaagttata | ggccgtcttg | tactatggt | aactgcgttg | 840 |
| tcctgctgtc | aagaggcata | tggagtcagt | gtgatcgtag | gtgttcctcc | tgattcacaa | 900 |
| aatttgtcga | tgaatcctat | gctgttgcta | agcggtcgta | catggaaggg | agctatattt | 960 |
| ggcggttttα | agagcaagga | tagtgttcca | aaacttgttg | ccgactttat | ggcgaagaag | 1020 |
| tttgctcttg | atcctttaat | tacacatgta | ttgccattcg | agaaaatcaa | tgaagggttt | 1080 |
| gatttgttaa | gaagtggtga | atctattcgt | acaattttaa | cttttttga | | 1128 |

<210> SEQ ID NO 2
<211> LENGTH: 1083
<212> TYPE: DNA
<213> ORGANISM: Saccharomyces cerevisiae

<400> SEQUENCE: 2

| | | | | | |
|---|---|---|---|---|---|
| atgtcttatc | ctgagaaatt | tgaaggtatc | gctattcaat | cacacgaaga | ttggaaaaac | 60 |
| ccaaagaaga | caaagtatga | cccaaaacca | ttttacgatc | atgacattga | cattaagatc | 120 |
| gaagcatgtg | gtgtctgcgg | tagtgatatt | cattgtgcag | ctggtcattg | gggcaatatg | 180 |
| aagatgccgc | tagtcgttgg | tcatgaaatc | gttggtaaag | ttgtcaagct | agggcccaag | 240 |
| tcaaacagtg | ggttgaaagt | cggtcaacgt | gttggtgtag | gtgctcaagt | cttttcatgc | 300 |
| ttggaatgtg | accgttgtaa | gaatgataat | gaaccatact | gcaccaagtt | tgttaccaca | 360 |
| tacagtcagc | cttatgaaga | cggctatgtg | tcgcagggtg | gctatgcaaa | ctacgtcaga | 420 |
| gttcatgaac | attttgtggt | gcctatccca | gagaatattc | catcacattt | ggctgctcca | 480 |
| ctattatgtg | gtggtttgac | tgtgtactct | ccattggttc | gtaacggttg | cggtccaggt | 540 |
| aaaaaagttg | gtatagttgg | tcttggtggt | atcggcagta | tgggtacatt | gatttccaaa | 600 |
| gccatggggg | cagagacgta | tgttatttct | cgttcttcga | gaaaaagaga | agatgcaatg | 660 |
| aagatgggcg | ccgatcacta | cattgctaca | ttagaagaag | gtgattgggg | tgaaaagtac | 720 |
| tttgacacct | cgacctgat | tgtagtctgt | gcttcctccc | ttaccgacat | tgacttcaac | 780 |
| attatgccaa | aggctatgaa | ggttggtggt | agaattgtct | caatctctat | accagaacaa | 840 |

```
cacgaaatgt tatcgctaaa gccatatggc ttaaaggctg tctccatttc ttacagtgct    900
ttaggttcca tcaaagaatt gaaccaactc ttgaaattag tctctgaaaa agatatcaaa    960
atttgggtgg aaacattacc tgttggtgaa gccggcgtcc atgaagcctt cgaaaggatg   1020
gaaaagggtg acgttagata tagatttacc ttagtcggct acgacaaaga attttcagac   1080
tag                                                                 1083

<210> SEQ ID NO 3
<211> LENGTH: 1086
<212> TYPE: DNA
<213> ORGANISM: Saccharomyces cerevisiae

<400> SEQUENCE: 3
atgctttacc cagaaaaatt tcagggcatc ggtatttcca acgcaaagga ttggaagcat     60
cctaaattag tgagttttga cccaaaaccc tttggcgatc atgacgttga tgttgaaatt    120
gaagcctgtg gtatctgcgg atctgatttt catatagccg ttggtaattg gggtccagtc    180
ccagaaaatc aaatccttgg acatgaaata attggccgcg tggtgaaggt tggatccaag    240
tgccacactg gggtaaaaat cggtgaccgt gttggtgttg gtgcccaagc cttggcgtgt    300
tttgagtgtg aacgttgcaa aagtgacaac gagcaatact gtaccaatga ccacgttttg    360
actatgtgga ctccttacaa ggacggctac atttcacaag gaggctttgc ctcccacgtg    420
aggcttcatg aacactttgc tattcaaata ccagaaaata ttccaagtcc gctagccgct    480
ccattattgt gtggtggtat tacagttttc tctccactac taagaaatgg ctgtggtcca    540
ggtaagaggg taggtattgt tggcatcggt ggtattgggc atgggggat tctgttggct    600 aaagctatgg gagccgaggt ttatgcgttt tcgcgaggcc actccaagcg ggaggattct    660
atgaaactcg gtgctgatca ctatattgct atgttgagg ataaaggctg acagaacaa    720 tactctaacg ctttggacct tcttgtcgtt tgctcatcat cttttgtcgaa agttaatttt    780 gacagtatcg ttaagattat gaagattgga ggctccatcg tttcaattgc tgctcctgaa    840
gttaatgaaa agcttgtttt aaaaccgttg ggcctaatgg gagtatcaat ctcaagcagt    900
gctatcggat ctaggaagga aatcgaacaa ctattgaaat tagttttccga aaagaatgtc    960 aaaatatggg tggaaaaact tccgatcagc gaagaaggcg tcagccatgc ctttacaagg   1020
atggaaagcg gagacgtcaa atacagattt actttggtcg attatgataa gaaattccat   1080
aaatag                                                              1086

<210> SEQ ID NO 4
<211> LENGTH: 1170
<212> TYPE: DNA
<213> ORGANISM: Clostridium acetobutylicum

<400> SEQUENCE: 4
atgctaagtt ttgattattc aataccaact aaagtttttt ttggaaaagg aaaaatagac    60
gtaattggag aagaaattaa gaaatatggc tcaagagtgc ttatagttta tggcggagga    120
agtataaaaa ggaacggtat atatgataga gcaacagcta tattaaaaga aaacaatata    180
gctttctatg aactttcagg agtagagcca atcctagga taacaacagt aaaaaaaggc    240
atagaaatat gtagagaaaa taatgtggat ttagtattag caatagggggg aggaagtgca    300 atagactgtt ctaaggtaat tgcagctgga gtttattatg atggcgatac atgggacatg    360
gttaaagatc catctaaaat aactaaagtt cttccaattg caagtatact tactctttca    420
gcaacagggt ctgaaatgga tcaaattgca gtaatttcaa atatggagac taatgaaaag    480
```

```
cttggagtag gacatgatga tatgagacct aaattttcag tgttagatcc tacatatact      540
tttacagtac ctaaaaatca aacagcagcg ggaacagctg acattatgag tcacaccttt      600
gaatcttact ttagtggtgt tgaaggtgct tatgtgcagg acggtatacg agaagcaatc      660
ttaagaacat gtataaagta tggaaaaata gcaatggaga agactgatga ttacgaggct      720
agagctaatt tgatgtgggc ttcaagttta gctataaatg gtctattatc acttggtaag      780
gatagaaaat ggagttgtca tcctatggaa cacgagttaa gtgcatatta tgatataaca      840
catggtgtag gacttgcaat tttaacacct aattggatgg aatatattct aaatgacgat      900
acacttcata aatttgtttc ttatggaata aatgtttggg gaatagacaa gaacaaagat      960
aactatgaaa tagcacgaga ggctattaaa aatacgagag aatactttaa ttcattgggt     1020
attccttcaa agcttagaga agttggaata ggaaaagata aactgaaact aatggcaaag     1080
caagctgtta gaaattctgg aggaacaata ggaagtttaa gaccaataaa tgcagaggat     1140
gttcttgaga tatttaaaaa atcttattaa                                      1170

<210> SEQ ID NO 5
<211> LENGTH: 1173
<212> TYPE: DNA
<213> ORGANISM: Clostridium acetobutylicum

<400> SEQUENCE: 5
atggttgatt tcgaatattc aataccaact agaattttt tcggtaaaga taagataaat        60
gtacttggaa gagagcttaa aaaatatggt tctaaagtgc ttatagttta tggtggagga      120
agtataaaga gaaatggaat atatgataaa gctgtaagta tacttgaaaa aaacagtatt      180
aaattttatg aacttgcagg agtagagcca atccaagag taactacagt tgaaaaagga      240
gttaaaatat gtagagaaaa tggagttgaa gtagtactag ctataggtgg aggaagtgca      300
atagattgcg caaaggttat agcagcagca tgtgaatatg atggaaatcc atgggatatt      360
gtgttagatg gctcaaaaat aaaaagggtg cttcctatag ctagtatatt aaccattgct      420
gcaacaggat cagaaatgga tacgtgggca gtaataaata tatggatac aaacgaaaaaa      480 ctaattgcgg cacatccaga tatggctcct aagttttcta tattagatcc aacgtatacg      540
tataccgtac ctaccaatca aacagcagca ggaacagctg atattatgag tcatatattt      600
gaggtgtatt ttagtaatac aaaaacagca tatttgcagg atagaatggc agaagcgtta      660
ttaagaactt gtattaaata tggaggaata gctcttgaga agccggatga ttatgaggca      720
agagccaatc taatgtgggc ttcaagtctt gcgataaatg acttttaac atatggtaaa      780 gacactaatt ggagtgtaca cttaatggaa catgaattaa gtgcttatta cgacataaca      840
cacggcgtag gcttgcaat tttaacacct aattggatgg agtatatttt aaataatgat      900
acagtgtaca gtttgttga atatggtgta aatgtttggg gaatagacaa agaaaaaaat      960
cactatgaca tagcacatca agcaatacaa aaacaagag attactttgt aaatgtacta     1020
ggtttaccat ctagactgag agatgttgga attgaagaag aaaaattgga cataatggca     1080
aaggaatcag taaagcttac aggaggaacc ataggaaacc taagaccagt aaacgcctcc     1140
gaagtcctac aaatattcaa aaaatctgtg taa                                  1173

<210> SEQ ID NO 6
<211> LENGTH: 1047
<212> TYPE: DNA
<213> ORGANISM: Achromobacter xylosoxidans
```

<400> SEQUENCE: 6

```
atgaaagctc tggtttatca cggtgaccac aagatctcgc ttgaagacaa gcccaagccc      60
acccttcaaa agcccacgga tgtagtagta cgggttttga agaccacgat ctgcggcacg     120
gatctcggca tctacaaagg caagaatcca gaggtcgccg acgggcgcat cctgggccat     180
gaagggtag gcgtcatcga ggaagtgggc gagagtgtca cgcagttcaa gaaaggcgac     240
aaggtcctga tttcctgcgt cacttcttgc ggctcgtgcg actactgcaa gaagcagctt     300
tactcccatt gccgcgacgg cgggtggatc ctgggttaca tgatcgatgg cgtgcaggcc     360
gaatacgtcc gcatcccgca tgccgacaac agcctctaca agatccccca gacaattgac     420
gacgaaatcg ccgtcctgct gagcgacatc ctgcccaccg ccacgaaat cggcgtccag     480
tatgggaatg tccagccggg cgatgcggtg gctattgtcg gcgcgggccc cgtcggcatg     540
tccgtactgt tgaccgccca gttctactcc ccctcgacca tcatcgtgat cgacatggac     600
gagaatcgcc tccagctcgc caaggagctc ggggcaacgc acaccatcaa ctccggcacg     660
gagaacgttg tcgaagccgt gcataggatt gcggcagagg agtcgatgt tgcgatcgag     720
gcggtgggca taccggcgac ttgggacatc tgccaggaga tcgtcaagcc ggcgcgcac     780
atcgccaacg tcggcgtgca tggcgtcaag gttgacttcg agattcagaa gctctggatc     840
aagaacctga cgatcaccac gggactggtg aacacgaaca cgacgcccat gctgatgaag     900
gtcgcctcga ccgacaagct tccgttgaag aagatgatta cccatcgctt cgagctggcc     960
gagatcgagc acgcctatca ggtattcctc aatggcgcca aggagaaggc gatgaagatc    1020
atcctctcga acgcaggcgc tgcctga                                        1047
```

<210> SEQ ID NO 7
<211> LENGTH: 981
<212> TYPE: DNA
<213> ORGANISM: Artificial sequence
<220> FEATURE:
<223> OTHER INFORMATION: Codon-optimized polynucleotide sequence-Bos
      taurus ARD

<400> SEQUENCE: 7

```
atggcggcga gctgcatttt gctgcacacc ggtcaaaaga tgccgctgat cggtctgggc      60
acctggaaat ctgacccagg tcaagtgaag gcggcaatta gtatgcgct gagcgtcggt     120
tatcgtcaca ttgactgcgc ggcaatctac ggcaatgaaa ccgagattgg cgaggcgttg     180
aaagagaacg tcggtccggg taagctggtc ccgcgtgaag aactgtttgt cacgagcaag     240
ctgtggaata ccaagcacca cccggaggac gtggaaccgg ctctgcgcaa accctggcc     300
gatctgcagt tggagtactt ggatctgtat ttgatgcact ggccgtatgc gtttgaacgc     360
ggtgactctc cgttcccgaa gaacgccgac ggcaccatcc gttacgacag cactcattat     420
aaagaaacct ggcgtgcgct ggaggcgctg gttgcaaaag gtctggtgcg tgccctgggt     480
ttgagcaatt ttaattctcg tcagatcgac gatgttctga gcgtggcctc tgtgcgtccg     540
gctgtgttgc aggtcgagtg tcacccttat ctggcgcaaa acgagctgat cgctcattgt     600
caagcgcgta atctgaagt gaccgcgtac tccccgctgg gtagcagcga ccgcgcctgg     660
cgtgatccgg aagaacctgt tctgctgaaa gaaccggtcg tgctggcgct ggctgaaaag     720
cacggtcgca gcccagcgca gatcttgctg cgttggcaag ttcagcgcaa agtttcttgc     780
atcccgaaat ctgtcacgcc gagccgtatt ctggagaaca ttcaagtttt cgacttcacc     840
tttagcccgg aagaaatgaa gcagctggac gccctgaaca agaatctgcg ttttattgtg    900
```

```
ccgatgttga ccgtggacgg caagcgcgtt ccgcgtgacg cgggtcaccc gttgtatcca    960
tttaacgatc cgtactaatg a                                              981
```

<210> SEQ ID NO 8
<211> LENGTH: 1125
<212> TYPE: DNA
<213> ORGANISM: Artificial sequence
<220> FEATURE:
<223> OTHER INFORMATION: Codon-optimized polynucleotide sequence-Rana perezi ADH8

<400> SEQUENCE: 8

```
atgtgcaccg ccggtaaaga tattacgtgt aaagcggcgg tcgcttggga gccgcataaa     60
ccgctgtccc tggaaacgat cacggttgca cctccaaaag cgcatgaggt gcgtattaaa    120
atcctggcgt ctggcatctg cggtagcgac agcagcgttc tgaaagagat catcccgagc    180
aagttcccgg tgattctggg tcatgaggcg gtgggcgtgg ttgagagcat cggtgcgggc    240
gttacgtgcg tgaaaccggg tgacaaggtg atcccgctgt cgtgccgcca atgtggttct    300
tgtcgcgcat gtaaaagcag caatagcaac ttctgtgaga gaatgatat gggcgcgaaa    360 acgggtttga tggcagacat gaccagccgt tttacgtgcc gtggtaagcc gatttataat    420
ctggtgggca ccagcaccct tacggagtac acggttgtgg ccgatatcgc ggtcgcaaag    480
atcgacccaa agccccgct ggagagctgc ctgatcggtt gtggttttgc gacgggttat    540
ggtgcagcgg ttaacacggc caaagttacc cctggcagca cctgtgcagt gtttggcctg    600
ggcggtgttg gtttcagcgc tattgttggt tgtaaagcag ctggcgcatc ccgtattatt    660
ggcgttggta ctcataagga taagttcccg aaggcaatcg aactgggcgc aactgagtgc    720
ctgaatccga aggactatga caaaccgatc tatgaggtta tttgcgagaa accaatggc    780 ggtgtggatt acgcggtcga gtgtgcgggt cgtattgaaa ctatgatgaa cgcattgcag    840
tcgacctatt gcggttctgg cgttactgtt gtgtttgggtc tggcgagccc gaacgagcgt    900
ctgccgctgg accgttgtt gctgctgacg ggccgttccc tgaaaggtag cgtgtttggc    960
ggctttaaag gtgaagaagt tagccgtctg gtggatgact acatgaagaa gaagatcaat   1020
gttaatttcc tggtgagcac caaactgacg ctggatcaga tcaacaaagc gttcgaattg   1080
ctgagcagcg gtcaaggcgt tcgtagcatt atgatctact aatga                   1125
```

<210> SEQ ID NO 9
<211> LENGTH: 1059
<212> TYPE: DNA
<213> ORGANISM: Artificial sequence
<220> FEATURE:
<223> OTHER INFORMATION: Codon-optimized polynucleotide sequence-Clostridium beijerinckii ADH

<400> SEQUENCE: 9

```
atgaaaggtt tcgctatgtt gggtattaat aagctgggtt ggattgagaa agagcgtccg     60
gtcgcaggca gctatgatgc aatcgttcgt ccgttggccg ttagcccgtg cacgagcgac    120
attcatacgg tgttcgaggg tgcactgggt gaccgtaaga acatgatcct gggtcatgag    180
gccgttggtg aagttgtcga agtcggtagc gaagtcaaag atttaaacc gggcgaccgt    240 gtcatcgttc catgcacgac gccagattgg cgtagcctgg aggtgcaggc aggtttccag    300
cagcatagca atggcatgct ggctggctgg aaattctcta atttcaagga tggtgtgttc    360
ggtgaatatt tccacgtgaa cgacgctgac atgaacctgg ctatcctgcc gaaggatatg    420
ccgctggaga acgcggtgat gatcacggat atgatgacta cggggttttca tggtgcggag    480
```

```
ctggcggaca tccaaatggg tagcagcgtg gtcgtcatcg gcatcggcgc tgtgggtctg      540
atgggcattg caggcgcaaa actgcgcggt gcgggtcgta tcatcggtgt gggtagccgc      600
cctatctgcg tggaggcggc gaagttttac ggtgcgactg acattctgaa ctataagaac      660
ggtcacattg ttgatcaagt gatgaagctg accaacggta aaggcgtgga tcgcgttatc      720
atggcgggtg gtggttcgga aacgctgagc caggcagtta gcatggtcaa gccgggtggc      780
attatcagca atattaatta ccacggtagc ggtgatgcgc tgctgatccc acgtgtcgag      840
tggggttgtg gtatggcaca aagaccatt aaaggcggtc tgtgcccggg tggtcgtttg       900
cgtgcggaaa tgctgcgtga tatggttgtc tataaccgtg ttgacctgag caagctggtg      960
acgcacgtct atcacggctt tgaccatatc gaagaggcgt tgctgctgat gaaggataaa     1020
ccgaaggacc tgattaaagc ggtcgtgatc ctgtaatga                             1059

<210> SEQ ID NO 10
<211> LENGTH: 1086
<212> TYPE: DNA
<213> ORGANISM: Artificial sequence
<220> FEATURE:
<223> OTHER INFORMATION: Codon-optimized polynucleotide sequence-
      Entamoeba histolytica ADH1

<400> SEQUENCE: 10
atgaagggcc tggcgatgct gggtatcggt cgtattggtt ggattgaaaa gaaaatcccg       60
gagtgcggcc cactggatgc gttggtccgt ccgctggcgc tggccccgtg caccagcgac      120
acccacaccg tgtgggctgg cgcaatcggc gaccgtcacg acatgattct gggtcacgaa      180
gcggtcggtc agatcgtgaa ggtgggttcc ctggtgaagc gtctgaaggt tggcgataag      240
gtgatcgtcc cggcgattac tccggactgg ggtgaagaag aaagccaacg tggttacccg      300
atgcatagcg gtggtatgct gggcggctgg aagttctcca atttcaagga cggtgtcttt      360
tccgaggtgt tccacgtgaa cgaggcggat gctaacctgg cactgctgcc gcgtgatatt      420
aaacctgaag atgcggtcat gctgagcgac atggtgacca ccggctttca cggtgccgaa      480
ttggcgaata ttaaactggg tgataccgtg tgcgttattg gtatcggccc agtgggtctg      540
atgagcgtgg ctggtgcgaa tcacctgggt gccggtcgca tcttcgcggt tggtagccgc      600
aaacactgtt gtgatatcgc tctggaatac ggcgcgactg atattatcaa ttacaagaat      660
ggcgacattg tggagcaaat tttgaaggcg accgatggta aaggcgttga caaggttgtt      720
attgcaggtg gcgatgttca tacgtttgca caagcggtca gatgattaa accgggtagc      780 gatattggta acgtgaatta tctgggtgaa ggcgataaca ttgacattcc gcgtagcgaa      840
tggggtgtgg gcatgggtca taaacacatc acggtggtt tgactcctgg cggtcgtgtc      900
cgcatggaaa agttggcttc gctgattagc accggcaaac tggacaccag caaactgatt      960
actcatcgtt tcgagggcct ggagaaggtg gaagatgcct tgatgctgat gaagaacaag     1020
ccggcagatc tgattaagcc ggttgtccgt attcactatg acgatgaaga tacgttgcac     1080
taatga                                                                1086

<210> SEQ ID NO 11
<211> LENGTH: 1047
<212> TYPE: DNA
<213> ORGANISM: Artificial sequence
<220> FEATURE:
<223> OTHER INFORMATION: Codon-optimized polynucleotide sequence-
      Beijerickia indica ADH
```

<400> SEQUENCE: 11

```
atgaaagcac tggtttaccg tggccctggc caaaagctgg tggaagaacg tcaaaagccg      60
gagctgaaag agccaggcga cgcgattgtg aaagtcacca aaacgaccat ctgtggtacg     120
gacttgcaca ttctgaaggg cgatgtggcg acgtgtaagc cgggtcgcgt gctgggtcac     180
gaaggtgtgg gtgttattga aagcgttggc agcggcgtta ccgcgttcca accgggtgat     240
cgcgtcctga tctcttgtat ttctagctgt ggcaagtgca gcttttgtcg ccgtggcatg     300
tttagccact gtaccactgg cggctggatt ctgggtaatg agattgacgg tacgcaggca     360
gagtacgttc gtgtcccgca tgccgacacc tctctgtatc gtattccagc gggtgcggac     420
gaagaggcgc tggtgatgct gagcgatatc ctgccgaccg gtttcgagtg tggtgtcctg     480
aatggtaagg ttgcgcctgg cagcagcgtt gcgatcgttg cgcaggccc tgtcggtttg      540
gccgcattgc tgacggcgca gttctactct ccggcagaga ttatcatgat tgatctggac     600
gacaaccgcc tggccctggc gaagcaattc ggcgcaacgc gtaccgttaa tagcaccggt     660
ggtaacgcag cagcagaggt caaggctctg acggagggcc tggtgttga cacggctatt     720
gaggctgttg catcccggc caccttcgag ctgtgccaga acattgtggc tccgggtggc     780
actattgcga atgtcggcgt tcacggttcg aaagtggatc tgcatctgga atctctgtgg     840
agccataatg tgactatcac gacgcgtctg gtggacacgg caacgacgcc gatgctgctg     900
aaaccgtgc aatctcataa actggacccg agccgtctga tcacccatcg ttttagcctg     960
gaccaaatcc tggatgcgta cgaaacgttt ggtcaggccg caagcaccca ggcgctgaag    1020
gttattatca gcatggaggc gtaatga                                        1047
```

<210> SEQ ID NO 12
<211> LENGTH: 1134
<212> TYPE: DNA
<213> ORGANISM: Artificial sequence
<220> FEATURE:
<223> OTHER INFORMATION: Codon-optimized polynucleotide sequence-Rattus
      norvegicus ADH1

<400> SEQUENCE: 12

```
atgagcaccg caggtaaagt gattaaatgc aaagcagcag ttctgtggga accgcataaa      60
ccgtttacca ttgaagatat tgaagttgca cctccgaaag cacatgaagt gcgcattaaa     120
atggttgcaa ccgtgtttg tcgttctgat gatcatgcag ttagcggtag cctgtttaca     180
ccgctgcctg cagttctggg tcatgaaggt gcaggtattg ttgaaagcat tggtgaaggt     240
gttacctgtg ttaaaccggg tgataaagtg attccgctgt tttctccgca gtgtggtaaa     300
tgtcgcattt gcaaacatcc ggaaagcaat ctgtgttgcc agaccaaaaa tctgacccag     360
ccgaaaggtg cactgctgga tggcaccagc cgtttagct gtcgtggtaa accgattcat     420
cattttatta gcaccagcac ctttagccag tataccgtgg ttgatgatat tgccgtggca     480
aaaattgatg cagcagcacc gctggataaa gtttgtctga ttggttgtgg ttttagcacc     540
ggttatggta gcgcagttca ggttgcaaaa gttacaccgg gtagcacctg tgcagttttt     600
ggtctgggtg tgttggtct gagcgttgtt attggttgta aaccgcagg cgcagcaaaa     660
attattgccg tggatattaa taaagataaa tttgccaaag ccaaagaact gggtgcaacc     720
gattgtatta atccgcagga ttataccaaa ccgattcagg aagttctgca ggaaatgacc     780
gatggtggtg tggatttag ctttgaagtg attggtcgtc tggataccat gaccagcgca     840
ctgctgagct gtcatagcgc atgtggtgtt agcgttattg ttggtgttcc tccgagcgca     900
```

| | |
|---|---|
| cagagcctga gcgttaatcc gatgagcctg ctgctgggtc gtacctggaa aggtgcaatt | 960 |
| tttggtggct ttaaaagcaa agatgccgtt ccgaaactgg ttgcagattt tatggccaaa | 1020 |
| aaatttccgc tggaaccgct gattacccat gttctgccgt ttgaaaaaat taatgaagcc | 1080 |
| tttgatctgc tgcgtgcagg taaaagcatt cgtaccgtgc tgacctttta ataa | 1134 |

<210> SEQ ID NO 13
<211> LENGTH: 1047
<212> TYPE: DNA
<213> ORGANISM: Artificial sequence
<220> FEATURE:
<223> OTHER INFORMATION: Codon-optimized polynucleotide sequence-Thermus
      sp. ATN1 ADH

<400> SEQUENCE: 13

| | |
|---|---|
| atgcgtgcag ttgtgtttga aacaaagaa cgcgtggccg ttaaagaagt taacgcaccg | 60 |
| cgtctgcagc atccgctgga tgcactggtt cgtgttcatc tggcaggtat tgtggtagc | 120 |
| gatctgcatc tgtatcatgg taaaattccg gttctgcctg gtagcgttct gggtcatgaa | 180 |
| tttgttggtc aggttgaagc agttggtgaa ggtattcagg atctgcagcc tggtgattgg | 240 |
| gttgttggtc gtttcatat tgcatgtggc acctgtccgt attgtcgtcg tcatcagtat | 300 |
| aatctgtgtg aacgtggtgg tgtttatggt tatggtccga tgtttggtaa tctgcagggt | 360 |
| gcacaggcag aaattctgcg tgttccgttt agcaatgtga atctgcgtaa actgcctccg | 420 |
| aatctgtctc cggaacgtgc aatttttgcc ggtgatattc tgagcaccgc ctatggtggt | 480 |
| ctgattcagg tcagctgcg tcctggtgat agcgttgcag ttattggtgc aggtccggtt | 540 |
| ggtctgatgg caattgaagt tgcacaggtt ctgggtgcaa gcaaaattct ggccattgat | 600 |
| cgtattccgg aacgtctgga acgtgcagca agcctgggtg caattccgat taatgccgaa | 660 |
| caggaaaatc cggttcgtcg cgttcgtagc gaaaccaatg atgaaggtcc ggatctggtt | 720 |
| ctggaagccg ttggtggtgc agcaaccctg agcctggcac tggaaatggt tcgtcctggt | 780 |
| ggtcgtgtta gcgcagttgg tgttgataat gcaccgagct ttccgttttcc gctggcaagc | 840 |
| ggtctggtta aagatctgac gtttcgtatt ggtctggcaa atgtgcatct gtatattgat | 900 |
| gcagttctgg cactgctggc cagcggtcgt ctgcagccgg aacgtattgt tagccattat | 960 |
| ctgccgctgg aagaagcacc tcgcggttac gaactgtttg atcgcaaaga agcactgaaa | 1020 |
| gttctgctgg ttgtgcgtgg ttaataa | 1047 |

<210> SEQ ID NO 14
<211> LENGTH: 1041
<212> TYPE: DNA
<213> ORGANISM: Artificial sequence
<220> FEATURE:
<223> OTHER INFORMATION: Codon-optimized polynucleotide sequence-
      Phenylobacteriaum zucineum HLK1 ADH

<400> SEQUENCE: 14

| | |
|---|---|
| atgaaagcac tggtttatgg tggtccgggt cagaaaagcc tggaagatcg tccgaaaccg | 60 |
| gaactgcagg caccgggtga tgcaattgtt cgtattgtga aaaccaccat tgtggcacc | 120 |
| gatctgcata ttctgaaagg tgatgttgca acctgtgcac cgggtcgtat tctgggtcat | 180 |
| gaaggtgttg gtattgttga tagcgttggt gcagcagtta ccgcatttcg tccgggtgat | 240 |
| catgttctga ttagctgtat tagcgcctgt ggtaaatgtg attattgccg tcgtggtatg | 300 |
| tatagccatt gtacaaccgg tgatggaatt ctgggtaatg aaattgatgg cacccaggca | 360 |
| gaatatgttc gtacaccgca tgcagatacc agcctgtatc cggttccggc aggcgcagat | 420 |

```
gaagaggcac tggttatgct gagcgatatt ctgccgaccg ttttgaatg tggtgtgctg    480 aatggtaaag ttgcaccggg tggcaccgtt gcaattgttg gtgcaggtcc gattggtctg    540
gcagcactgc tgaccgcaca gttttattct ccggcagaaa ttattatgat tgatctggat    600
gataatcgtc tgggtattgc acgtcagttt ggtgcaaccc agaccattaa tagcggtgat    660
ggtcgtgcag cagaaaccgt taaagcactg accggtggtc gtggtgttga taccgcaatt    720
gaagcagttg tgttccggc aacctttgaa ctgtgtcagg atctggttgg tcctggtggt    780
gttattgcaa atattggtgt gcatggtcgt aaagttgatc tgcatctgga tcgtctgtgg    840
agccagaata ttgcaattac acccgtctg gttgataccg ttagcacccc gatgctgctg    900
aaaaccgttc agagccgtaa actggacccg agccagctga ttacccatcg ttttcgcctg    960
gatgaaattc tggcagccta tgatacctt gcacgtgcag cagataccca ggcactgaaa   1020
gttattattg cagcctaata a                                              1041
```

<210> SEQ ID NO 15
<211> LENGTH: 1041
<212> TYPE: DNA
<213> ORGANISM: Artificial sequence
<220> FEATURE:
<223> OTHER INFORMATION: Codon-optimized polynucleotide sequence-
      Methlyoceclla silvestris BL2 ADH

<400> SEQUENCE: 15

```
atgaaagcac tggtttatca tggtccgggt cagaaagcac tggaagaacg tccgaaaccg    60
cagattgaag caagcggtga tgccattgtt aaaattgtga aaaccaccat ttgtggcacc   120
gatctgcata ttctgaaagg tgatgttgca acctgtgcac cgggtcgtat tctgggtcat   180
gaaggtgtgg gtattattga tagcgttggt gccggtgtta ccgcatttca gcctggtgat   240
cgtgttctga ttagctgtat tagcagctgt ggcaaatgtg attattgtcg tcgtggtctg   300
tatagccatt gtacaaccgg tggttggatt ctgggtaatg aaattgatgg cacccaggca   360
gaatatgttc gtacaccgca tgcagatacc agcctgtatc gtattccggc aggcgcagat   420
gaagaggcac tggttatgct gagcgatatt ctgccgaccg ttttgaatg tggtgtgctg    480 aatggtaaag ttgaaccggg tagcaccgtt gcaattgttg gtgcaggtcc gattggtctg    540
gcagcactgc tgaccgcaca gttttatgca ccgggtgata ttattatgat tgatctggat    600
gataatcgtc tggatgttgc acgtcgtttt ggtgcaaccc ataccattaa tagcggtgat    660
ggtaaagcag cagaagcagt taaagcactg accggtggta ttggtgttga taccgcaatt    720
gaagccgttg tattccggc aacctttctg ctgtgtgaag atattgttgc accgggtggt    780
gttattgcaa atgttggtgt gcatggtgtt aaagttgatc tgcatctgga acgtctgtgg    840
gcacataata ttaccattac acccgtctg gttgataccg ttaccacccc gatgctgctg    900
aaaaccgttc agagcaaaaa actggacccg ctgcagctga ttacccatcg ttttaccctg    960
gatcatattc tggatgccta tgatacctt agccgtgcag cagataccaa agccctgaaa   1020
gttattgtga gcgcctaata a                                              1041
```

<210> SEQ ID NO 16
<211> LENGTH: 1086
<212> TYPE: DNA
<213> ORGANISM: Artificial sequence
<220> FEATURE:
<223> OTHER INFORMATION: Codon-optimized polynucleotide sequence-
      Acinetobacter baumannii AYE ADH

<400> SEQUENCE: 16

```
atggaaaata ttatgaaagc aatggtgtat tatggcgatc atgatattcg ttttgaagaa      60
cgcaaaaaac cggaactgat tgatccgacc gatgccatta ttaaaatgac caaaaccacc     120
atttgtggca ccgatctggg tatttataaa ggcaaaaatc cggaaattga acagaaagaa     180
caggaaaaaa acggcagctt taatggtcgt attctgggtc atgaaggtat tggtattgtg     240
gagcagattg gtagcagcgt gaaaaacatt aaagtgggcg ataaagttat tgttagctgc     300
gttagccgtt gtggcacctg tgaaaattgt gccaacagc tgtatagcca ttgtcgtaat     360
gatggtggtt ggattatggg ctatatgatt gatggcaccc aggcagaata tgttcgtacc     420
ccgtttgcag ataccagcct gtatgttctg ccggaaggtc tgaatgaaga tgttgcagtt     480
ctgctgtctg atgcactgcc gaccgcacat gaaattggtg ttcagaatgg cgatattaaa     540
ccgggtgata ccgttgcaat tgttggtgca ggtccggttg gtatgagcgc actgctgacc     600
gctcagtttt atagcccgag ccagattatt atgattgata tggatgaaaa tcgtctggca     660
atggcaaaag aactgggtgc aaccgatacc attaatagcg caccgaaga tgcaattgca     720
cgtgttatgg aactgaccaa tcagcgtggt gttgattgtg caattgaagc cgttggtatt     780
gaaccgacct gggatatttg tcagaatatt gtgaagaag tggtcatct ggcaaatgtt     840
ggtgttcatg gcaaaagcgt gaattttagc ctggaaaaac tgtggattaa aaatctgacc     900
attaccaccg gtctggttaa tgcaaatacc accggtatgc tgctgaaaag ctgttgtagc     960
ggtaaactgc cgatggaaaa actggcaacc catcatttta aatttaatga aattgaaaag    1020
gcctatgatg tgtttattaa tgcagccaaa gaaaaagcca tgaaagtgat tattgatttt    1080
taataa                                                              1086
```

<210> SEQ ID NO 17
<211> LENGTH: 1044
<212> TYPE: DNA
<213> ORGANISM: Artificial sequence
<220> FEATURE:
<223> OTHER INFORMATION: Codon-optimized polynucleotide sequence-
Geobacillus sp. WCH70 ADH

<400> SEQUENCE: 17

```
atgaaagcac tgacctatct gggtccgggt aaaaagaag tgatggaaaa accgaaaccg      60
aaaattgaaa agaaaccga tgccattgtg aaaattacca aaaccaccat tgtggcacc     120
gatctgcata ttctgagcgg tgatgttccg accgttgaag aaggtcgtat tctgggtcat     180
gaaggtgtgg gtattattga agaagttggc tctggcgtta aaatttttaa aaaggcgat     240
cgcgttctga ttagctgtat taccagctgt ggcaaatgcg aaaattgcaa aaaaggcctg     300
tatgcccatt gtgaagatgg tggttggatt ctggccatc tgattgatgg cacccaggca     360
gaatatgttc gtattccgca tgcagataat agcctgtatc cgattccgga aggtgttgat     420
gaagaggcac tggttatgct gagcgatatt ctgccgaccg ttttgaaat tggtgtgctg     480
aatggtaaag ttcagcctgg tcagaccgtt gcaattattg gtgcaggtcc ggttggtatg     540
gcagcactgc tgaccgcaca gttttattct ccggcagaaa ttattatggt ggatctggat     600
gataatcgtc tggaagtggc caaaaaattt ggtgcaaccc aggttgttaa tagcgcagat     660
ggtaaagccg tggaaaaaat tatggaactg accggtggca aggtgtgga tgttgcaatg     720
gaagcagttg gtattccggt gacctttgat atttgccagg aaattgttaa acctggcggt     780
tatattgcaa atattggcgt gcatggtaaa agcgtggaat tcatattga aaaactgtgg     840
```

| | |
|---|---|
| attcgcaaca ttaccctgac caccggtctg gttaataccg cctctacccc gatgctgctg | 900 |
| aaaaccgttc agagcaaaaa actgaaaccg aacagctga ttacccatcg ttttgccttt | 960 |
| gccgatatta tgaaagccta tgaagtgttt ggtaatgcag ccaaagaaaa agccctgaaa | 1020 |
| gtgattatta gcaatgatta taa | 1044 |

```
<210> SEQ ID NO 18
<211> LENGTH: 1086
<212> TYPE: DNA
<213> ORGANISM: Artificial sequence
<220> FEATURE:
<223> OTHER INFORMATION: Codon-optimized polynucleotide sequence-
      Vanderwaltozyma polyspora DSM 70294 ADH

<400> SEQUENCE: 18
```

| | |
|---|---|
| atgagctatc cggaaaaatt tcagggtatt ggcattacca atcgcgaaga ttggaaacat | 60 |
| ccgaaaaaag tgacctttga accgaaacag tttaatgata agatgtgga tattaaaatt | 120 |
| gaagcctgcg gtgtttgtgg ttctgatgtt cattgtgcag caagccattg ggtccggtt | 180 |
| gcagaaaaac aggttgtggg ccatgaaatt attggtcgtg tgctgaaagt tggtccgaaa | 240 |
| tgtaccaccg gtattaaagt tggtgatcgt gttggtgttg gtgcacaggc atggtcttgt | 300 |
| ctggaatgta gccgttgcaa aagcgataat gaaagctatt gtccgaaaag cgtttggacc | 360 |
| tatagcattc gtatattga tggttatgtt agccagggtg ttatgcaag ccatattcgc | 420 |
| ctgcatgaac attttgcaat tccgattccg gataaactga gcaatgaact ggcagcaccg | 480 |
| ctgctgtgtg tggtattac cgtttattct ccgctgctgc gtaatggttg tggtccgggt | 540 |
| aaaaaagttg gtattgtggg cattggtggt attggtcaca tgggtctgct gtttgcaaaa | 600 |
| ggtatgggtg ccgaagttta tgcatttagc cgcacccata gcaaagaggc agacgccaaa | 660 |
| aaactgggtg ccgatcattt tattgcaacc ctggaagata agattggac caccaaatat | 720 |
| tttgatagccc tggatctgct ggttatttgt gcaagcagcc tgaccgatat taattttgat | 780 |
| gaactgacca aaattatgaa agtgaatacc aaaattatta gcattagcgc accggcagca | 840 |
| gatgaagttc tgaccctgaa accgtttggt ctgattggtg tgaccattgg taatagcgca | 900 |
| attggtagcc gtcgtgaaat tgaacatctg ctgaattttg tggccgaaaa agatattaaa | 960 |
| ccgtgggttg aaaccctgcc ggttggtgaa gccggtgtta tgaagcatt tgaacgcatg | 1020 |
| gataaaggtg atgtgaaata tcgttttacc ctggtggatt ttgataaaga atttggcaat | 1080 |
| taataa | 1086 |

```
<210> SEQ ID NO 19
<211> LENGTH: 1050
<212> TYPE: DNA
<213> ORGANISM: Artificial sequence
<220> FEATURE:
<223> OTHER INFORMATION: Codon-optimized polynucleotide sequence-Mucor
      circinelloides ADH

<400> SEQUENCE: 19
```

| | |
|---|---|
| atgagcgaag aaacctttac cgcatgggca tgtaaaagca aagcgcacc gctggaaccg | 60 |
| atggaaatga ccttttgcca ttgggatgat gatatggttc agatggatgt tatttgttgt | 120 |
| ggtgtttgtg gcaccgatct gcataccgtt gatgaaggtt ggggtccgac cgaatttccg | 180 |
| tgtgttgtgg gccatgaaat tattggcaat gtgaccaaag tgggtaaaaa tgtgaccccgt | 240 |
| attaaagttg gtgatcgttg tggtgttggt gtcagagcg caagctgtgg taaatgcgat | 300 |
| ttttgcaaaa aaggcatgga aaatctgtgt agcacccatg cagtttggac ctttaatgat | 360 |

```
cgctatgata atgccaccaa agataaaacc tatggtggct ttgcaaaaaa atggcgtggc     420
aatcaggatt ttgttgttca tgtgccgatg gattttctc cggaagttgc agcaagcttt     480
ctgtgtggtg gtgttaccac ctatgcaccg ctgaaacgtt atggtgttgg taaaggtagc     540
aaagttgcag ttctgggtct gggtggtctg ggccattttg gtgttcagtg ggcaaaagca     600
atgggtgcag aagttgttgc ctttgacgtg attccggata agtggatga tgccaaaaaa     660 ctgggctgtg atgattatgt tctgatgcag aagaagagc agatggaacc gcattataat     720
acctttaccc atattctggc caccaaaatt gtgaataaat gctgggatca gtattttaaa     780
atgctgaaaa ataatggcat ttttatgctg tgcgatattc cggaagttcc gctgagcggt     840
atgagcgcat ttgttatggc aggtaaacag ctgaccattg caggcacctt tattggtagc     900
ccgagcgtta ttcaggaatg tctggatttt gcagccaagc ataatgttcg tacctggggtt    960 aatacctttc cgatggaaaa aattaatgaa gcctttgaat tgttcgtca ggcaaaaccg     1020 cgttatcgtg ccgttgtgat gaattaataa                                     1050

<210> SEQ ID NO 20
<211> LENGTH: 1056
<212> TYPE: DNA
<213> ORGANISM: Artificial sequence
<220> FEATURE:
<223> OTHER INFORMATION: Codon-optimized polynucleotide sequence-
      Rhodococcus erythropolis PR4 ADH

<400> SEQUENCE: 20
atgtttaccg ttaatgcacg tagcaccagc gcaccgggtg taccgtttga agcagttgtt      60
attgaacgtc gtgatccggg tccgggtgat gttgttattg atattgcctt tagcggtatt     120
tgtcataccg atgttagccg tgcacgtagc gaatttggca ccacccatta tccgctggtt     180
ccgggtcatg aaattgccgg tgttgttagc aaagttggtt ccgatgttac caaatttgca     240
gttggtgatc gtgttggtgt tggttgtatt gttgatagct gccgtgaatg tgattattgt     300
cgtgcaggtc tggaaccgta ttgtcgtaaa gatcatgtgc gcacctataa agcatgggt      360 cgtgatggtc gtattacccct gggtggttat agcgaaaaaa ttgtggtgga tgaaggttat     420
gttctgcgta ttccggatgc aattccgctg atcaggcag caccgctgct gtgtgcaggt     480
attaccatgt attctccgct gcgtcattgg aaagcaggtc cgggtagccg tattgcaatt     540
gttggttttg gtggtctggg tcatgttggt gttgcaattg cacgtgcact gggtgcacat     600
accaccgttt ttgatctgac gatggataaa catgatgatg caattcgtct gggtgcagat     660
gattatcgtc tgagcaccga tgcaggcatt tttaaagaat ttgaaggtgc ctttgaactg     720
attgttagca ccgttccggc aaatctggat atgaccctgt ttctgaaaat gctggcactg     780
gatggcacct ttgttcagct gggtgttccg cataatccgg ttagcctgga tgtttttagc     840
ctgttttata tcgtcgtag cctggcaggc accctggttg gtggtattgg tgaaacccag     900
gaaatgctgg attttgcgc agaacatagc attgttgccg aaattgaaac cgttggtgcc     960
gatgaaattg atagcgccta tgatcgtgtt gcagccggtg atgttcgtta tcgtatggtt    1020
ctggatgttg gcaccctggc aacccagcgt taataa                               1056

<210> SEQ ID NO 21
<211> LENGTH: 375
<212> TYPE: PRT
<213> ORGANISM: Equus caballus

<400> SEQUENCE: 21
```

Met Ser Thr Ala Gly Lys Val Ile Lys Cys Lys Ala Ala Val Leu Trp
1               5                   10                  15

Glu Glu Lys Lys Pro Phe Ser Ile Glu Val Glu Val Ala Pro Pro
            20                  25                  30

Lys Ala His Glu Val Arg Ile Lys Met Val Ala Thr Gly Ile Cys Arg
        35                  40                  45

Ser Asp Asp His Val Val Ser Gly Thr Leu Val Thr Pro Leu Pro Val
50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Thr Pro
                85                  90                  95

Gln Cys Gly Lys Cys Arg Val Cys Lys His Pro Glu Gly Asn Phe Cys
            100                 105                 110

Leu Lys Asn Asp Leu Ser Met Pro Arg Gly Thr Met Gln Asp Gly Thr
        115                 120                 125

Ser Arg Phe Thr Cys Arg Gly Lys Pro Ile His His Phe Leu Gly Thr
130                 135                 140

Ser Thr Phe Ser Gln Tyr Thr Val Val Asp Glu Ile Ser Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Lys Val Ala Lys Val Thr Gln
            180                 185                 190

Gly Ser Thr Cys Ala Val Phe Gly Leu Gly Gly Val Gly Leu Ser Val
        195                 200                 205

Ile Met Gly Cys Lys Ala Ala Gly Ala Ala Arg Ile Ile Gly Val Asp
210                 215                 220

Ile Asn Lys Asp Lys Phe Ala Lys Ala Lys Glu Val Gly Ala Thr Glu
225                 230                 235                 240

Cys Val Asn Pro Gln Asp Tyr Lys Lys Pro Ile Gln Glu Val Leu Thr
                245                 250                 255

Glu Met Ser Asn Gly Gly Val Asp Phe Ser Phe Glu Val Ile Gly Arg
            260                 265                 270

Leu Asp Thr Met Val Thr Ala Leu Ser Cys Cys Gln Glu Ala Tyr Gly
        275                 280                 285

Val Ser Val Ile Val Gly Val Pro Pro Asp Ser Gln Asn Leu Ser Met
290                 295                 300

Asn Pro Met Leu Leu Leu Ser Gly Arg Thr Trp Lys Gly Ala Ile Phe
305                 310                 315                 320

Gly Gly Phe Lys Ser Lys Asp Ser Val Pro Lys Leu Val Ala Asp Phe
                325                 330                 335

Met Ala Lys Lys Phe Ala Leu Asp Pro Leu Ile Thr His Val Leu Pro
            340                 345                 350

Phe Glu Lys Ile Asn Glu Gly Phe Asp Leu Leu Arg Ser Gly Glu Ser
        355                 360                 365

Ile Arg Thr Ile Leu Thr Phe
370                 375

<210> SEQ ID NO 22
<211> LENGTH: 360
<212> TYPE: PRT
<213> ORGANISM: Saccharomyces cerevisiae

<400> SEQUENCE: 22

```
Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60

Val Val Gly His Glu Ile Val Gly Lys Val Lys Leu Gly Pro Lys
65                  70                  75                  80

Ser Asn Ser Gly Leu Lys Val Gly Gln Arg Val Gly Val Gly Ala Gln
            85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
            115                 120                 125

Tyr Val Ser Gln Gly Gly Tyr Ala Asn Tyr Val Arg Val His Glu His
        130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
        210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255

Ile Asp Phe Asn Ile Met Pro Lys Ala Met Lys Val Gly Gly Arg Ile
            260                 265                 270

Val Ser Ile Ser Ile Pro Glu Gln His Glu Met Leu Ser Leu Lys Pro
        275                 280                 285

Tyr Gly Leu Lys Ala Val Ser Ile Ser Tyr Ser Ala Leu Gly Ser Ile
        290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
                340                 345                 350

Gly Tyr Asp Lys Glu Phe Ser Asp
        355                 360
```

<210> SEQ ID NO 23
<211> LENGTH: 361
<212> TYPE: PRT
<213> ORGANISM: Saccharomyces cerevisiae

<400> SEQUENCE: 23

Met Leu Tyr Pro Glu Lys Phe Gln Gly Ile Gly Ile Ser Asn Ala Lys
1               5                   10                  15

Asp Trp Lys His Pro Lys Leu Val Ser Phe Asp Pro Lys Pro Phe Gly
            20                  25                  30

Asp His Asp Val Asp Val Glu Ile Glu Ala Cys Gly Ile Cys Gly Ser
            35                  40                  45

Asp Phe His Ile Ala Val Gly Asn Trp Gly Pro Val Pro Glu Asn Gln
    50                  55                  60

Ile Leu Gly His Glu Ile Ile Gly Arg Val Val Lys Val Gly Ser Lys
65                  70                  75                  80

Cys His Thr Gly Val Lys Ile Gly Asp Arg Val Gly Val Gly Ala Gln
                85                  90                  95

Ala Leu Ala Cys Phe Glu Cys Glu Arg Cys Lys Ser Asp Asn Glu Gln
                100                 105                 110

Tyr Cys Thr Asn Asp His Val Leu Thr Met Trp Thr Pro Tyr Lys Asp
            115                 120                 125

Gly Tyr Ile Ser Gln Gly Gly Phe Ala Ser His Val Arg Leu His Glu
    130                 135                 140

His Phe Ala Ile Gln Ile Pro Glu Asn Ile Pro Ser Pro Leu Ala Ala
145                 150                 155                 160

Pro Leu Leu Cys Gly Gly Ile Thr Val Phe Ser Pro Leu Leu Arg Asn
                165                 170                 175

Gly Cys Gly Pro Gly Lys Arg Val Ile Val Gly Ile Gly Gly Ile
                180                 185                 190

Gly His Met Gly Ile Leu Leu Ala Lys Ala Met Gly Ala Glu Val Tyr
                195                 200                 205

Ala Phe Ser Arg Gly His Ser Lys Arg Glu Asp Ser Met Lys Leu Gly
    210                 215                 220

Ala Asp His Tyr Ile Ala Met Leu Glu Asp Lys Gly Trp Thr Glu Gln
225                 230                 235                 240

Tyr Ser Asn Ala Leu Asp Leu Leu Val Val Cys Ser Ser Ser Leu Ser
                245                 250                 255

Lys Val Asn Phe Asp Ser Ile Val Lys Ile Met Lys Ile Gly Gly Ser
                260                 265                 270

Ile Val Ser Ile Ala Ala Pro Glu Val Asn Glu Lys Leu Val Leu Lys
            275                 280                 285

Pro Leu Gly Leu Met Gly Val Ser Ile Ser Ser Ala Ile Gly Ser
    290                 295                 300

Arg Lys Glu Ile Glu Gln Leu Leu Lys Leu Val Ser Glu Lys Asn Val
305                 310                 315                 320

Lys Ile Trp Val Glu Lys Leu Pro Ile Ser Glu Glu Gly Val Ser His
                325                 330                 335

Ala Phe Thr Arg Met Glu Ser Gly Asp Val Lys Tyr Arg Phe Thr Leu
            340                 345                 350

Val Asp Tyr Asp Lys Lys Phe His Lys
    355                 360

<210> SEQ ID NO 24
<211> LENGTH: 389
<212> TYPE: PRT
<213> ORGANISM: Clostridium acetobutylicum

<400> SEQUENCE: 24

Met Leu Ser Phe Asp Tyr Ser Ile Pro Thr Lys Val Phe Phe Gly Lys
1               5                   10                  15

```
Gly Lys Ile Asp Val Ile Gly Glu Glu Ile Lys Lys Tyr Gly Ser Arg
             20                  25                  30

Val Le

<400> SEQUENCE: 25

```
Met Val Asp Phe Glu Tyr Ser Ile Pro Thr Arg Ile Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Leu Ala Ile Gly
                85                  90                  95

Gly Gly Ser Ala Ile Asp Cys Ala Lys Val Ile Ala Ala Ala Cys Glu
                100                 105                 110

Tyr Asp Gly Asn Pro Trp Asp Ile Val Leu Asp Gly Ser Lys Ile Lys
            115                 120                 125

Arg Val Leu Pro Ile Ala Ser Ile Leu Thr Ile Ala Ala Thr Gly Ser
130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
            195                 200                 205

Thr Ala Tyr Leu Gln Asp Arg Met Ala Glu Ala Leu Leu Arg Thr Cys
210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
            275                 280                 285

Thr Pro Asn Trp Met Glu Tyr Ile Leu Asn Asn Asp Thr Val Tyr Lys
290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
            355                 360                 365

Gly Thr Ile Gly Asn Leu Arg Pro Val Asn Ala Ser Glu Val Leu Gln
370                 375                 380

Ile Phe Lys Lys Ser Val
385                 390
```

<210> SEQ ID NO 26

<211> LENGTH: 348
<212> TYPE: PRT
<213> ORGANISM: Achromobacter xylosoxidans

<400> SEQUENCE: 26

| Met | Lys | Ala | Leu | Val | Tyr | His | Gly | Asp | His | Lys | Ile | Ser | Leu | Glu | Asp |
|---|---|---|---|---|---|---|---|---|---|---|---|---|---|---|---|
| 1 | | | | 5 | | | | | 10 | | | | | 15 | |

Lys Pro Lys Pro Thr Leu Gln Lys Pro Thr Asp Val Val Arg Val
            20                  25                  30

Leu Lys Thr Thr Ile Cys Gly Thr Asp Leu Gly Ile Tyr Lys Gly Lys
                35                  40                  45

Asn Pro Glu Val Ala Asp Gly Arg Ile Leu Gly His Glu Gly Val Gly
 50                  55                  60

Val Ile Glu Glu Val Gly Glu Ser Val Thr Gln Phe Lys Lys Gly Asp
 65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
        275                 280                 285

Leu Val Asn Thr Asn Thr Thr Pro Met Leu Met Lys Val Ala Ser Thr
    290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345

<210> SEQ ID NO 27
<211> LENGTH: 325
<212> TYPE: PRT
<213> ORGANISM: Bos taurus

<400> SEQUENCE: 27

Met Ala Ala Ser Cys Ile Leu Leu His Thr Gly Gln Lys Met Pro Leu
1               5                   10                  15

Ile Gly Leu Gly Thr Trp Lys Ser Asp Pro Gly Gln Val Lys Ala Ala
            20                  25                  30

Ile Lys Tyr Ala Leu Ser Val Gly Tyr Arg His Ile Asp Cys Ala Ala
        35                  40                  45

Ile Tyr Gly Asn Glu Thr Glu Ile Gly Glu Ala Leu Lys Glu Asn Val
    50                  55                  60

Gly Pro Gly Lys Leu Val Pro Arg Glu Glu Leu Phe Val Thr Ser Lys
65                  70                  75                  80

Leu Trp Asn Thr Lys His His Pro Glu Asp Val Glu Pro Ala Leu Arg
                85                  90                  95

Lys Thr Leu Ala Asp Leu Gln Leu Glu Tyr Leu Asp Leu Tyr Leu Met
            100                 105                 110

His Trp Pro Tyr Ala Phe Glu Arg Gly Asp Ser Pro Phe Pro Lys Asn
        115                 120                 125

Ala Asp Gly Thr Ile Arg Tyr Asp Ser Thr His Tyr Lys Glu Thr Trp
    130                 135                 140

Arg Ala Leu Glu Ala Leu Val Ala Lys Gly Leu Val Arg Ala Leu Gly
145                 150                 155                 160

Leu Ser Asn Phe Asn Ser Arg Gln Ile Asp Asp Val Leu Ser Val Ala
                165                 170                 175

Ser Val Arg Pro Ala Val Leu Gln Val Glu Cys His Pro Tyr Leu Ala
            180                 185                 190

Gln Asn Glu Leu Ile Ala His Cys Gln Ala Arg Asn Leu Glu Val Thr
        195                 200                 205

Ala Tyr Ser Pro Leu Gly Ser Ser Asp Arg Ala Trp Arg Asp Pro Glu
    210                 215                 220

Glu Pro Val Leu Leu Lys Glu Pro Val Val Leu Ala Leu Ala Glu Lys
225                 230                 235                 240

His Gly Arg Ser Pro Ala Gln Ile Leu Leu Arg Trp Gln Val Gln Arg
                245                 250                 255

Lys Val Ser Cys Ile Pro Lys Ser Val Thr Pro Ser Arg Ile Leu Glu
            260                 265                 270

Asn Ile Gln Val Phe Asp Phe Thr Phe Ser Pro Glu Glu Met Lys Gln
        275                 280                 285

Leu Asp Ala Leu Asn Lys Asn Leu Arg Phe Ile Val Pro Met Leu Thr
    290                 295                 300

Val Asp Gly Lys Arg Val Pro Arg Asp Ala Gly His Pro Leu Tyr Pro
305                 310                 315                 320

Phe Asn Asp Pro Tyr
                325

<210> SEQ ID NO 28
<211> LENGTH: 373
<212> TYPE: PRT
<213> ORGANISM: Rama perezi

<400> SEQUENCE: 28

Met Cys Thr Ala Gly Lys Asp Ile Thr Cys Lys Ala Ala Val Ala Trp
1               5                   10                  15

Glu Pro His Lys Pro Leu Ser Leu Glu Thr Ile Thr Val Ala Pro Pro
            20                  25                  30

Lys Ala His Glu Val Arg Ile Lys Ile Leu Ala Ser Gly Ile Cys Gly

-continued

```
        35                  40                  45

Ser Asp Ser Ser Val Leu Lys Glu Ile Ile Pro Ser Lys Phe Pro Val
    50                  55                  60

Ile Leu Gly His Glu Ala Val Gly Val Val Glu Ser Ile Gly Ala Gly
65                  70                  75                  80

Val Thr Cys Val Lys Pro Gly Asp Lys Val Ile Pro Leu Phe Val Pro
                85                  90                  95

Gln Cys Gly Ser Cys Arg Ala Cys Lys Ser Ser Asn Ser Asn Phe Cys
            100                 105                 110

Glu Lys Asn Asp Met Gly Ala Lys Thr Gly Leu Met Ala Asp Met Thr
        115                 120                 125

Ser Arg Phe Thr Cys Arg Gly Lys Pro Ile Tyr Asn Leu Val Gly Thr
    130                 135                 140

Ser Thr Phe Thr Glu Tyr Thr Val Val Ala Asp Ile Ala Val Ala Lys
145                 150                 155                 160

Ile Asp Pro Lys Ala Pro Leu Glu Ser Cys Leu Ile Gly Cys Gly Phe
                165                 170                 175

Ala Thr Gly Tyr Gly Ala Ala Val Asn Thr Ala Lys Val Thr Pro Gly
            180                 185                 190

Ser Thr Cys Ala Val Phe Gly Leu Gly Gly Val Gly Phe Ser Ala Ile
        195                 200                 205

Val Gly Cys Lys Ala Ala Gly Ala Ser Arg Ile Ile Gly Val Gly Thr
    210                 215                 220

His Lys Asp Lys Phe Pro Lys Ala Ile Glu Leu Gly Ala Thr Glu Cys
225                 230                 235                 240

Leu Asn Pro Lys Asp Tyr Asp Lys Pro Ile Tyr Glu Val Ile Cys Glu
                245                 250                 255

Lys Thr Asn Gly Gly Val Asp Tyr Ala Val Glu Cys Ala Gly Arg Ile
            260                 265                 270

Glu Thr Met Met Asn Ala Leu Gln Ser Thr Tyr Cys Gly Ser Gly Val
        275                 280                 285

Thr Val Val Leu Gly Leu Ala Ser Pro Asn Glu Arg Leu Pro Leu Asp
    290                 295                 300

Pro Leu Leu Leu Leu Thr Gly Arg Ser Leu Lys Gly Ser Val Phe Gly
305                 310                 315                 320

Gly Phe Lys Gly Glu Glu Val Ser Arg Leu Val Asp Asp Tyr Met Lys
                325                 330                 335

Lys Lys Ile Asn Val Asn Phe Leu Val Ser Thr Lys Leu Thr Leu Asp
            340                 345                 350

Gln Ile Asn Lys Ala Phe Glu Leu Leu Ser Ser Gly Gln Gly Val Arg
        355                 360                 365

Ser Ile Met Ile Tyr
    370

<210> SEQ ID NO 29
<211> LENGTH: 351
<212> TYPE: PRT
<213> ORGANISM: Clostridium beijerinckii

<400> SEQUENCE: 29

Met Lys Gly Phe Ala Met Leu Gly Ile Asn Lys Leu Gly Trp Ile Glu
1               5                   10                  15

Lys Glu Arg Pro Val Ala Gly Ser Tyr Asp Ala Ile Val Arg Pro Leu
            20                  25                  30

```
Ala Val Ser Pro Cys Thr Ser Asp Ile His Thr Val Phe Glu Gly Ala
         35                  40                  45

Leu Gly Asp Arg Lys Asn Met Ile Leu Gly His Glu Ala Val Gly Glu
 50                  55                  60

Val Val Glu Val Gly Ser Glu Val Lys Asp Phe Lys Pro Gly Asp Arg
 65                  70                  75                  80

Val Ile Val Pro Cys Thr Thr Pro Asp Trp Arg Ser Leu Glu Val Gln
                 85                  90                  95

Ala Gly Phe Gln Gln His Ser Asn Gly Met Leu Ala Gly Trp Lys Phe
            100                 105                 110

Ser Asn Phe Lys Asp Gly Val Phe Gly Glu Tyr Phe His Val Asn Asp
        115                 120                 125

Ala Asp Met Asn Leu Ala Ile Leu Pro Lys Asp Met Pro Leu Glu Asn
130                 135                 140

Ala Val Met Ile Thr Asp Met Met Thr Thr Gly Phe His Gly Ala Glu
145                 150                 155                 160

Leu Ala Asp Ile Gln Met Gly Ser Ser Val Val Ile Gly Ile Gly
            165                 170                 175

Ala Val Gly Leu Met Gly Ile Ala Gly Ala Lys Leu Arg Gly Ala Gly
        180                 185                 190

Arg Ile Ile Gly Val Gly Ser Arg Pro Ile Cys Val Glu Ala Ala Lys
    195                 200                 205

Phe Tyr Gly Ala Thr Asp Ile Leu Asn Tyr Lys Asn Gly His Ile Val
            210                 215                 220

Asp Gln Val Met Lys Leu Thr Asn Gly Lys Gly Val Asp Arg Val Ile
225                 230                 235                 240

Met Ala Gly Gly Gly Ser Glu Thr Leu Ser Gln Ala Val Ser Met Val
                245                 250                 255

Lys Pro Gly Gly Ile Ile Ser Asn Ile Asn Tyr His Gly Ser Gly Asp
            260                 265                 270

Ala Leu Leu Ile Pro Arg Val Glu Trp Gly Cys Gly Met Ala His Lys
        275                 280                 285

Thr Ile Lys Gly Gly Leu Cys Pro Gly Gly Arg Leu Arg Ala Glu Met
    290                 295                 300

Leu Arg Asp Met Val Val Tyr Asn Arg Val Asp Leu Ser Lys Leu Val
305                 310                 315                 320

Thr His Val Tyr His Gly Phe Asp His Ile Glu Glu Ala Leu Leu Leu
                325                 330                 335

Met Lys Asp Lys Pro Lys Asp Leu Ile Lys Ala Val Val Ile Leu
        340                 345                 350

<210> SEQ ID NO 30
<211> LENGTH: 360
<212> TYPE: PRT
<213> ORGANISM: Entamoeba histolytica

<400> SEQUENCE: 30

Met Lys Gly Leu Ala Met Leu Gly Ile Gly Arg Ile Gly Trp Ile Glu
1               5                   10                  15

Lys Lys Ile Pro Glu Cys Gly Pro Leu Asp Ala Leu Val Arg Pro Leu
            20                  25                  30

Ala Leu Ala Pro Cys Thr Ser Asp Thr His Thr Val Trp Ala Gly Ala
        35                  40                  45

Ile Gly Asp Arg His Asp Met Ile Leu Gly His Glu Ala Val Gly Gln
    50                  55                  60
```

```
Ile Val Lys Val Gly Ser Leu Val Lys Arg Leu Lys Val Gly Asp Lys
 65                  70                  75                  80

Val Ile Val Pro Ala Ile Thr Pro Asp Trp Gly Glu Glu Glu Ser Gln
                 85                  90                  95

Arg Gly Tyr Pro Met His Ser Gly Gly Met Leu Gly Gly Trp Lys Phe
            100                 105                 110

Ser Asn Phe Lys Asp Gly Val Phe Ser Glu Val Phe His Val Asn Glu
        115                 120                 125

Ala Asp Ala Asn Leu Ala Leu Leu Pro Arg Asp Ile Lys Pro Glu Asp
    130                 135                 140

Ala Val Met Leu Ser Asp Met Val Thr Thr Gly Phe His Gly Ala Glu
145                 150                 155                 160

Leu Ala Asn Ile Lys Leu Gly Asp Thr Val Cys Val Ile Gly Ile Gly
                165                 170                 175

Pro Val Gly Leu Met Ser Val Ala Gly Ala Asn His Leu Gly Ala Gly
            180                 185                 190

Arg Ile Phe Ala Val Gly Ser Arg Lys His Cys Cys Asp Ile Ala Leu
        195                 200                 205

Glu Tyr Gly Ala Thr Asp Ile Ile Asn Tyr Lys Asn Gly Asp Ile Val
    210                 215                 220

Glu Gln Ile Leu Lys Ala Thr Asp Gly Lys Gly Val Asp Lys Val Val
225                 230                 235                 240

Ile Ala Gly Gly Asp Val His Thr Phe Ala Gln Ala Val Lys Met Ile
                245                 250                 255

Lys Pro Gly Ser Asp Ile Gly Asn Val Asn Tyr Leu Gly Glu Gly Asp
            260                 265                 270

Asn Ile Asp Ile Pro Arg Ser Glu Trp Gly Val Gly Met Gly His Lys
        275                 280                 285

His Ile His Gly Gly Leu Thr Pro Gly Gly Arg Val Arg Met Glu Lys
    290                 295                 300

Leu Ala Ser Leu Ile Ser Thr Gly Lys Leu Asp Thr Ser Lys Leu Ile
305                 310                 315                 320

Thr His Arg Phe Glu Gly Leu Glu Lys Val Glu Asp Ala Leu Met Leu
                325                 330                 335

Met Lys Asn Lys Pro Ala Asp Leu Ile Lys Pro Val Val Arg Ile His
            340                 345                 350

Tyr Asp Asp Glu Asp Thr Leu His
        355                 360

<210> SEQ ID NO 31
<211> LENGTH: 347
<212> TYPE: PRT
<213> ORGANISM: Beijerickia indica

<400> SEQUENCE: 31

Met Lys Ala Leu Val Tyr Arg Gly Pro Gly Gln Lys Leu Val Glu Glu
  1               5                  10                  15

Arg Gln Lys Pro Glu Leu Lys Glu Pro Gly Asp Ala Ile Val Lys Val
                 20                  25                  30

Thr Lys Thr Thr Ile Cys Gly Thr Asp Leu His Ile Leu Lys Gly Asp
             35                  40                  45

Val Ala Thr Cys Lys Pro Gly Arg Val Leu Gly His Glu Gly Val Gly
     50                  55                  60

Val Ile Glu Ser Val Gly Ser Gly Val Thr Ala Phe Gln Pro Gly Asp
```

```
            65                  70                  75                  80
Arg Val Leu Ile Ser Cys Ile Ser Ser Cys Gly Lys Cys Ser Phe Cys
                    85                  90                  95

Arg Arg Gly Met Phe Ser His Cys Thr Thr Gly Gly Trp Ile Leu Gly
                    100                 105                 110

Asn Glu Ile Asp Gly Thr Gln Ala Glu Tyr Val Arg Val Pro His Ala
                    115                 120                 125

Asp Thr Ser Leu Tyr Arg Ile Pro Ala Gly Ala Asp Glu Glu Ala Leu
            130                 135                 140

Val Met Leu Ser Asp Ile Leu Pro Thr Gly Phe Glu Cys Gly Val Leu
145                 150                 155                 160

Asn Gly Lys Val Ala Pro Gly Ser Ser Val Ala Ile Val Gly Ala Gly
                    165                 170                 175

Pro Val Gly Leu Ala Ala Leu Leu Thr Ala Gln Phe Tyr Ser Pro Ala
                    180                 185                 190

Glu Ile Ile Met Ile Asp Leu Asp Asp Asn Arg Leu Gly Leu Ala Lys
                    195                 200                 205

Gln Phe Gly Ala Thr Arg Thr Val Asn Ser Thr Gly Gly Asn Ala Ala
            210                 215                 220

Ala Glu Val Lys Ala Leu Thr Glu Gly Leu Gly Val Asp Thr Ala Ile
225                 230                 235                 240

Glu Ala Val Gly Ile Pro Ala Thr Phe Glu Leu Cys Gln Asn Ile Val
                    245                 250                 255

Ala Pro Gly Gly Thr Ile Ala Asn Val Gly Val His Gly Ser Lys Val
                    260                 265                 270

Asp Leu His Leu Glu Ser Leu Trp Ser His Asn Val Thr Ile Thr Thr
                    275                 280                 285

Arg Leu Val Asp Thr Ala Thr Thr Pro Met Leu Leu Lys Thr Val Gln
            290                 295                 300

Ser His Lys Leu Asp Pro Ser Arg Leu Ile Thr His Arg Phe Ser Leu
305                 310                 315                 320

Asp Gln Ile Leu Asp Ala Tyr Glu Thr Phe Gly Gln Ala Ala Ser Thr
                    325                 330                 335

Gln Ala Leu Lys Val Ile Ile Ser Met Glu Ala
                    340                 345

<210> SEQ ID NO 32
<211> LENGTH: 376
<212> TYPE: PRT
<213> ORGANISM: Rattus norvegicus

<400> SEQUENCE: 32

Met Ser Thr Ala Gly Lys Val Ile Lys Cys Lys Ala Ala Val Leu Trp
1               5                   10                  15

Glu Pro His Lys Pro Phe Thr Ile Glu Asp Ile Glu Val Ala Pro Pro
                    20                  25                  30

Lys Ala His Glu Val Arg Ile Lys Met Val Ala Thr Gly Val Cys Arg
            35                  40                  45

Ser Asp Asp His Ala Val Ser Gly Ser Leu Phe Thr Pro Leu Pro Ala
        50                  55                  60

Val Leu Gly His Glu Gly Ala Gly Ile Val Glu Ser Ile Gly Glu Gly
65                  70                  75                  80

Val Thr Cys Val Lys Pro Gly Asp Lys Val Ile Pro Leu Phe Ser Pro
                    85                  90                  95
```

```
Gln Cys Gly Lys Cys Arg Ile Cys Lys His Pro Glu Ser Asn Leu Cys
                100                 105                 110

Cys Gln Thr Lys Asn Leu Thr Gln Pro Lys Gly Ala Leu Leu Asp Gly
            115                 120                 125

Thr Ser Arg Phe Ser Cys Arg Gly Lys Pro Ile His His Phe Ile Ser
        130                 135                 140

Thr Ser Thr Phe Ser Gln Tyr Thr Val Val Asp Ile Ala Val Ala
145                 150                 155                 160

Lys Ile Asp Ala Ala Pro Leu Asp Lys Val Cys Leu Ile Gly Cys
                165                 170                 175

Gly Phe Ser Thr Gly Tyr Gly Ser Ala Val Gln Val Ala Lys Val Thr
            180                 185                 190

Pro Gly Ser Thr Cys Ala Val Phe Gly Leu Gly Gly Val Gly Leu Ser
        195                 200                 205

Val Val Ile Gly Cys Lys Thr Ala Gly Ala Ala Lys Ile Ile Ala Val
        210                 215                 220

Asp Ile Asn Lys Asp Lys Phe Ala Lys Ala Lys Glu Leu Gly Ala Thr
225                 230                 235                 240

Asp Cys Ile Asn Pro Gln Asp Tyr Thr Lys Pro Ile Gln Glu Val Leu
                245                 250                 255

Gln Glu Met Thr Asp Gly Gly Val Asp Phe Ser Phe Glu Val Ile Gly
            260                 265                 270

Arg Leu Asp Thr Met Thr Ser Ala Leu Leu Ser Cys His Ser Ala Cys
            275                 280                 285

Gly Val Ser Val Ile Val Gly Val Pro Pro Ser Ala Gln Ser Leu Ser
        290                 295                 300

Val Asn Pro Met Ser Leu Leu Leu Gly Arg Thr Trp Lys Gly Ala Ile
305                 310                 315                 320

Phe Gly Gly Phe Lys Ser Lys Asp Ala Val Pro Lys Leu Val Ala Asp
                325                 330                 335

Phe Met Ala Lys Lys Phe Pro Leu Glu Pro Leu Ile Thr His Val Leu
            340                 345                 350

Pro Phe Glu Lys Ile Asn Glu Ala Phe Asp Leu Leu Arg Ala Gly Lys
        355                 360                 365

Ser Ile Arg Thr Val Leu Thr Phe
        370                 375

<210> SEQ ID NO 33
<211> LENGTH: 347
<212> TYPE: PRT
<213> ORGANISM: Thermus sp. ATN1

<400> SEQUENCE: 33

Met Arg Ala Val Val Phe Glu Asn Lys Glu Arg Val Ala Val Lys Glu
1               5                   10                  15

Val Asn Ala Pro Arg Leu Gln His Pro Leu Asp Ala Leu Val Arg Val
                20                  25                  30

His Leu Ala Gly Ile Cys Gly Ser Asp Leu His Leu Tyr His Gly Lys
            35                  40                  45

Ile Pro Val Leu Pro Gly Ser Val Leu Gly His Glu Phe Val Gly Gln
        50                  55                  60

Val Glu Ala Val Gly Glu Gly Ile Gln Asp Leu Gln Pro Gly Asp Trp
65                  70                  75                  80

Val Val Gly Pro Phe His Ile Ala Cys Gly Thr Cys Pro Tyr Cys Arg
                85                  90                  95
```

Arg His Gln Tyr Asn Leu Cys Glu Arg Gly Gly Val Tyr Gly Tyr Gly
                100                 105                 110

Pro Met Phe Gly Asn Leu Gln Gly Ala Gln Ala Glu Ile Leu Arg Val
                115                 120                 125

Pro Phe Ser Asn Val Asn Leu Arg Lys Leu Pro Pro Asn Leu Ser Pro
            130                 135                 140

Glu Arg Ala Ile Phe Ala Gly Asp Ile Leu Ser Thr Ala Tyr Gly Gly
145                 150                 155                 160

Leu Ile Gln Gly Gln Leu Arg Pro Gly Asp Ser Val Ala Val Ile Gly
                165                 170                 175

Ala Gly Pro Val Gly Leu Met Ala Ile Glu Val Ala Gln Val Leu Gly
            180                 185                 190

Ala Ser Lys Ile Leu Ala Ile Asp Arg Ile Pro Glu Arg Leu Glu Arg
        195                 200                 205

Ala Ala Ser Leu Gly Ala Ile Pro Ile Asn Ala Glu Gln Glu Asn Pro
210                 215                 220

Val Arg Arg Val Arg Ser Glu Thr Asn Asp Glu Gly Pro Asp Leu Val
225                 230                 235                 240

Leu Glu Ala Val Gly Gly Ala Ala Thr Leu Ser Leu Ala Leu Glu Met
                245                 250                 255

Val Arg Pro Gly Gly Arg Val Ser Ala Val Gly Val Asp Asn Ala Pro
            260                 265                 270

Ser Phe Pro Phe Pro Leu Ala Ser Gly Leu Val Lys Asp Leu Thr Phe
        275                 280                 285

Arg Ile Gly Leu Ala Asn Val His Leu Tyr Ile Asp Ala Val Leu Ala
290                 295                 300

Leu Leu Ala Ser Gly Arg Leu Gln Pro Glu Arg Ile Val Ser His Tyr
305                 310                 315                 320

Leu Pro Leu Glu Glu Ala Pro Arg Gly Tyr Glu Leu Phe Asp Arg Lys
                325                 330                 335

Glu Ala Leu Lys Val Leu Leu Val Val Arg Gly
            340                 345

<210> SEQ ID NO 34
<211> LENGTH: 345
<212> TYPE: PRT
<213> ORGANISM: Phenylobacterium zucineum HLK1

<400> SEQUENCE: 34

Met Lys Ala Leu Val Tyr Gly Gly Pro Gly Gln Lys Ser Leu Glu Asp
1               5                   10                  15

Arg Pro Lys Pro Glu Leu Gln Ala Pro Gly Asp Ala Ile Val Arg Ile
            20                  25                  30

Val Lys Thr Thr Ile Cys Gly Thr Asp Leu His Ile Leu Lys Gly Asp
        35                  40                  45

Val Ala Thr Cys Ala Pro Gly Arg Ile Leu Gly His Glu Gly Val Gly
    50                  55                  60

Ile Val Asp Ser Val Gly Ala Ala Val Thr Ala Phe Arg Pro Gly Asp
65                  70                  75                  80

His Val Leu Ile Ser Cys Ile Ser Ala Cys Gly Lys Cys Asp Tyr Cys
                85                  90                  95

Arg Arg Gly Met Tyr Ser His Cys Thr Thr Gly Gly Trp Ile Leu Gly
            100                 105                 110

Asn Glu Ile Asp Gly Thr Gln Ala Glu Tyr Val Arg Thr Pro His Ala

```
                115                 120                 125
Asp Thr Ser Leu Tyr Pro Val Pro Ala Gly Ala Asp Glu Glu Ala Leu
    130                 135                 140

Val Met Leu Ser Asp Ile Leu Pro Thr Gly Phe Glu Cys Gly Val Leu
145                 150                 155                 160

Asn Gly Lys Val Ala Pro Gly Gly Thr Val Ala Ile Val Gly Ala Gly
                165                 170                 175

Pro Ile Gly Leu Ala Ala Leu Leu Thr Ala Gln Phe Tyr Ser Pro Ala
            180                 185                 190

Glu Ile Ile Met Ile Asp Leu Asp Asp Asn Arg Leu Gly Ile Ala Arg
        195                 200                 205

Gln Phe Gly Ala Thr Gln Thr Ile Asn Ser Gly Asp Gly Arg Ala Ala
    210                 215                 220

Glu Thr Val Lys Ala Leu Thr Gly Gly Arg Gly Val Asp Thr Ala Ile
225                 230                 235                 240

Glu Ala Val Gly Val Pro Ala Thr Phe Glu Leu Cys Gln Asp Leu Val
                245                 250                 255

Gly Pro Gly Gly Val Ile Ala Asn Ile Gly Val His Gly Arg Lys Val
            260                 265                 270

Asp Leu His Leu Asp Arg Leu Trp Ser Gln Asn Ile Ala Ile Thr Thr
        275                 280                 285

Arg Leu Val Asp Thr Val Ser Thr Pro Met Leu Leu Lys Thr Val Gln
    290                 295                 300

Ser Arg Lys Leu Asp Pro Ser Gln Leu Ile Thr His Arg Phe Arg Leu
305                 310                 315                 320

Asp Glu Ile Leu Ala Ala Tyr Asp Thr Phe Ala Arg Ala Ala Asp Thr
                325                 330                 335

Gln Ala Leu Lys Val Ile Ala Ala
            340                 345

<210> SEQ ID NO 35
<211> LENGTH: 345
<212> TYPE: PRT
<213> ORGANISM: Methyloceclla silvestris BL2

<400> SEQUENCE: 35

Met Lys Ala Leu Val Tyr His Gly Pro Gly Gln Lys Ala Leu Glu Glu
1               5                   10                  15

Arg Pro Lys Pro Gln Ile Glu Ala Ser Gly Asp Ala Ile Val Lys Ile
                20                  25                  30

Val Lys Thr Thr Ile Cys Gly Thr Asp Leu His Ile Leu Lys Gly Asp
            35                  40                  45

Val Ala Thr Cys Ala Pro Gly Arg Ile Leu Gly His Glu Gly Val Gly
        50                  55                  60

Ile Ile Asp Ser Val Gly Ala Gly Val Thr Ala Phe Gln Pro Gly Asp
65                  70                  75                  80

Arg Val Leu Ile Ser Cys Ile Ser Ser Cys Gly Lys Cys Asp Tyr Cys
                85                  90                  95

Arg Arg Gly Leu Tyr Ser His Cys Thr Thr Gly Gly Trp Ile Leu Gly
            100                 105                 110

Asn Glu Ile Asp Gly Thr Gln Ala Glu Tyr Val Arg Thr Pro His Ala
        115                 120                 125

Asp Thr Ser Leu Tyr Arg Ile Pro Ala Gly Ala Asp Glu Glu Ala Leu
    130                 135                 140
```

```
Val Met Leu Ser Asp Ile Leu Pro Thr Gly Phe Glu Cys Gly Val Leu
145                 150                 155                 160

Asn Gly Lys Val Glu Pro Gly Ser Thr Val Ala Ile Val Gly Ala Gly
                165                 170                 175

Pro Ile Gly Leu Ala Ala Leu Leu Thr Ala Gln Phe Tyr Ala Pro Gly
            180                 185                 190

Asp Ile Ile Met Ile Asp Leu Asp Asp Asn Arg Leu Asp Val Ala Arg
        195                 200                 205

Arg Phe Gly Ala Thr His Thr Ile Asn Ser Gly Asp Gly Lys Ala Ala
    210                 215                 220

Glu Ala Val Lys Ala Leu Thr Gly Gly Ile Gly Val Asp Thr Ala Ile
225                 230                 235                 240

Glu Ala Val Gly Ile Pro Ala Thr Phe Leu Leu Cys Glu Asp Ile Val
                245                 250                 255

Ala Pro Gly Gly Val Ile Ala Asn Val Gly Val His Gly Val Lys Val
            260                 265                 270

Asp Leu His Leu Glu Arg Leu Trp Ala His Asn Ile Thr Ile Thr Thr
        275                 280                 285

Arg Leu Val Asp Thr Val Thr Thr Pro Met Leu Leu Lys Thr Val Gln
    290                 295                 300

Ser Lys Lys Leu Asp Pro Leu Gln Leu Ile Thr His Arg Phe Thr Leu
305                 310                 315                 320

Asp His Ile Leu Asp Ala Tyr Asp Thr Phe Ser Arg Ala Ala Asp Thr
                325                 330                 335

Lys Ala Leu Lys Val Ile Val Ser Ala
            340                 345

<210> SEQ ID NO 36
<211> LENGTH: 360
<212> TYPE: PRT
<213> ORGANISM: Acinetobacter baumannii AYE

<400> SEQUENCE: 36

Met Glu Asn Ile Met Lys Ala Met Val Tyr Tyr Gly Asp His Asp Ile
1               5                   10                  15

Arg Phe Glu Glu Arg Lys Lys Pro Glu Leu Ile Asp Pro Thr Asp Ala
                20                  25                  30

Ile Ile Lys Met Thr Lys Thr Thr Ile Cys Gly Thr Asp Leu Gly Ile
            35                  40                  45

Tyr Lys Gly Lys Asn Pro Glu Ile Glu Gln Lys Glu Gln Glu Lys Asn
        50                  55                  60

Gly Ser Phe Asn Gly Arg Ile Leu Gly His Glu Gly Ile Gly Ile Val
65                  70                  75                  80

Glu Gln Ile Gly Ser Ser Val Lys Asn Ile Lys Val Gly Asp Lys Val
                85                  90                  95

Ile Val Ser Cys Val Ser Arg Cys Gly Thr Cys Glu Asn Cys Ala Lys
            100                 105                 110

Gln Leu Tyr Ser His Cys Arg Asn Asp Gly Gly Trp Ile Met Gly Tyr
        115                 120                 125

Met Ile Asp Gly Thr Gln Ala Glu Tyr Val Arg Thr Pro Phe Ala Asp
    130                 135                 140

Thr Ser Leu Tyr Val Leu Pro Glu Gly Leu Asn Glu Asp Val Ala Val
145                 150                 155                 160

Leu Leu Ser Asp Ala Leu Pro Thr Ala His Glu Ile Gly Val Gln Asn
                165                 170                 175
```

```
Gly Asp Ile Lys Pro Gly Asp Thr Val Ala Ile Val Gly Ala Gly Pro
            180                 185                 190

Val Gly Met Ser Ala Leu Leu Thr Ala Gln Phe Tyr Ser Pro Ser Gln
        195                 200                 205

Ile Ile Met Ile Asp Met Asp Glu Asn Arg Leu Ala Met Ala Lys Glu
    210                 215                 220

Leu Gly Ala Thr Asp Thr Ile Asn Ser Gly Thr Glu Asp Ala Ile Ala
225                 230                 235                 240

Arg Val Met Glu Leu Thr Asn Gln Arg Gly Val Asp Cys Ala Ile Glu
                245                 250                 255

Ala Val Gly Ile Glu Pro Thr Trp Asp Ile Cys Gln Asn Ile Val Lys
            260                 265                 270

Glu Gly Gly His Leu Ala Asn Val Gly Val His Gly Lys Ser Val Asn
        275                 280                 285

Phe Ser Leu Glu Lys Leu Trp Ile Lys Asn Leu Thr Ile Thr Thr Gly
    290                 295                 300

Leu Val Asn Ala Asn Thr Thr Gly Met Leu Leu Lys Ser Cys Cys Ser
305                 310                 315                 320

Gly Lys Leu Pro Met Glu Lys Leu Ala Thr His His Phe Lys Phe Asn
                325                 330                 335

Glu Ile Glu Lys Ala Tyr Asp Val Phe Ile Asn Ala Ala Lys Glu Lys
            340                 345                 350

Ala Met Lys Val Ile Ile Asp Phe
        355                 360

<210> SEQ ID NO 37
<211> LENGTH: 346
<212> TYPE: PRT
<213> ORGANISM: Geobacillus sp. WCH70

<400> SEQUENCE: 37

Met Lys Ala Leu Thr Tyr Leu Gly Pro Gly Lys Glu Val Met Glu
1               5                   10                  15

Lys Pro Lys Pro Lys Ile Glu Lys Glu Thr Asp Ala Ile Val Lys Ile
            20                  25                  30

Thr Lys Thr Thr Ile Cys Gly Thr Asp Leu His Ile Leu Ser Gly Asp
        35                  40                  45

Val Pro Thr Val Glu Glu Gly Arg Ile Leu Gly His Glu Gly Val Gly
    50                  55                  60

Ile Ile Glu Glu Val Gly Ser Gly Val Lys Asn Phe Lys Lys Gly Asp
65                  70                  75                  80

Arg Val Leu Ile Ser Cys Ile Thr Ser Cys Gly Lys Cys Glu Asn Cys
                85                  90                  95

Lys Lys Gly Leu Tyr Ala His Cys Glu Asp Gly Gly Trp Ile Leu Gly
            100                 105                 110

His Leu Ile Asp Gly Thr Gln Ala Glu Tyr Val Arg Ile Pro His Ala
        115                 120                 125

Asp Asn Ser Leu Tyr Pro Ile Pro Glu Gly Val Asp Glu Glu Ala Leu
    130                 135                 140

Val Met Leu Ser Asp Ile Leu Pro Thr Gly Phe Glu Ile Gly Val Leu
145                 150                 155                 160

Asn Gly Lys Val Gln Pro Gly Gln Thr Val Ala Ile Ile Gly Ala Gly
                165                 170                 175

Pro Val Gly Met Ala Ala Leu Leu Thr Ala Gln Phe Tyr Ser Pro Ala
```

```
            180                 185                 190
Glu Ile Ile Met Val Asp Leu Asp Asp Asn Arg Leu Glu Val Ala Lys
                195                 200                 205

Lys Phe Gly Ala Thr Gln Val Val Asn Ser Ala Asp Gly Lys Ala Val
            210                 215                 220

Glu Lys Ile Met Glu Leu Thr Gly Gly Lys Gly Val Asp Val Ala Met
225                 230                 235                 240

Glu Ala Val Gly Ile Pro Val Thr Phe Asp Ile Cys Gln Glu Ile Val
                245                 250                 255

Lys Pro Gly Gly Tyr Ile Ala Asn Ile Gly Val His Gly Lys Ser Val
            260                 265                 270

Glu Phe His Ile Glu Lys Leu Trp Ile Arg Asn Ile Thr Leu Thr Thr
                275                 280                 285

Gly Leu Val Asn Thr Thr Ser Thr Pro Met Leu Leu Lys Thr Val Gln
            290                 295                 300

Ser Lys Lys Leu Lys Pro Glu Gln Leu Ile Thr His Arg Phe Ala Phe
305                 310                 315                 320

Ala Asp Ile Met Lys Ala Tyr Glu Val Phe Gly Asn Ala Ala Lys Glu
                325                 330                 335

Lys Ala Leu Lys Val Ile Ile Ser Asn Asp
            340                 345

<210> SEQ ID NO 38
<211> LENGTH: 360
<212> TYPE: PRT
<213> ORGANISM: Vanderwaltozyma polyspora DSM 70294

<400> SEQUENCE: 38

Met Ser Tyr Pro Glu Lys Phe Gln Gly Ile Gly Ile Thr Asn Arg Glu
1               5                   10                  15

Asp Trp Lys His Pro Lys Lys Val Thr Phe Glu Pro Lys Gln Phe Asn
            20                  25                  30

Asp Lys Asp Val Asp Ile Lys Ile Glu Ala Cys Gly Val Cys Gly Ser
        35                  40                  45

Asp Val His Cys Ala Ala Ser His Trp Gly Pro Val Ala Glu Lys Gln
    50                  55                  60

Val Val Gly His Glu Ile Ile Gly Arg Val Leu Lys Val Gly Pro Lys
65                  70                  75                  80

Cys Thr Thr Gly Ile Lys Val Gly Asp Arg Val Gly Val Gly Ala Gln
                85                  90                  95

Ala Trp Ser Cys Leu Glu Cys Ser Arg Cys Lys Ser Asp Asn Glu Ser
            100                 105                 110

Tyr Cys Pro Lys Ser Val Trp Thr Tyr Ser Ile Pro Tyr Ile Asp Gly
        115                 120                 125

Tyr Val Ser Gln Gly Gly Tyr Ala Ser His Ile Arg Leu His Glu His
    130                 135                 140

Phe Ala Ile Pro Ile Pro Asp Lys Leu Ser Asn Glu Leu Ala Ala Pro
145                 150                 155                 160

Leu Leu Cys Gly Gly Ile Thr Val Tyr Ser Pro Leu Leu Arg Asn Gly
                165                 170                 175

Cys Gly Pro Gly Lys Lys Val Gly Ile Val Gly Ile Gly Gly Ile Gly
            180                 185                 190

His Met Gly Leu Leu Phe Ala Lys Gly Met Gly Ala Glu Val Tyr Ala
        195                 200                 205
```

```
Phe Ser Arg Thr His Ser Lys Glu Ala Asp Ala Lys Lys Leu Gly Ala
    210                 215                 220

Asp His Phe Ile Ala Thr Leu Glu Asp Lys Asp Trp Thr Thr Lys Tyr
225                 230                 235                 240

Phe Asp Thr Leu Asp Leu Leu Val Ile Cys Ala Ser Ser Leu Thr Asp
                245                 250                 255

Ile Asn Phe Asp Glu Leu Thr Lys Ile Met Lys Val Asn Thr Lys Ile
                260                 265                 270

Ile Ser Ile Ser Ala Pro Ala Asp Glu Val Leu Thr Leu Lys Pro
            275                 280                 285

Phe Gly Leu Ile Gly Val Thr Ile Gly Asn Ser Ala Ile Gly Ser Arg
    290                 295                 300

Arg Glu Ile Glu His Leu Leu Asn Phe Val Ala Glu Lys Asp Ile Lys
305                 310                 315                 320

Pro Trp Val Glu Thr Leu Pro Val Gly Glu Ala Gly Val Asn Glu Ala
                325                 330                 335

Phe Glu Arg Met Asp Lys Gly Asp Val Lys Tyr Arg Phe Thr Leu Val
                340                 345                 350

Asp Phe Asp Lys Glu Phe Gly Asn
            355                 360

<210> SEQ ID NO 39
<211> LENGTH: 348
<212> TYPE: PRT
<213> ORGANISM: Mucor circinelloides

<400> SEQUENCE: 39

Met Ser Glu Glu Thr Phe Thr Ala Trp Ala Cys Lys Ser Lys Ser Ala
1               5                   10                  15

Pro Leu Glu Pro Met Glu Met Thr Phe Cys His Trp Asp Asp Asp Met
                20                  25                  30

Val Gln Met Asp Val Ile Cys Cys Gly Val Cys Gly Thr Asp Leu His
            35                  40                  45

Thr Val Asp Glu Gly Trp Gly Pro Thr Glu Phe Pro Cys Val Val Gly
50                  55                  60

His Glu Ile Ile Gly Asn Val Thr Lys Val Gly Lys Asn Val Thr Arg
65                  70                  75                  80

Ile Lys Val Gly Asp Arg Cys Gly Val Gly Cys Gln Ser Ala Ser Cys
                85                  90                  95

Gly Lys Cys Asp Phe Cys Lys Lys Gly Met Glu Asn Leu Cys Ser Thr
                100                 105                 110

His Ala Val Trp Thr Phe Asn Asp Arg Tyr Asp Asn Ala Thr Lys Asp
            115                 120                 125

Lys Thr Tyr Gly Gly Phe Ala Lys Lys Trp Arg Gly Asn Gln Asp Phe
    130                 135                 140

Val Val His Val Pro Met Asp Phe Ser Pro Glu Val Ala Ala Ser Phe
145                 150                 155                 160

Leu Cys Gly Gly Val Thr Thr Tyr Ala Pro Leu Lys Arg Tyr Gly Val
                165                 170                 175

Gly Lys Gly Ser Lys Val Ala Val Leu Gly Leu Gly Gly Leu Gly His
                180                 185                 190

Phe Gly Val Gln Trp Ala Lys Ala Met Gly Ala Glu Val Val Ala Phe
            195                 200                 205

Asp Val Ile Pro Asp Lys Val Asp Asp Ala Lys Lys Leu Gly Cys Asp
    210                 215                 220
```

```
Asp Tyr Val Leu Met Gln Lys Glu Glu Gln Met Glu Pro His Tyr Asn
225                 230                 235                 240

Thr Phe Thr His Ile Leu Ala Thr Lys Ile Val Asn Lys Cys Trp Asp
            245                 250                 255

Gln Tyr Phe Lys Met Leu Lys Asn Asn Gly Ile Phe Met Leu Cys Asp
        260                 265                 270

Ile Pro Glu Val Pro Leu Ser Gly Met Ser Ala Phe Met Ala Gly
    275                 280                 285

Lys Gln Leu Thr Ile Ala Gly Thr Phe Ile Gly Ser Pro Ser Val Ile
290                 295                 300

Gln Glu Cys Leu Asp Phe Ala Ala Lys His Asn Val Arg Thr Trp Val
305                 310                 315                 320

Asn Thr Phe Pro Met Glu Lys Ile Asn Glu Ala Phe Glu Phe Val Arg
            325                 330                 335

Gln Ala Lys Pro Arg Tyr Arg Ala Val Val Met Asn
            340                 345

<210> SEQ ID NO 40
<211> LENGTH: 350
<212> TYPE: PRT
<213> ORGANISM: Rhodococcus erythropolis PR4

<400> SEQUENCE: 40

Met Phe Thr Val Asn Ala Arg Ser Thr Ser Ala Pro Gly Ala Pro Phe
1               5                   10                  15

Glu Ala Val Val Ile Glu Arg Arg Asp Pro Gly Pro Gly Asp Val Val
            20                  25                  30

Ile Asp Ile Ala Phe Ser Gly Ile Cys His Thr Asp Val Ser Arg Ala
        35                  40                  45

Arg Ser Glu Phe Gly Thr Thr His Tyr Pro Leu Val Pro Gly His Glu
    50                  55                  60

Ile Ala Gly Val Val Ser Lys Val Gly Ser Asp Val Thr Lys Phe Ala
65                  70                  75                  80

Val Gly Asp Arg Val Gly Val Gly Cys Ile Val Asp Ser Cys Arg Glu
                85                  90                  95

Cys Asp Tyr Cys Arg Ala Gly Leu Glu Pro Tyr Cys Arg Lys Asp His
            100                 105                 110

Val Arg Thr Tyr Asn Ser Met Gly Arg Asp Gly Arg Ile Thr Leu Gly
        115                 120                 125

Gly Tyr Ser Glu Lys Ile Val Asp Glu Gly Tyr Val Leu Arg Ile
    130                 135                 140

Pro Asp Ala Ile Pro Leu Asp Gln Ala Ala Pro Leu Leu Cys Ala Gly
145                 150                 155                 160

Ile Thr Met Tyr Ser Pro Leu Arg His Trp Lys Ala Gly Pro Gly Ser
                165                 170                 175

Arg Ile Ala Ile Val Gly Phe Gly Gly Leu Gly His Val Gly Val Ala
            180                 185                 190

Ile Ala Arg Ala Leu Gly Ala His Thr Thr Val Phe Asp Leu Thr Met
        195                 200                 205

Asp Lys His Asp Asp Ala Ile Arg Leu Gly Ala Asp Tyr Arg Leu
    210                 215                 220

Ser Thr Asp Ala Gly Ile Phe Lys Glu Phe Glu Gly Ala Phe Glu Leu
225                 230                 235                 240

Ile Val Ser Thr Val Pro Ala Asn Leu Asp Tyr Asp Leu Phe Leu Lys
```

```
                   245                 250                 255
Met Leu Ala Leu Asp Gly Thr Phe Val Gln Leu Gly Val Pro His Asn
            260                 265                 270

Pro Val Ser Leu Asp Val Phe Ser Leu Phe Tyr Asn Arg Arg Ser Leu
        275                 280                 285

Ala Gly Thr Leu Val Gly Ile Gly Glu Thr Gln Glu Met Leu Asp
    290                 295                 300

Phe Cys Ala Glu His Ser Ile Val Ala Glu Ile Glu Thr Val Gly Ala
305                 310                 315                 320

Asp Glu Ile Asp Ser Ala Tyr Asp Arg Val Ala Ala Gly Asp Val Arg
                325                 330                 335

Tyr Arg Met Val Leu Asp Val Gly Thr Leu Ala Thr Gln Arg
            340                 345                 350

<210> SEQ ID NO 41
<211> LENGTH: 34
<212> TYPE: DNA
<213> ORGANISM: Artificial Sequence
<220> FEATURE:
<223> OTHER INFORMATION: SadBXhoI-f primer

<400> SEQUENCE: 41
ccatggaatc tcgagatgaa agctctggtt tacc                                34

<210> SEQ ID NO 42
<211> LENGTH: 26
<212> TYPE: DNA
<213> ORGANISM: Artificial Sequence
<220> FEATURE:
<223> OTHER INFORMATION: SadBKpnI-r primer

<400> SEQUENCE: 42
gatccccggg taccgagctc gaattc                                         26

<210> SEQ ID NO 43
<211> LENGTH: 32
<212> TYPE: DNA
<213> ORGANISM: Artificial Sequence
<220> FEATURE:
<223> OTHER INFORMATION: ADH6_XhoI_f primer

<400> SEQUENCE: 43
caagaaaact cgagatcatg tcttatcctg ag                                  32

<210> SEQ ID NO 44
<211> LENGTH: 31
<212> TYPE: DNA
<213> ORGANISM: Artificial Sequence
<220> FEATURE:
<223> OTHER INFORMATION: ADH6_KpnI_r primer

<400> SEQUENCE: 44
gagcttggta ccctagtctg aaaattcttt g                                   31

<210> SEQ ID NO 45
<211> LENGTH: 31
<212> TYPE: DNA
<213> ORGANISM: Artificial Sequence
<220> FEATURE:
<223> OTHER INFORMATION: ADH7_XhoI_f primer

<400> SEQUENCE: 45
ctgaaaaact cgagaaaaaa atgctttacc c                                   31
```

<210> SEQ ID NO 46
<211> LENGTH: 31
<212> TYPE: DNA
<213> ORGANISM: Artificial Sequence
<220> FEATURE:
<223> OTHER INFORMATION: ADH7_KpnI_r primer

<400> SEQUENCE: 46
gaaaaatatt aggtacctag actatttatg g         31

<210> SEQ ID NO 47
<211> LENGTH: 62
<212> TYPE: DNA
<213> ORGANISM: Artificial Sequence
<220> FEATURE:
<223> OTHER INFORMATION: N1176 Primer

<400> SEQUENCE: 47
gcatagcaat ctaatctaag ttccagctga ggatgacaac agattactca tcaccagcat    60
at                                                                   62

<210> SEQ ID NO 48
<211> LENGTH: 62
<212> TYPE: DNA
<213> ORGANISM: Artificial Sequence
<220> FEATURE:
<223> OTHER INFORMATION: N1177 Primer

<400> SEQUENCE: 48
atcaacacac aaacactaaa tcaaagctga ggatggattt atttgagtca ttagcacaaa    60
aa                                                                   62

<210> SEQ ID NO 49
<211> LENGTH: 44
<212> TYPE: DNA
<213> ORGANISM: Artificial Sequence
<220> FEATURE:
<223> OTHER INFORMATION: N822 Primer

<400> SEQUENCE: 49
cgcctcagct ttgatttagt gtttgtgtgt tgataagcag ttgc                     44

<210> SEQ ID NO 50
<211> LENGTH: 63
<212> TYPE: DNA
<213> ORGANISM: Artificial Sequence
<220> FEATURE:
<223> OTHER INFORMATION: N1178 Primer

<400> SEQUENCE: 50
ggtatcgata agcttgatat cgaattcctg cgcccgggcc actagtcaga tgccgcgggc    60
act                                                                  63

<210> SEQ ID NO 51
<211> LENGTH: 10934
<212> TYPE: DNA
<213> ORGANISM: Artificial Sequence
<220> FEATURE:
<223> OTHER INFORMATION: pRS423::TEF(M4)-xpk1+ENO1-eutD plasmid

<400> SEQUENCE: 51
ggtggagctc cagcttttgt tccctttagt gagggttaat tgcgcgcttg gcgtaatcat    60

```
ggtcatagct gtttcctgtg tgaaattgtt atccgctcac aattccacac aacataggag    120
ccggaagcat aaagtgtaaa gcctggggtg cctaatgagt gaggtaactc acattaattg    180
cgttgcgctc actgcccgct ttccagtcgg gaaacctgtc gtgccagctg cattaatgaa    240
tcggccaacg cgcggggaga ggcggtttgc gtattgggcg ctcttccgct tcctcgctca    300
ctgactcgct gcgctcggtc gttcggctgc ggcgagcggt atcagctcac tcaaaggcgg    360
taatacggtt atccacagaa tcaggggata cgcaggaaa gaacatgtga gcaaaaggcc    420
agcaaaaggc caggaaccgt aaaaaggccg cgttgctggc gtttttccat aggctccgcc    480
cccctgacga gcatcacaaa aatcgacgct caagtcagag gtggcgaaac ccgacaggac    540
tataaagata ccaggcgttt ccccctggaa gctccctcgt gcgctctcct gttccgaccc    600
tgccgcttac cggatacctg tccgcctttc tcccttcggg aagcgtggcg ctttctcata    660
gctcacgctg taggtatctc agttcggtgt aggtcgttcg ctccaagctg ggctgtgtgc    720
acgaaccccc cgttcagccc gaccgctgcg ccttatccgg taactatcgt cttgagtcca    780
acccggtaag acacgactta tcgccactgg cagcagccac tggtaacagg attagcagag    840
cgaggtatgt aggcggtgct acagagttct tgaagtggtg gcctaactac ggctacacta    900
gaaggacagt atttggtatc tgcgctctgc tgaagccagt taccttcgga aaaagagttg    960
gtagctcttg atccggcaaa caaaccaccg ctggtagcgg tggtttttt gtttgcaagc   1020 agcagattac gcgcagaaaa aaggatctca agaagatcc tttgatcttt tctacggggt   1080
ctgacgctca gtggaacgaa aactcacgtt aagggatttt ggtcatgaga ttatcaaaaa   1140
ggatcttcac ctagatcctt ttaaattaaa aatgaagttt taaatcaatc taagtatat   1200 atgagtaaac ttggtctgac agttaccaat gcttaatcag tgaggcacct atctcagcga   1260
tctgtctatt tcgttcatcc atagttgcct gactccccgt cgtgtagata actacgatac   1320
gggagggctt accatctggc cccagtgctg caatgatacc gcgagaccca cgctcaccgg   1380
ctccagattt atcagcaata aaccagccag ccggaagggc cgagcgcaga agtggtcctg   1440
caactttatc cgcctccatc cagtctatta attgttgccg ggaagctaga gtaagtagtt   1500
cgccagttaa tagtttgcgc aacgttgttg ccattgctac aggcatcgtg gtgtcacgct   1560
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc cttttttcaat   2100 attattgaag catttatcag ggttattgtc tcatgagcgg atacatattt gaatgtattt   2160
agaaaaataa acaaataggg gttccgcgca catttccccg aaaagtgcca cctgaacgaa   2220
gcatctgtgc ttcattttgt agaacaaaaa tgcaacgcga gagcgctaat ttttcaaaca   2280
aagaatctga gctgcatttt tacagaacag aaatgcaacg cgaaagcgct attttaccaa   2340
cgaagaatct gtgcttcatt tttgtaaaac aaaaatgcaa cgcgagagcg ctaatttttc   2400
aaacaaagaa tctgagctgc atttttacag aacagaaatg caacgcgaga gcgctatttt   2460
```

```
accaacaaag aatctatact tcttttttgt tctacaaaaa tgcatcccga gagcgctatt   2520
tttctaacaa agcatcttag attactttt ttctcctttg tgcgctctat aatgcagtct   2580
cttgataact ttttgcactg taggtccgtt aaggttagaa gaaggctact ttggtgtcta   2640
ttttctcttc cataaaaaaa gcctgactcc acttcccgcg tttactgatt actagcgaag   2700
ctgcgggtgc atttttcaa gataaaggca tccccgatta tattctatac cgatgtggat   2760
tgcgcatact ttgtgaacag aaagtgatag cgttgatgat tcttcattgg tcagaaaatt   2820
atgaacggtt tcttctattt tgtctctata tactacgtat aggaaatgtt tacattttcg   2880
tattgttttc gattcactct atgaatagtt cttactacaa ttttttttgtc taaagagtaa   2940 tactagagat aaacataaaa aatgtagagg tcgagtttag atgcaagttc aaggagcgaa   3000
aggtggatgg gtaggttata tagggatata gcacagagat atatagcaaa gagatacttt   3060
tgagcaatgt ttgtggaagc ggtattcgca atattttagt agctcgttac agtccggtgc   3120
gttttttggt ttttgaaagt gcgtcttcag agcgcttttg gttttcaaaa gcgctctgaa   3180
gttcctatac tttctagaga ataggaactt cggaatagga acttcaaagc gtttccgaaa   3240
acgagcgctt ccgaaaatgc aacgcgagct gcgcacatac agctcactgt tcacgtcgca   3300
cctatatctg cgtgttgcct gtatatatat atacatgaga agaacggcat agtgcgtgtt   3360
tatgcttaaa tgcgtactta tatgcgtcta tttatgtagg atgaaaggta gtctagtacc   3420
tcctgtgata ttatcccatt ccatgcgggg tatcgtatgc ttccttcagc actacccttt   3480
agctgttcta tatgctgcca ctcctcaatt ggattagtct catccttcaa tgctatcatt   3540
tcctttgata ttggatcatc taagaaacca ttattatcat gacattaacc tataaaaata   3600
ggcgtatcac gaggcccttt cgtctcgcgc gtttcggtga tgacggtgaa aacctctgac   3660
acatgcagct cccggagacg gtcacagctt gtctgtaagc ggatgccggg agcagacaag   3720
cccgtcaggg cgcgtcagcg ggtgttggcg ggtgtcgggg ctggcttaac tatgcggcat   3780
cagagcagat tgtactgaga gtgcaccata aattcccgtt taagagcttt ggtgagcgct   3840
aggagtcact gccaggtatc gtttgaacac ggcattagtc agggaagtca taacacagtc   3900
ctttcccgca atttttcttt tctattactc ttggcctcct ctagtacact ctatattttt   3960
ttatgcctcg gtaatgattt tcatttttt ttttccccta gcggatgact cttttttttt   4020
cttagcgatt ggcattatca cataatgaat tatacattat ataaagtaat gtgatttctt   4080
cgaagaatat actaaaaaat gagcaggcaa gataaacgaa ggcaaagatg acagagcaga   4140
aagccctagt aaagcgtatt acaaatgaaa ccaagattca gattgcgatc tctttaaagg   4200
gtggtcccct agcgatagag cactcgatct tcccagaaaa agaggcagaa gcagtagcag   4260
aacaggccac acaatcgcaa gtgattaacg tccacacagg tatagggttt ctggaccata   4320
tgatacatgc tctggccaag cattccggct ggtcgctaat cgttgagtgc attggtgact   4380
tacacataga cgaccatcac accactgaag actgcgggat tgctctcggt caagctttta   4440
aagaggccct actggcgcgt ggagtaaaaa ggtttggatc aggatttgcg cctttggatg   4500
aggcactttc cagagcggtg gtagatcttt cgaacaggcc gtacgcagtt gtcgaacttg   4560
gtttgcaaag ggagaaagta ggagatctct cttgcgagat gatcccgcat tttcttgaaa   4620
gctttgcaga ggctagcaga attaccctcc acgttgattg tctgcgaggc aagaatgatc   4680
atcaccgtag tgagagtgcg ttcaaggctc ttgcggttgc cataagagaa gccacctcgc   4740
ccaatggtac caacgatgtt ccctccacca aaggtgttct tatgtagtga caccgattat   4800
```

```
ttaaagctgc agcatacgat atatatacat gtgtatatat gtatacctat gaatgtcagt    4860
aagtatgtat acgaacagta tgatactgaa gatgacaagg taatgcatca ttctatacgt    4920
gtcattctga acgaggcgcg cttttccttt ttcttttgc tttttctttt tttttctctt    4980
gaactcgacg gatctatgcg gtgtgaaata ccgcacagat gcgtaaggag aaaataccgc    5040
atcaggaaat tgtaaacgtt aatattttgt taaaattcgc gttaaatttt tgttaaatca    5100
gctcattttt taaccaatag gccgaaatcg gcaaaatccc ttataaatca aaagaataga    5160
ccgagatagg gttgagtgtt gttccagttt ggaacaagag tccactatta agaacgtgg    5220 actccaacgt caaagggcga aaaaccgtct atcagggcga tggcccacta cgtgaaccat    5280
caccctaatc aagttttttg gggtcgaggt gccgtaaagc actaaatcgg aaccctaaag    5340 ggagccccg atttagagct tgacggggaa agccggcgaa cgtggcgaga aggaaggga    5400 agaaagcgaa aggagcgggc gctagggcgc tggcaagtgt agcggtcacg ctgcgcgtaa    5460
ccaccacacc cgccgcgctt aatgcgccgc tacagggcgc gtcgcgccat tcgccattca    5520
ggctgcgcaa ctgttgggaa gggcgatcgg tgcgggcctc ttcgctatta cgccagctgg    5580
cgaaaggggg atgtgctgca aggcgattaa gttgggtaac gccagggttt tcccagtcac    5640
gacgttgtaa aacgacggcc agtgagcgcg cgtaatacga ctcactatag ggcgaattgg    5700
gtaccgggcc ccccctcgag gtcgacggta tcgataagct tgatatcgaa ttcctgcgcc    5760
cgggccacta gtcagatgcc gcgggcactt gagcacctca tgcacagcaa taacacaaca    5820
caatggttag tagcaacctg aattcggtca ttgatgcatg catgtgccgt gaagcgggac    5880
aaccagaaaa gtcgtctata aatgccgca cgtgcgatca tcgtggcggg gttttaagag    5940
tgcatatcac aaattgtcgc attaccgcgg aaccgccaga tattcattac ttgacgcaaa    6000
agcgtttgaa ataatgacga aaagaagga agaaaaaaaa agaaaaatac cgcttctagg    6060
cgggttatct actgatccga gcttccacta ggatagcacc caaacacctg catatttgga    6120
cgacctttac ttacaccacc aaaaaccact ttcgcctctc ccgcccctga taacgtccac    6180
taattgagcg attacctgag cggtcctctt ttgtttgcag catgagactt gcatactgca    6240
aatcgtaagt agcaacgtct caaggtcaaa actgtatgga aaccttgtca cctcacttaa    6300
ttctagctag cctaccctgc aagtcaagag gtctccgtga ttcctagcca cctcaaggta    6360
tgcctctccc cggaaactgt ggccttttct ggcacacatg atctccacga tttcaacata    6420
taaatagctt ttgataatgg caatattaat caaatttatt ttacttcttt cttgtaacat    6480
ctctcttgta atcccttatt ccttctagct atttttcata aaaaaccaag caactgctta    6540
tcaacacaca aacactaaat caaagctgag gatggattta tttgagtcat tagcacaaaa    6600
aattactggt aaagatcaaa caattgtttt ccctgaagga actgaacccc gaattgtcgg    6660
tgcggcagcg cgattagctg cagacggctt ggttaagccg attgttttag gtgcaacgga    6720
caaagttcag gctgtggcta acgatttgaa tgcggattta acaggcgttc aagtccttga    6780
tcctgcgaca tacccggctg aagataagca agcaatgctt gatgccctcg ttgaacggcg    6840
gaaaggtaag aatacgccag aacaagcggc taaaatgctg gaagatgaaa actactttgg    6900
cacgatgctc gttatatgg gcaaagcgga tgggatggtt tcaggtgcaa tccatccaac    6960
tggtgatacg gtacggccag cgttacaaat tattaagacc aagcccggtt cacaccgaat    7020
ctcgggtgca tttatcatgc aaaagggtga ggaacgctac gtctttgctg actgtgccat    7080
caatattgat cccgatgccg atacgttagc ggaaattgcc actcagagtg cggctactgc    7140
taaggtcttc gatattgacc cgaaagttgc gatgctcagc ttctcaacta agggttcggc    7200
```

```
taagggtgaa atggtcacta aagtgcaaga agcaacggcc aaggcgcaag ctgctgaacc    7260
ggaattggct atcgatggtg aacttcaatt tgacgcggcc ttcgttgaaa aagttggttt    7320
gcaaaaggct cctggttcca aagtagctgg tcatgccaat gtctttgtat ttccagagct    7380
tcagtctggt aatattggct ataagattgc gcaacgattt ggtcattttg aagcggtggg    7440
tcctgtcttg caaggcctga acaagccggt ctccgacttg tcacgtggat gcagtgaaga    7500
agacgtttat aaggttgcga ttattacagc agcccaagga ttagcttaat taattaagag    7560
taagcgaatt tcttatgatt tatgattttt attattaaat aagttataaa aaaaataagt    7620
gtatacaaat tttaaagtga ctcttaggtt ttaaaacgaa aattcttatt cttgagtaac    7680
tctttcctgt aggtcaggtt gctttctcag gtatagcatg aggtcgctct tattgaccac    7740
acctctaccg gcatgccgag caaatgcctg caaatcgctc cccatttcac ccaattgtag    7800
atatgctaac tccagcaatg agttgatgaa tctcggtgtg tattttatgt cctcagagga    7860
caacacctgt ggtactagtt ctagagcggc cgcccgcaaa ttaaagcctt cgagcgtccc    7920
aaaaccttct caagcaaggt tttcagtata atgttacatg cgtacacgcg tttgtacaga    7980
aaaaaaagaa aaatttgaaa tataaataac gttcttaata ctaacataac tattaaaaaa    8040
aataaatagg gacctagact tcaggttgtc taactccttc cttttcggtt agagcggatg    8100
tgggaggagg gcgtgaatgt aagcgtgaca taactaatta catgattaat taattatttt    8160
aaacccttcc attgccaatc attaacttct ggcaagtcag ttccggcatc ccggatatag    8220
gcattgtgtt tagcaagcat attatccatg gattgaacga aggccgcacc agtgtttttcc   8280 attgctggtt gcgccgcaat tgccgactta gctaagtcga agcggtccat ctggttcatg    8340
acccgtacgt cgaatggtgt ggtaaatatca ccattttcac ggtaaccgtg gacgtataag   8400
ttatggttgt gacgatcaaa gaagatgtca cgaactaagt cttcgtaacc gtggaaagca    8460
aagaccactg gtttgtcctt agtaaagtaa tggtcaaact cagcatctga caagccccgc    8520
ggatcctttt caggactacg taacttcaag atgtcgacca cgttcacgaa acgaatcttc    8580
atctctggga aactgtcgtg tagtaattgg atggcagcca acgtttcaag cgttggttcc    8640
gtcccagcag ctgcaaagac aatgtctggt tcgctaccttt ggtccgtact tgcccaatca   8700
atgataccaa gaccattgtc aactaattgc ttagcttctt caatgctgaa ccattgttga    8760
cgtgggtgtt ttgacgtaac cacgtagttg atcttttctt ggctccggaa aatgacgtca    8820
ccgacagcta ataacgtgtt ggcatcggct ggtaaatatt cacgaatgta ttctggtttc    8880
ttttcggcca aatgagttaa tgcacctgga tcttggtggg tataaccatt atggtcttgt    8940
tggaatacag ttgaagccgc gataatgtta agtgatgggt actttttacg ccaatcaagt    9000
tcattggctt tacgtaacca cttgaagtgt tgcgtcaaca ttgagtccac aacgcgtagg    9060
aaggcttcat aactggcaaa taacccatga cgtccagtta agacgtaacc ttctaaccaa    9120
ccttcagctt ggtgttcaga taactgagca tctaagaccc ggccagctgg tgcttcatat    9180
tggtcactat ctggatgaat gtcttccatc cattgacgat tagtggtttc gaagacacca    9240
tataaacggt tagacatggt ttcatcaggt ccgaacaacc ggaagttatc aggatttttc    9300
ttgatgacat cccgcaaata gtctgaccaa acgatcatat cttgcttaac attcgcgcct    9360
tctttggacg tatcgaccgc ataatcacgg aagtttggta agttcaaggc tttcggatcg    9420
accccaccat tggtgattgg gttagcagcc atccgactgt ccccagtagg aataatttct    9480
ttaatatcat ccttcaaaga gccatcttca ttgaagagtt cttttggttg atatgattcg    9540
```

| | | |
|---|---|---|
| agccaatcaa ctaaagcatc cgcatgttcc atgtcatttt gatcaacagg aatcggaatt | 9600 |
| tgatgagcac ggaatgaacc ttcgatctta tcaccgtccc atgacttcgg accagtccag | 9660 |
| cccttaggtg cgcggaagac gatcattggc catactggca atgttgcatc gttattttcg | 9720 |
| cgagcatgct tctggattgc cttgatcttt tcaacggctt catccatggc cttagctaag | 9780 |
| gctgggtgaa cctttttcagg atcgtcacct tcaacgaaga ttggttccca attcatgctt | 9840 |
| tcgaagtatt ccttaatctt agcatcagaa gtccgaccaa aaatcgttgg attagaaatc | 9900 |
| ttaaaaccat ttaagttcaa gattggtaaa acagcccgt cgttgattgg gttaatgaac | 9960 |
| ttcgttgatt gccatgaagt tgctaatgga cccgtttcgg attccccatc accaacaaca | 10020 |
| accgcggcga tttcgtcagg attgtcaaga attgccccaa ccccgtgtga aattgagtaa | 10080 |
| ccaagttcgc caccttcgtg gattgaaccg ggtgtttcag gtgccgcatg ggaagcaacc | 10140 |
| ccacctggga atgagaattg cttgaagagc ttttgcatcc cttcaacatc ctgcgtaatt | 10200 |
| tctggataaa tatcggtgta agtaccgtca aggtaagagt ttgaaaccat cacttgacca | 10260 |
| ccatgacctg gaccttcaac gtagaacatc ttcaaaccgt acttgttgat gacccggtta | 10320 |
| agatgagcat agataaagtt ttgaccggca atcgtccccc agtgaccaat tggatgaacc | 10380 |
| ttaacgtcac tggccttcaa tggccgttgt aatagtggat tatcttttaa ataaagttga | 10440 |
| ccaactgata agtagttggc agcacgccag tacttatcaa ctttttgcaa atatgctggt | 10500 |
| gatgagtaat ctgttgtcat cctcagctgg aacttagatt agattgctat gctttctctc | 10560 |
| taacgagcaa gaagtaaaaa aagttgtaat agaacaagaa aaatgaaact gaagcttgag | 10620 |
| aaattgaaga ccgtttatta gcttaaatat caatgggagg tcatcgaaag agaaaaaaat | 10680 |
| caagaaagaa actctcaaga aaaagaaacg tgataaaaat ttttattgcc tctctcgacg | 10740 |
| aagagaaaga aacgaggcgg tcccttttt cttttccaaa cctttagtac gggtaattag | 10800 |
| cgacacccta gaggaagaaa gaggggaaat ttagtatgct gtgcttgggt gtcttgaagt | 10860 |
| ggtacggcga tgcgcggagt ccgagaaaat ctggaagagt aaaaaggggg tagaagcgtt | 10920 |
| ttgaagctat ccgc | 10934 |

```
<210> SEQ ID NO 52
<211> LENGTH: 38
<212> TYPE: DNA
<213> ORGANISM: Artificial Sequence
<220> FEATURE:
<223> OTHER INFORMATION: N821 Primer

<400> SEQUENCE: 52
```

| | |
|---|---|
| cgcccgggcc actagtcaga tgccgcgggc acttgagc | 38 |

```
<210> SEQ ID NO 53
<211> LENGTH: 30
<212> TYPE: DNA
<213> ORGANISM: Artificial Sequence
<220> FEATURE:
<223> OTHER INFORMATION: N1115 Primer

<400> SEQUENCE: 53
```

| | |
|---|---|
| tttttgtgct aatgactcaa ataaatccat | 30 |

```
<210> SEQ ID NO 54
<211> LENGTH: 30
<212> TYPE: DNA
<213> ORGANISM: Artificial Sequence
<220> FEATURE:
<223> OTHER INFORMATION: N1110 Primer
```

```
<400> SEQUENCE: 54
gcgatttaat ctctaattat tagttaaagt                                         30

<210> SEQ ID NO 55
<211> LENGTH: 30
<212> TYPE: DNA
<213> ORGANISM: Artificial Sequence
<220> FEATURE:
<223> OTHER INFORMATION: N1114 Primer

<400> SEQUENCE: 55
atatgctggt gatgagtaat ctgttgtcat                                         30

<210> SEQ ID NO 56
<211> LENGTH: 22
<212> TYPE: DNA
<213> ORGANISM: Artificial Sequence
<220> FEATURE:
<223> OTHER INFORMATION: N160SeqF5 Primer

<400> SEQUENCE: 56
cctgaagtct aggtccctat tt                                                 22

<210> SEQ ID NO 57
<211> LENGTH: 38
<212> TYPE: DNA
<213> ORGANISM: Artificial Sequence
<220> FEATURE:
<223> OTHER INFORMATION: BK468 Primer

<400> SEQUENCE: 57
gcctcgagtt ttaatgttac ttctcttgca gttaggga                                38

<210> SEQ ID NO 58
<211> LENGTH: 9220
<212> TYPE: DNA
<213> ORGANISM: Artificial Sequence
<220> FEATURE:
<223> OTHER INFORMATION: pUC19-URA3::pdc1::TEF(M4)-xpk1::kan Plasmid

<400> SEQUENCE: 58
ccgcattgcg gattacgtat tctaatgttc agataacttc gtataatgta tgctatacga        60
agttatcgaa cagagaaact aaatccacat taattgagag ttctatctat tagaaaatgc       120
aaactccaac taaatgggaa aacagataac ctcttttatt ttttttttaat gtttgatatt      180 cgagtctttt tcttttgtta ggtttatatt catcatttca atgaataaaa gaagcttctt       240
attttggttg caaagaatga aaaaaaagga ttttttcata cttctaaagc ttcaattata       300
accaaaaatt ttataaatga agagaaaaaa tctagtagta tcaagttaaa cttagaaaaa       360
ctcatcgagc atcaaatgaa actgcaattt attcatatca ggattatcaa taccatattt       420
ttgaaaaagc cgtttctgta atgaaggaga aaactcaccg aggcagttcc ataggatggc       480
aagatcctgg tatcggtctg cgattccgac tcgtccaaca tcaatacaac ctattaattt      540
cccctcgtca aaataaggt tatcaagtga gaaatcacca tgagtgacga ctgaatccgg       600
tgagaatggc aaaagcttat gcatttcttt ccagacttgt tcaacaggcc agccattacg      660
ctcgtcatca aaatcactcg catcaaccaa accgttattc attcgtgatt gcgcctgagc      720
gagacgaaat acgcgatcgc tgttaaaagg acaattacaa acaggaatcg aatgcaaccg      780
gcgcaggaac actgccagcg catcaacaat attttcacct gaatcaggat attcttctaa      840
```

```
tacctggaat gctgttttgc cggggatcgc agtggtgagt aaccatgcat catcaggagt    900
acggataaaa tgcttgatgg tcggaagagg cataaattcc gtcagccagt ttagtctgac    960
catctcatct gtaacatcat tggcaacgct acctttgcca tgtttcagaa acaactctgg   1020
cgcatcgggc ttcccataca atcgatagat tgtcgcacct gattgcccga cattatcgcg   1080
agcccattta tacccatata atcagcatc catgttggaa tttaatcgcg gcctcgaaac    1140
gtgagtcttt tccttaccca tctcgagttt taatgttact tctcttgcag ttagggaact   1200
ataatgtaac tcaaaataag attaaacaaa ctaaaataaa aagaagttat acagaaaaac   1260
ccatataaac cagtactaat ccataataat aatacacaaa aaaactatca aataaaacca   1320
gaaaacagat tgaatagaaa aattttttcg atctcctttt atattcaaaa ttcgatatat   1380
gaaaagggga actctcagaa aatcaccaaa tcaatttaat tagattttc ttttccttct    1440
agcgttggaa agaaaaattt ttcttttttt ttttagaaat gaaaaatttt tgccgtagga   1500
atcaccgtat aaaccctgta taaacgctac tctgttcacc tgtgtaggct atgattgacc   1560
cagtgttcat tgttattgcg agagagcggg agaaaagaac cgatacaaga gatccatgct   1620
ggtatagttg tctgtccaac actttgatga acttgtagga cgatgatgtg tatttagacg   1680
agtacgtgtg tgactattaa gtagttatga tagagaggtt tgtacggtgt gttctgtgta   1740
attcgattga gaaatggtt atgaatccct agataacttc gtataatgta tgctatacga    1800
agttatccag tgatgataca acgagttagc caaggtgggg gatcctctag agtcttaagg   1860
ccgcccgcaa attaaagcct tcgagcgtcc caaaaccttc tcaagcaagg ttttcagtat   1920
aatgttacat gcgtacacgc gtttgtacag aaaaaaaaga aaaatttgaa atataaataa   1980
cgttcttaat actaacataa ctattaaaaa aaataaatag ggacctagac ttcaggttgt   2040
ctaactcctt cctttcggt tagagcggat gtgggaggag ggcgtgaatg taagcgtgac    2100
ataactaatt acatgattaa ttaattattt taaacccttc cattgccaat cattaacttc   2160
tggcaagtca gttccggcat cccgatata ggcattgtgt ttagcaagca tattatccat    2220
ggattgaacg aaggccgcac cagtgttttc cattgctggt tgcgccgcaa ttgccgactt   2280
agctaagtcg aagcggtcca tctggttcat gacccgtacg tcgaatggtg tggtaatatc   2340
accattttca cggtaaccgt ggacgtataa gttatggttg tgacgatcaa agaagatgtc   2400
acgaactaag tcttcgtaac cgtggaaagc aaagaccact ggtttgtcct tagtaaagta   2460
atggtcaaac tcagcatctg acaagccccg cggatccttt tcaggactac gtaacttcaa   2520
gatgtcgacc acgttcacga aacgaatctt catctctggg aaactgtcgt gtagtaattg   2580
gatggcagcc aacgtttcaa gcgttggttc cgtcccagca gctgcaaaga caatgtctgg   2640
ttcgctacct tggtccgtac ttgcccaatc aatgatacca agaccattgt caactaattg   2700
cttagcttct tcaatgctga accattgttg acgtgggtgt tttgacgtaa ccacgtagtt   2760
gatcttttct tggctccgga aaatgacgtc accgacagct aataacgtgt tggcatcggc   2820
tggtaaatat tcacgaatgt attctggttt cttttcggcc aaatgagtta atgcacctgg   2880
atcttggtgg gtataaccat tatggtcttg ttggaataca gttgaagccg cgataatgtt   2940
aagtgatggg tacttttac gccaatcaag ttcattggct ttacgtaacc acttgaagtg    3000
ttgcgtcaac attgagtcca caacgcgtag gaaggcttca taactggcaa ataacccatg   3060
acgtccagtt aagacgtaac cttctaacca accttcagct tggtgttcag ataactgagc   3120
atctaagacc cggccagctg gtgcttcata ttggtcacta tctggatgaa tgtcttccat   3180
ccattgacga ttagtggttt cgaagacacc atataaacgg ttagacatgg tttcatcagg   3240
```

```
tccgaacaac cggaagttat caggattttt cttgatgaca tcccgcaaat agtctgacca    3300
aacgatcata tcttgcttaa cattcgcgcc ttctttggac gtatcgaccg cataatcacg    3360
gaagtttggt aagttcaagg ctttcggatc gaccccacca ttggtgattg ggttagcagc    3420
catccgactg tccccagtag gaataatttc tttaatatca tccttcaaag agccatcttc    3480
attgaagagt tcttttggtt gatatgattc gagccaatca actaaagcat ccgcatgttc    3540
catgtcattt tgatcaacag gaatcggaat ttgatgagca cggaatgaac cttcgatctt    3600
atcaccgtcc catgacttcg gaccagtcca gcccttaggt gcgcggaaga cgatcattgg    3660
ccatactggc aatgttgcat cgttattttc gcgagcatgc ttctggattg ccttgatctt    3720
ttcaacggct tcatccatgg ccttagctaa ggctgggtga accttttcag gatcgtcacc    3780
ttcaacgaag attggttccc aattcatgct ttcgaagtat tccttaatct tagcatcaga    3840
agtccgacca aaaatcgttg gattagaaat cttaaaacca tttaagttca agattggtaa    3900
aacagccccg tcgttgattg ggttaatgaa cttcgttgat tgccatgaag ttgctaatgg    3960
acccgtttcg gattccccat caccaacaac aaccgcggcg atttcgtcag gattgtcaag    4020
aattgcccca accccgtgtg aaattgagta accaagttcg ccaccttcgt ggattgaacc    4080
gggtgtttca ggtgccgcat gggaagcaac cccacctggg aatgagaatt gcttgaagag    4140
cttttgcatc ccttcaacat cctgcgtaat ttctggataa atatcggtgt aagtaccgtc    4200
aaggtaagag tttgaaacca tcacttgacc accatgacct ggaccttcaa cgtagaacat    4260
cttcaaaccg tacttgttga tgacccggtt aagatgagca tagataaagt tttgaccggc    4320
aatcgtcccc cagtgaccaa ttggatgaac cttaacgtca ctggccttca atggccgttg    4380
taatagtgga ttatctttta aataaagttg accaactgat aagtagttgg cagcacgcca    4440
gtacttatca acttttttgca aatatgctgg tgatgagtaa tctgttgtca tcctcagctg    4500
gaacttagat tagattgcta tgcttttctct ctaacgagca agaagtaaaa aaagttgtaa    4560
tagaacaaga aaaatgaaac tgaagcttga gaaattgaag accgtttatt agcttaaata    4620
tcaatgggag gtcatcgaaa gagaaaaaaa tcaagaaaga aactctcaag aaaaagaaac    4680
gtgataaaaa ttttttattgc ctctctcgac gaagagaaag aaacgaggcg gtcccttttt    4740
tcttttccaa acctttagta cgggtaatta gcgacaccct agaggaagaa agagggaaa    4800 tttagtatgc tgtgcttggg tgtcttgaag tggtacggcg atgcgcggag tccgagaaaa    4860
tctggaagag taaaagggg gtagaagcgt tttgaagcta tccgcggtgg ttaagcctaa    4920
ccaggccaat tcaacagact gtcggcaact tcttgtctgg tctttccatg gtaagtgaca    4980
gtgcagtaat aatatgaacc aatttatttt tcgttacata aaaatgctta taaaacttta    5040
actaataatt agagattaaa tcgcaaacgg ccggccaatg tggctgtggt ttcagggtcc    5100
ataaagcttt tcaattcatc tttttttttt ttgttctttt ttttgattcc ggtttctttg    5160 aaatttttt gattcggtaa tctccgagca gaaggaagaa cgaaggaagg agcacagact    5220
tagattggta tatatacgca tatgtggtgt tgaagaaaca tgaaattgcc cagtattctt    5280
aacccaactg cacagaacaa aaacctgcag gaaacgaaga taaatcatgt cgaaagctac    5340
atataaggaa cgtgctgcta ctcatcctag tcctgttgct gccaagctat ttaatatcat    5400
gcacgaaaag caaacaaact tgtgtgcttc attggatgtt cgtaccacca aggaattact    5460
ggagttagtt gaagcattag gtcccaaaat ttgtttacta aaaacacatg tggatatctt    5520
gactgatttt tccatggagg gcacagttaa gccgctaaag gcattatccg ccaagtacaa    5580
```

```
tttttttactc ttcgaagaca gaaaatttgc tgacattggt aatacagtca aattgcagta    5640
ctctgcgggt gtatacagaa tagcagaatg ggcagacatt acgaatgcac acggtgtggt    5700
gggcccaggt attgttagcg gtttgaagca ggcggcggaa gaagtaacaa aggaacctag    5760
aggccttttg atgttagcag aattgtcatg caagggctcc ctagctactg agaatatac    5820 taagggtact gttgacattg cgaagagcga caaagatttt gttatcggct ttattgctca    5880
aagagacatg ggtggaagag atgaaggtta cgattggttg attatgacac ccggtgtggg    5940
tttagatgac aagggagacg cattgggtca acagtataga accgtggatg atgtggtctc    6000
tacaggatct gacattatta ttgttggaag aggactattt gcaaagggaa gggatgctaa    6060
ggtagagggt gaacgttaca gaaaagcagg ctgggaagca tatttgagaa gatgcggcca    6120
gcaaaactaa aaaactgtat tataagtaaa tgcatgtata ctaaactcac aaattagagc    6180
ttcaatttaa ttatatcagt tattacccgg gaatctcggt cgtaatgatt tctataatga    6240
cgaaaaaaaa aaaattggaa agaaaaagct tcatggcctt gcggccgctt aattaatcta    6300
gagtcgacct gcaggcatgc aagcttggcg taatcatggt catagctgtt tcctgtgtga    6360
aattgttatc cgctcacaat tccacacaac atacgagccg aagcataaa gtgtaaagcc    6420 tggggtgcct aatgagtgag ctaactcaca ttaattgcgt tgcgctcact gcccgctttc    6480
cagtcgggaa acctgtcgtg ccagctgcat taatgaatcg gccaacgcgc ggggagaggc    6540
ggtttgcgta ttgggcgctc ttccgcttcc tcgctcactg actcgctgcg ctcggtcgtt    6600
cggctgcggc gagcggtatc agctcactca aaggcggtaa tacggttatc cacagaatca    6660
ggggataacg caggaaagaa catgtgagca aaaggccagc aaaaggccag gaaccgtaaa    6720
aaggccgcgt tgctggcgtt tttccatagg ctccgccccc ctgacgagca tcacaaaaat    6780
cgacgctcaa gtcagaggtg gcgaaacccg acaggactat aaagatacca ggcgtttccc    6840
cctggaagct ccctcgtgcg ctctcctgtt ccgaccctgc cgcttaccgg atacctgtcc    6900
gcctttctcc cttcgggaag cgtggcgctt tctcatagct cacgctgtag gtatctcagt    6960
tcggtgtagg tcgttcgctc caagctgggc tgtgtgcacg aaccccccgt tcagcccgac    7020
cgctgcgcct tatccggtaa ctatcgtctt gagtccaacc cggtaagaca cgacttatcg    7080
ccactggcag cagccactgg taacaggatt agcagagcga ggtatgtagg cggtgctaca    7140
gagttcttga agtggtggcc taactacggc tacactagaa ggacagtatt tggtatctgc    7200
gctctgctga agccagttac cttcggaaaa agagttggta gctcttgatc cggcaaacaa    7260
accaccgctg gtagcggtgg tttttttgtt tgcaagcagc agattacgcg cagaaaaaaa    7320
ggatctcaag aagatccttt gatcttttct acggggtctg acgctcagtg gaacgaaaac    7380
tcacgttaag ggattttggt catgagatta tcaaaaagga tcttcaccta gatcctttta    7440
aattaaaaat gaagttttaa atcaatctaa agtatatatg agtaaacttg gtctgacagt    7500
taccaatgct taatcagtga ggcacctatc tcagcgatct gtctatttcg ttcatccata    7560
gttgcctgac tccccgtcgt gtagataact acgatacggg agggcttacc atctggcccc    7620
agtgctgcaa tgataccgcg agacccacgc tcaccggctc cagatttatc agcaataaac    7680
cagccagccg aagggccga gcgcagaagt ggtcctgcaa ctttatccgc ctccatccag    7740
tctattaatt gttgccggga agctagagta agtagttcgc cagttaatag tttgcgcaac    7800
gttgttgcca ttgctacagg catcgtggtg tcacgctcgt cgtttggtat ggcttcattc    7860
agctccggtt cccaacgatc aaggcgagtt acatgatccc ccatgttgtg caaaaaagcg    7920
gttagctcct tcggtcctcc gatcgttgtc agaagtaagt tggccgcagt gttatcactc    7980
```

```
atggttatgg cagcactgca taattctctt actgtcatgc catccgtaag atgcttttct    8040
gtgactggtg agtactcaac caagtcattc tgagaatagt gtatgcggcg accgagttgc    8100
tcttgcccgg cgtcaatacg ggataatacc gcgccacata gcagaacttt aaaagtgctc    8160
atcattggaa aacgttcttc ggggcgaaaa ctctcaagga tcttaccgct gttgagatcc    8220
agttcgatgt aacccactcg tgcacccaac tgatcttcag catcttttac tttcaccagc    8280
gtttctgggt gagcaaaaac aggaaggcaa aatgccgcaa aaaagggaat aagggcgaca    8340
cggaaatgtt gaatactcat actcttcctt tttcaatatt attgaagcat ttatcagggt    8400
tattgtctca tgagcggata catatttgaa tgtatttaga aaaataaaca ataggggtt     8460 ccgcgcacat ttccccgaaa agtgccacct gacgtctaag aaaccattat tatcatgaca    8520
ttaacctata aaaataggcg tatcacgagg ccctttcgtc tcgcgcgttt cggtgatgac    8580
ggtgaaaacc tctgacacat gcagctcccg gagacggtca cagcttgtct gtaagcggat    8640
gccgggagca gacaagcccg tcagggcgcg tcagcgggtg ttggcgggtg tcgggctgg     8700 cttaactatg cggcatcaga gcagattgta ctgagagtgc accatatgcg gtgtgaaata    8760
ccgcacagat gcgtaaggag aaaataccgc atcaggcgcc attcgccatt caggctgcgc    8820
aactgttggg aagggcgatc ggtgcgggcc tcttcgctat tacgccagct ggcgaaaggg    8880
ggatgtgctg caaggcgatt aagttgggta acgccagggt tttcccagtc acgacgttgt    8940
aaaacgacgg ccagtgaatt cgagctcggt acccggggat ccggcgcgcc gttttatttg    9000
tatcgaggtg tctagtcttc tattacacta atgcagtttc agggttttgg aaaccacact    9060
gtttaaacag tgttccttaa tcaaggatac ctctttttt ttccttggtt ccactaattc     9120
atcggttttt tttttggaag acatcttttc caacgaaaag aatatacata tcgtttaaga    9180
gaaattctcc aaatttgtaa agaagcggac ccagacttaa                          9220
```

<210> SEQ ID NO 59
<211> LENGTH: 20
<212> TYPE: DNA
<213> ORGANISM: Artificial Sequence
<220> FEATURE:
<223> OTHER INFORMATION: N886 Primer

<400> SEQUENCE: 59
caatgattgt tggtaaaggg                                                20

<210> SEQ ID NO 60
<211> LENGTH: 30
<212> TYPE: DNA
<213> ORGANISM: Artificial Sequence
<220> FEATURE:
<223> OTHER INFORMATION: N1214 Primer

<400> SEQUENCE: 60
aaaaaggggg tagaagcgtt ttgaagctat                                     30

<210> SEQ ID NO 61
<211> LENGTH: 22
<212> TYPE: DNA
<213> ORGANISM: Artificial Sequence
<220> FEATURE:
<223> OTHER INFORMATION: oBP512 Primer

<400> SEQUENCE: 61
aaagttggca tagcggaaac tt                                             22

<210> SEQ ID NO 62
<211> LENGTH: 19
<212> TYPE: DNA
<213> ORGANISM: Artificial Sequence
<220> FEATURE:
<223> OTHER INFORMATION: N160SeqR5 Primer

<400> SEQUENCE: 62
tgagcccgaa agagaggat                                                19

<210> SEQ ID NO 63
<211> LENGTH: 21
<212> TYPE: DNA
<213> ORGANISM: Artificial Sequence
<220> FEATURE:
<223> OTHER INFORMATION: oBP540 Primer

<400> SEQUENCE: 63
taggcataat caccgaagaa g                                             21

<210> SEQ ID NO 64
<211> LENGTH: 60
<212> TYPE: DNA
<213> ORGANISM: Artificial Sequence
<220> FEATURE:
<223> OTHER INFORMATION: oBP835 Primer

<400> SEQUENCE: 64
cacaaacgtt gaatcatgag ttttatgtta attagctttg ttcttcttgt tattgtattg   60

<210> SEQ ID NO 65
<211> LENGTH: 60
<212> TYPE: DNA
<213> ORGANISM: Artificial Sequence
<220> FEATURE:
<223> OTHER INFORMATION: oBP836 Primer

<400> SEQUENCE: 65
caaagagaac aacacaatac aataacaaga agaacaaagc taattaacat aaaactcatg   60

<210> SEQ ID NO 66
<211> LENGTH: 60
<212> TYPE: DNA
<213> ORGANISM: Artificial Sequence
<220> FEATURE:
<223> OTHER INFORMATION: oBP837 Primer

<400> SEQUENCE: 66
ttgaaaagct ttatggaccc tgaaaccaca gccacattaa gtaaataaat taatcagcat   60

<210> SEQ ID NO 67
<211> LENGTH: 60
<212> TYPE: DNA
<213> ORGANISM: Artificial Sequence
<220> FEATURE:
<223> OTHER INFORMATION: oBP838 Primer

<400> SEQUENCE: 67
tttattattt aattttatgc tgattaattt atttacttaa tgtggctgtg gtttcagggt   60

<210> SEQ ID NO 68
<211> LENGTH: 60
<212> TYPE: DNA
<213> ORGANISM: Artificial Sequence
<220> FEATURE:
<223> OTHER INFORMATION: oBP839 Primer

<400> SEQUENCE: 68
gatgatggtc gagggggagt agaactgggc ggtcaacaaa ggccatgaag cttttctttt    60

<210> SEQ ID NO 69
<211> LENGTH: 60
<212> TYPE: DNA
<213> ORGANISM: Artificial Sequence
<220> FEATURE:
<223> OTHER INFORMATION: oBP840 Primer

<400> SEQUENCE: 69
aaaaaaaaaa aattggaaag aaaaagcttc atggcctttg ttgaccgccc agttctactc    60

<210> SEQ ID NO 70
<211> LENGTH: 22
<212> TYPE: DNA
<213> ORGANISM: Artificial Sequence
<220> FEATURE:
<223> OTHER INFORMATION: oBP841 Primer

<400> SEQUENCE: 70
tcaggcagcg cctgcgttcg ag    22

<210> SEQ ID NO 71
<211> LENGTH: 30
<212> TYPE: DNA
<213> ORGANISM: Artificial Sequence
<220> FEATURE:
<223> OTHER INFORMATION: Ura3-end Primer

<400> SEQUENCE: 71
gcatatttga aagatgcgg ccagcaaaac    30

<210> SEQ ID NO 72
<211> LENGTH: 21
<212> TYPE: DNA
<213> ORGANISM: Artificial Sequence
<220> FEATURE:
<223> OTHER INFORMATION: oBP541 Primer

<400> SEQUENCE: 72
aaaatggtaa gcagctgaaa g    21

<210> SEQ ID NO 73
<211> LENGTH: 33
<212> TYPE: DNA
<213> ORGANISM: Artificial Sequence
<220> FEATURE:
<223> OTHER INFORMATION: oBP530 Primer

<400> SEQUENCE: 73
aattggcgcg ccatgaaagc tctggtttat cac    33

<210> SEQ ID NO 74
<211> LENGTH: 49
<212> TYPE: DNA
<213> ORGANISM: Artificial Sequence
<220> FEATURE:
<223> OTHER INFORMATION: oBP531 Primer

<400> SEQUENCE: 74
tgaatcatga gttttatgtt aattagctca ggcagcgcct gcgttcgag    49

<210> SEQ ID NO 75

<211> LENGTH: 15539
<212> TYPE: DNA
<213> ORGANISM: Artificial Sequence
<220> FEATURE:
<223> OTHER INFORMATION: pLH468 Plasmid

<400> SEQUENCE: 75

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accataaatt cccgttttaa gagcttggtg agcgctagga gtcactgcca ggtatcgttt | 240 |
| gaacacggca ttagtcaggg aagtcataac acagtccttt cccgcaattt tctttttcta | 300 |
| ttactcttgg cctcctctag tacactctat atttttttat gcctcggtaa tgattttcat | 360 |
| ttttttttt ccacctagcg gatgactctt ttttttttctt agcgattggc attatcacat | 420 |
| aatgaattat acattatata agtaatgtg atttcttcga agaatatact aaaaaatgag | 480 |
| caggcaagat aaacgaaggc aaagatgaca gagcagaaag ccctagtaaa gcgtattaca | 540 |
| aatgaaacca agattcagat tgcgatctct ttaaagggtg gtccctagc gatagagcac | 600 |
| tcgatcttcc cagaaaaaga ggcagaagca gtagcagaac aggccacaca atcgcaagtg | 660 |
| attaacgtcc acacaggtat agggtttctg gaccatatga tacatgctct ggccaagcat | 720 |
| tccggctggt cgctaatcgt tgagtgcatt ggtgacttac acatagacga ccatcacacc | 780 |
| actgaagact gcgggattgc tctcggtcaa gcttttaaag aggccctagg ggccgtgcgt | 840 |
| ggagtaaaaa ggtttggatc aggatttgcg cctttggatg aggcactttc cagagcggtg | 900 |
| gtagatcttt cgaacaggcc gtacgcagtt gtcgaacttg gtttgcaaag ggagaaagta | 960 |
| ggagatctct cttgcgagat gatcccgcat tttcttgaaa gctttgcaga ggctagcaga | 1020 |
| attaccctcc acgttgattg tctgcgaggc aagaatgatc atcaccgtag tgagagtgcg | 1080 |
| ttcaaggctc ttgcggttgc cataagagaa gccacctcgc ccaatggtac caacgatgtt | 1140 |
| ccctccacca aggtgttct tatgtagtga caccgattat ttaaagctgc agcatacgat | 1200 |
| atatatacat gtgtatatat gtataccat gaatgtcagt aagtatgtat acgaacagta | 1260 |
| tgatactgaa gatgacaagg taatgcatca ttctatacgt gtcattctga acgaggcgcg | 1320 |
| cttttccttttt ttcttttttgc ttttttctttt ttttctctt gaactcgacg gatctatgcg | 1380 |
| gtgtgaaata ccgcacagat gcgtaaggag aaaataccgc atcaggaaat tgtaagcgtt | 1440 |
| aatattttgt taaaattcgc gttaaatttt tgttaaatca gctcatttttt taaccaatag | 1500 |
| gccgaaatcg gcaaaatccc ttataaatca aagaataga ccgagatagg gttgagtgtt | 1560 |
| gttccagttt ggaacaagag tccactatta agaacgtgg actccaacgt caaagggcga | 1620 |
| aaaaccgtct atcagggcga tggcccacta cgtgaaccat caccctaatc aagttttttg | 1680 |
| gggtcgaggt gccgtaaagc actaaatcgg aaccctaaag ggagccccg atttagagct | 1740 |
| tgacggggaa agccggcgaa cgtggcgaga aggaaggga agaaagcgaa aggagcgggc | 1800 |
| gctagggcgc tggcaagtgt agcggtcacg ctgcgcgtaa ccaccacacc cgccgcgctt | 1860 |
| aatgcgccgc tacagggcgc gtccattcgc cattcaggct gcgcaactgt tgggaagggc | 1920 |
| gcggtgcggg cctcttcgct attacgccag ctggcgaaag gggatgtgc tgcaaggcga | 1980 |
| ttaagttggg taacgccagg gttttcccag tcacgacgtt gtaaaacgac ggccagtgag | 2040 |
| cgcgcgtaat acgactcact ataggggaa ttggtaccg ggccccccct cgaggtcgac | 2100 |
| ggcgcgccac tggtagagag cgactttgta tgccccaatt gcgaaacccg cgatatcctt | 2160 |

```
ctcgattctt tagtacccga ccaggacaag gaaaaggagg tcgaaacgtt tttgaagaaa    2220
caagaggaac tacacggaag ctctaaagat ggcaaccagc cagaaactaa gaaaatgaag    2280
ttgatggatc caactggcac cgctggcttg aacaacaata ccagccttcc aacttctgta    2340
aataacggcg gtacgccagt gccaccagta ccgttacctt tcggtatacc tccttttcccc   2400 atgtttccaa tgcccttcat gcctccaacg gctactatca caaatcctca tcaagctgac    2460
gcaagcccta gaaatgaat aacaatactg acagtactaa ataattgcct acttggcttc     2520
acatacgttg catacgtcga tatagataat aatgataatg acagcaggat tatcgtaata    2580
cgtaatagct gaaaatctca aaaatgtgtg ggtcattacg taaataatga taggaatggg    2640
attcttctat ttttccttt tccattctag cagccgtcgg gaaaacgtgg catcctctct     2700
ttcgggctca attggagtca cgctgccgtg agcatcctct ctttccatat ctaacaactg    2760
agcacgtaac caatggaaaa gcatgagctt agcgttgctc caaaaagta ttggatggtt    2820 aataccattt gtctgttctc ttctgacttt gactcctcaa aaaaaaaat ctacaatcaa    2880 cagatcgctt caattacgcc ctcacaaaaa cttttttcct tcttcttcgc ccacgttaaa   2940
ttttatccct catgttgtct aacggatttc tgcacttgat ttattataaa agacaaaga    3000 cataatactt ctctatcaat ttcagttatt gttcttcctt gcgttattct tctgttcttc   3060
tttttctttt gtcatatata accataacca agtaatacat attcaaacta gtatgactga   3120
caaaaaaact cttaaagact taagaaatcg tagttctgtt tacgattcaa tggttaaatc    3180
acctaatcgt gctatgttgc gtgcaactgg tatgcaagat gaagactttg aaaaacctat    3240
cgtcggtgtc atttcaactt gggctgaaaa cacaccttgt aatatccact tacatgactt    3300 tggtaaaacta gccaaagtcg gtgttaagga agctggtgct tggccagttc agttcggaac    3360
aatcacggtt tctgatggaa tcgccatggg aacccaagga atgcgtttct ccttgacatc    3420
tcgtgatatt attgcagatt ctattgaagc agccatggga ggtcataatg cggatgcttt    3480
tgtagccatt ggcggttgtg ataaaaacat gcccggttct gttatcgcta tggctaacat    3540
ggatatccca gccatttttg cttacggcgg aacaattgca cctggtaatt tagacggcaa    3600
agatatcgat ttagtctctg tctttgaagg tgtcggccat tggaaccacg gcgatatgac    3660
caaagaagaa gttaaagctt tggaatgtaa tgcttgtccc ggtcctggag gctgcggtgg    3720
tatgtatact gctaacacaa tggcgacagc tattgaagtt tgggactta gccttccggg     3780 ttcatcttct cacccggctg aatccgcaga aagaaagca gatattgaag aagctggtcg    3840
cgctgttgtc aaaatgctcg aaatgggctt aaaaccttct gacattttaa cgcgtgaagc    3900
ttttgaagat gctattactg taactatggc tctgggaggt tcaaccaact caaccccttca    3960 cctcttagct attgcccatg ctgctaatgt ggaattgaca cttgatgatt tcaatacttt    4020
ccaagaaaaa gttcctcatt tggctgattt gaaaccttct ggtcaatatg tattccaaga    4080
cctttacaag gtcggagggg taccagcagt tatgaaatat ctccttaaaa atggcttcct    4140
tcatggtgac cgtatcactt gtactggcaa aacagtcgct gaaaatttga aggcttttga   4200
tgatttaaca cctggtcaaa aggttattat gccgcttgaa atcctaaac gtgaagatgg     4260 tccgctcatt attctccatg gtaacttggc tccagacggt gccgttgcca agtttctgg     4320 tgtaaaagtg cgtcgtcatg tcggtcctgc taaggtcttt aattctgaag aagaagccat    4380
tgaagctgtc ttgaatgatg atattgttga tggtgatgtt gttgtcgtac gttttgtagg    4440
accaaagggc ggtcctggta tgcctgaaat gctttccctt tcatcaatga ttgttggtaa    4500
```

-continued

```
agggcaaggt gaaaaagttg cccttctgac agatggccgc ttctcaggtg gtacttatgg    4560
tcttgtcgtg ggtcatatcg ctcctgaagc acaagatggc ggtccaatcg cctacctgca    4620
aacaggagac atagtcacta ttgaccaaga cactaaggaa ttacactttg atatctccga    4680
tgaagagtta aaacatcgtc aagagaccat tgaattgcca ccgctctatt cacgcggtat    4740
ccttggtaaa tatgctcaca tcgtttcgtc tgcttctagg ggagccgtaa cagacttttg    4800
gaagcctgaa gaaactggca aaaatgttg tcctggttgc tgtggttaag cggccgcgtt     4860
aattcaaatt aattgatata gttttttaat gagtattgaa tctgtttaga ataatggaa     4920
tattattttt atttatttat ttatattatt ggtcggctct tttcttctga aggtcaatga    4980
caaaatgata tgaaggaaat aatgatttct aaaattttac aacgtaagat atttttacaa    5040
aagcctagct catcttttgt catgcactat tttactcacg cttgaaatta acggccagtc    5100
cactgcggag tcatttcaaa gtcatcctaa tcgatctatc gttttgata gctcattttg     5160
gagttcgcga ttgtcttctg ttattcacaa ctgttttaat ttttatttca ttctggaact    5220
cttcgagttc tttgtaaagt ctttcatagt agcttacttt atcctccaac atatttaact    5280
tcatgtcaat ttcggctctt aaattttcca catcatcaag ttcaacatca tctttaact    5340
tgaatttatt ctctagctct tccaaccaag cctcattgct ccttgattta ctggtgaaaa    5400
gtgatacact ttgcgcgcaa tccaggtcaa aactttcctg caaagaattc accaatttct    5460
cgacatcata gtacaatttg ttttgttctc ccatcacaat ttaatatacc tgatggattc    5520
ttatgaagcg ctgggtaatg acgtgtcac tctacttcgc cttttccct actccttta      5580
gtacggaaga caatgctaat aaataagagg gtaataataa tattattaat cggcaaaaaa    5640
gattaaacgc caagcgttta attatcagaa agcaaacgtc gtaccaatcc ttgaatgctt    5700
cccaattgta tattaagagt catcacagca acatattctt gttattaaat taattattat    5760
tgattttttga tattgtataa aaaaccaaa tatgtataaa aaagtgaat aaaaaatacc     5820
aagtatggag aaatatatta gaagtctata cgttaaacca cccgggcccc ccctcgaggt    5880
cgacggtatc gataagcttg atatcgaatt cctgcagccc ggggatcca ctagttctag    5940
agcggccgct ctagaactag taccacaggt gttgtcctct gaggacataa aatacacacc    6000
gagattcatc aactcattgc tggagttagc atatctacaa ttgggtgaaa tggggagcga    6060
tttgcaggca tttgctcggc atgccggtag aggtgtggtc aataagagcg acctcatgct    6120
atacctgaga aagcaacctg acctacagga aagagttact caagaataag aattttcgtt    6180
ttaaaaccta agagtcactt taaaatttgt atacacttat ttttttata acttatttaa     6240
taataaaaat cataaatcat aagaaattcg cttactctta attaatcaaa aagttaaaat    6300
tgtacgaata gattcaccac ttcttaacaa atcaaaccct tcattgattt tctcgaatgg    6360
caatacatgt gtaattaaag gatcaagagc aaacttcttc gccataaagt cggcaacaag    6420
ttttggaaca ctatccttgc tcttaaaacc gccaaatata gctcccttcc atgtacgacc    6480
gcttagcaac agcataggat tcatcgacaa attttgtgaa tcaggaggaa cacctacgat    6540
cacactgact ccatatgcct cttgacagca ggacaacgca gttaccatag tatcaagacg    6600
gcctataact tcaaaagaga aatcaactcc accgtttgac atttcagtaa ggacttcttg    6660
tattggtttc ttataatctt gagggttaac acattcagta gccccgacct ccttagcttt    6720
tgcaaatttg tccttattga tgtctacacc tataatcctc gctgcgcctg cagctttaca    6780
ccccataata acgcttagtc ctactcctcc taaaccgaat actgcacaag tcgaccctg     6840
tgtaaccttt gcaactttaa ctgcggaacc gtaaccggtg gaaaatccgc accctatcaa    6900
```

```
gcaaactttt tccagtggtg aagctgcatc gattttagcg acagatatct cgtccaccac    6960
tgtgtattgg gaaaatgtag aagtaccaag gaaatggtgt ataggtttcc ctctgcatgt    7020
aaatctgctt gtaccatcct gcatagtacc tctaggcata gacaaatcat ttttaaggca    7080
gaaattaccc tcaggatgtt tgcagactct acacttacca cattgaggag tgaacagtgg    7140
gatcacttta tcaccaggac gaacagtggt aacaccttca cctatggatt caacgattcc    7200
ggcagcctcg tgtcccgcga ttactggcaa aggagtaact agagtgccac tcaccacatg    7260
gtcgtcggat ctacagattc cggtggcaac catcttgatt ctaacctcgt gtgcttttgg    7320
tggcgctact tctacttctt ctatgctaaa cggcttttc tcttcccaca aaactgccgc     7380
tttacactta ataactttac cggctgttga catcctcagc tagctattgt aatatgtgtg    7440
tttgtttgga ttattaagaa gaataattac aaaaaaaatt acaaaggaag gtaattacaa    7500
cagaattaag aaaggacaag aaggaggaag agaatcagtt cattatttct tctttgttat    7560
ataacaaacc caagtagcga tttggccata cattaaaagt tgagaaccac cctccctggc    7620
aacagccaca actcgttacc attgttcatc acgatcatga aactcgctgt cagctgaaat    7680
ttcacctcag tggatctctc tttttattct tcatcgttcc actaaccttt ttccatcagc    7740
tggcagggaa cggaaagtgg aatcccattt agcgagcttc ctcttttctt caagaaaaga    7800
cgaagcttgt gtgtgggtgc gcgcgctagt atctttccac attaagaaat ataccataaa    7860
ggttacttag acatcactat ggctatatat atatatatat atatatgtaa cttagcacca    7920
tcgcgcgtgc atcactgcat gtgttaaccg aaaagtttgg cgaacacttc accgacacgg    7980
tcatttagat ctgtcgtctg cattgcacgt cccttagcct taaatcctag gcgggagcat    8040
tctcgtgtaa ttgtgcagcc tgcgtagcaa ctcaacatag cgtagtctac ccagtttttc    8100
aagggtttat cgttagaaga ttctcccttt tcttcctgct cacaaatctt aaagtcatac    8160
attgcacgac taaatgcaag catgcggatc ccccgggctg caggaattcg atatcaagct    8220
tatcgatacc gtcgactggc cattaatctt tcccatatta gatttcgcca agccatgaaa    8280
gttcaagaaa ggtctttaga cgaattaccc ttcatttctc aaactggcgt caagggatcc    8340
tggtatggtt ttatcgtttt atttctggtt cttatagcat cgttttggac ttctctgttc    8400
ccattaggcg gttcaggagc cagcgcagaa tcattctttg aaggatactt atcctttcca    8460
attttgattg tctgttacgt tggacataaa ctgtatacta gaaattggac tttgatggtg    8520
aaactagaag atatggatct tgataccggc agaaaacaag tagatttgac tcttcgtagg    8580
gaagaaatga ggattgagcg agaaacatta gcaaaaagat ccttcgtaac aagattttta    8640
catttctggt gttgaaggga agatatgag ctatacagcg gaatttccat atcactcaga    8700
ttttgttatc taattttttc cttcccacgt ccgcgggaat ctgtgtatat tactgcatct    8760
agatatatgt tatcttatct tggcgcgtac atttaatttt caacgtattc tataagaaat    8820
tgcgggagtt ttttttcatgt agatgatact gactgcacgc aaatataggc atgatttata    8880
ggcatgattt gatggctgta ccgataggaa cgctaagagt aacttcagaa tcgttatcct    8940
ggcgaaaaaa attcatttgt aaactttaaa aaaaaaagcc aatatcccca aaattattaa    9000
gagcgcctcc attattaact aaaatttcac tcagcatcca caatgtatca ggtatctact    9060
acagatatta catgtggcga aaaagacaag aacaatgcaa tagcgcatca agaaaaaaca    9120
caaagctttc aatcaatgaa tcgaaaatgt cattaaaata gtatataaat tgaaactaag    9180
tcataaagct ataaaagaa aatttattta aatgcaagat ttaaagtaaa ttcacggccc    9240
```

```
tgcaggcctc agctcttgtt ttgttctgca aataacttac ccatcttttt caaaacttta   9300
ggtgcaccct cctttgctag aataagttct atccaataca tcctatttgg atctgcttga   9360
gcttctttca tcacggatac gaattcattt tctgttctca caattttgga cacaactctg   9420
tcttccgttg ccccgaaact ttctggcagt tttgagtaat tccacatagg aatgtcatta   9480
taactctggt tcggaccatg aatttccctc tcaaccgtgt aaccatcgtt attaatgata   9540
aagcagattg ggtttatctt ctctctaatg gctagtccta attcttggac agtcagttgc   9600
aatgatccat ctccgataaa caataaatgt ctagattctt tatctgcaat ttggctgcct   9660
agagctgcgg ggaaagtgta tcctatagat ccccacaagg gttgaccaat aaaatgtgat   9720
ttcgatttca gaaatataga tgaggcaccg aagaagaag tgccttgttc agccacgatc    9780
gtctcattac tttgggtcaa attttcgaca gcttgccaca gtctatcttg tgacaacagc   9840
gcgttagaag gtacaaaatc ttcttgcttt ttatctatgt acttgccttt atattcaatt   9900
tcggacaagt caagaagaga tgatatcagg gattcgaagt cgaaattttg gattctttcg   9960
ttgaaaattt taccttcatc gatattcaag gaaatcattt tattttcatt aagatggtga  10020
gtaaatgcac ccgtactaga atcggtaagc tttacaccca acataagaat aaaatcagca  10080
gattccacaa attccttcaa gtttggctct gacagagtac cgttgtaaat ccccaaaaat  10140
gagggcaatg cttcatcaac agatgattta ccaaagttca agtagtaat aggtaactta    10200 gtctttgaaa taaactgagt aacagtcttc tctaggccga acgatataat ttcatggcct  10260
gtgattacaa ttggtttctt ggcattcttc agactttcct gtattttgtt cagaatctct  10320
tgatcagatg tattcgacgt ggaattttcc ttcttaagag gcaaggatgg tttttcagcc  10380
ttagcggcag ctacatctac aggtaaattg atgtaaaccg gctttctttc ctttagtaag  10440
gcagacaaca ctctatcaat ttcaacagtt gcattctcgg ctgtcaataa agtcctggca  10500
gcagtaaccg gttcgtgcat cttcataaag tgcttgaaat caccatcagc caacgtatgg  10560
tgaacaaact taccttcgtt ctgcactttc gaggtaggag atcccacgat ctcaacaaca  10620
ggcaggttct cagcatagga gcccgctaag ccattaactg cggataattc gccaacacca  10680
aatgtagtca agaatgccgc agccttttc gttcttgcgt acccgtcggc catataggag   10740
gcatttaact cattagcatt tcccacccat ttcatatctt tgtgtgaaat aatttgatct  10800
agaaattgca aattgtagtc acctggtact ccgaatattt cttctatacc taattcgtgt  10860
aatctgtcca acagatagtc acctactgta tacattttgt ttactagttt atgtgtgttt  10920
attcgaaact aagttcttgg tgttttaaaa ctaaaaaaaa gactaactat aaaagtagaa  10980
tttaagaagt ttaagaaata gatttacaga attacaatca atacctaccg tctttatata  11040
cttattagtc aagtagggga ataatttcag ggaactggtt tcaacctttt ttttcagctt  11100
tttccaaatc agagagagca gaaggtaata gaaggtgtaa gaaaatgaga tagatacatg  11160
cgtgggtcaa ttgccttgtg tcatcattta ctccaggcag gttgcatcac tccattgagg  11220
ttgtgcccgt tttttgcctg tttgtgcccc tgttctctgt agttgcgcta agagaatgga  11280
cctatgaact gatggttggt gaagaaaaca atattttggt gctgggattc tttttttttc  11340
tggatgccag cttaaaaagc gggctccatt atatttagtg gatgccagga ataaactgtt  11400
cacccagaca cctacgatgt tatatattct gtgtaacccg cccctatttt tgggcatgta  11460
cgggttacag cagaattaaa aggctaattt tttgactaaa taagttagg aaaatcacta    11520 ctattaatta tttcgtgtatt ctttgaaatg gcagtattga taatgataaa ctcgaactga  11580
aaaagcgtgt ttttattca aaatgattct aactcccctta cgtaatcaag gaatctttttt 11640
```

```
gccttggcct ccgcgtcatt aaacttcttg ttgttgacgc taacattcaa cgctagtata   11700
tattcgtttt tttcaggtaa gttcttttca acgggtctta ctgatgaggc agtcgcgtct   11760
gaacctgtta agaggtcaaa tatgtcttct tgaccgtacg tgtcttgcat gttattagct   11820
ttgggaattt gcatcaagtc ataggaaaat ttaaatcttg gctctcttgg gctcaaggtg   11880
acaaggtcct cgaaaatagg gcgcgcccca ccgcggtgga gctccagctt tgttcccttt   11940
tagtgagggt taattgcgcg cttggcgtaa tcatggtcat agctgtttcc tgtgtgaaat   12000
tgttatccgc tcacaattcc acacaacata cgagccggaa gcataaagtg taaagcctgg   12060
ggtgcctaat gagtgagcta actcacatta attgcgttgc gctcactgcc cgctttccag   12120
tcgggaaacc tgtcgtgcca gctgcattaa tgaatcggcc aacgcgcggg gagaggcggt   12180
ttgcgtattg ggcgctcttc cgcttcctcg ctcactgact cgctgcgctc ggtcgttcgg   12240
ctgcggcgag cggtatcagc tcactcaaag gcggtaatac ggttatccac agaatcaggg   12300
gataacgcag gaaagaacat gtgagcaaaa ggccagcaaa aggccaggaa ccgtaaaaag   12360
gccgcgttgc tggcgttttt ccataggctc cgcccccctg acgagcatca caaaaatcga   12420
cgctcaagtc agaggtggcg aaacccgaca ggactataaa gataccaggc gtttccccct   12480
ggaagctccc tcgtgcgctc tcctgttccg accctgccgc ttaccggata cctgtccgcc   12540
tttctccctt cgggaagcgt ggcgctttct catagctcac gctgtaggta tctcagttcg   12600
gtgtaggtcg ttcgctccaa gctgggctgt gtgcacgaac cccccgttca gcccgaccgc   12660
tgcgccttat ccggtaacta tcgtcttgag tccaacccgg taagacacga cttatcgcca   12720
ctggcagcag ccactggtaa caggattagc agagcgaggt atgtaggcgg tgctacagag   12780
ttcttgaagt ggtggcctaa ctacggctac actagaagaa cagtatttgg tatctgcgct   12840
ctgctgaagc cagttacctt cggaaaaaga gttggtagct cttgatccgg caaacaaacc   12900
accgctggta gcggtggttt ttttgtttgc aagcagcaga ttacgcgcag aaaaaaagga   12960
tctcaagaag atcctttgat cttttctacg gggtctgacg ctcagtggaa cgaaaactca   13020
cgttaaggga ttttggtcat gagattatca aaaaggatct tcacctagat ccttttaaat   13080
taaaaatgaa gttttaaatc aatctaaagt atatatgagt aaacttggtc tgacagttac   13140
caatgcttaa tcagtgaggc acctatctca gcgatctgtc tatttcgttc atccatagtt   13200
gcctgactcc ccgtcgtgta gataactacg atacgggagg gcttaccatc tggccccagt   13260
gctgcaatga taccgcgaga cccacgctca ccggctccag atttatcagc aataaaccag   13320
ccagccggaa gggccgagcg cagaagtggt cctgcaactt tatccgcctc catccagtct   13380
attaattgtt gccgggaagc tagagtaagt agttcgccag ttaatagttt gcgcaacgtt   13440
gttgccattg ctacaggcat cgtggtgtca cgctcgtcgt ttggtatggc ttcattcagc   13500
tccggttccc aacgatcaag gcgagttaca tgatccccca tgttgtgcaa aaaagcggtt   13560
agctccttcg gtcctccgat cgttgtcaga agtaagttgg ccgcagtgtt atcactcatg   13620
gttatggcag cactgcataa ttctcttact gtcatgccat ccgtaagatg cttttctgtg   13680
actggtgagt actcaaccaa gtcattctga gaatagtgta tgcggcgacc gagttgctct   13740
tgcccggcgt caatacggga taataccgcg ccacatagca gaactttaaa agtgctcatc   13800
attggaaaac gttcttcggg gcgaaaactc tcaaggatct taccgctgtt gagatccagt   13860
tcgatgtaac ccactcgtgc acccaactga tcttcagcat cttttacttt caccagcgtt   13920
tctgggtgag caaaaacagg aaggcaaaat gccgcaaaaa agggaataag ggcgacacgg   13980
```

-continued

```
aaatgttgaa tactcatact cttcctttt caatattatt gaagcattta tcagggttat   14040
tgtctcatga gcggatacat atttgaatgt atttagaaaa ataaacaaat aggggttccg   14100
cgcacatttc cccgaaaagt gccacctgaa cgaagcatct gtgcttcatt ttgtagaaca   14160
aaaatgcaac gcgagagcgc taattttca aacaaagaat ctgagctgca ttttacaga    14220
acagaaatgc aacgcgaaag cgctattta ccaacgaaga atctgtgctt cattttgta    14280
aaacaaaaat gcaacgcgag agcgctaatt tttcaaacaa agaatctgag ctgcatttt   14340
acagaacaga aatgcaacgc gagagcgcta tttaccaac aaagaatcta tacttctttt   14400
ttgttctaca aaaatgcatc ccgagagcgc tatttttcta acaaagcatc ttagattact   14460
tttttctcc tttgtgcgct ctataatgca gtctcttgat aactttttgc actgtaggtc   14520
cgttaaggtt agaagaaggc tactttggtg tctattttct cttccataaa aaagcctga    14580
ctccacttcc cgcgtttact gattactagc gaagctgcgg gtgcattttt tcaagataaa   14640
ggcatccccg attatattct ataccgatgt ggattgcgca tactttgtga acagaaagtg   14700
atagcgttga tgattcttca ttggtcagaa aattatgaac ggtttcttct atttgtctc    14760
tatatactac gtataggaaa tgtttacatt ttcgtattgt tttcgattca ctctatgaat   14820
agttcttact acaattttt tgtctaaaga gtaatactag ataaacat aaaaaatgta    14880
gaggtcgagt ttagatgcaa gttcaaggag cgaaaggtgg atgggtaggt tatataggga   14940
tatagcacag agatatatag caaagagata cttttgagca atgtttgtgg aagcggtatt   15000
cgcaatattt tagtagctcg ttacagtccg gtgcgttttt ggttttttga aagtgcgtct   15060
tcagagcgct tttggttttc aaaagcgctc tgaagttcct atactttcta gagaatagga   15120
acttcggaat aggaacttca aagcgtttcc gaaaacgagc gcttccgaaa atgcaacgcg   15180
agctgcgcac atacagctca ctgttcacgt cgcacctata tctgcgtgtt gcctgtatat   15240
atatatacat gagaagaacg gcatagtgcg tgtttatgct aaatgcgta cttatatgcg    15300
tctatttatg taggatgaaa ggtagtctag tacctcctgt gatattatcc cattccatgc   15360
ggggtatcgt atgcttcctt cagcactacc ctttagctgt tctatatgct gccactcctc   15420
aattggatta gtctcatcct tcaatgctat catttccttt gatattggat catactaaga   15480
aaccattatt atcatgacat taacctataa aaataggcgt atcacgaggc cctttcgtc    15539
```

<210> SEQ ID NO 76
<211> LENGTH: 1123
<212> TYPE: DNA
<213> ORGANISM: Artificial Sequence
<220> FEATURE:
<223> OTHER INFORMATION: BiADH coding region (codon optimized for yeast)
      plus 5'homology to GPM promoter and 3'homology to ADH1 terminator

<400> SEQUENCE: 76

```
gaattccaaa caaacacaca tattacaata gctagctgag gatgaaagca ttagtgtata     60
ggggcccagg ccagaagttg gtggaagaga cacagaagcc agagcttaag gaacctggtg    120
acgctatagt gaaggtaaca aagactacaa tttgcggaac cgatctacac attcttaaag    180
gtgacgttgc gacttgtaaa cccggtcgtg tattagggca tgaaggagtg ggggttattg    240
aatcagtcgg atctggggtt actgcttcc aaccaggcga tagagttttg atatcatgta    300
tatcgagttg cggaaaagtgc tcattttgta gaagaggaat gttcagtcac tgtacgaccg    360
ggggttggat tctgggcaac gaaattgatg gtacccaagc agagtacgta agagtaccac    420
atgctgacac atcccttat cgtattccgg caggtgcgga tgaagaggcc ttagtcatgt     480
```

```
tatcagatat tctaccaacg ggttttgagt gcggagtcct aaacggcaaa gtcgcacctg    540
gttcttcggt ggctatagta ggtgctggtc ccgttggttt ggccgcctta ctgacagcac    600
aattctactc cccagctgaa atcataatga tcgatcttga tgataacagg ctgggattag    660
ccaaacaatt tggtgccacc agaacagtaa actccacggg tggtaacgcc gcagccgaag    720
tgaaagctct tactgaaggc ttaggtgttg atactgcgat tgaagcagtt gggatacctg    780
ctacatttga attgtgtcag aatatcgtag ctcccggtgg aactatcgct aatgtcggcg    840
ttcacggtag caaagttgat ttgcatcttg aaagtttatg gtcccataat gtcacgatta    900
ctacaaggtt ggttgacacg gctaccaccc cgatgttact gaaaactgtt caaagtcaca    960
agctagatcc atctagattg ataacacata gattcagcct ggaccagatc ttggacgcat   1020
atgaaacttt tggccaagct gcgtctactc aagcactaaa agtcatcatt tcgatggagg   1080
cttgattaat taagagtaag cgaatttctt atgatttgga tcc                     1123
```

<210> SEQ ID NO 77
<211> LENGTH: 26
<212> TYPE: DNA
<213> ORGANISM: Artificial Sequence
<220> FEATURE:
<223> OTHER INFORMATION: N1092 Primer

<400> SEQUENCE: 77
agagttttga tatcatgtat atcgag                                          26

<210> SEQ ID NO 78
<211> LENGTH: 26
<212> TYPE: DNA
<213> ORGANISM: Artificial Sequence
<220> FEATURE:
<223> OTHER INFORMATION: N1093 Primer

<400> SEQUENCE: 78
tttcaagatg caaatcaact ttgcta                                          26

<210> SEQ ID NO 79
<211> LENGTH: 398
<212> TYPE: PRT
<213> ORGANISM: Pseudomonas Putida

<400> SEQUENCE: 79

```
Ser Gly Asn Arg Gly Val Val Tyr Leu Gly Ser Gly Lys Val Glu Val
1               5                   10                  15

Gln Lys Ile Asp Tyr Pro Lys Met Gln Asp Pro Arg Gly Lys Lys Ile
            20                  25                  30

Glu His Gly Val Ile Leu Lys Val Val Ser Thr Asn Ile Cys Gly Ser
        35                  40                  45

Asp Gln His Met Val Arg Gly Arg Thr Thr Ala Gln Val Gly Leu Val
    50                  55                  60

Leu Gly His Glu Ile Thr Gly Glu Val Ile Glu Lys Gly Arg Asp Val
65                  70                  75                  80

Glu Asn Leu Gln Ile Gly Asp Leu Val Ser Val Pro Phe Asn Val Ala
                85                  90                  95

Cys Gly Arg Cys Arg Ser Cys Lys Glu Met His Thr Gly Val Cys Leu
            100                 105                 110

Thr Val Asn Pro Ala Arg Ala Gly Gly Ala Tyr Gly Tyr Val Asp Met
        115                 120                 125

Gly Asp Trp Thr Gly Gly Gln Ala Glu Tyr Val Leu Val Pro Tyr Ala
```

```
                130                 135                 140
Asp Phe Asn Leu Leu Lys Leu Pro Asp Arg Asp Lys Ala Met Glu Lys
145                 150                 155                 160

Ile Arg Asp Leu Thr Cys Leu Ser Asp Ile Leu Pro Thr Gly Tyr His
                165                 170                 175

Gly Ala Val Thr Ala Gly Val Gly Pro Gly Ser Thr Val Tyr Val Ala
            180                 185                 190

Gly Ala Gly Pro Val Gly Leu Ala Ala Ala Ser Ala Arg Leu Leu
        195                 200                 205

Gly Ala Ala Val Val Ile Val Gly Asp Leu Asn Pro Ala Arg Leu Ala
    210                 215                 220

His Ala Lys Ala Gln Gly Phe Glu Ile Ala Asp Leu Ser Leu Asp Thr
225                 230                 235                 240

Pro Leu His Glu Gln Ile Ala Ala Leu Leu Gly Glu Pro Glu Val Asp
                245                 250                 255

Cys Ala Val Asp Ala Val Gly Phe Glu Ala Arg Gly His Gly His Glu
                260                 265                 270

Gly Ala Lys His Glu Ala Pro Ala Thr Val Leu Asn Ser Leu Met Gln
            275                 280                 285

Val Thr Arg Val Ala Gly Lys Ile Gly Ile Pro Gly Leu Tyr Val Thr
        290                 295                 300

Glu Asp Pro Gly Ala Val Asp Ala Ala Lys Ile Gly Ser Leu Ser
305                 310                 315                 320

Ile Arg Phe Gly Leu Gly Trp Ala Lys Ser His Ser Phe His Thr Gly
                325                 330                 335

Gln Thr Pro Val Met Lys Tyr Asn Arg Ala Leu Met Gln Ala Ile Met
            340                 345                 350

Trp Asp Arg Ile Asn Ile Ala Glu Val Val Gly Val Gln Val Ile Ser
        355                 360                 365

Leu Asp Asp Ala Pro Arg Gly Tyr Gly Glu Phe Asp Ala Gly Val Pro
    370                 375                 380

Lys Lys Phe Val Ile Asp Pro His Lys Thr Phe Ser Ala Ala
385                 390                 395

<210> SEQ ID NO 80
<211> LENGTH: 348
<212> TYPE: PRT
<213> ORGANISM: Pyrococcus horikoshii

<400> SEQUENCE: 80

Met Ser Glu Lys Met Val Ala Ile Met Lys Thr Lys Pro Gly Tyr Gly
1               5                   10                  15

Ala Glu Leu Val Glu Val Asp Val Pro Lys Pro Gly Pro Gly Glu Val
                20                  25                  30

Leu Ile Lys Val Leu Ala Thr Ser Ile Cys Gly Thr Asp Leu His Ile
            35                  40                  45

Tyr Glu Trp Asn Glu Trp Ala Gln Ser Arg Ile Lys Pro Pro Gln Ile
        50                  55                  60

Met Gly His Glu Val Ala Gly Glu Val Val Glu Ile Gly Pro Gly Val
65                  70                  75                  80

Glu Gly Ile Glu Val Gly Asp Tyr Val Ser Val Glu Thr His Ile Val
                85                  90                  95

Cys Gly Lys Cys Tyr Ala Cys Arg Arg Gly Gln Tyr His Val Cys Gln
                100                 105                 110
```

```
Asn Thr Lys Ile Phe Gly Val Asp Thr Asp Gly Val Phe Ala Glu Tyr
            115                 120                 125
Ala Val Val Pro Ala Gln Asn Ile Trp Lys Asn Pro Lys Ser Ile Pro
        130                 135                 140
Pro Glu Tyr Ala Thr Leu Gln Glu Pro Leu Gly Asn Ala Val Asp Thr
145                 150                 155                 160
Val Leu Ala Gly Pro Ile Ser Gly Lys Ser Val Leu Ile Thr Gly Ala
                165                 170                 175
Gly Pro Leu Gly Leu Leu Gly Ile Ala Val Ala Lys Ala Ser Gly Ala
            180                 185                 190
Tyr Pro Val Ile Val Ser Glu Pro Ser Asp Phe Arg Arg Glu Leu Ala
        195                 200                 205
Lys Lys Val Gly Ala Asp Tyr Val Ile Asn Pro Phe Glu Glu Asp Val
    210                 215                 220
Val Lys Glu Val Met Asp Ile Thr Asp Gly Asn Gly Val Asp Val Phe
225                 230                 235                 240
Leu Glu Phe Ser Gly Ala Pro Lys Ala Leu Glu Gln Gly Leu Gln Ala
                245                 250                 255
Val Thr Pro Ala Gly Arg Val Ser Leu Leu Gly Leu Tyr Pro Gly Lys
            260                 265                 270
Val Thr Ile Asp Phe Asn Asn Leu Ile Ile Phe Lys Ala Leu Thr Ile
        275                 280                 285
Tyr Gly Ile Thr Gly Arg His Leu Trp Glu Thr Trp Tyr Thr Val Ser
    290                 295                 300
Arg Leu Leu Gln Ser Gly Lys Leu Asn Leu Asp Pro Ile Ile Thr His
305                 310                 315                 320
Lys Tyr Lys Gly Phe Asp Lys Tyr Glu Glu Ala Phe Glu Leu Met Arg
                325                 330                 335
Ala Gly Lys Thr Gly Lys Val Val Phe Met Leu Lys
            340                 345

<210> SEQ ID NO 81
<211> LENGTH: 11017
<212> TYPE: DNA
<213> ORGANISM: Artificial sequence
<220> FEATURE:
<223> OTHER INFORMATION: pRS426::GPD-xpk1+ADH-eutD plasmid

<400> SEQUENCE: 81
gatccccggg gctgcaggaa ttcgatatca agcttatcga taccgtcgac ctcgaggggg    60
ggcccggtac ccaattcgcc ctatagtgag tcgtattacg cgcgctcact ggccgtcgtt   120
ttacaacgtc gtgactggga aaaccctggc gttacccaac ttaatcgcct tgcagcacat   180
ccccctttcg ccagctggcg taatagcgaa gaggcccgca ccgatcgccc ttcccaacag   240
ttgcgcagcc tgaatggcga atggcgcgac gcgcctgta gcggcgcatt aagcgcggcg   300
ggtgtggtgg ttacgcgcag cgtgaccgct acacttgcca gcgccctagc gcccgctcct   360
ttcgctttct tcccttcctt tctcgccacg ttcgccggct ttccccgtca gctctaaat    420
cgggggctcc ctttagggtt ccgatttagt gctttacggc acctcgaccc caaaaaactt   480
gattagggtg atggttcacg tagtgggcca tcgccctgat agacggtttt tcgccctttg   540
acgttggagt ccacgttctt taatagtgga ctcttgttcc aaactggaac aacactcaac   600
cctatctcgg tctattcttt tgatttataa gggattttgc cgatttcggc ctattggtta   660
aaaaatgagc tgatttaaca aaaatttaac gcgaatttta caaaaatatt aacgtttaca   720
```

```
atttcctgat gcggtatttt ctccttacgc atctgtgcgg tatttcacac cgcatagggt    780
aataactgat ataattaaat tgaagctcta atttgtgagt ttagtataca tgcatttact    840
tataatacag ttttttagtt ttgctggccg catcttctca aatatgcttc ccagcctgct    900
tttctgtaac gttcaccctc taccttagca tcccttccct ttgcaaatag tcctcttcca    960
acaataataa tgtcagatcc tgtagagacc acatcatcca cggttctata ctgttgaccc   1020
aatgcgtctc ccttgtcatc taaacccaca ccgggtgtca taatcaacca atcgtaacct   1080
tcatctcttc cacccatgtc tctttgagca ataaagccga taacaaaatc tttgtcgctc   1140
ttcgcaatgt caacagtacc cttagtatat tctccagtag ataggagcc cttgcatgac    1200 aattctgcta acatcaaaag gcctctaggt tcctttgtta cttcttctgc cgcctgcttc   1260
aaaccgctaa caatacctgg gcccaccaca ccgtgtgcat tcgtaatgtc tgcccattct   1320
gctattctgt atacacccgc agagtactgc aatttgactg tattaccaat gtcagcaaat   1380
tttctgtctt cgaagagtaa aaattgtac ttggcggata atgcctttag cggcttaact    1440
gtgccctcca tggaaaaatc agtcaagata tccacatgtg tttttagtaa acaaattttg   1500
ggacctaatg cttcaactaa ctccagtaat tccttggtgg tacgaacatc caatgaagca   1560
cacaagtttg tttgcttttc gtgcatgata ttaaatagct tggcagcaac aggactagga   1620
tgagtagcag cacgttcctt atatgtagct ttcgacatga tttatcttcg tttcctgcag   1680 gttttgttc tgtgcagttg ggttaagaat actgggcaat ttcatgtttc ttcaacacta    1740
catatgcgta tatataccaa tctaagtctg tgctccttcc ttcgttcttc cttctgttcg   1800
gagattaccg aatcaaaaaa atttcaaga aaccgaaatc aaaaaaaga ataaaaaaa      1860 aatgatgaat tgaattgaaa agctgtggta tggtgcactc tcagtacaat ctgctctgat   1920
gccgcatagt taagccagcc ccgacacccg ccaacacccg ctgacgcgcc ctgacgggct   1980
tgtctgctcc cggcatccgc ttacagacaa gctgtgaccg tctccgggag ctgcatgtgt   2040
cagaggtttt caccgtcatc accgaaacgc gcgagacgaa agggcctcgt gatacgccta   2100
tttttatagg ttaatgtcat gataataatg gtttcttagt atgatccaat atcaaaggaa   2160
atgatagcat tgaaggatga gactaatcca attgaggagt ggcagcatat agaacagcta   2220
aagggtagtg ctgaaggaag catacgatac cccgcatgga atgggataat atcacaggag   2280
gtactagact acctttcatc ctacataaat agacgcatat aagtacgcat ttaagcataa   2340
acacgcacta tgccgttctt ctcatgtata tatatataca ggcaacacgc agatataggt   2400
gcgacgtgaa cagtgagctg tatgtgcgca gctcgcgttg cattttcgga agcgctcgtt   2460
ttcggaaacg cttttgaagtt cctattccga agttcctatt ctctagaaag tataggaact   2520
tcagagcgct tttgaaaacc aaaagcgctc tgaagacgca cttttcaaaaa accaaaaacg   2580 caccggactg taacgagcta ctaaaatatt gcgaataccg cttccacaaa cattgctcaa   2640
aagtatctct ttgctatata tctctgtgct atatccctat ataacctacc catccacctt   2700
tcgctccttg aacttgcatc taaactcgac ctctacattt tttatgttta tctctagtat   2760
tactctttag acaaaaaaat tgtagtaaga actattcata gagtgaatcg aaaacaatac   2820
gaaaatgtaa acatttccta tacgtagtat atagagacaa aatagaagaa accgttcata   2880
attttctgac caatgaagaa tcatcaacgc tatcactttc tgttcacaaa gtatgcgcaa   2940
tccacatcgg tatagaatat aatcggggat gcctttatct tgaaaaaatg cacccgcagc   3000
ttcgctagta atcagtaaac gcgggaagtg gagtcaggct ttttttatgg aagagaaaat   3060
agacaccaaa gtagccttct tctaaccctta acggacctac agtgcaaaaa gttatcaaga   3120
```

```
gactgcatta tagagcgcac aaaggagaaa aaaagtaatc taagatgctt tgttagaaaa    3180
atagcgctct cgggatgcat ttttgtagaa caaaaaagaa gtatagattc tttgttggta    3240
aaatagcgct ctcgcgttgc atttctgttc tgtaaaaatg cagctcagat tctttgtttg    3300
aaaaattagc gctctcgcgt tgcattttg ttttacaaaa atgaagcaca gattcttcgt    3360
tggtaaaata gcgctttcgc gttgcatttc tgttctgtaa aaatgcagct cagattcttt    3420
gtttgaaaaa ttagcgctct cgcgttgcat ttttgttcta caaatgaag cacagatgct    3480 tcgttcaggt ggcacttttc ggggaaatgt gcgcggaacc cctatttgtt tattttctta    3540
aatacattca aatatgtatc cgctcatgag acaataaccc tgataaatgc ttcaataata    3600
ttgaaaaagg aagagtatga gtattcaaca tttccgtgtc gcccttattc cctttttgc    3660 ggcatttgc cttcctgttt ttgctcaccc agaaacgctg gtgaaagtaa aagatgctga    3720
agatcagttg ggtgcacgag tgggttacat cgaactggat ctcaacagcg gtaagatcct    3780
tgagagtttt cgccccgaag aacgttttcc aatgatgagc acttttaaag ttctgctatg    3840
tggcgcggta ttatcccgta ttgacgccgg gcaagagcaa ctcggtcgcc gcatacacta    3900
ttctcagaat gacttggttg agtactcacc agtcacagaa aagcatctta cggatggcat    3960
gacagtaaga gaattatgca gtgctgccat aaccatgagt gataacactg cggccaactt    4020
acttctgaca acgatcggag gaccgaagga gctaaccgct tttttgcaca acatggggga    4080
tcatgtaact cgccttgatc gttgggaacc ggagctgaat gaagccatac caaacgacga    4140
gcgtgacacc acgatgcctg tagcaatggc aacaacgttg cgcaaactat taactggcga    4200
actacttact ctagcttccc ggcaacaatt aatagactgg atggaggcgg ataaagttgc    4260
aggaccactt ctgcgctcgg cccttccggc tggctggttt attgctgata atctggagc    4320 cggtgagcgt gggtctcgcg gtatcattgc agcactgggg ccagatggta agccctcccg    4380
tatcgtagtt atctacacga cggggagtca ggcaactatg gatgaacgaa atagacagat    4440
cgctgagata ggtgcctcac tgattaagca ttggtaactg tcagaccaag tttactcata    4500
tatactttag attgatttaa aacttcattt ttaatttaaa aggatctagg tgaagatcct    4560
ttttgataat ctcatgacca aaatccctta acgtgagttt cgttccact gagcgtcaga    4620 ccccgtagaa aagatcaaag gatcttcttg agatcctttt tttctgcgcg taatctgctg    4680
cttgcaaaca aaaaaaccac cgctaccagc ggtggtttgt ttgccggatc aagagctacc    4740
aactcttttt ccgaaggtaa ctggcttcag cagagcgcag ataccaaata ctgtccttct    4800
agtgtagccg tagttaggcc accacttcaa gaactctgta gcaccgccta catacctcgc    4860
tctgctaatc ctgttaccag tggctgctgc cagtggcgat aagtcgtgtc ttaccgggtt    4920
ggactcaaga cgatagttac cggataaggc gcagcggtcg ggctgaacgg ggggttcgtg    4980
cacacagccc agcttggagc gaacgaccta caccgaactg agatacctac agcgtgagct    5040
atgagaaagc gccacgcttc ccgaagggag aaaggcggac aggtatccgg taagcggcag    5100
ggtcggaaca ggagagcgca cgagggagct tccaggggga aacgcctggt atctttatag    5160
tcctgtcggg tttcgccacc tctgacttga gcgtcgattt ttgtgatgct cgtcaggggg    5220
gcggagccta tggaaaaacg ccagcaacgc ggccttttta cggttcctgg ccttttgctg    5280
gccttttgct cacatgttct ttcctgcgtt atccctgat tctgtggata accgtattac    5340
cgcctttgag tgagctgata ccgctcgccg cagccgaacg accgagcgca gcgagtcagt    5400
gagcgaggaa gcggaagagc gcccaatacg caaaccgcct ctccccgcgc gttggccgat    5460
```

```
tcattaatgc agctggcacg acaggtttcc cgactggaaa gcgggcagtg agcgcaacgc   5520
aattaatgtg agttacctca ctcattaggc accccaggct ttacacttta tgcttccggc   5580
tcctatgttg tgtggaattg tgagcggata caatttcac acaggaaaca gctatgacca    5640
tgattacgcc aagcgcgcaa ttaaccctca ctaaagggaa caaaagctgg agctccaccg   5700
cggatagatc tagttcgagt ttatcattat caatactgcc atttcaaaga atacgtaaat   5760
aattaatagt agtgattttc ctaactttat ttagtcaaaa aattagcctt ttaattctgc   5820
tgtaacccgt acatgcccaa ataggggc gggttacaca gaatatataa catcgtaggt     5880
gtctgggtga acagtttatt cctggcatcc actaaatata atggagcccg cttttttaagc  5940
tggcatccag aaaaaaaaag aatcccagca ccaaatatt gttttcttca ccaaccatca    6000
gttcataggt ccattctctt agcgcaacta cagagaacag gggcacaaac aggcaaaaaa   6060
cgggcacaac ctcaatggag tgatgcaacc tgcctggagt aaatgatgac acaaggcaat   6120
tgacccacgc atgtatctat ctcattttct tacaccttct attacttct gctctctctg    6180
atttggaaaa agctgaaaaa aaaggttgaa accagttccc tgaaattatt cccctacttg   6240
actaataagt atataaagac ggtaggtatt gattgtaatt ctgtaaatct atttcttaaa   6300
cttcttaaat tctacttta tagttagtct tttttttagt tttaaaacac caagaactta    6360
gtttcgaata aacacacata aacgctgagg atgacaacag attactcatc accagcatat   6420
ttgcaaaaag ttgataagta ctggcgtgct gccaactact tatcagttgg tcaactttat   6480
ttaaagata atccactatt acaacggcca ttgaaggcca gtgacgttaa ggttcatcca    6540
attggtcact gggggacgat tgccggtcaa aactttatct atgctcatct taaccgggtc   6600
atcaacaagt acggtttgaa gatgttctac gttgaaggtc caggtcatgg tggtcaagtg   6660
atggtttcaa actcttacct tgacggtact tacaccgata tttatccaga aattacgcag   6720
gatgttgaag ggatgcaaaa gctcttcaag caattctcat tcccaggtgg ggttgcttcc   6780
catgcggcac ctgaaacacc cggttcaatc cacgaaggtg cgaacttgg ttactcaatt    6840
tcacacgggg ttggggcaat tcttgacaat cctgacgaaa tcgccgcggt tgttgttggt   6900
gatggggaat ccgaaacggg tccattagca acttcatggc aatcaacgaa gttcattaac   6960
ccaatcaacg acgggctgt tttaccaatc ttgaacttaa atggttttaa gatttctaat    7020
ccaacgatt ttggtcggac ttctgatgct aagattaagg aatacttcga aagcatgaat    7080
tgggaaccaa tcttcgttga aggtgacgat cctgaaaagg ttcacccagc cttagctaag   7140
gccatggat aagccgttga aaagatcaag gcaatccaga agcatgctcg cgaaaataac    7200
gatgcaacat tgccagtatg gccaatgatc gtcttccgcg cacctaaggg ctggactggt   7260
ccgaagtcat gggacggtga taagatcgaa ggttcattcc gtgctcatca aattccgatt   7320
cctgttgatc aaaatgacat ggaacatgcg gatgctttag ttgattggct cgaatcatat   7380
caaccaaaag aactcttcaa tgaagatggc tctttgaagg atgatattaa agaaattatt   7440
cctactgggg acagtcggat ggctgctaac ccaatcacca atggtggggt cgatccgaaa   7500
gccttgaact taccaaactt ccgtgattat gcggtcgata cgtccaaaga aggcgcgaat   7560
gttaagcaag atatgatcgt ttggtcgac tatttgcggg atgtcatcaa gaaaaatcct    7620
gataacttcc ggttgttcgg acctgatgaa accatgtcta accgtttata tggtgtcttc   7680
gaaaccacta atcgtcaatg gatggaagac attcatccag atagtgacca atatgaagca   7740
ccagctggcc gggtcttaga tgctcagtta tctgaacacc aagctgaagg ttggttagaa   7800
ggttacgtct taactggacg tcatgggtta tttgccagtt atgaagcctt cctacgcgtt   7860
```

```
gtggactcaa tgttgacgca acacttcaag tggttacgta aagccaatga acttgattgg    7920
cgtaaaaagt acccatcact taacattatc gcggcttcaa ctgtattcca acaagaccat    7980
aatggttata cccaccaaga tccaggtgca ttaactcatt tggccgaaaa gaaaccagaa    8040
tacattcgtg aatatttacc agccgatgcc aacacgttat tagctgtcgg tgacgtcatt    8100
ttccggagcc aagaaaagat caactacgtg gttacgtcaa acacccacg tcaacaatgg     8160
ttcagcattg aagaagctaa gcaattagtt gacaatggtc ttggtatcat tgattgggca    8220
agtacggacc aaggtagcga accagacatt gtctttgcag ctgctgggac ggaaccaacg    8280
cttgaaacgt tggctgccat ccaattacta cacgacagtt tcccagagat gaagattcgt    8340
ttcgtgaacg tggtcgacat cttgaagtta cgtagtcctg aaaaggatcc gcgggcttg     8400
tcagatgctg agtttgacca ttactttact aaggacaaac cagtggtctt tgctttccac    8460
ggttacgaag acttagttcg tgacatcttc tttgatcgtc acaaccataa cttatacgtc    8520
cacggttacc gtgaaaatgg tgatattacc acaccattcg acgtacgggt catgaaccag    8580
atggaccgct tcgacttagc taagtcggca attgcggcgc aaccagcaat ggaaaacact    8640
ggtgcggcct tcgttcaatc catggataat atgcttgcta acacaatgc ctatatccgg     8700
gatgccggaa ctgacttgcc agaagttaat gattggcaat ggaagggttt aaaataatta    8760
attaatcatg taattagtta tgtcacgctt acattcacgc cctcctccca catccgctct    8820
aaccgaaaag gaaggagtta gacaacctga agtctaggtc cctatttatt tttttaata    8880
gttatgttag tattaagaac gttatttata tttcaaattt ttcttttttt tctgtacaaa    8940
cgcgtgtacg catgtaacat tatactgaaa accttgcttg agaaggtttt gggacgctcg    9000
aaggctttaa tttgcgggcg ccgctctag aactagtacc acaggtgttg tcctctgagg     9060
acataaaata cacaccgaga ttcatcaact cattgctgga gttagcatat ctacaattgg    9120
gtgaaatggg gagcgatttg caggcatttg ctcggcatgc cggtagaggt gtggtcaata    9180
agagcgacct catgctatac ctgagaaagc aacctgacct acaggaaaga gttactcaag    9240
aataagaatt ttcgttttaa aacctaagag tcactttaaa atttgtatac acttattttt    9300
tttataactt atttaataat aaaaatcata aatcataaga aattcgctta ctcttaatta    9360
attaagctaa tccttgggct gctgtaataa tcgcaacctt ataaacgtct tcttcactgc    9420
atccacgtga caagtcggag accggcttgt tcaggccttg caagacagga cccaccgctt    9480
caaaatgacc aaatcgttgc gcaatcttat agccaatatt accagactga agctctggaa    9540
atacaaagac attggcatga ccagctactt tggaaccagg agccttttgc aaaccaactt    9600
tttcaacgaa ggccgcgtca aattgaagtt caccatcgat agccaattcc ggttcagcag    9660
cttgcgcctt ggccgttgct tcttgcactt tagtgaccat ttcaccctta gccgaaccct    9720
tagttgagaa gctgagcatc gcaactttcg ggtcaatatc gaagacctta gcagtagccg    9780
cactctgagt ggcaatttcc gctaacgtat cggcatcggg atcaatattg atggcacagt    9840
cagcaaagac gtagcgttcc tcacccttt gcatgataaa tgcacccgag attcggtgtg    9900
aaccgggctt ggtcttaata atttgtaacg ctggccgtac cgtatcacca gttggatgga    9960
ttgcacctga aaccatccca tccgcttttgc ccatataaac gagcatcgtg ccaaagtagt    10020
tttcatcttc cagcatttta gccgcttgtt ctggcgtatt cttacctttc gccgttcaa     10080
cgagggcatc aagcattgct tgcttatctt cagcccggta tgtcgcagga tcaaggactt    10140
gaacgcctgt taaatccgca ttcaaatcgt tagccacagc ctgaactttg tccgttgcac    10200
```

```
ctaaaacaat cggcttaacc aagccgtctg cagctaatcg cgctgccgca ccgacaattc    10260
ggggttcagt tccttcaggg aaaacaattg tttgatcttt accagtaatt ttttgtgcta    10320
atgactcaaa taaatccatc ctcagcgaga tagttgattg tatgcttggt atagcttgaa    10380
atattgtgca gaaaaagaaa caaggaagaa agggaacgag aacaatgacg aggaaacaaa    10440
agattaataa ttgcaggtct atttatactt gatagcaaga cagcaaactt ttttttattt    10500
caaattcaag taactggaag gaaggccgta taccgttgct cattagagag tagtgtgcgt    10560
gaatgaagga aggaaaaagt ttcgtgtgct tcgagatacc cctcatcagc tctggaacaa    10620
cgacatctgt tggtgctgtc tttgtcgtta atttttcct ttagtgtctt ccatcatttt     10680
tttgtcattg cggatatggt gagacaacaa cggggagag agaaaagaaa aaaaagaaa      10740 agaagttgca tgcgcctatt attacttcaa tagatggcaa atggaaaaag ggtagtgaaa    10800
cttcgatatg atgatggcta tcaagtctag ggctacagta ttagttcgtt atgtaccacc    10860
atcaatgagg cagtgtaatt ggtgtagtct tgtttagccc attatgtctt gtctggtatc    10920
tgttctattg tatatctccc ctccgccacc tacatgttag ggagaccaac gaaggtatta    10980
taggaatccc gatgtatggg tttggttgcc agaaaag                            11017
```